US012742209B2

(12) United States Patent
Tainer et al.

(10) Patent No.: US 12,742,209 B2
(45) Date of Patent: Sep. 22, 2026

(54) METHODS FOR TREATING CANCERS WITH INHIBITORS TARGETING THE ROLE OF GRB2 IN DNA REPAIR

(71) Applicant: Board of Regents, The University of Texas System, Austin, TX (US)

(72) Inventors: John A. Tainer, Houston, TX (US); Zamal Ahmed, Houston, TX (US); Zu Ye, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 636 days.

(21) Appl. No.: 18/245,571

(22) PCT Filed: Aug. 3, 2021

(86) PCT No.: PCT/US2021/044288
§ 371 (c)(1),
(2) Date: Mar. 16, 2023

(87) PCT Pub. No.: WO2022/060477
PCT Pub. Date: Mar. 24, 2022

(65) Prior Publication Data

US 2023/0366033 A1 Nov. 16, 2023

Related U.S. Application Data

(60) Provisional application No. 63/079,386, filed on Sep. 16, 2020.

(51) Int. Cl.
*C12Q 1/6886* (2018.01)
*A61K 45/06* (2006.01)

(52) U.S. Cl.
CPC ............ *C12Q 1/6886* (2013.01); *A61K 45/06* (2013.01); *C12Q 2600/106* (2013.01); *C12Q 2600/158* (2013.01)

(58) Field of Classification Search
CPC . C12Q 1/6886; C12Q 2600/158; A61K 45/06
See application file for complete search history.

(56) References Cited

U.S. PATENT DOCUMENTS

2019/0352418 A1* 11/2019 Wilson .................. C07K 14/71
2022/0151991 A1* 5/2022 Ahmed .............. A61K 31/5377

FOREIGN PATENT DOCUMENTS

WO WO 2018/053232 A1 3/2018
WO WO 2020/186202 9/2020

OTHER PUBLICATIONS

Ashizawa, A. T. et al., "BP1001, a Novel Therapeutic for Chronic Myelogenous Leukemia," *Blood*, 128.22 (2016): 4239, 1-2.

Faruqi, A. et al., "Cytarabine—StarPearls—NCBI Bookshelf," last updated 2023: 1-6 https://www.ncbi.nlm.nih.gov/books/NBK557680/.

Klinakis, A. et al., "Targeting DNA repair in cancer: current state and novel approaches," *Cellular and Molecular Life Sciences*, 77 (2020): 677-703.

Maes, K. et al., "The Role of DNA Damage and Repair in Decitabine-Mediated Apoptosis in Multiple Myeloma," *Oncotarget*, 5.10 (2014): 3115-3129.

O'Conner, W. et al., "Bio-Path Announces Patient Dosing in Amended Phase 2 Prexigebersen Trial in Acute Myeloid Leukemia," *Bio-Path Holdings, Inc.*, (2019): 1-3.

Ohanian, M. et al., "Liposomal Grb2 antisense oligodeoxynucleotide (BP1001) in patients with refractory or relapsed haematological malignancies: a single-centre, open-label, dose-escalation, phase 1/1b trial," *Lancet Haematol.*, 18 (2018): 30021-8, 1-15.

Pen, S. et al., "Dasatinib induces DNA damage and activates DNA repair pathways leading to senescence in non-small cell lung cancer cell lines with kinase-inactivating BRAF mutations," *Oncotarget*, 7.1 (2015): 565-579.

Slade, D., "PARP and PARG inhibitors in cancer treatment," *Genes & Development*, 34 (2020): 360-394.

Ye, Z. et al., "GRB2 enforces homology-directed repair initiation by MRE11," *Science Advances*, 7 (2021): eabe9254, 1-17.

Ahmed, Z. et al., "Direct binding of Grb2 SH3 domain to FGFR2 regulates SHP2 function," *Cellular Signaling*, 22.1 (2010): 23-33.

Ahmed, Z. et al., "Grb2 controls phosphorylation of FGFR2 by inhibiting receptor kinase and Shp2 phosphatase activity," *The Journal of Cell Biology*, 200.4 (2013): 493-504.

Ahmed, Z. et al., "Grb2 monomer-dimer equilibrium determines normal versus oncogenic function," *Nature Communications*, 6.7354 (2015): 1-11.

Ashworth, A. et al., "Synthetic lethal therapies for cancer: what's next after PARP inhibitors?" *Nat Rev Clin Oncol*, 15.9 (2018): 564-576.

Bacolla, A. et al., "Heritable pattern of oxidized DNA base repair coincides with pre-targeting of repair complexes to open chromatin," *Nucleic Acids Research*, 49.1 (2013): 221-243.

Bai, W. et al., "C1QBP Promotes Homologous Recombination by Stabilizing MRE11 and Controlling the Assembly and Activation of MRE11/RAD50/NBS1 Complex," *Molecular Cell*, 75 (2019): 1299-1314.

Blackford, A. N. et al., "ATM, ATR, and DNA-PK: The Trinity at the Heart of the DNA Damage Response," *Molecular Cell*, 66 (2017): 801-817.

Chang, E. Y-C. et al., "MRE11-RAD50-NBS1 promotes Fanconi Anemia R-loop suppression at transcription-replication conflicts," *Nature Communications*, 10.4265 (2019): 1-15.

Chapman, J. R. et al., "Phospho-dependent interactions between NBS1 and MDC1 mediate chromatin retention of the MRN complex at sites of DNA damage," *EMBO Reports*, 9.8 (2008): 795-801.

Chardin, P. et al., "Human Sos1: a guanine nucleotide exchange factor for Ras that binds to GRB2," *Science*, 260.5112 (1993): 1338-1343.

(Continued)

*Primary Examiner* — Sarae L Bausch
(74) *Attorney, Agent, or Firm* — pH IP Law

(57) ABSTRACT

Provided herein are methods for selecting and treating cancers that are homology-directed repair (HDR) proficient. As such, methods for sensitizing cancers to PARP inhibitor therapy and ionizing radiation are also provided. In some aspects, cancers are treated with a combination of a GRB2 inhibitor and a PARP inhibitor or a GRB2 inhibitor and ionizing radiation.

11 Claims, 47 Drawing Sheets

Specification includes a Sequence Listing.

(56) References Cited

OTHER PUBLICATIONS

Chen, Y. et al., "Lymecycline reverses acquired EGFR-TKI resistance in non-small-cell lung cancer by targeting GRB2," *Pharmacological Research*, 159 (2020): 105007, 1-15.
Cheng, A. M. et al., "Mammalian Grb2 regulates multiple steps in embryonic development and malignant transformation," *Cell*, 95 (1998): 793-803.
Cook, P. J. et al., "Tyrosine dephosphorylation of H2AX modulates apoptosis and survival decisions," *Nature*, 458.7238 (2009): 591-596.
Deshpande, R. A. et al., "ATP-driven Rad50 conformations regulate DNA tethering, end resection, and ATM checkpoint signaling," *The EMBO Journal*, 33.5 (2014): 482-500.
Dutta, A. et al., "Microhomology-mediated end joining is activated in irradiated human cells due to phosphorylation-dependent formation of the XRCCI repair complex," *Nucleic Acids Research*, 45.5 (2017): 2585-2599.
Eckelmann, B. J. et al., "XRCC1 promotes replication restart, nascent fork degradation and mutagenic DNA repair in BRCA2-deficient cells," *NAR Cancer*, 2.3 (2020): 1-15.
Feng, L. et al., "The E3 ligase RNF8 regulates KU80 removal and NHEJ repair," *Nat Struct Mol Biol.*, 19.2 (2012): 201-206.
Hogrel, G. et al., "Physical and functional interplay between PCNA DNA clamp and Mre11-Rad50 complex from the archaeon Pyrococcus furiosus," *Nucleic Acids Research*, 46.11 (2018): 5651-5663.
Hou, B. et al., "Grb2 binds to PTEN and regulates its nuclear translocation to maintain the genomic stability in DNA damage response," *Cell Death and Disease*, 10 (2019): 546, 1-14.
Houl, J. H. et al., "Selective small molecule PARG inhibitor causes replication fork stalling and cancer cell death," *Nature Communications*, 10. 5654 (2019): 1-15.
Keung, M. Y. et al., "Response of Breast Cancer Cells to PARP Inhibitors Is Independent of BRCA Status," *Journal of Clinical Medicine*, 9 (2020): 940, 1-15.
Lloyd, J. et al., "A supramodular FHA/BRCT-repeat architecture mediates Nbs1 adaptor function in response to DNA damage," *Cell*, 139 (2009): 100-111.
Lowenstein, E. J. et al., "The SH2 and SH3 domain-containing protein GRB2 links receptor tyrosine kinases to ras signaling," *Cell*, 70 (1992): 431-442.
Lv, J. et al., "Deubiquitinase PSMD14 enhances hepatocellular carcinoma growth and metastasis by stabilizing GRB2," *Cancer Letters*, 469 (2020): 22-34.
Melander, F. et al., "Phosphorylation of SDT repeats in the MDC1 N terminus triggers retention of NBS1 at the DNA damage-modified chromatin," *The Journal of Cell Biology*, 181.2 (2008): 213-226.
Miotto, B. et al., "The RBBP6/ZBTB38/MCM10 axis regulates DNA replication and common fragile site stability," *Cell Reports*, 7 (2014): 575-587.
Mol, C. D. et al., "DNA-bound structures and mutants reveal abasic DNA binding by APE1 and DNA repair coordination [corrected]," *Nature*, 403 (2000): 451-456.
Park, Y. B. et al., "Crystal structure of human Mre11: understanding tumorigenic mutations," *Structure*, 19 (2011): 1591-1602.
Paull, T. T. et al., "The Mre11/Rad50/Nbs1 complex: recent insights into catalytic activities and ATP-driven conformational changes," *Exp Cell Res.*, 329.1 (2014): 139-147).
Paull, T. T, "20 Years of Mre11 Biology: No. End in Sight," *Molecular Cell*, 71 (2018): 419-427.
Paull, T. T. et al., "A critical role for histone H2AX in recruitment of repair factors to nuclear foci after DNA damage," *Current Biology*, 10 (2000): 886-895.
PCT International Search Report and Written Opinion issued in International Patent Application No. PCT/US2021/044288, mailed Feb. 28, 2022.
PCT Preliminary Report on Patentability issued in International Patent Application No. PCT/US2021/044288, mailed Mar. 30, 2023.
Rogakou, E. P. et al., "Megabase Chromatin Domains Involved in DNA Double-Strand Breaks In Vivo," *The Journal of Cell Biology*, 146.5 (1999): 905-916.
Rogakou, E. P. et al., "DNA double-stranded breaks induce histone H2AX phosphorylation on serine 139," The Journal of Biological Chemistry, 273.10 (1998): 5858-5868.
Sakai, Y. et al., "cDNA Sequence and Chromosomal Localization of a Novel Human Protein, RBQ-1 (RBBP6), That Binds to the Retinoblastoma Gene Product," *Genomics*, 30.1 (1995): 98-101.
Sfeir, A. et al., "Microhomology-Mediated End Joining: A Back-up Survival Mechanism or Dedicated Pathway?" *Trends in Biochemical Sciences*, 40.11 (2015): 701-714.
Shen, W. H. et al., "Essential role for nuclear PTEN in maintaining chromosomal integrity," *Cell*, 128 (2007): 157-170.
Shibata, A. et al., "DNA double-strand break repair pathway choice is directed by distinct MRE11 nuclease activities," *Molecular Cell*, 53 (2013): 7-18.
Songyang, Z. et al., "Specific motifs recognized by the SH2 domains of Csk, 3BP2, fps/fes, GRB-2, HCP, SHC, Syk, and Vav," Molecular and Cellular Biology, 14.4 (1994): 2777-2785.
Spycher, C. et al., "Constitutive phosphorylation of MDC1 physically links the MRE11-RAD50-NBS1 complex to damaged chromatin," *The Journal of Cell Biology*, 181.2 (2008): 227-240.
Stucki, M. et al., "MDC1 directly binds phosphorylated histone H2AX to regulate cellular responses to DNA double-strand breaks," *Cell*, 123 (2005): 1213-1226.
Syed, A. et al., "The MRE11-RAD50-NBS1 Complex Conducts the Orchestration of Damage Signaling and Outcomes to Stress in DNA Replication and Repair," *Annual Review of Biochemistry*, 87 (2018): 263-294.
Symington, L., "Mechanism and regulation of DNA end resection in eukaryotes," *Crit Rev Biochem Mol Biol*, 51.3 (2016): 195-212.
Verbeek, B. S. et al., "Grb2 overexpression in nuclei and cytoplasm of human breast cells: a histochemical and biochemical study of normal and neoplastic mammary tissue specimens," *J Pathol*, 183 (1997): 195-203.
Wang, Q. et al., "Rad17 recruits the MRE11-RAD50-NBS1 complex to regulate the cellular response to DNA double-strand breaks," *EMBO Journal*, 33.8 (2014): 862-877.
Williams, S. et al., "Mre11 dimers coordinate DNA end bridging and nuclease processing in double-strand-break repair," *Cell*, 135 (2008): 97-109.
Williams, G. et al., "Mre11-Rad50-Nbs1 conformations and the control of sensing, signaling, and effector responses at DNA double-strand breaks," *DNA Repair*, 9.12 (2010): 1299-1306, 2010.
Wu, L. et al., "MDC1 regulates intra-S-phase checkpoint by targeting NBS1 to DNA double-strand breaks," *PNAS*, 105.32 (2008): 11200-11205.
Xiao, A. et al., "WSTF regulates the H2A.X DNA damage response via a novel tyrosine kinase activity," *Nature*, 457 (2009): 57-62.
Yamazaki, T. et al., "Role of Grb2 in EGF-stimulated EGFR internalization," *Journal of Cell Science*, 115 (2002): 1791-1802.
Zhong, Z-H. et al., "Disruption of telomere maintenance by depletion of the MRE11/RAD50/NBS1 complex in cells that use alternative lengthening of telomeres," *The Journal of Biological Chemistry*, 282.40 (2007): 29314-29322.

* cited by examiner

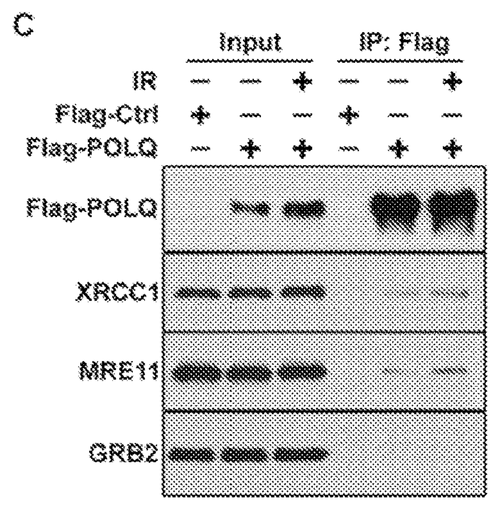
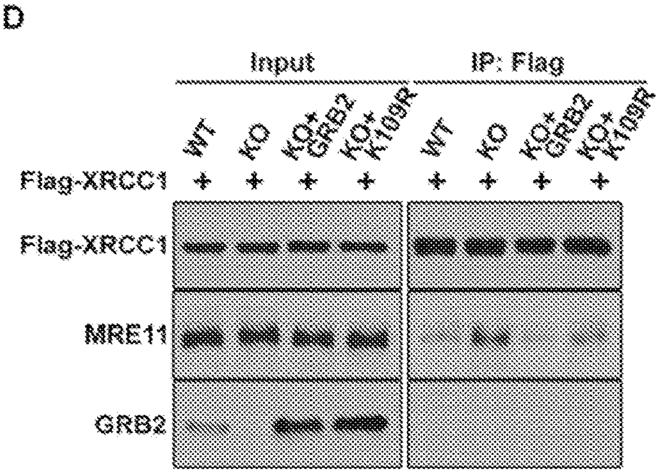
FIGS. 6C-6D
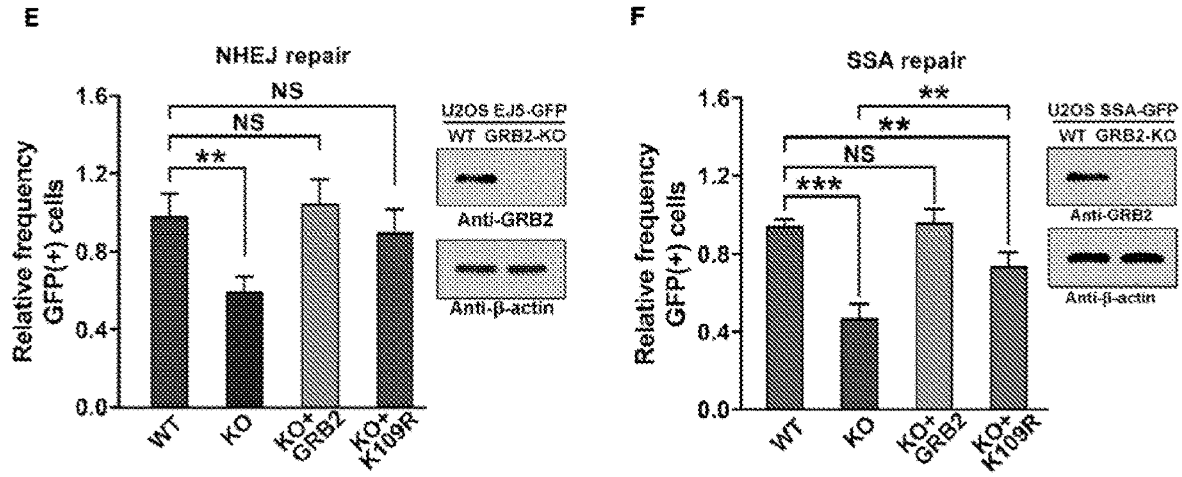
FIGS. 6E-6F

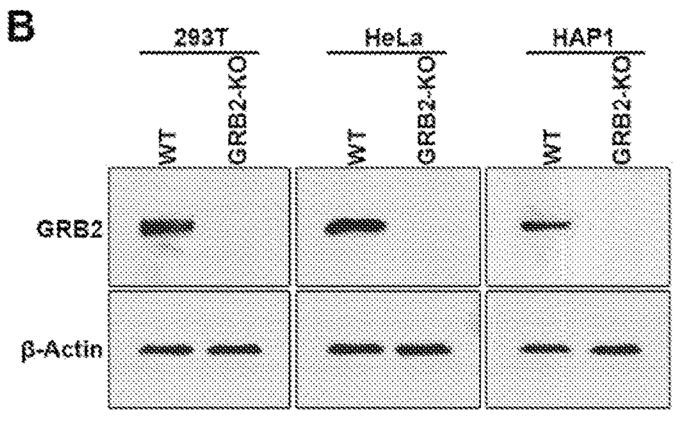
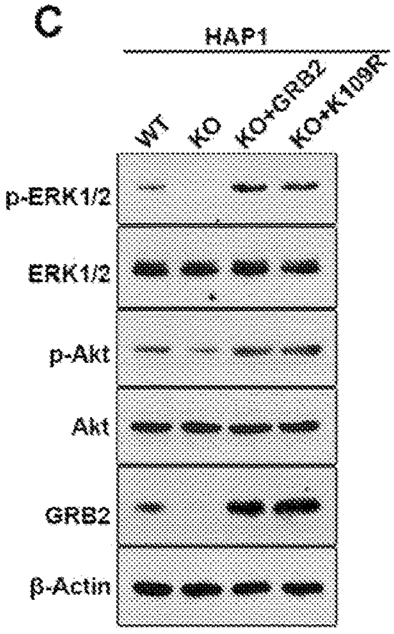
FIGS. 11B-11C
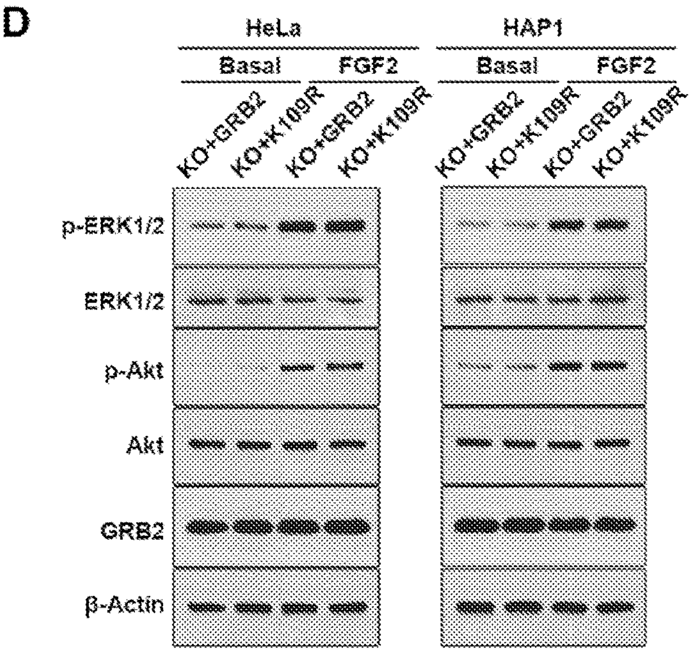
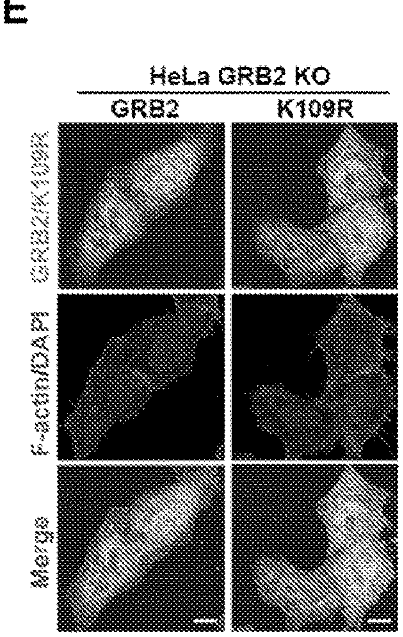
FIGS. 11D-11E

| GRB2 interactors involved in DNA repair | | |
|---|---|---|
| H2AX | NONO | SFPQ |
| HMGB1 | PCNA | SMC3 |
| MRE11 | RPA70 | SUPT16H |

C

D

NIH-3T3 cells

H

I

B

C

METHODS FOR TREATING CANCERS WITH INHIBITORS TARGETING THE ROLE OF GRB2 IN DNA REPAIR

REFERENCE TO RELATED APPLICATIONS

The present application is a national phase application under 35 U.S.C. § 371 of International Application No. PCT/US2021/044288, filed Aug. 3, 2021, which claims the priority benefit of U.S. provisional application No. 63/079,386, filed Sep. 16, 2020, the entire contents of each of which are incorporated herein by reference.

REFERENCE TO A SEQUENCE LISTING

The instant application contains a Sequence Listing, which has been submitted in ASCII format via EFS-Web and is hereby incorporated by reference in its entirety. Said ASCII copy, created on Jul. 30, 2021, is named UTFCP1507WO_ST25.txt and is 4.5 kilobytes in size.

BACKGROUND

I. Field

The present disclosure relates in general to the fields of chemistry and medicine, specifically to compositions of matter and methods of their use in medical indications, such as cancer.

II. Description of Related Art

Double-strand breaks (DSBs), the most toxic and mutagenic form of DNA damage, are repaired by multiple proteins but the meiotic recombination 11 homolog (MRE11) complex with RAD50 ATPase and NBS1 phospho-binding protein (MRN) complex plays a central initiating and orchestrating role (Deshpande et al., 2014; Paull & Deshpande, 2014; Paull, 2018; Syed & Tainer, 2018; Williams et al., 2010). At DSBs, the variant histone H2AX, which is inserted within ~2-25% of the nucleosome core particles throughout the genome, is constitutively phosphorylated on tyrosine 142 (Y142) by the ATP-dependent chromatin remodeling complex Williams Syndrome Transcription Factor WSTF (Fernandez-Capetillo et al., 2004; Xiao et al., 2009). In response to DNA damage, serine 139 undergoes phosphorylation (pS139, aka γH2AX) on each side of a DNA double-strand break by phosphatidylinositol 3-kinase-related kinases (Blackford and Jackson, 2017; Rogakou et al., 1999; Rogakou et al., 1998). H2AX thus provides a critical signal and platform for the recruitment of DNA damage repair proteins proximal to DNA damage sites (Paull et al., 2000). Early DNA damage signaling is dominated by H2AX dually phosphorylated on Y142 and S139 (pH2AX). Yet, around two hours after DNA damage, a switch to the γH2AX state of S139 phosphorylation is required to complete repair (Xiao et al., 2009). The transcriptional coactivator eyes absent (EYA) phosphatase facilitates Y142 dephosphorylation (Cook et al., 2009). MRN can be recruited to the DSB site through multiple independent processes. Many cell-based assays establish that γH2AX plays a pivotal role in MRN recruitment to chromatin through the association of NBS1-MDC1-H2AX (Chapman & Jackson, 2008; Melander et al., 2008; Spycher et al., 2008; Wu et al., 2008). The NBS1 FHA domain interacts with phosphorylated Mediator of DNA damage checkpoint protein 1 (MDC1), which in turn binds to γH2AX, establishing a mode of MRN recruitment to the DNA damage site (Lloyd et al., 2009; Stucki et al., 2005). Rad17, through its association with NBS1, also indirectly recruits MRE11 to DSBs at an early stage, independent of MDC1 (Wang et al., 2014). Evolutionarily conserved complement component 1 Q subcomponent-binding protein (C1QBP) interacts with MRE11-RAD50 to form a complex without NBS1, stabilizing MRE11 but preventing its DNA binding (Bai et al., 2019). Thus, a constitutive MRN complex may not be constant in cells and multiple independent processes may enrich MRE11 assembly at DSBs, rendering efficient DSB repair timing critical for cell survival and genome stability. Overall, timely MRE11 recruitment dictates DSB repair initiation and the efficiency, as critical for cell survival and genome stability (Syed & Tainer, 2018).

Growth factor receptor-bound protein 2 (GRB2) is a metazoan cytoplasmic adapter protein essential for receptor tyrosine kinase (RTK)-induced RAS/MAPK activation (Buday et al., 1994; Chardin et al., 1993; Dearth et al., 2007; Gale et al., 1993; Giubellino et al., 2008; Li et al., 1993; Lowenstein et al., 1992; Simon et al., 1991; Timsah et al., 2016; Wagner et al., 2013). Functionally, GRB2 acts in early signaling complexes (ESCs): within seconds after RTK activation, GRB2-SOS complex is recruited by the receptor to the membrane for RAS activation (Aoki et al., 2011). GRB2 is essential for RTK-induced RAS activation and thus GRB2-knockout (KO) mice are embryonically lethal due to defective endodermal cell differentiation and epiblast formation (Cheng et al., 1998). Although the nuclear localization of GRB2 was first reported over 20 years ago (Verbeek et al., 1997; Yamazaki et al., 2002), no function was assigned. Recently, GRB2-mediated nuclear localization of PTEN was reported. Based primarily upon inferential evidence, a GRB2-PTEN signaling axis was recently proposed to act in DNA repair and genomic stability with possible implications in DNA damage response (DDR) pathways in HeLa and 293T cells (Hou et al., 2019). Yet, a substantial presence and role of GRB2 in the nucleus and its possible detailed molecular and cellular functions remain enigmatic. As such, an understanding of the molecular basis for GRB2 as a bonafide DDR protein, including possible nuclear activities, is needed as a foundation for future GRB2 research.

In breast cancer, a study of 560 whole genomes and subsequent studies revealed that one gene signature—'Signature 3'—corresponds to a defect in the homologous recombination (HR) machinery. This signature is observed in tumors with complete inactivation of BRCA1/2. This inactivation can occur by germline and somatic point mutations, loss of heterozygosity (LOH) due to structural variations, hyper-methylation of BRCA1 promoters, or loss-of-function mutations of PALB2 and RAD51D. Experimentally, Signature 3 was observed in BRCA −/− isogenic cell lines, providing direct evidence of its association with HR defect. A recent study using breast cancer organoids, for example, has shown that the high burden of Signature 3 mutations is associated with a better response to PARP (poly [ADP-ribose] polymerase) inhibitors. Inhibitors of PARP enzymes cause multiple double-strand breaks, and tumor cells that cannot repair the breaks due to homology-directed repair (HDR) defects do not survive. However, methods of treating cancer that lack Signature 3 mutations, and thus are HDR proficient, are needed.

SUMMARY

In some aspects, the present disclosure provides methods of treating cancer in a patient, the methods comprising administering to the patient a combined effective amount of a GRB2 inhibitor and a DNA damaging agent or DNA repair inhibitor. In some embodiments, the cancer has been identified as being homology-directed repair (HDR) proficient. In some embodiments, the methods further comprise administering to the patient an Alt-EJ inhibitor (e.g., a polymerase theta inhibitor).

In other aspects, the present disclosure provides methods of treating a patient having a cancer, the method comprising (a) determining or having determined whether the cancer is HDR proficient; (b) selecting or having selected the patient for treatment with a GRB2 inhibitor in combination with a DNA damaging agent or DNA repair inhibitor when the cancer is HDR proficient; and (c) administering or having administered to the selected patient a combined effective amount of a GRB2 inhibitor and a DNA damaging agent or DNA repair inhibitor. In some embodiments. In some embodiments, the methods further comprise administering to the patient an Alt-EJ inhibitor (e.g., a polymerase theta inhibitor).

In some embodiments, the method is further defined as a method of sensitizing cancer cells to a DNA damaging agent or DNA repair inhibitor.

In still other aspects, the present disclosure provides methods for selecting a cancer patient for treatment with a GRB2 inhibitor in combination with a PARP inhibitor, the method comprising (a) determining or having determined whether the cancer is HDR proficient; and (b) selecting or having selected the patient for treatment with a GRB2 inhibitor in combination with a DNA damaging agent or DNA repair inhibitor when the cancer is HDR proficient. In some embodiments, step (a) comprises (i) obtaining or having obtained a biological sample from the patient; and (ii) performing or having performed an assay on the biological sample to determine whether the cancer is HDR proficient. In some embodiments, the methods further comprise (c) administering or having administered to the selected patient a combined effective amount of a GRB2 inhibitor and a DNA damaging agent or DNA repair inhibitor. In some embodiments, the methods further comprise administering to the patient an Alt-EJ inhibitor (e.g., a polymerase theta inhibitor). In some embodiments, the methods further comprise determining whether the cancer expresses high levels of MRE11 relative to a reference level, wherein if the cancer is both HDR proficient and expresses high levels of MRE11, then the patient is selected for treatment with a GRB2 inhibitor in combination with a DNA damaging agent or DNA repair inhibitor. In some embodiments, the methods further comprise administering or having administered to the selected patient a combined effective amount of a GRB2 inhibitor and a DNA damaging agent or DNA repair inhibitor. In some embodiments, the methods further comprise determining whether the cancer expresses high levels of GRB2 relative to a reference level, wherein if the cancer is both HDR proficient and expresses high levels of GRB2, then the patient is selected for treatment with a GRB2 inhibitor in combination with a DNA damaging agent or DNA repair inhibitor. In some embodiments, the methods further comprise administering or having administered to the selected patient a combined effective amount of a GRB2 inhibitor and a DNA damaging agent or DNA repair inhibitor. In some embodiments, the methods further comprise determining whether the cancer expresses high levels of GRB2 and high levels of MRE11 relative to a reference level, wherein if the cancer is both HDR proficient and expresses high levels of GRB2 and high levels of MRE11, then the patient is selected for treatment with a GRB2 inhibitor in combination with a DNA damaging agent or DNA repair inhibitor. In some embodiments, the methods further comprise administering or having administered to the selected patient a therapeutically effective amount of a GRB2 inhibitor and a DNA damaging agent or DNA repair inhibitor. In some embodiments, the methods further comprise administering to the patient an Alt-EJ inhibitor (e.g., a polymerase theta inhibitor).

In some embodiments, the reference level is a level in a sample sourced from healthy or non-cancerous tissue from the patient. In some embodiments, the reference level is a level in a sample sourced from a healthy subject. In some embodiments, the GRB2 inhibitor is a small molecule GRB2 inhibitor or an anti-GRB2 inhibitory nucleic acid. In some embodiments, the DNA damaging agent or DNA repair inhibitor is a PARP inhibitor, a PARG inhibitor, a DNAPK inhibitor, a polymerase theta inhibitor, an MRE11 inhibitor, or an ATR inhibitor. In some embodiments, the PARP inhibitor is olaparib, ABT-888 (Veliparib), BSI-201 (Iniparib), BMN 673, Rucaparib (AG-014699, PF-01367338), AG14361, INO-1001, A-966492, PJ34, MK-4827, or Fluzoparib. In some embodiments, the method is further defined as a method of sensitizing cancer cells to a PARP inhibitor. In some embodiments, the GRB2 inhibitor and the DNA damaging agent or DNA repair inhibitor are administered concurrently or essentially simultaneously. In some embodiments, the GRB2 inhibitor is administered before the DNA damaging agent or DNA repair inhibitor. In some embodiments, the methods further comprise administering at least one additional therapeutic to the subject. In some embodiments, the at least one additional therapeutic is selected from the group consisting of surgical therapy, chemotherapy, radiation therapy, cryotherapy, hormonal therapy, toxin therapy, immunotherapy, or cytokine therapy. In some embodiments, the at least one additional therapeutic comprises ionizing radiation. In some embodiments, the cancer is colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, or glioblastoma.

In yet other aspects, the present disclosure provides methods of treating cancer in a patient, the method comprising administering to the patient a combined effective amount of a DNA damaging agent or DNA repair inhibitor, wherein the cancer has been identified as expressing a decrease level of GRB2 relative to a reference level. In some embodiments, the methods further comprise administering to the patient an Alt-EJ inhibitor (e.g., a polymerase theta inhibitor).

In other aspects, the present disclosure provides methods of treating a patient having a cancer, the method comprising (a) determining or having determined whether the cancer expresses a decrease level of GRB2 relative to a reference level; (b) selecting or having selected the patient for treatment with a DNA damaging agent or DNA repair inhibitor when the cancer expresses a decrease level of GRB2 relative to a reference level; and (c) administering or having administered to the selected patient an effective amount of a DNA damaging agent or DNA repair inhibitor. In some embodiments, the methods further comprise administering to the patient an Alt-EJ inhibitor (e.g., a polymerase theta inhibitor).

In still other aspects, the present disclosure provides methods for selecting a cancer patient for treatment with a DNA damaging agent or DNA repair inhibitor, the method comprising (a) determining or having determined whether the cancer expresses a decrease level of GRB2 relative to a reference level; and (b) selecting or having selected the patient for treatment with a DNA damaging agent or DNA repair inhibitor when the cancer expresses a decrease level of GRB2 relative to a reference level. In some embodiments, step (a) comprises (i) obtaining or having obtained a biological sample from the patient; and (ii) performing or having performed an assay on the biological sample to determine whether the cancer expresses a decrease level of GRB2 relative to a reference level. In some embodiments, the methods further comprise (c) administering or having administered to the selected patient an effective amount of a DNA damaging agent or DNA repair inhibitor. In some embodiments, the methods further comprise administering to the patient an Alt-EJ inhibitor (e.g., a polymerase theta inhibitor).

In some embodiments, the reference level is a level in a sample sourced from healthy or non-cancerous tissue from the patient. In some embodiments, the reference level is a level in a sample sourced from a healthy subject. In some embodiments, the DNA damaging agent or DNA repair inhibitor is a PARP inhibitor, a PARG inhibitor, a DNAPK inhibitor, a polymerase theta inhibitor, an MRE11 inhibitor, or an ATR inhibitor. In some embodiments, the PARP inhibitor is olaparib, ABT-888 (Veliparib), BSI-201 (Iniparib), BMN 673, Rucaparib (AG-014699, PF-01367338), AG14361, INO-1001, A-966492, PJ34, MK-4827, or Fluzoparib. In some embodiments, the methods further comprise administering at least one additional therapeutic to the subject. In some embodiments, the at least one additional therapeutic is selected from the group consisting of surgical therapy, chemotherapy, radiation therapy, cryotherapy, hormonal therapy, toxin therapy, immunotherapy, or cytokine therapy. In some embodiments, the at least one additional therapeutic comprises ionizing radiation. In some embodiments, the cancer is colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, or glioblastoma.

In yet other aspects, the present disclosure provides methods of treating cancer in a patient, the method comprising administering to the patient a combined effective amount of a GRB2 inhibitor and ionizing radiation. In some embodiments, the methods further comprise administering to the patient an Alt-EJ inhibitor (e.g., a polymerase theta inhibitor). In some embodiments, the cancer has been identified as being homology-directed repair (HDR) proficient.

In other aspects, the present disclosure provides methods of treating a patient having a cancer, the method comprising (a) determining or having determined whether the cancer is HDR proficient; (b) selecting or having selected the patient for treatment with a GRB2 inhibitor in combination with ionizing radiation when the cancer is HDR proficient; and (c) administering or having administered to the selected patient a combined effective amount of a GRB2 inhibitor and ionizing radiation. In some embodiments, the methods further comprise administering to the patient an Alt-EJ inhibitor (e.g., a polymerase theta inhibitor). In some embodiments, the method is further defined as a method of sensitizing cancer cells to ionizing radiation.

In still other aspects, the present disclosure provides methods for selecting a cancer patient for treatment with a GRB2 inhibitor in combination with ionizing radiation, the method comprising (a) determining or having determined whether the cancer is HDR proficient; and (b) selecting or having selected the patient for treatment with a GRB2 inhibitor in combination with ionizing radiation when the cancer is HDR proficient. In some embodiments, step (a) comprises (i) obtaining or having obtained a biological sample from the patient; and (ii) performing or having performed an assay on the biological sample to determine whether the cancer is HDR proficient. In some embodiments, the methods further comprise (c) administering or having administered to the selected patient a combined effective amount of a GRB2 inhibitor and ionizing radiation. In some embodiments, the methods further comprise administering to the patient an Alt-EJ inhibitor (e.g., a polymerase theta inhibitor). In some embodiments, the methods further comprise determining whether the cancer expresses high levels of MRE11 relative to a reference level, wherein if the cancer is both HDR proficient and expresses high levels of MRE11, then the patient is selected for treatment with a GRB2 inhibitor in combination with ionizing radiation. In some embodiments, the methods further comprise administering or having administered to the selected patient a combined effective amount of a GRB2 inhibitor and ionizing radiation. In some embodiments, the methods further comprise determining whether the cancer expresses high levels of GRB2 relative to a reference level, wherein if the cancer is both HDR proficient and expresses high levels of GRB2, then the patient is selected for treatment with a GRB2 inhibitor in combination with ionizing radiation. In some embodiments, the methods further comprise administering or having administered to the selected patient a combined effective amount of a GRB2 inhibitor and ionizing radiation. In some embodiments, the methods further comprise determining whether the cancer expresses high levels of GRB2 and high levels of MRE11 relative to a reference level, wherein if the cancer is both HDR proficient and expresses high levels of GRB2 and high levels of MRE11, then the patient is selected for treatment with a GRB2 inhibitor in combination with ionizing radiation. In some embodiments, the methods further comprise administering or having administered to the selected patient a therapeutically effective amount of a GRB2 inhibitor and ionizing radiation. In some embodiments, the methods further comprise administering to the patient an Alt-EJ inhibitor (e.g., a polymerase theta inhibitor).

In some embodiments, the reference level is a level in a sample sourced from healthy or non-cancerous tissue from the patient. In some embodiments, the reference level is a level in a sample sourced from a healthy subject. In some embodiments, the GRB2 inhibitor is a small molecule GRB2 inhibitor or an anti-GRB2 inhibitory nucleic acid. In some embodiments, the GRB2 inhibitor and the ionizing radiation are administered concurrently or essentially simultaneously. In some embodiments, the GRB2 inhibitor is administered before the ionizing radiation. In some embodiments, the methods further comprise administering at least one additional therapeutic to the subject. In some embodiments, the at least one additional therapeutic is selected from the group consisting of surgical therapy, chemotherapy, radiation therapy, cryotherapy, hormonal therapy, toxin therapy, immunotherapy, or cytokine therapy. In some embodiments, the at least one additional therapeutic comprises a DNA damaging agent or DNA repair inhibitor. In some embodiments, the DNA damaging agent or DNA repair inhibitor is a PARP inhibitor, a PARG inhibitor, a DNAPK inhibitor, a polymerase theta inhibitor, an MRE11 inhibitor, or an ATR inhibitor. In some embodiments, the PARP inhibitor is olaparib, ABT-888 (Veliparib), BSI-201 (Iniparib), BMN 673, Rucaparib (AG-014699, PF-01367338), AG14361, INO-1001, A-966492, PJ34, MK-4827, or Fluzoparib. In some embodiments, the cancer is colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, or glioblastoma.

In yet other aspects, the present disclosure provides pharmaceutical compositions comprising a GRB2 inhibitor and a DNA damaging agent or DNA repair inhibitor. In some embodiments, the compositions further comprise an Alt-EJ inhibitor (e.g., a polymerase theta inhibitor). In some embodiments, the GRB2 inhibitor is a small molecule GRB2 inhibitor or an anti-GRB2 inhibitory nucleic acid. In some embodiments, the DNA damaging agent or DNA repair inhibitor is a PARP inhibitor, a PARG inhibitor, a DNAPK inhibitor, a polymerase theta inhibitor, an MRE11 inhibitor, or an ATR inhibitor. In some embodiments, the PARP inhibitor is olaparib, ABT-888 (Veliparib), BSI-201 (Iniparib), BMN 673, Rucaparib (AG-014699, PF-01367338), AG14361, INO-1001, A-966492, PJ34, MK-4827, or Fluzoparib.

In other aspects, the present disclosure provides compositions of the present disclosure for use in the treatment of cancer, preferably wherein the cancer is HDR proficient.

In still other aspects, the present disclosure provides first pharmaceutical therapies comprising a GRB2 inhibitor for use as a medicament for treating a cancer in a patient in combination with a second pharmaceutical therapy comprising a DNA damaging agent or DNA repair inhibitor.

In yet other aspects, the present disclosure provides first pharmaceutical therapies comprising a GRB2 inhibitor for use as a medicament for treating a cancer in a patient in combination with a second pharmaceutical therapy comprising ionizing radiation.

In other aspects, the present disclosure provides methods of rendering an HDR proficient cell HDR deficient, the method comprising contacting the cell with a GRB2 inhibitor.

With respect to any of the above aspects, in some embodiments, the GRB2 inhibitor is a compound of the formula:

(I-A)

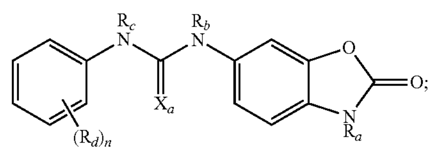

wherein:

n is 2, 3, 4, or 5;

$X_a$ is O or S;

$R_a$ is hydrogen; or alkyl$_{(C\leq12)}$, aralkyl$_{(C\leq12)}$, heteroaralkyl$_{(C\leq12)}$, or a substituted version of any of these groups;

$R_b$ and $R_c$ are each independently hydrogen, alkyl$_{(C\leq12)}$, or substituted alkyl$_{(C\leq12)}$; and $R_d$ is in each instance independently halo, hydroxy, cyano, nitro, alkyl$_{(C\leq12)}$, substituted alkyl$_{(C\leq12)}$, alkoxy$_{(C\leq12)}$, or substituted alkoxy$_{(C\leq12)}$; or a compound of the formula:

(I)

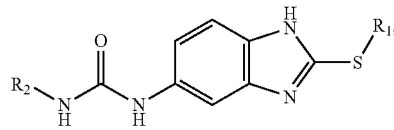

wherein:

$R_1$ is hydrogen; or alkyl$_{(C\leq12)}$, aralkyl$_{(C\leq12)}$, heteroaralkyl$_{(C\leq12)}$, or a substituted version of any of these groups; and $R_2$ is aralkyl$_{(C\leq12)}$, heteroaryl$_{(C\leq12)}$, heteroaralkyl$_{(C\leq12)}$, or a substituted version of any of these groups; or a group of the formula:

(Ia)

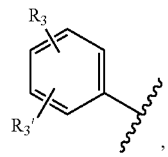

, wherein:

$R_3$ is hydrogen, hydroxy, halo, amino, nitro, cyano, carboxy, or mercapto; or alkyl$_{(C\leq12)}$, alkoxy$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)N$R_{3a}R_{3b}$, wherein:

$R_{3a}$ and $R_{3b}$ are each independently hydrogen, alkyl$_{(C\leq12)}$, or substituted alkyl$_{(C\leq12)}$;

$R_3$' is hydrogen, hydroxy, halo, amino, nitro, cyano, carboxy, or mercapto; or alkyl$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)N$R_{3c}R_{3d}$, wherein:

$R_{3c}$ and $R_{3d}$ are each independently hydrogen, alkyl$_{(C\leq12)}$, or substituted alkyl$_{(C\leq12)}$; or $R_3$ and $R_3$' are taken together and are alkenediyl$_{(C\leq12)}$ or substituted alkenediyl$_{(C\leq12)}$;

or a pharmaceutically acceptable salt and/or tautomer of either of these formulae.

In some embodiments, the compounds are further defined as:

(I-A)

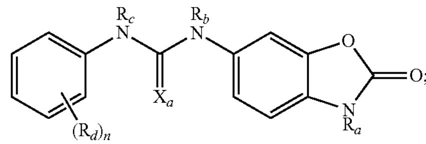

wherein:

n is 2, 3, 4, or 5;

$X_a$ is O or S;

$R_a$ is hydrogen; or alkyl$_{(C\leq12)}$, aralkyl$_{(C\leq12)}$, heteroaralkyl$_{(C\leq12)}$, or a substituted version of any of these groups;

$R_b$ and $R_c$ are each independently hydrogen, alkyl$_{(C\leq12)}$, or substituted alkyl$_{(C\leq12)}$; and $R_d$ is in each instance independently halo, hydroxy, cyano, nitro, alkyl$_{(C\leq12)}$, substituted alkyl$_{(C\leq12)}$, alkoxy$_{(C\leq12)}$, or substituted alkoxy$_{(C\leq12)}$;

or a pharmaceutically acceptable salt and/or tautomer thereof.

In further embodiments, the compounds are further defined as:

(I-B)

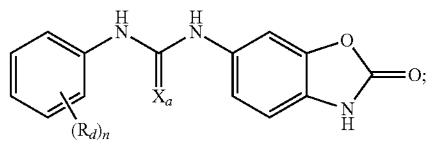

wherein:

n is 2, 3, 4, or 5;

$X_a$ is O or S; and $R_d$ is in each instance independently halo, hydroxy, cyano, nitro, alkyl$_{(C\leq12)}$, substituted alkyl$_{(C\leq12)}$, alkoxy$_{(C\leq12)}$, or substituted alkoxy$_{(C\leq12)}$;

or a pharmaceutically acceptable salt and/or tautomer thereof.

In some embodiments, $X_a$ is O. In other embodiments, $X_a$ is S. In some embodiments, n is 2 or 3. In some embodiments, n is 2. In other embodiments, n is 3. In some embodiments, $R_d$ is hydroxy. In other embodiments, $R_d$ is halo, such as chloro or fluoro. In still other embodiments, $R_d$ is alkyl$_{(C\leq12)}$ or substituted alkyl$_{(C\leq12)}$. In some embodiments, $R_d$ is alkyl$_{(C\leq12)}$, such as methyl. In yet other embodiments, $R_d$ is alkoxy$_{(C\leq12)}$ or substituted alkoxy$_{(C\leq12)}$. In some embodiments, alkoxy$_{(C\leq12)}$, such as methoxy.

In some embodiments the compound is defined as:

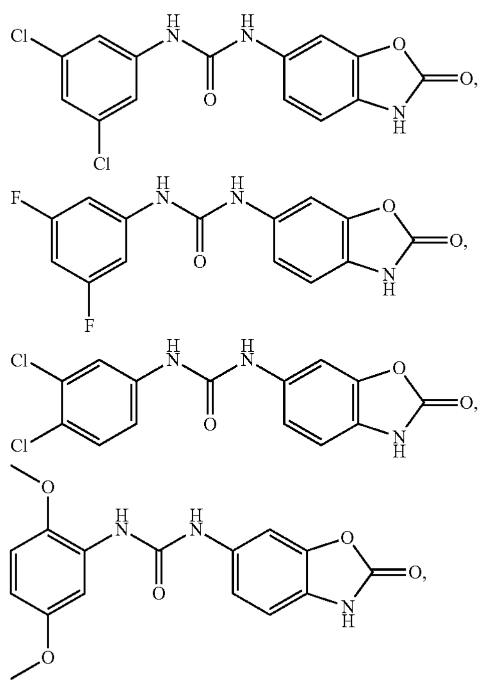

-continued

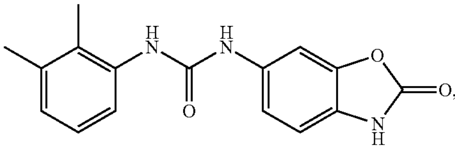

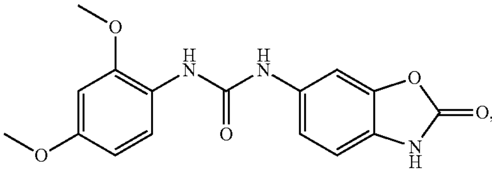

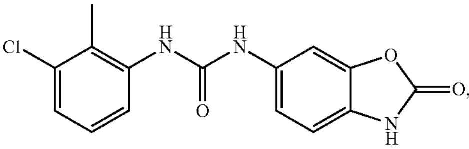

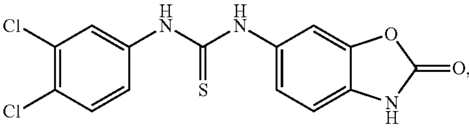

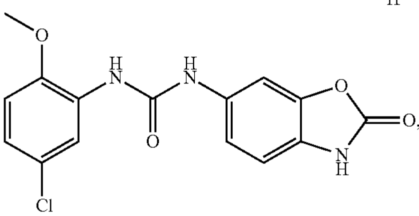

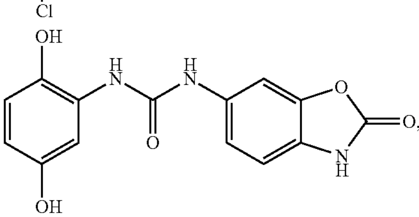

or

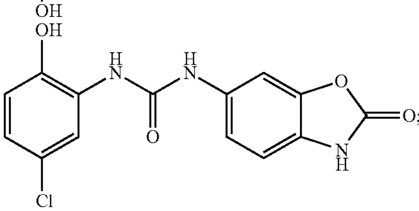

or a pharmaceutically acceptable salt and/or tautomer thereof.

In some embodiments, the compounds are of the formula:

(I)

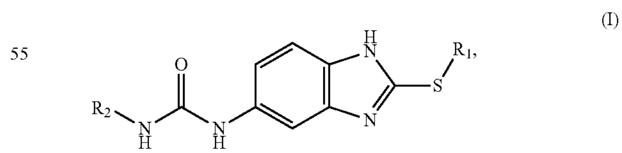

wherein:

$R_1$ is hydrogen; or alkyl$_{(C\leq12)}$, aralkyl$_{(C\leq12)}$, heteroaralkyl$_{(C\leq12)}$, or a substituted version of any of these groups; and $R_2$ is aralkyl$_{(C\leq12)}$, heteroaryl$_{(C\leq12)}$, heteroaralkyl$_{(C\leq12)}$, or a substituted version of any of these groups; or a group of the formula:

(Ia)

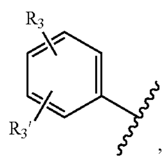

wherein:

$R_3$ is hydrogen, hydroxy, halo, amino, nitro, cyano, carboxy, or mercapto; or alkyl$_{(C\leq12)}$, alkoxy$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3a}$R$_{3b}$, wherein:

$R_{3a}$ and $R_{3b}$ are each independently hydrogen, alkyl$_{(C\leq12)}$, or substituted alkyl$_{(C\leq12)}$;

$R_3$' is hydrogen, hydroxy, halo, amino, nitro, cyano, carboxy, or mercapto; or alkyl$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3c}$R$_{3d}$, wherein:

$R_{3c}$ and $R_{3d}$ are each independently hydrogen, alkyl$_{(C\leq12)}$, or substituted alkyl$_{(C\leq12)}$; or $R_3$ and $R_3$' are taken together and are alkenediyl$_{(C\leq12)}$ or substituted alkenediyl$_{(C\leq12)}$;

or a pharmaceutically acceptable salt and/or tautomer thereof.

In some embodiments, the compounds are further defined as:

(I)

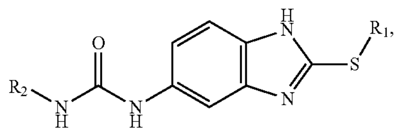

wherein:

$R_1$ is hydrogen; or alkyl$_{(C\leq12)}$, aralkyl$_{(C\leq12)}$, heteroaralkyl$_{(C\leq12)}$, or a substituted version of any of these groups; and $R_2$ is aralkyl$_{(C\leq12)}$, or a substituted version of any of these groups; or a group of the formula:

(Ia)

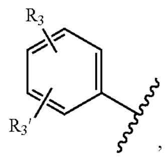

wherein:

$R_3$ is hydrogen, hydroxy, halo, amino, nitro, cyano, carboxy, or mercapto; or alkyl$_{(C\leq12)}$, alkoxy$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3a}$R$_{3b}$, wherein:

$R_{3a}$ and $R_{3b}$ are each independently hydrogen, alkyl$_{(C\leq12)}$, or substituted alkyl$_{(C\leq12)}$;

$R_3$' is hydrogen, hydroxy, halo, amino, nitro, cyano, carboxy, or mercapto; or alkyl$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3c}$R$_{3d}$, wherein:

$R_{3c}$ and $R_{3d}$ are each independently hydrogen, alkyl$_{(C\leq12)}$, or substituted alkyl$_{(C\leq12)}$; or $R_3$ and $R_3$' are taken together and are alkenediyl$_{(C\leq12)}$ or substituted alkenediyl$_{(C\leq12)}$;

or a pharmaceutically acceptable salt and/or tautomer thereof.

In further embodiments, the compounds are further defined as:

(I)

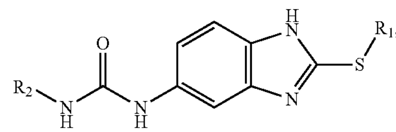

wherein:

$R_1$ is hydrogen; or alkyl$_{(C\leq12)}$, substituted alkyl$_{(C\leq12)}$, aralkyl$_{(C\leq12)}$, or substituted aralkyl$_{(C\leq12)}$; and $R_2$ is aralkyl$_{(C\leq12)}$ or substituted aralkyl$_{(C\leq12)}$; or a group of the formula:

(Ia)

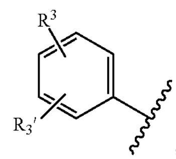

wherein:

$R_3$ is hydrogen, hydroxy, halo, amino, nitro, cyano, carboxy, or mercapto; or alkyl$_{(C\leq12)}$, alkoxy$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3a}$R$_{3b}$, wherein:

$R_{3a}$ and $R_{3b}$ are each independently hydrogen, alkyl$_{(C\leq12)}$, or substituted alkyl$_{(C\leq12)}$;

$R_3$' is hydrogen, hydroxy, halo, amino, nitro, cyano, carboxy, or mercapto; or alkyl$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3c}$R$_{3d}$, wherein:

$R_{3c}$ and $R_{3d}$ are each independently hydrogen, alkyl$_{(C\leq12)}$, or substituted alkyl$_{(C\leq12)}$; or $R_3$ and $R_3$' are taken together and are alkenediyl$_{(C\leq12)}$ or substituted alkenediyl$_{(C\leq12)}$;

or a pharmaceutically acceptable salt and/or tautomer thereof.

In some embodiments, $R_2$ is aralkyl$_{(C\leq12)}$ or substituted aralkyl$_{(C\leq12)}$. In further embodiments, $R_2$ is substituted aralkyl$_{(C\leq12)}$, such as 4-fluorobenzyl.

In other embodiments, the compounds are further defined as:

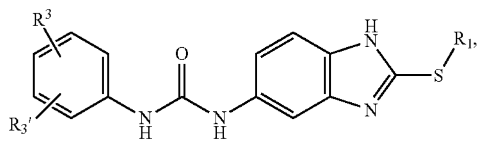

(II)

wherein:

$R_1$ is hydrogen; or alkyl$_{(C\leq12)}$, substituted alkyl$_{(C\leq12)}$, aralkyl$_{(C\leq12)}$, or substituted aralkyl$_{(C\leq12)}$; and $R_3$ is hydrogen, hydroxy, halo, amino, nitro, cyano, carboxy, or mercapto; or alkyl$_{(C\leq12)}$, alkoxy$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3a}$R$_{3b}$, wherein:

$R_{3a}$ and $R_{3b}$ are each independently hydrogen, alkyl$_{(C\leq12)}$, or substituted alkyl$_{(C\leq12)}$;

$R_3$' is hydrogen, hydroxy, halo, amino, nitro, cyano, carboxy, or mercapto; or alkyl$_{(C\leq12)}$, alkylamino$_{(C\leq12)}$, dialkylamino$_{(C\leq12)}$, acyl$_{(C\leq12)}$, acyloxy$_{(C\leq12)}$, amido$_{(C\leq12)}$, or a substituted version of any of these groups; or —C(O)NR$_{3c}$R$_{3d}$, wherein:

$R_{3c}$ and $R_{3d}$ are each independently hydrogen, alkyl$_{(C\leq12)}$, or substituted alkyl$_{(C\leq12)}$; or $R_3$ and $R_3$' are taken together and are alkenediyl$_{(C\leq12)}$ or substituted alkenediyl$_{(C\leq12)}$;

or a pharmaceutically acceptable salt and/or tautomer thereof.

In some embodiments, $R_1$ is hydrogen. In other embodiments, $R_1$ is aralkyl$_{(C\leq12)}$ or substituted aralkyl$_{(C\leq12)}$. In further embodiments, $R_1$ is substituted aralkyl$_{(C\leq12)}$, such as 4-fluorobenzyl. In some embodiments, $R_3$ is hydrogen. In other embodiments, $R_3$ is cyano. In still other embodiments, $R_3$ is halo, such as fluoro. In yet other embodiments, $R_3$ is alkyl$_{(C\leq12)}$ or substituted alkyl$_{(C\leq12)}$. In further embodiments, $R_3$ is alkyl$_{(C\leq12)}$, such as methyl. In still other embodiments, $R_3$ is alkoxy$_{(C\leq12)}$ or substituted alkoxy$_{(C\leq12)}$. In further embodiments, $R_3$ is alkoxy$_{(C\leq12)}$, such as methoxy. In still other embodiments, $R_3$ is acyl$_{(C\leq12)}$ or substituted acyl$_{(C\leq12)}$. In further embodiments, $R_3$ is acyl$_{(C\leq12)}$, such as acetyl. In some embodiments, $R_3$' is hydrogen. In other embodiments, $R_3$' is cyano. In still other embodiments, $R_3$' is halo, such as fluoro. In yet other embodiments, $R_3$' is alkyl$_{(C\leq12)}$ or substituted alkyl$_{(C\leq12)}$. In further embodiments, $R_3$' is alkyl$_{(C\leq12)}$, such as methyl. In still other embodiments, $R_3$' is acyl$_{(C\leq12)}$ or substituted acyl$_{(C\leq12)}$. In further embodiments, $R_3$' is acyl$_{(C\leq12)}$, such as acetyl.

In some embodiments, the compounds are further defined as:

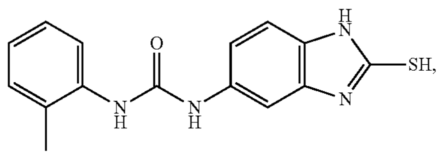

-continued

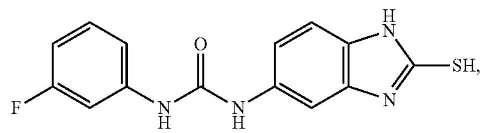

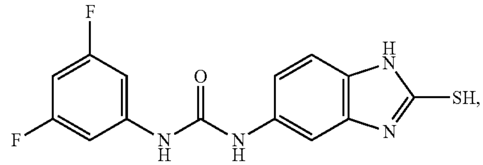

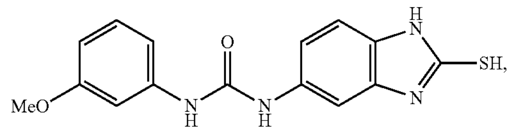

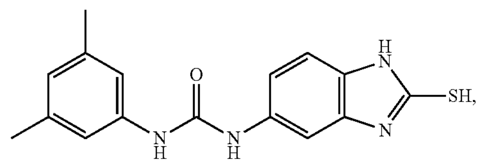

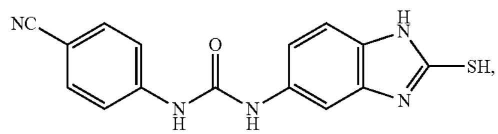

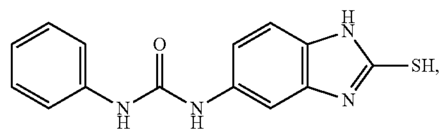

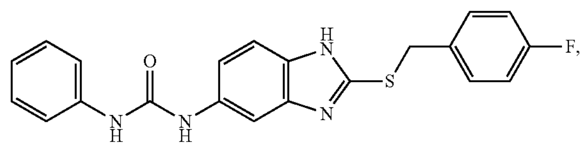

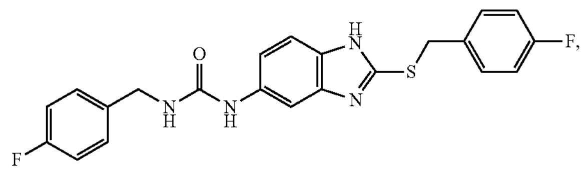

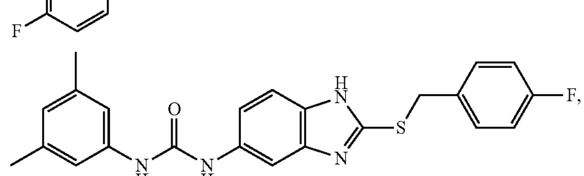

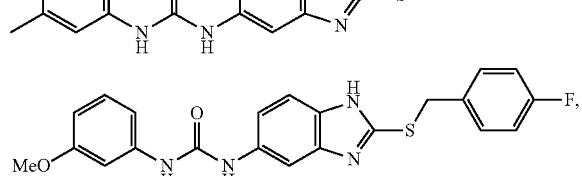

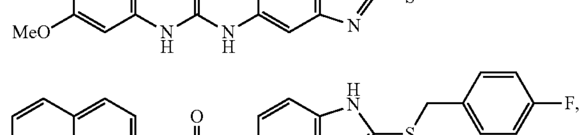

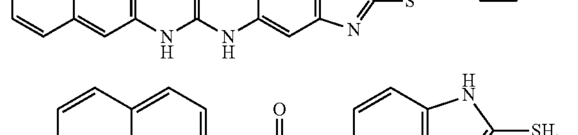

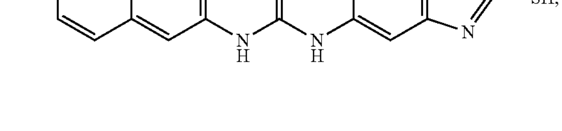

-continued

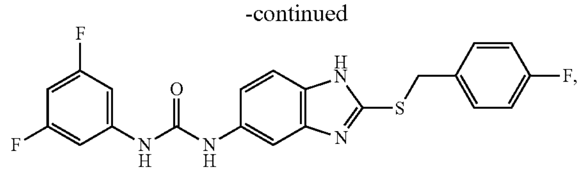

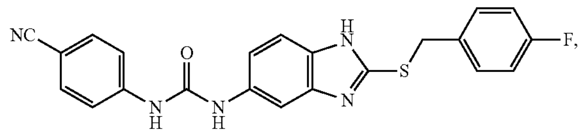

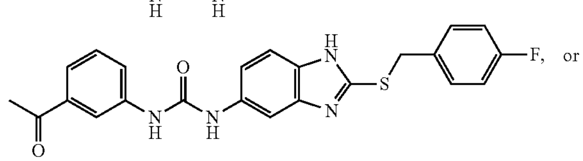

or

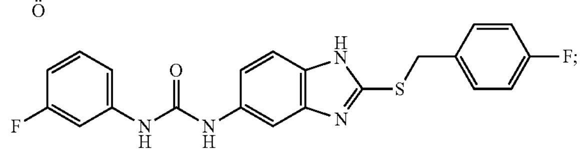

or a pharmaceutically acceptable salt and/or tautomer thereof.

In further embodiments, the compounds are further defined as:

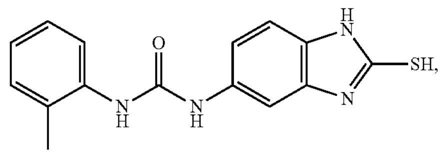

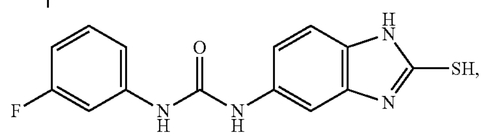

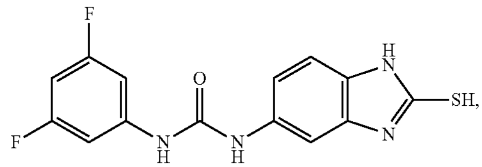

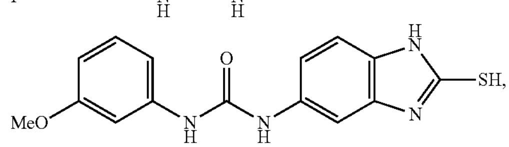

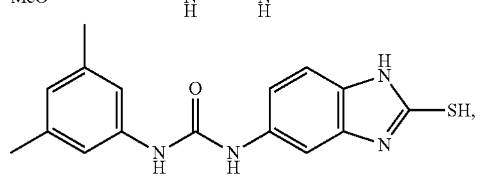

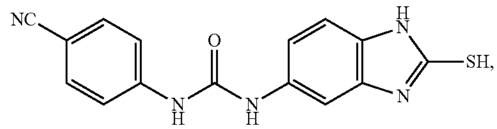

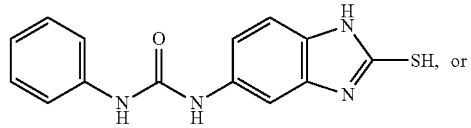

or

-continued

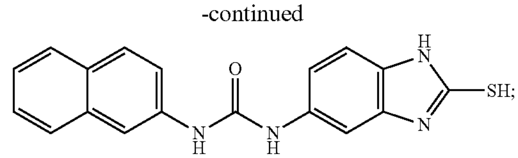

or a pharmaceutically acceptable salt and/or tautomer thereof.

In still further embodiments, the compounds are further defined as:

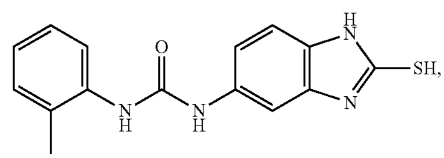

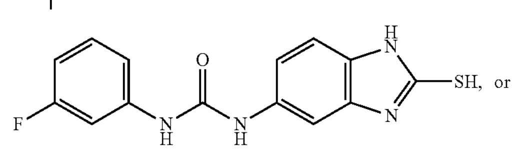

or

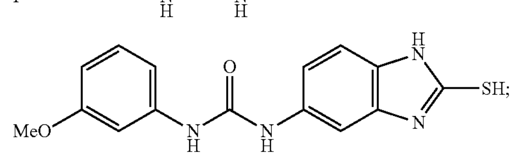

or a pharmaceutically acceptable salt and/or tautomer thereof.

In other embodiments, the compounds are further defined as:

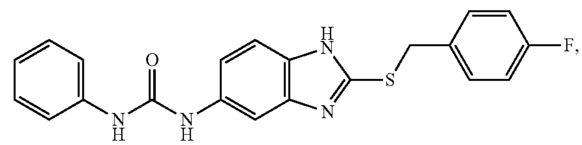

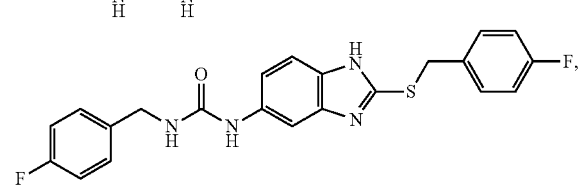

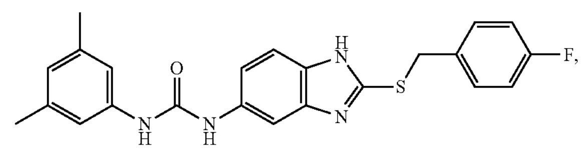

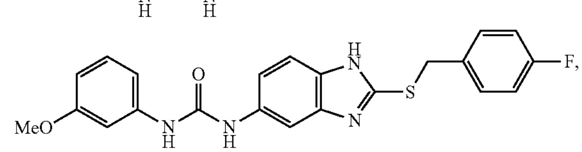

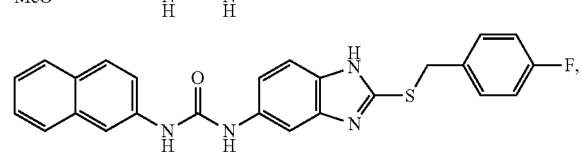

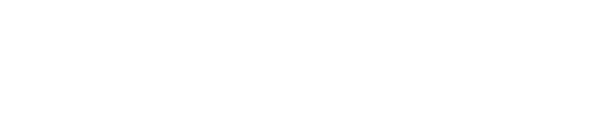

-continued
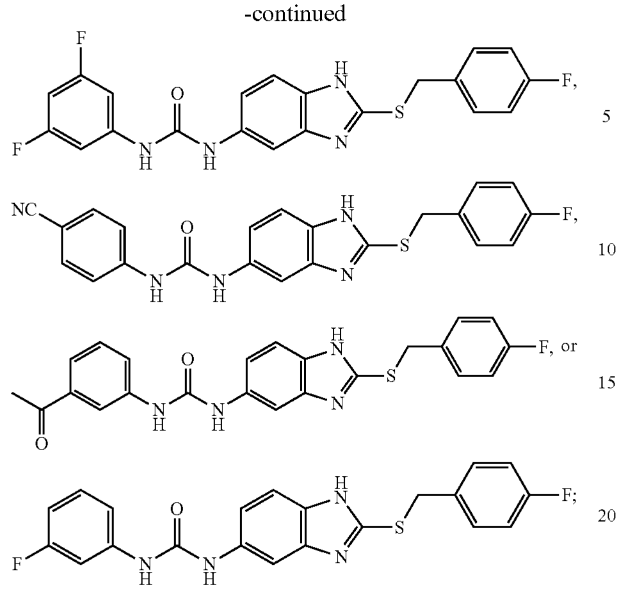
or
or a pharmaceutically acceptable salt and/or tautomer thereof.
In another aspect, the present disclosure provides compounds of the formula:
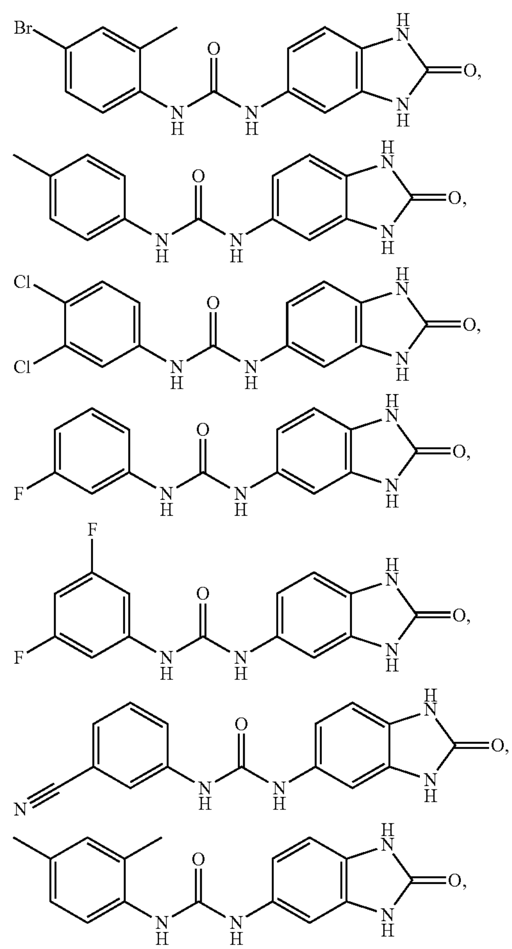
-continued
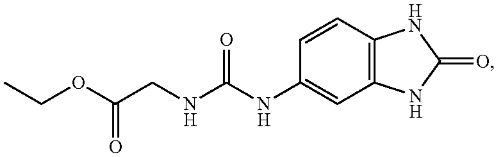
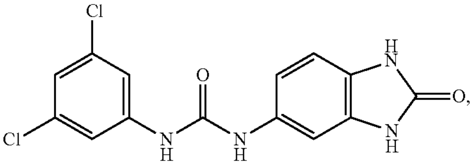
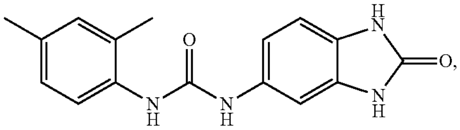
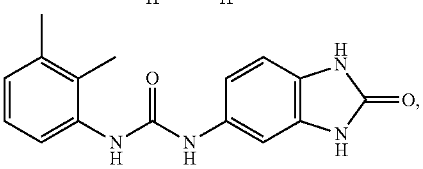
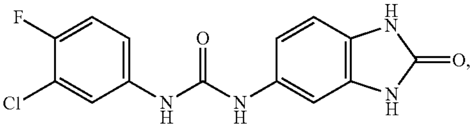
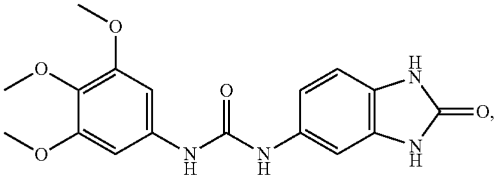
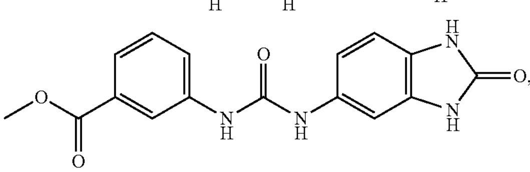
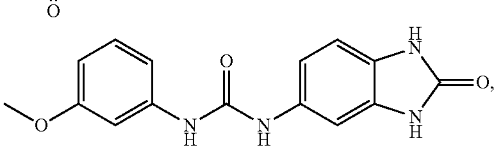
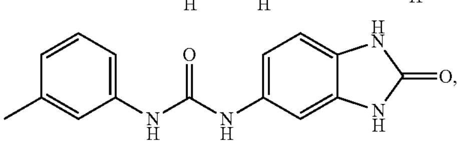
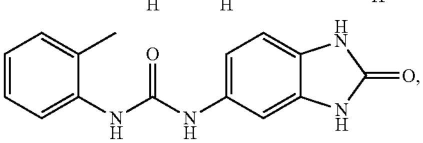
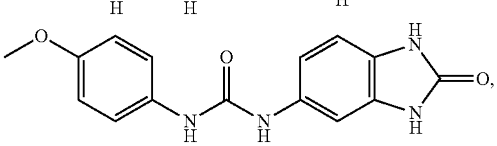
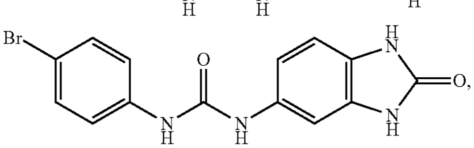

-continued
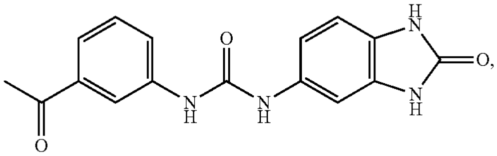
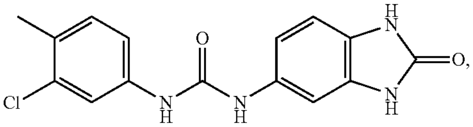
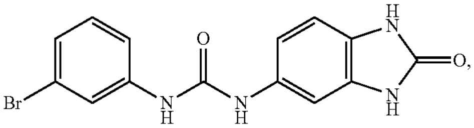
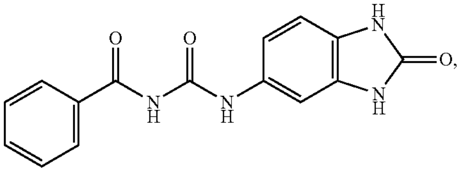
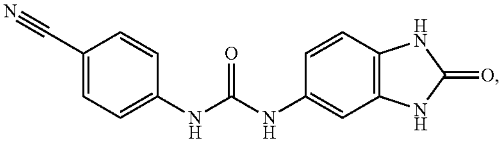
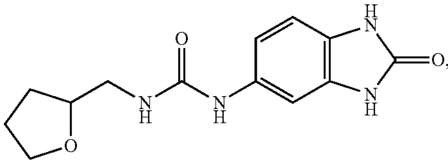
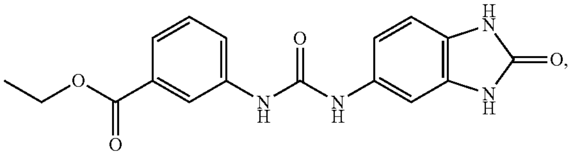
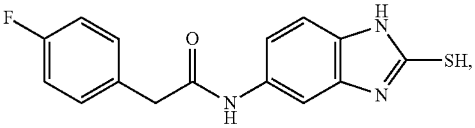
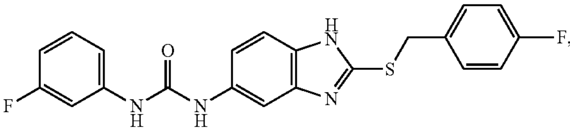
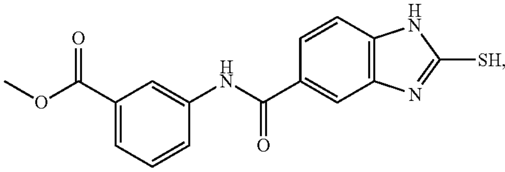
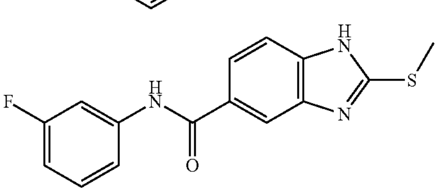
,
-continued
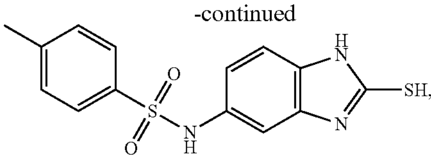
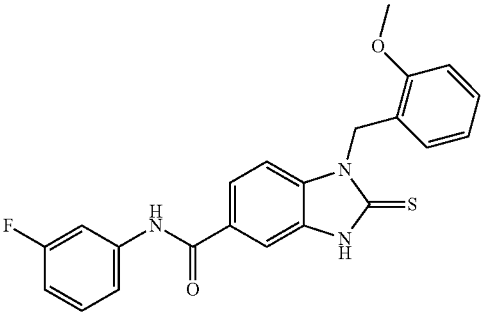
,
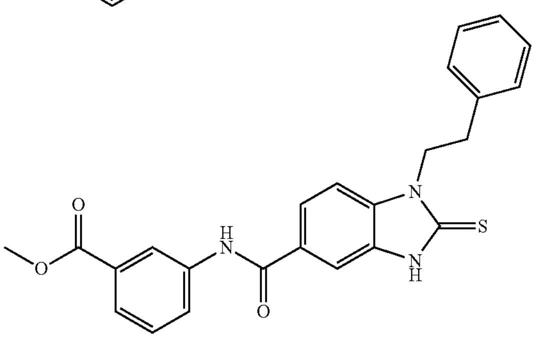
,
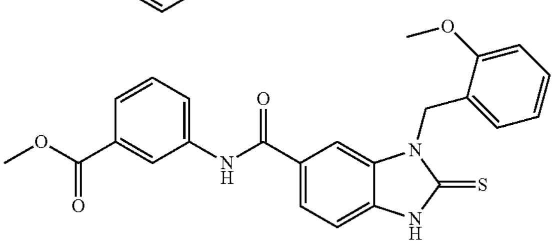
,
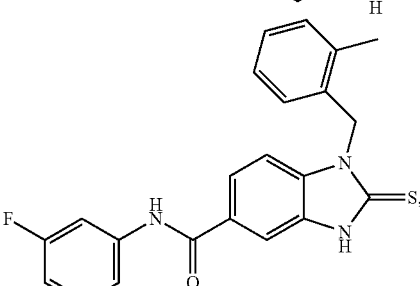
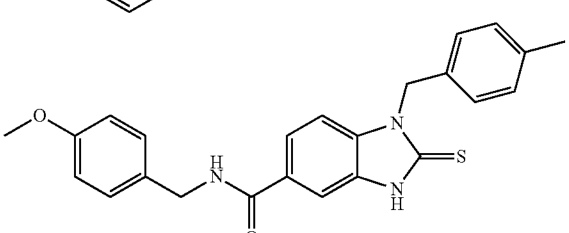
,
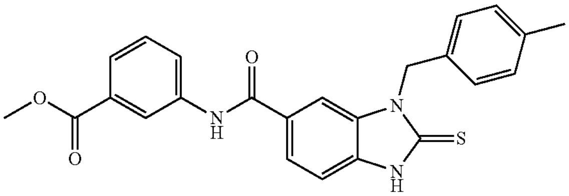
, -continued
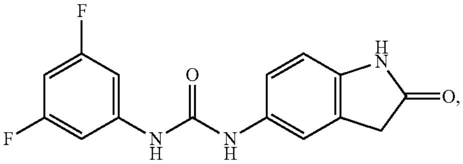
,
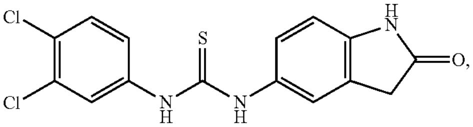
,
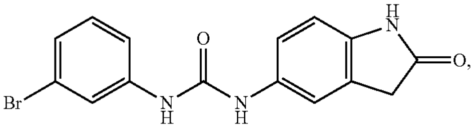
,
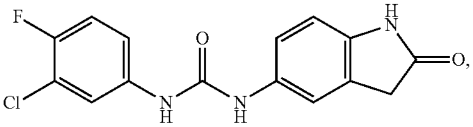
,
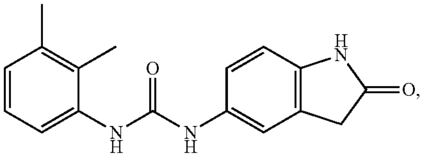
,
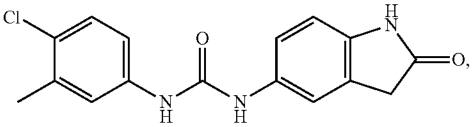
,
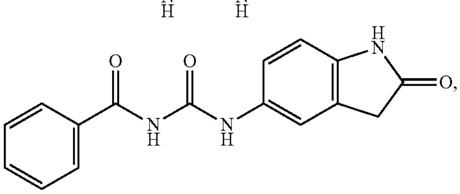
,
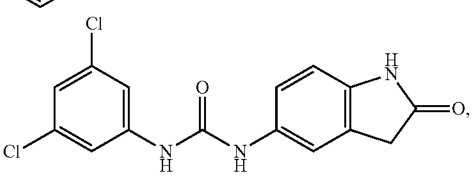
,
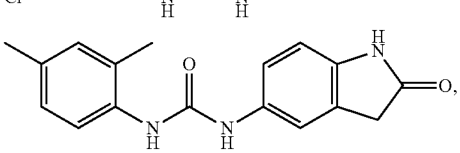
,
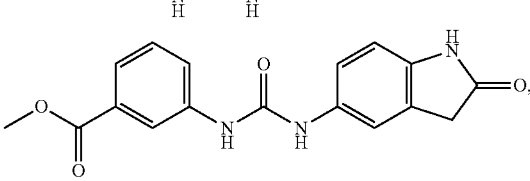
,
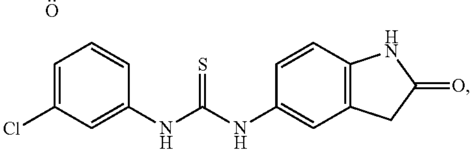
,
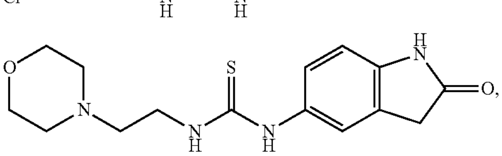
,
-continued
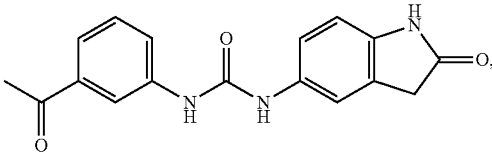
,
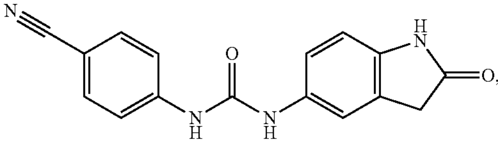
,
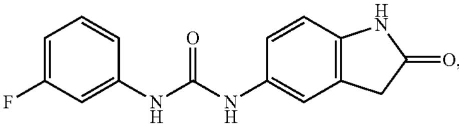
,
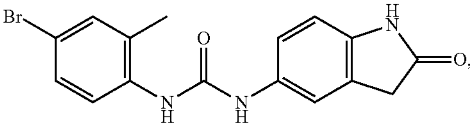
,
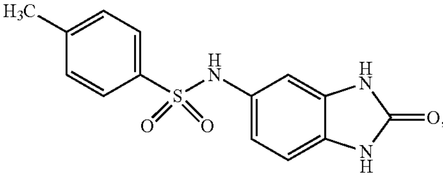
,
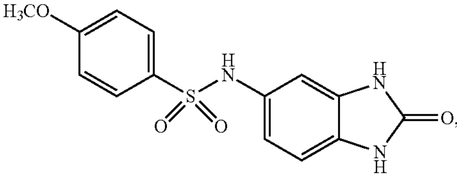
,
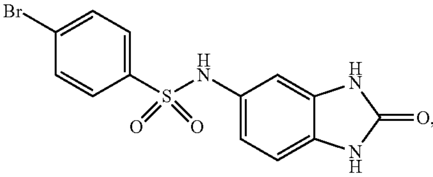
,
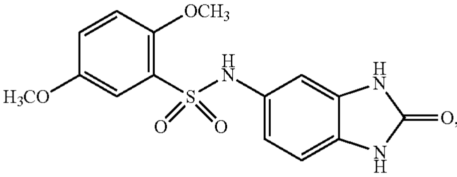
,
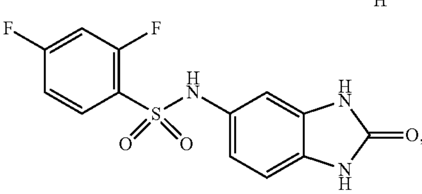
,
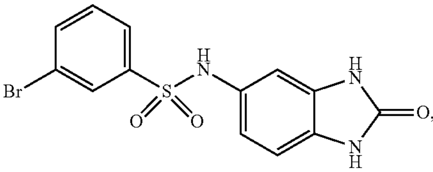
, -continued
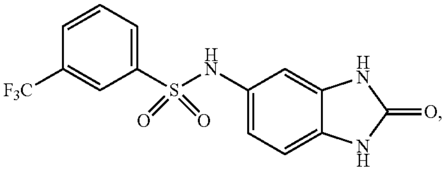
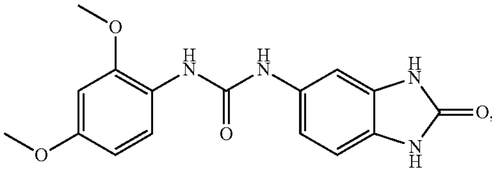
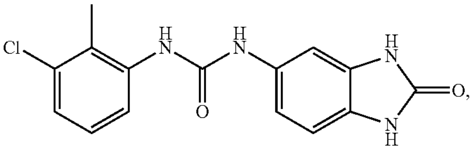
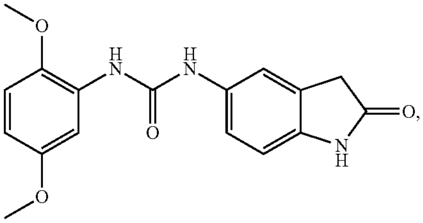
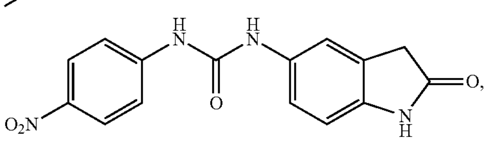
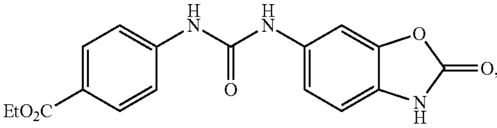
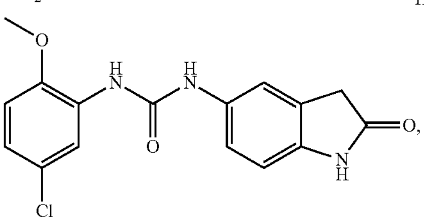
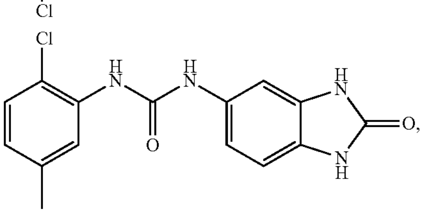
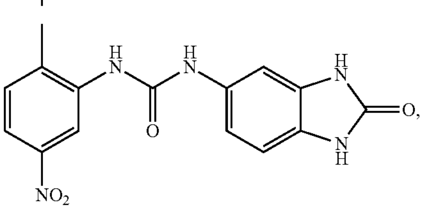
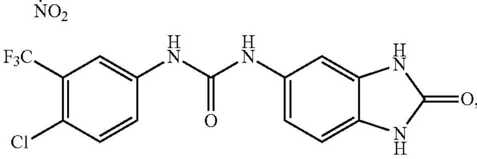
-continued
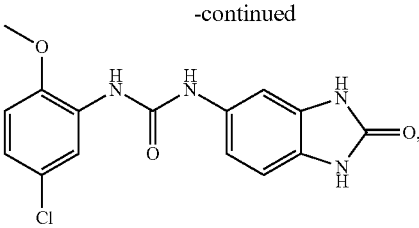
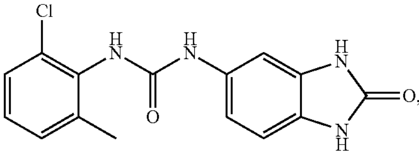
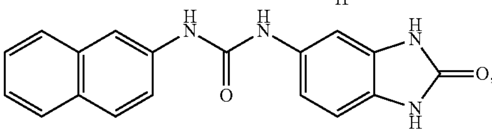
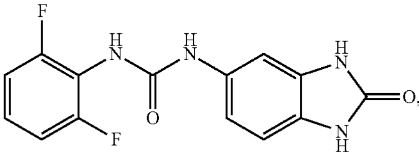
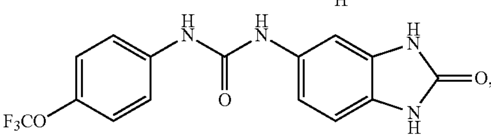
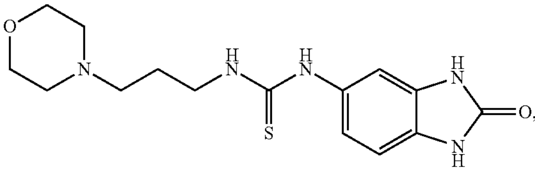
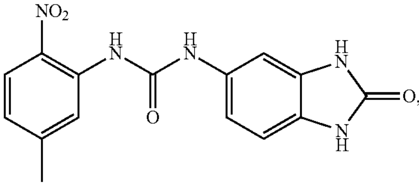
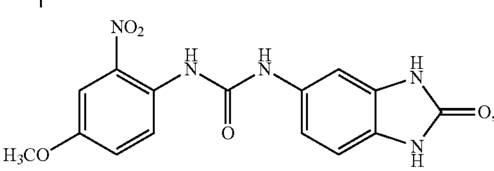
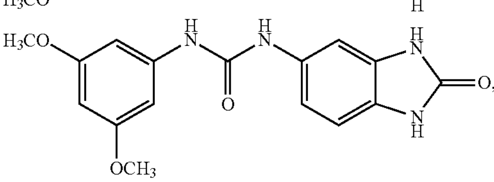
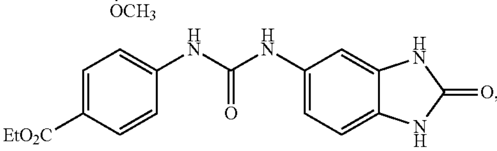
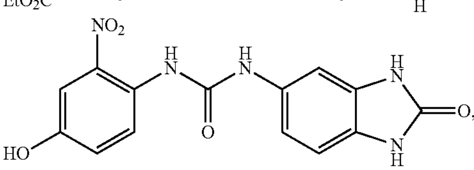

-continued
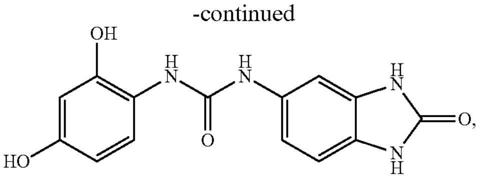
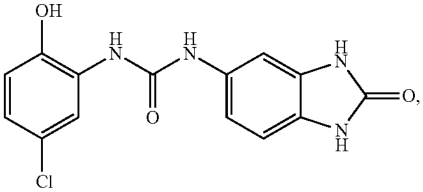
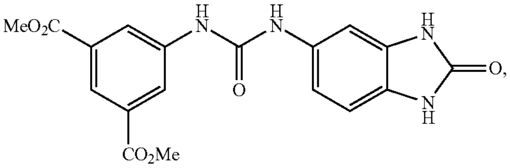
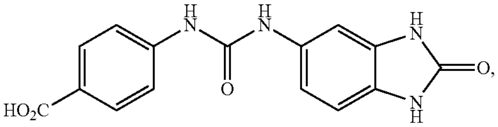
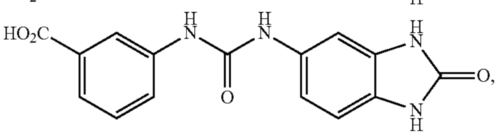
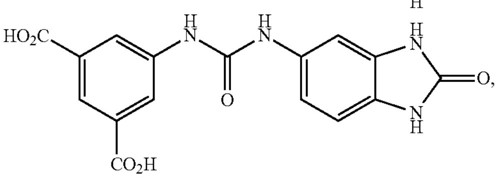
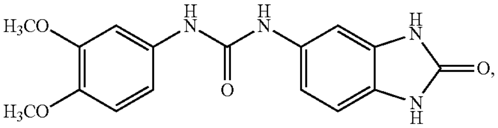
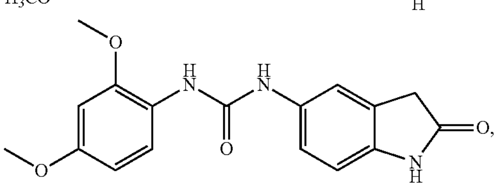
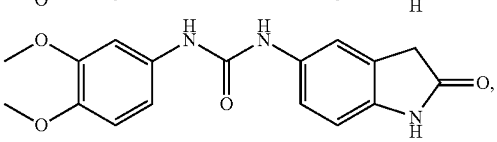
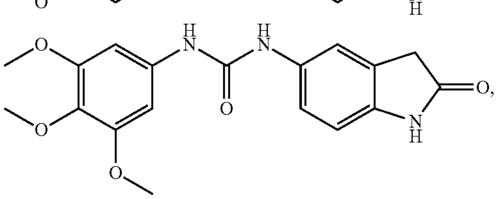
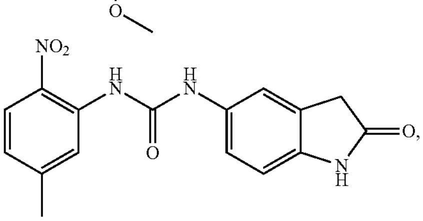
-continued
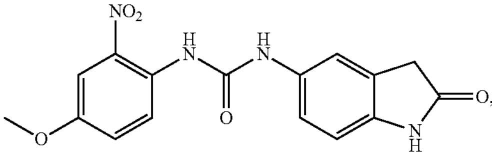
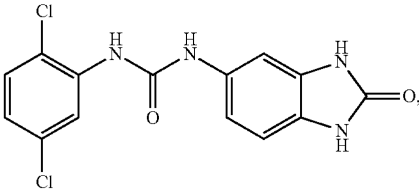
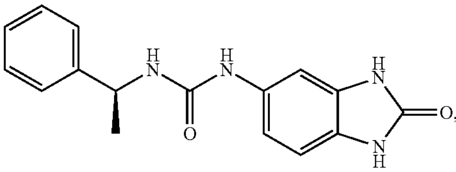
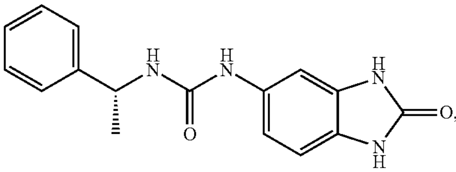
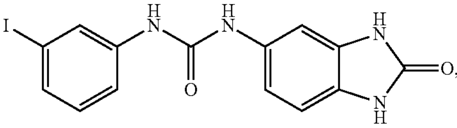
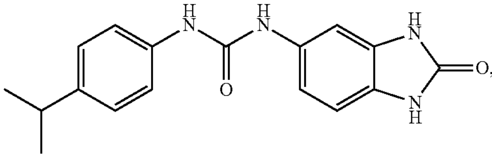
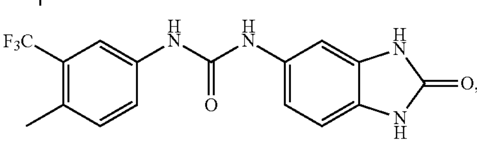
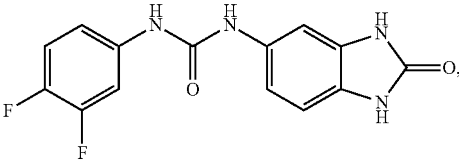
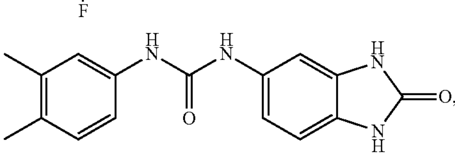
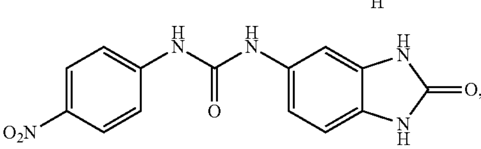
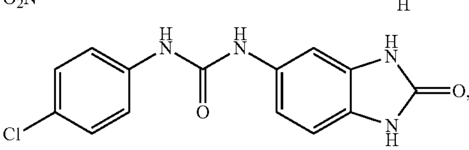

-continued

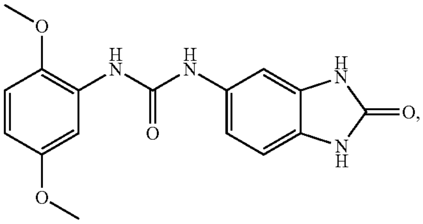

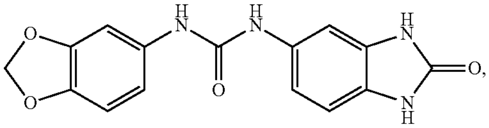

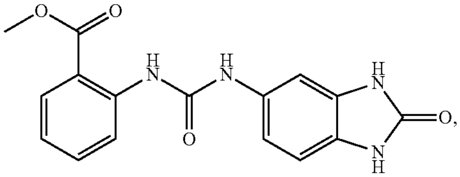

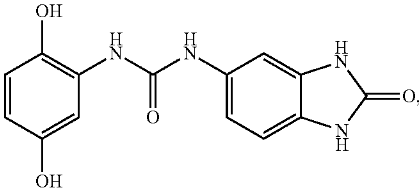 [SMILES: O=C(Nc1ccc2[nH]c(=O)[nH]c2c1)Nc1cc(O)ccc1O]

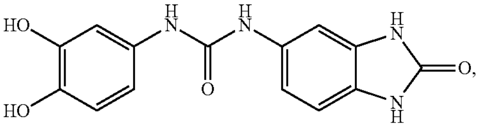

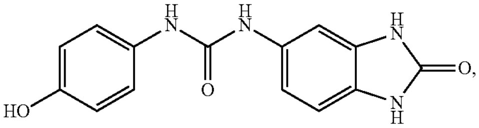

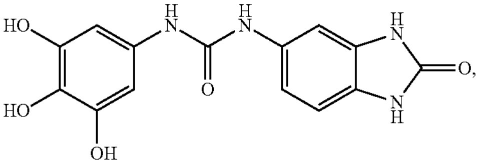

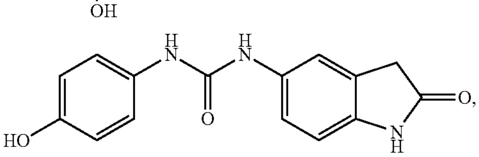

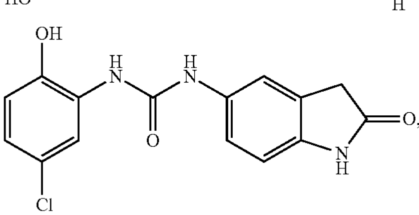

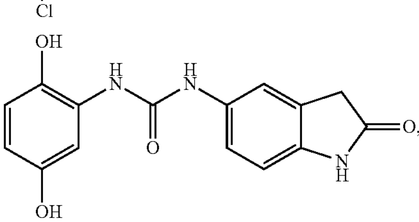

or

-continued

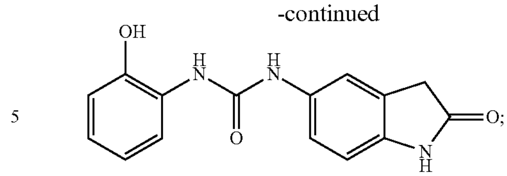

or a pharmaceutically acceptable salt and/or tautomer thereof.

The use of the word "a" or "an" when used in conjunction with the term "comprising" in the claims and/or the specification may mean "one," but it is also consistent with the meaning of "one or more," "at least one," and "one or more than one."

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. The skilled artisan will understand that typically there is no limit on the number of items or terms in any combination, unless otherwise apparent from the context.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

For a more complete understanding of the features and advantages of the present disclosure, reference is now made to the detailed description of the disclosure along with the accompanying figures and in which:

(FIG. 1A) Immunohistochemical (IHC) analysis of GRB2 expression in mouse and human tissue samples stained with anti-GRB2 antibody. Scale bars, 50 μm. Zoomed insets shown (upper left corners). (FIG. 1B) H-score quantification of nuclear GRB2 IHC staining for different mouse and human tissues. The top bar of each pair represents Mouse; the bottom bar of each pair represents Human. (FIG. 1C) Subcellular fraction analysis of GRB2 expression patterns. GAPDH, E-cadherin (E-cad) and Lamin A are markers of cytoplasm (C), plasma membrane (M) and nucleus (N), respectively. (FIG. 1D) GRB2 is ubiquitinated in the nucleus. Strep-GRB2 with Strep-tag alone (Ctrl) were precipitated from the nuclear extracts of HEK293T cells with Strep-Tactin beads and analyzed with GRB2 (upper left) or ubiquitin (right) antibodies. Lamin A was a loading control. (FIG. 1E) Strep-tagged K44R or K109R mutant GRB2 were precipitated from the nuclear extracts of HEK293T cells and immunoblotted with anti-GRB2 antibody. Long exposure (top panel), short exposure (middle panel) and Lamin A as an input loading control are shown. (FIG. 1F) Wild-type (WT)HeLa cells, GRB2-knockout (KO) cells, and KO cells reconstituted with WT-GRB2 or K109R-GRB2 were immunoblotted with indicated antibodies. (FIG. 1G) Strep-GRB2 was immunoprecipitated from the nuclear extracts of CBLL1-, RING2- or RBBP6-knockdown (KD) HEK293T cells and immunoblotted with indicated antibodies. Knockdown levels were determined with the respective antibody in input. Lamin A was a loading control. (FIG. 1H) Live HeLa cells with or without RBBP6 knockdown were micro-irradiated, pre-extracted, fixed and processed for IF staining with anti-RBBP6 and anti-γH2AX antibodies. (FIG. 1I) Live HeLa and HAP1 cells were micro-irradiated, pre-extracted and IF stained with anti-RBBP6 and anti-γH2AX antibodies. (FIG. 1J) HeLa cells were treated as in FIGS. 1H and 1F stained with anti-GRB2 and anti-γH2AX antibodies. (FIG. 1K) HEK293T cells stably expressing either WT or K109R mutant GRB2 were exposed to 5 Gy IR (152 sec), and then either immediately lysed (t=0) or allowed to recover for the indicated time before lysis and nuclear fractionation. GRB2 was precipitated using Strep-Tactin beads from nuclear extractions and immunoblotted with anti-GRB2 antibody. Lamin A was used as an input loading control. All data are representative of three independent experiments. Scale bars, 5 μm.

(FIG. 2A) Mass spectrometry identifies nuclear GRB2-associated proteins that are involved in DNA damage repair. Mean of coverage and unique peptides from three independent data sets are shown. (FIG. 2B) Strep-Tactin precipitation of Strep-GRB2 precipitated from HEK293T cells followed by western blotting with indicated antibodies. (FIG. 2C) GRB2 preferentially co-precipitate MRE11 without RAD50 or NBS1. Strep-GRB2 expressed HEK293T cells treated with or without 5 Gy IR were lysed immediately followed by Strep-Tactin precipitation and immunoblotting with indicated antibodies. (FIG. 2D) Immunoprecipitation of NBS1. HEK293T cells were co-transfected with RFP-GRB2 and GFP-NBS1 or GFP alone as control. Total cell lysates were precipitated with GFP-trap beads and immunoblotted with indicated antibodies. (FIG. 2E) Immunoprecipitation of RAD50. HEK293T cells expressing Flag-RAD50 or Flag-Ctrl were co-transfected with RFP-GRB2 for 24 h. Unperturbed cells were immunoprecipitated with Flag-M2 beads and immunoblotted with indicated antibodies. β-Actin was used as a loading control. (FIG. 2F) Immunoprecipitation of MRE11. HEK293T cells expressing Flag-MRE11 were co-transfected with Strep-GRB2 or Strep-Ctrl for 24 h. Unperturbed or IR treated (5 Gy) cells were immunoprecipitated with Flag-M2 beads and immunoblotted with indicated antibodies. β-Actin was used as a loading control. (FIG. 2G) Strep-Tactin precipitation of WT and K109R mutant Strep-GRB2 from HEK293T cells that were unperturbed or IR treated (5 Gy) and lysed, followed by western blot detection with the indicated antibodies. β-Actin was used as an internal loading control. (FIG. 2H) MST isotherms of 100 nM Atto488-labelled WT, K109R or K109A mutant to titrating concentrations (0.5 nM to 10 μM) of human MRE11 (residue 1-411). All data are representative of three independent experiments.

(FIG. 3A) Schematic DDR binding-motifs (circles) on GRB2 within its domain architecture. Approximate non-canonical binding motifs are shown. (FIG. 3B) GST-SH domains pulldown of HEK293T cell-extracts followed by immunoblotting with indicated antibodies. (FIG. 3C) GST pulldown of bacterially expressed and purified human MRE11 with indicated GRB2 SH-domains. (FIG. 3D) OB1 fold binding motifs sequence alignment (top). MST isotherms of 50 nM Atto488-labelled RPA70 N-terminal domain (residue 1-120) binding to titrating concentrations (2 nM to 20 μM) of GRB2 or GRB2-derived OB1 peptide. The binding affinity (Kd) is shown. (FIG. 3E) Strep-Tactin precipitation of WT and DF/AA mutant from HEK293T cells that were either untreated (normal) or immediately after IR treated (5 Gy) and lysed, followed by western blot detection with the indicated antibodies. (FIG. 3F) MST-binding isotherms of an Atto488-labelled GRB2-SH2 domain (100 nM) binding to titrating concentrations (30 nM to 500 μM) of synthetic peptides derived from indicated proteins. (FIG. 3G) MST-isotherms of 100 nM Atto488-labelled K109R GRB2 mutant binding to titrating concentrations (30 nM to 200 μM) of synthetic peptides derived from the indicated proteins. Each isotherm was derived from the raw data and fitted according to the law of mass action to yield an apparent Kd. (FIG. 3H) Molecular docking overlay model of GRB2-SH2 domain with (PDB: 3wa4) and without (PDB: 1gri) showing S88 and S90 movement ~4.7 Å when bound to phosphotyrosine peptide (PDB: 3wa4). K109R shown modeled, which could engage with the loop containing S88 and S90 residues. (FIG. 3I) Docking of pH2AX, MRE11 and pEGFR peptide into GRB2 SH2 domain pocket. The relative docking orientation of each peptide is shown.

(FIG. 4A) Live-cell MRE11 recruitment in HeLa cells. GFP-MRE11 was transfected into the indicated stable cells, followed by UV-LMI imaging. Scale bars, 10 μm. (FIG. 4B) Kinetics of recruitment to micro-irradiated regions. GFP-MRE11 track intensity values from 20 cells at every 30 sec were quantified with ImageJ, and normalized average intensities are shown with the standard deviation. (FIG. 4C) Kinetics of GFP-RPA70 recruitment to micro-irradiated regions in HeLa cells. GFP-RPA70 was transfected into the indicated stable cells, followed by UV-LMI imaging. Track intensities were calculated as described in FIG. 4B. (FIG. 4D) Irradiation induced transient chromatin-bound GRB2 ubiquitination. HeLa cells exposed to 5 Gy IR (152 sec) were either immediately lysed (0 min) or allowed to recover for the indicated time. The chromatin fractions and the soluble nuclear fractions of the cells were analyzed with indicated antibodies. (FIG. 4E) Cells were either untreated (UT) or irradiated with 5 Gy IR (152 sec), then lysed immediately (0 min) or allowed to recover for the indicated time. Chromatin fractions were analyzed by western blot with the indicated antibodies (left panel). Direct comparison of MRE11 recruitment onto chromatin between WT and GRB2-KO HeLa cells (middle panel). Comparison of GRB2-KO HeLa cells reconstituted with either wild-type (KO+GRB2) or K109A (KO+K109A) mutant GRB2 (right panel).

(FIG. 5A) Representative images of live-cell GFP-MRE11 recruitment in WT and H2AX-KO MEFs. GFP-MRE11 was transfected into the cells, followed by laser treatment and microscopy imaging. Scale bars, 10 μm. (FIG. 5B) Kinetics of recruitment to micro-irradiated regions. GFP-MRE11 track intensity values from 20 cells at every 30 sec were quantified, and normalized average intensities are shown with standard deviations.

(FIG. 5C) WT and H2AX-KO MEFs were either untreated (UT) or irradiated with 5 Gy IR 1012 (152 sec), then lysed immediately (0 min) or allowed to recover for the indicated time. Chromatin and soluble nuclear fractions were analyzed by western blotting with indicated antibodies. All data are representative of three independent experiments. (FIG. 5D) H2AX-KO MEF cells reconstituted with either WT-H2AX or S139A and Y142F mutant were treated as above and the chromatin fractions were analyzed by western blotting with the indicated antibodies. (FIG. 5E) Quantitative analysis of γH2AX foci from GRB2-KO HeLa and KO cells stably reconstituted with WT or K109R mutant GRB2, treated with 5 Gy IR and then fixed at the indicated post-IR times. The numbers of γH2AX foci were counted and represented. WT HeLa cells served as control. For each time point, the columns represent, from left to right, WT, KO, KO+GRB2, and KO+K109R. (FIG. 5F) Colony survival assay of WT HeLa cells, GRB2-KO cells and stable GRB2-KO cells reconstituted with WT or K109R mutant GRB2, cultured for 10 days after exposure to IR (1 Gy). For each treatment type, the columns represent, from left to right, WT, GRB2 KO, KO+GRB2, and KO+K109R. The significance was analyzed by two-sided student's t-test. *, p≤0.001; **, p≤0.0001; NS, not significant.

FIGS. 6A-6F. GRB2 KO suppresses HDR. (FIG. 6A) DR-GFP reporter assay for control (WT), GRB2-KO (KO) and indicated reconstituted U2OS cells. The percentage of GFP-positive cells was determined by fluorescence-activated cell sorting (FACS) 72 h after transfection. Normalized data are shown. Insert showing western analysis of GRB2 expression in WT and GRB2-KO U2OS cells containing GFP reporter. (FIG. 6B) Normalized data showing a measurable increase in Alt-EJ in GRB2-KO cells. The upregulation was suppressed with either WT GRB2 or K109R mutant reconstitution. (FIG. 6C) HEK293T cells overexpressing Flag-tagged POLQ was immunoprecipitated immediately after 5Gy IR treatment or without treatment, and immunoblotted with indicated antibodies. (FIG. 6D) Parental control (WT), GRB2-KO (KO), $^{WT}$GRB2 (KO+GRB2) and $^{K109R}$GRB2 (KO+K109R) reconstituted HEK293T cells were transfected with flag-tagged XRCC1. After 24 h, XRCC1 was immunoprecipitated and the resulting co-immunoprecipitants were analyzed by western blotting with indicated antibodies. β-Actin was used as a loading control. (FIG. 6E) Normalized data showing a significant reduction in NHEJ in GRB2-KO cells that was rescued by reconstitution of either WT GRB2 or K109R mutant. (FIG. 6F) Normalized data showing GRB2-KO and reconstituted cells for single-stranded annealing (SSA) repair. The K109R mutant only partially rescued the GRB2-KO phenotype. Immunoblot inserts showing the GRB2 knockout level. All data are representative of four independent experiments. The significance was analyzed by two-sided student's t-test. *, p≤0.05; , p≤0.01; *, p≤0.001; ****, p≤0.0001; NS, not significant.

(FIG. 7A) MRE11 depletion levels with two different shRNA (KD1 and KD2) in U2OS cells with normal level of GRB2 (Ctrl) and GRB2-knockout (KO). (FIG. 7B) DR-GFP reporter assay in MRE11 knockdown control (Ctrl) and GRB2-KO U2OS cells. (FIG. 7C) DR-GFP reporter assay in PTEN-knockdown and/or GRB2-KO U2OS cells. (FIG. 7D) SRB assay of olaparib-induced cytotoxicity in control HeLa cells, GRB2-KO cells and GRB2-KO cells reconstituted with WT or K109R mutant GRB2. $IC_{50}$ values are shown. (FIG. 7E) Clonogenic assay evaluating the effect of a PARPi on colony formation of HeLa cells. Cells were treated with the indicated concentrations of the PARPi olaparib and cultured for 10 days, then the resulting colonies were visualized with crystal violet staining and counted by Gelcount instrument. Parental control (WT), GRB2-KO (KO), $^{WT}$GRB2 (KO+GRB2) and $^{K109R}$GRB2 (KO+K109R) reconstituted HeLa cells. For each concentration on the X-axis, the columns represent, from left to right, WT, GRB2 KO, KO+GRB2, and KO+K109R. ***, p≤0.001; NS, not significant. (FIG. 7F) Bar graph representing Annexin-V/propidium iodide combined labeling and flow cytometry analysis of olaparib-treated control (WT), GRB2-KO, reconstituted $^{WT}$GRB2(KO+GRB2) and K109R mutant (KO+K109R) HeLa cells. Cells were treated with either DMSO or 50 μM olaparib for 72 h. For each treatment group on the X-axis, the columns represent, from left to right, WT, GRB2 KO, KO+GRB2, and KO+K109R. All data are representative of three independent experiments. The significance was analyzed by two-sided student's t-test. *, p≤0.05; , p≤0.01; *, p≤0.001; NS, not significant.

(FIG. 8A) GRB2 expression is upregulated in the majority of human cancers. Analysis of GRB2 expression in TCGA tumors and matched normal tissues. Log p-values were from Wilcoxon tests, with greater values indicating stronger differences; GRB2 expression was higher in tumors than in matched controls in BRCA, KIRP, HNSC, LIHC, ESCA, THCA and UCEC but lower in tumor than in controls in LUAD, LUSC, KICH and COAD. Datasets with >10 normal samples were included. Box-plots display the interquartile range (IQR) from Q1 to Q3 (25-75% percentiles), median (center line), whiskers extending to the minimum (Q1−1.5*IQR) and maximum (Q3+1.5*IQR) and outliers (dots). For each tumor type, the left column represents Normal and the right column represents Tumor. (FIG. 8B) GRB2 expression in breast tumor tissue-array. Scale bars, 50 μm. (FIG. 8C) H-score quantification of nuclear GRB2 IHC staining for 100 BRCA and 10 normal tissue samples. The significance was analyzed by two-sided student's t-test. *, p≤0.05; ****, p≤0.0001. (FIG. 8D) Schematic diagram of BRCA patient stratification according to MRE11 expression and signature 3. (FIGS. 8E-8F) Kaplan-Meier survival curves and hazard ratios for TCGA breast cancer patients with high (above mean) MRE11 expression scored positive (n=285; Sig3+[FIG. 8E]) or negative (n=226; Sig3− [FIG. 8F]) for signature 3 mutations and low (at or below mean) or high (above mean) GRB2 expression; p-values from log-rank tests. For each, the curve that does not reach 0.00 on the Y-axis is "Low GRB2."

(FIG. 9A) HEK293T cells expressing Strep-GRB2 were treated with 5Gy IR, lysed immediately (0) or allowed to recover for the designated time. Strep-tagged GRB2 was precipitated and immunoblotted with MRE11 antibody. Input controls are shown in the bottom three panels. (FIG. 9B) Control or RBBP6-knockdown 1 (KD1) HEK293T cells overexpressing Strep-GRB2 were treated with 5Gy IR, lysed immediately or allowed to recover for the designated time. Strep-GRB2 was precipitated from total extract and immunoblotted with indicated antibodies along with Input controls. (FIG. 9C) Strep-tagged $^{WT}$GRB2 or $^{K109A}$GRB2 K109A mutant precipitated from 5Gy IR-treated (0) or post-recovery (2h) and analyzed with indicated antibodies. (FIG. 9D) DR-GFP reporter assay for control (Ctrl) and two RBBP6-KD U2OS cells. (FIG. 9E) DR-GFP reporter assay for control, GRB2-KO (KO) and K109A reconstituted (KO+K109A) U2OS cells. The significance was analyzed by two-sided student's t-test. , p≤0.01; *, p≤0.001. (FIG. 9F) A schematic proposed model depicting the role of GRB2 in the DSB repair. Ionizing radiation (IR) creates DSBs and phosphorylation of H2AX, which serves as a docking site for the recruitment of the GRB2-MRE11 complex. Ubiquitination of GRB2 at K109 by RBBP6 releases GRB2 from MRE11, while deubiquitination of GRB2 possibly by PSMD14 enables GRB2-MRE11 re-association.

(FIGS. 10A-10B) Representative images of GRB2 IHC staining for different mouse and human tissues. Mouse tissues and human tissue microarrays from Biomax Inc. were stained with anti-GRB2 antibody and hematoxylin for the nucleus. Scale bars, 50 mm. (FIG. 10C) Subcellular localization of GRB2 in HeLa, HAP1, A431 and NIH3T3 cells analyzed by confocal microscopy. Cells were stained with DAPI for nuclei, phalloidin for F-actin and anti-GRB2 antibody for GRB2. Scale bars, 10 μm. Zoomed images of boxed areas shown (right).

FIGS. 11A-11I. Identification and characterization of GRB2 K109 as the RBBP6 ubiquitination site. (FIG. 11A) Schematic depiction and guide RNA sequence used to create GRB2-KO cells. The top sequence is SEQ ID NO: 1 and the bottom sequence is SEQ ID NO: 2. (FIG. 11B) Western blots confirming GRB2-KO in HeLa, HAP1 and HEK293T cells. Total cell lysates were analyzed with indicated antibodies. (FIG. 11C) Characterization of the K109R GRB2 mutant in HAP1 cells under normal growth conditions. The cytoplasmic functions were monitored by immunoblotting with indicated antibodies. (FIG. 11D) Characterization of the K109R mutant GRB2 in HeLa and HAP1 cells following growth factor receptor stimulation. Cells were serum starved overnight, left untreated (basal) or treated with 10 ng/ml FGF2 for 15 min (FGF2); cells were then lysed and analyzed with indicated antibodies. (FIG. 11E) Immunofluorescence comparison of cellular localization of WT and K109R mutant GRB2 in HeLa GRB2-KO cells. Strep-tagged WT and K109R GRB2 were detected with anti-GRB2 antibody, the actin cytoskeleton was labeled with phalloidin and the nucleus stained with DAPI. Scale bars, 10 μm. (FIG. 11F) Comparison of the dimerization and SOS binding propensity between wild-type GRB2 and K109R mutant. GRB2-KO HEK293T cells were co-transfected with Strep- and GFP-tagged GRB2. Strep-GRB2 precipitation of GFP-GRB2 was compared between the WT and K109R mutant (upper panel). SOS binding between WT and K109R GRB2 was also investigated with anti-SOS1 antibody. (FIG. 11G) Venn diagram showing the overlap of the enriched E3 ligases identified in three independent immunoprecipitation-mass spectrometry (IP-MS) experiments in HEK293T cells. Four shared proteins and mean of the coverage and unique peptides from three independent data sets are listed. (FIG. 11H) Co-immunoprecipitation validation of RBBP6 interaction with GRB2 in HEK293T cells. (FIG. 11I) Ubiquitinated GRB2 is not degraded by proteasomes. HEK293T cells were treated with 10 μM MG132 for 1 h before IR-treatment and the indicated recovery time. Nuclear extracts were analyzed using a pan-ubiquitin antibody (left panel) or precipitated with strep-tactin and probed with anti-GRB2 antibody (right panel).

(FIG. 12A) Schematic overview of the nuclear Strep-GRB2 purification and mass spectrometry analysis. (FIG. 12B) Coomassie staining of SDS-PAGE gels from three independent immunoprecipitations (IP 1-3) from nuclear extracts of HEK293T cells used for mass spectrometry analysis. (FIG. 12C) Zoomed classification of the identified GRB2-associated DNA damage response nuclear proteins into different groups according to their known functions. From a string diagram showing the nuclear GRB2 interaction network, color coded according to the p-value. Table insert shows key GRB2-interacting proteins involved in DNA damage repair. (FIG. 12D) Bacterially purified proteins used for biophysical binding assay. Purification was done by standard 6×His tagged protein isolation using immobilized metal affinity chromatography (IMAC) followed by size exclusion chromatography (SEC). SEC fractions from each protein purification are shown.

(FIG. 13A) MST binding isotherms comparing Y111 phosphorylated MRE11 peptide binding to full-length and GRB2-SH2 domain. Kd values are shown. (FIG. 13B) Direct comparison of HDR protein recruitment onto chromatin between GRB2-KO HeLa cells reconstituted with either wild-type GRB2 (KO+GRB2) or GRB2 DF/AA mutant (KO+DF/AA). Cells were either untreated (UT) or irradiated with 5 Gy IR (152 sec), then lysed immediately (0 min) or allowed to recover for the indicated time. Chromatin fractions were analyzed by western blot with the indicated antibody. (FIG. 13C) HeLa sub-cellar fractionation and western analysis of GRB2 cellular compartmentalization immediately following 5Gy IR (0) or following 2 h recovery. Plasma membrane (PM), cytoplasm (C), Chromatin bound (Chr) and soluble nuclear (SN) were analyzed with anti-GRB2 antibody. GAPDH, E-cadherin, Histone H3 and Lamin A was used as control marker for the representing cellular compartments. (FIG. 13D) Total lysates probed with anti-GRB2 antibody of the samples used for fractionation in FIG. 13C. (FIG. 13E) Wild-type (WT) control and GRB2-KO HeLa cells are treated with or without IR (5GY), recovered for 2 h, pre-extracted, fixed and processed for IF staining with indicated antibodies. Representative confocal microscopy images and quantification data are presented. For each treatment type, the left column is WT and the right column is KO. Scale bar, 5 μm. Significance was analyzed by two-sided student's t-test. *, p≤0.05; **, p≤0.01; NS, not significant. All data are from three independent experiments.

(FIG. 14A) Western blots verifying the level of GRB2 knockdown (KD) in A431 and NIH-3T3 cells. (FIG. 14B) Representative confocal microscopy images of gH2AX foci for wild-type (Ctrl) and GRB2-KD A431 cells fixed at indicated times after IR (5 Gy) treatment. Zoomed boxed images are shown (bottom). Scale bar, 10 μm. (FIG. 14C) Quantification of observed numbers of gH2AX foci per cell in FIG. 14B. For each time point, the left column is Control and the right column is GRB2KD. (FIG. 14D) Representative confocal microscopy images of γH2AX foci for wild-type (Ctrl) and GRB2-KD NIH-3T3 cells fixed at indicated times after IR (5 Gy) treatment. Zoomed boxed images are shown (bottom). Scale bar, 10 μm. (FIG. 14E) Quantification of observed numbers of γH2AX foci per cell in FIG. 14D. For each time point, the left column is Control and the right column is GRB2 KD. (FIG. 14F) Representative images of an alkaline comet assay from control and GRB2-KD A431 cells exposed to IR (5 Gy) either left untreated or allowed to recover for 8 h. Scale bars, 50 μm. (FIG. 14G) Statistical analysis of comet tail lengths from three independent experiments in FIG. 14F. For each treatment type, the left column is Control and the right column is GRB2 KD. (FIG. 14H) Colony survival assay of control and GRB2-KD A431 cells cultured for 10 days after IR (1 Gy). Representative colony images from each group. (FIG. 14I) Statistical analysis of FIG. 14H from three independent experiments. For each treatment type, the left column is Control and the right column is GRB2 KD. (FIG. 14J) Quantification and representative colony images of the clonogenic survival assay comparing the control and GRB2-KD NIH-3T3 cells with 1 Gy IR treatment. For each treatment type, the left column is Control and the right column is GRB2-KD. Colony numbers from three independent experiments are shown. The significance was analyzed by two-sided student's t-test. , $p \leq 0.01$; **, $p \leq 0.0001$; NS, not significant.

(FIG. 15A) Western analysis of GRB2 expression in WT and GRB2-KO U2OS cells containing GFP reporter. (FIGS. 15B-15E) Raw flow cytometry data showing the effect of GRB2 KO on DNA damage repair pathways. (FIG. 15F) Raw flow cytometry data showing the effect of MRE11 knockdown in HDR repair efficiency in control and GRB2 KO U2OS cells. (FIG. 15G) Western analysis showing PTEN knockdown efficiency in U2OS cells with and without GRB2 knockout. Beta-actin was used as loading control. Two different shRNA (KD1 and KD2) was used to knock down PTEN in this study. (FIG. 15H) Raw flow cytometry data showing the effect of PTEN knockdown in HDR repair efficiency in control and GRB2 KO U2OS cells. (FIG. 15I) Clonogenic assay evaluating the effect of a PARPi on colony formation of HeLa cells. Cells were treated with the indicated concentrations of the PARPi olaparib for 10 days, and the resulting colonies were visualized with crystal violet staining.

(FIG. 16A) UV-LMI PARP recruitment in HeLa cells. Fixed-time point static images from live-cell UV-LMI experiments using control cells with a normal level of GRB2 and GRB2-KO (KO) cells. We also tested GRB2-KO cells reconstituted with either WT-GRB2 (KO+GRB2) or K109R mutant (KO+K109R). The results showing that in all tested conditions, GRB2 had no impact on PARP recruitment to the DNA damage site. (FIG. 16B) Kinetics of PARP recruitment to micro-irradiated regions. Cells were imaged every 30 seconds, and GFP-PARP1 intensity values from 20 cells were quantified with ImageJ. Averages are shown with standard deviations. (FIG. 16C) Annexin-V/Propidium Iodide combined labeling and flow cytometry analysis of olaparib treated control (WT), GRB2-KO, reconstituted $^{WT}$GRB2 (KO+GRB2) and K109R mutant (KO+K109R) HeLa cells. Cells were treated with either DMSO or 50 μM Olaparib for 72 h. (FIG. 16D) Western analysis of GRB2-knockout (KO) and wild-type (WT) or K109R mutant GRB2 reconstituted HeLa cells, as well as control WT HeLa cells, were treated for 72 hours with DMSO or Olaparib (50 μM), then immunoblotted with indicated antibodies. β-Actin was a loading control. All data are representative of three independent experiments.

(FIGS. 17A-17B)Kaplan-Meier survival curves and hazard ratios for TCGA breast cancer patients with low (at or below mean; n=536, FIG. 17A) and high (above mean; n=558, FIG. 17B) MRE11 expression and low or high GRB2 expression. Patients with high expression levels of MRE11 and GRB2 had significantly reduced overall survival; p-values from log-rank tests. For each graph, the curve with the higher overall survival at year 10 is Low GRB2. (FIGS. 17C-17D) Kaplan-Meier survival curves and hazard ratios for TCGA breast cancer patients with low (at or below mean) MRE11 expression with (FIG. 17C) or without (FIG. 17D) signature 3 mutations, and low (at or below mean) or high (above mean) GRB2 expression. For FIG. 17C, the curve with the higher overall survival at year 10 is High GRB2. For FIG. 17D, the curve with the higher overall survival at year 10 is Low GRB2. (FIG. 17E-17F) Kaplan-Meier survival curves and hazard ratios for TCGA breast cancer patients with (FIG. 17E) or without (FIG. 17F) signature 3 mutations and high (above mean) or low (at or below mean) GRB2 expression. For FIG. 17E, the curve with the higher overall survival at year 10 is Low GRB2. For FIG. 17F, the curve with the higher overall survival at year 10 is High GRB2.

DETAILED DESCRIPTION

Figures 1A, 1B:
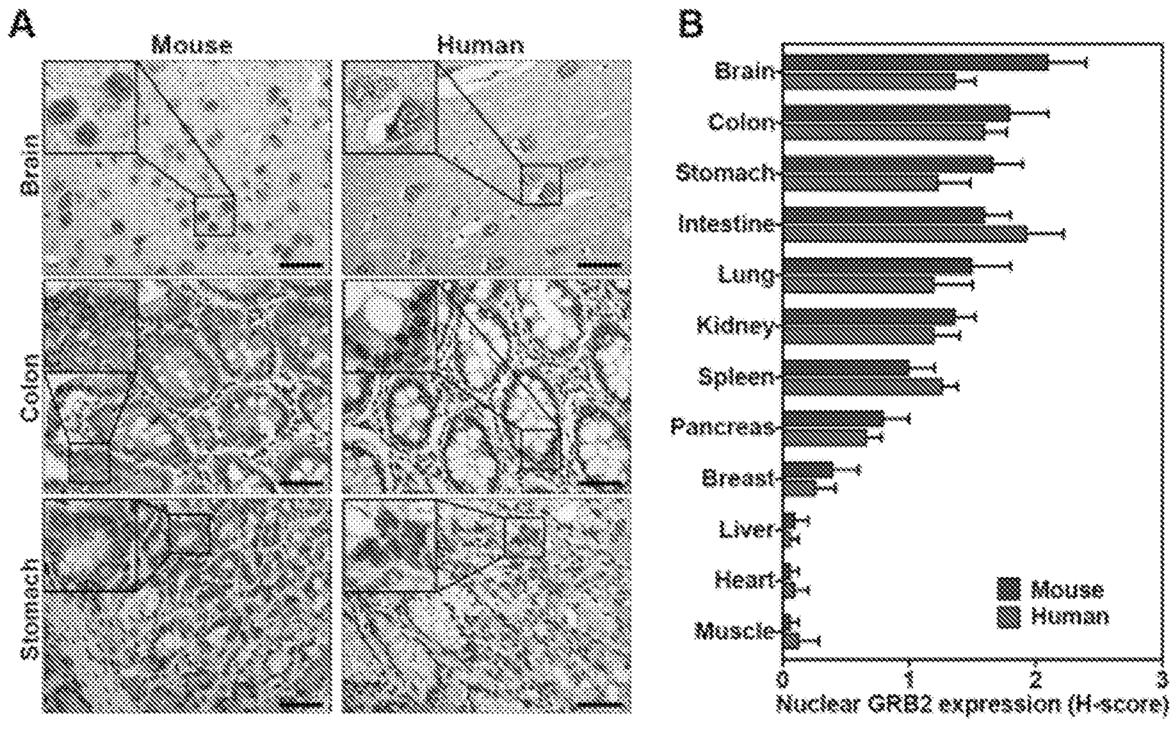
FIGS. 1A-1K. Nuclear GRB2 is poly-ubiquitinated by RBBP6 at the K109 site.

Provided herein is an examination of GRB2 in multiple human cells and tissues that provides comprehensive and systematic evidence of GRB2's nuclear localization. In the nucleus, GRB2 is ubiquitinated on lysine 109 (K109) by the retinoblastoma binding protein 6 (RBBP6) E3 ubiquitin ligase acting in maintaining common fragile site stability (Sakai et al., 1995), (Miotto et al., 2014). RBBP6 forms a complex with nuclear GRB2 (nGRB2) that upon initiation of DNA damage migrates at the damage site and co-localize with GRB2 and γH2AX. Furthermore, key DNA damage response factors MRE11, H2AX and RPA70 interaction sites and direct binding affinities with GRB2 are identified. The inventors identified a conserved RPA70 OB1 fold binding motif at the nSH3 domain of GRB2 that facilitate GRB2-RPA70 interactions while the GRB2-SH2 domain binds both MRE11 and γH2AX with unique binding modes. These results define a new molecular mechanism for timely functional recruitment of MRE11 to DSBs via GRB2, where GRB2 forms a constitutive GRB2-MRE11 (GM) complex without RAD50 and NBS1. The GM complex is recruited to the damage site using phosphorylated H2AX as the docking site where GRB2 ubiquitination at K109 site by RBBP6 releases MRE11 in the vicinity of the damaged DNA. GRB2-mediated MRE11 recruitment is indispensable for a timely DNA repair process. GRB2 knockout (KO) or reconstitution of a GRB2-MRE11 disrupting $^{K109R}$GRB2 mutant cell-lines show prolonged repair activity. Whereas GRB2 depletion affects DNA repair, the direct measurements provided herein indicate limited correlation between PTEN and GRB2 in DNA repair. Instead, the present results define a novel nucleoplasmic GRB2-MRE11 (GM) complex as an MRE11 pool possibly distinct from its canonical MRN complex (Syed & Tainer, 2018). Moreover, GRB2 preferentially promotes homology-directed repair (HDR) and suppresses alternative end-joining (Alt-EJ), GRB2-KO is synthetically lethal to the loss of PARP function, and GRB2-mediated MRE11 recruitment to phosphorylated H2AX was indispensable for timely HDR.

At DNA damage sites, MRE11 release enabling efficient HDR was regulated by GRB2 ubiquitination on lysine 109 (K109). Release was controlled by the E3 ubiquitin ligase retinoblastoma binding protein 6 (RBBP6), which acts in maintaining common fragile site stability (Miotto et al., 2014). Mutant cell lines with GRB2-KO, reconstitution of GM interaction disrupting GRB2 mutants, and RBBP6 depletion showed HDR defects. This repair axis linking GRB2 and MRE11 is further supported by an analysis of TCGA data from patients with breast cancer, where high GRB2 expression showed worse survival only in HDR-proficient patients with high MRE11 expression. Provocatively, immunohistochemical (IHC) analysis of human normal and breast cancer tissues supported correlation between cancer progression stage and nuclear GRB2, where high levels of nuclear-GRB2 occur in late-stage patients. Therefore, these data define a ubiquitination-regulated GRB2 function in timely and robust MRE11 recruitment and consequentially HDR pathway efficiency. These findings suggest GRB2 and MRE11 co-expression levels merit testing as a prognostic biomarker in HDR-proficient patients, paving the way to identify patient groups without BRCA mutations who may favorably respond to PARP inhibitor (PARPi). Consequently, GRB2 and MRE11 expression levels can be used as prognostic biomarkers for predicting PARPi sensitivity in HDR-proficient patients, providing for the selection of patients lacking BRCA mutations to likely benefit from PARPi treatment. Overall, the inventors find an unexpected GRB2 function in timely and robust recruitment and ubiquitination-regulated release of MRE11 that promotes HDR and suppresses Alt-EJ, suggesting that the GM complex acts in maintaining genome integrity.

I. GRB2 Inhibitors

A "GRB2 inhibitor" as used herein includes any molecule that interferes with the function of, blocks, and/or neutralizes a relevant activity of GRB2. Thus, a GRB2 inhibitor includes an antagonist small molecule as well as an inhibitory nucleic acid that prevents expression of GRB2 protein.

A GRB2 inhibitory nucleic acid may be a single-stranded antisense RNA molecule, a single-stranded antisense DNA molecule, or a single-stranded antisense polynucleotide comprising both DNA and RNA. In some cases, the inhibitory nucleic acid may be an antisense oligonucleotide (ASO) therapeutic agent, which is a single stranded nucleic acid therapeutic, typically about 16 to 30 nucleotides in length, and are complementary to a target nucleic acid sequence in the target cell, either in culture or in an organism. An antisense molecule is complementary to a sequence within the target mRNA, e.g., a GRB2 mRNA. Antisense molecules can inhibit translation in a stoichiometric manner by base pairing to the mRNA and physically obstructing the translation machinery. The antisense molecule may have about 15-30 nucleotides that are complementary to the target mRNA. For example, the antisense molecule may have a sequence of at least 15, 16, 17, 18, 19, 20, 21, 22, 23, 24 or 25 or more contiguous nucleotides that are complementary to the target mRNA. siRNA (e.g., siNA) are well known in the art. For example, siRNA and double-stranded RNA have been described in U.S. Pat. Nos. 6,506,559 and 6,573,099, as well as in U.S. Patent Applications 2003/0051263, 2003/0055020, 2004/0265839, 2002/0168707, 2003/0159161, and 2004/0064842, all of which are herein incorporated by reference in their entirety. As exosomes are known to comprise DICER and active RNA processing RISC complex (see PCT Publn. WO 2014/152622, which is incorporated herein by reference in its entirety), shRNA transfected into exosomes can mature into RISC-complex bound siRNA within the exosomes themselves. Alternatively, mature siRNA or ASO can itself be transfected into exosomes or liposomes. Any inhibitory nucleic acid can be applied in the compositions and methods of the present invention if such inhibitory nucleic acid has been found by any source to be a validated downregulator of GRB2.

A GRB2 antagonist small molecule (e.g., a small molecule stabilizer of dimeric GRB2) may be depicted by a structural formula as shown below in Table 1. Non-limiting examples of small molecule GRB2 inhibitors that may be employed in the present methods and pharmaceutical compositions are disclosed in International Patent Application No. PCT/US2020/022722, which is incorporated by reference herein.

TABLE 1

Exemplary small molecule GRB2 inhibitors.

| ID | Structure |
|---|---|
| GRB020 | 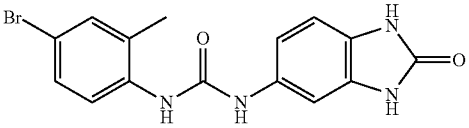 [SMILES: Cc1cc(Br)ccc1NC(=O)Nc1ccc2[nH]c(=O)[nH]c2c1] |
| GRB021 | 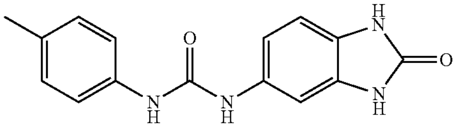 [SMILES: Cc1ccc(NC(=O)Nc2ccc3[nH]c(=O)[nH]c3c2)cc1] |
| GRB022 | 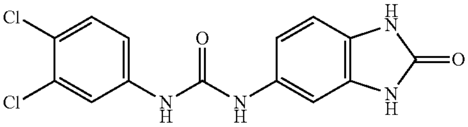 |
| GRB023 | 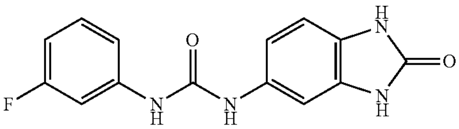 [SMILES: O=C(Nc1cccc(F)c1)Nc1ccc2[nH]c(=O)[nH]c2c1] |

TABLE 1-continued
| Exemplary small molecule GRB2 inhibitors. | |
|---|---|
| ID | Structure |
| GRB024 | 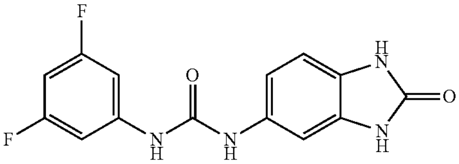 [SMILES: O=C(Nc1cc(F)cc(F)c1)Nc1ccc2[nH]c(=O)[nH]c2c1] |
| GRB025 | 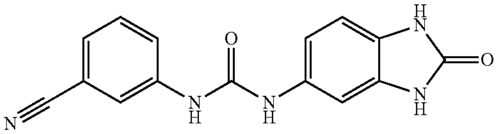 [SMILES: N#Cc1cccc(NC(=O)Nc2ccc3[nH]c(=O)[nH]c3c2)c1] |
| GRB026 | 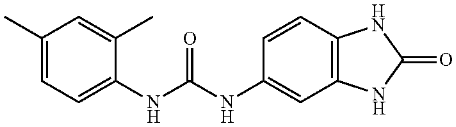 [SMILES: Cc1ccc(NC(=O)Nc2ccc3[nH]c(=O)[nH]c3c2)c(C)c1] |
| GRB027 | 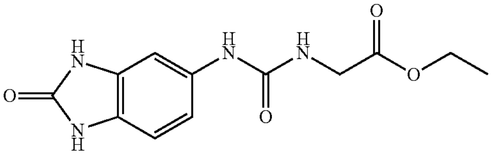 [SMILES: CCOC(=O)CNC(=O)Nc1ccc2[nH]c(=O)[nH]c2c1] |
| GRB028 | 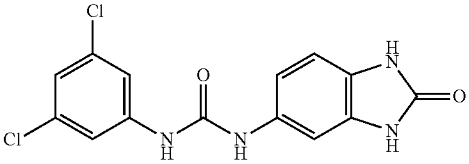 [SMILES: O=C(Nc1cc(Cl)cc(Cl)c1)Nc1ccc2[nH]c(=O)[nH]c2c1] |
| GRB029 | 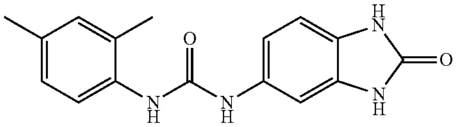 [SMILES: Cc1ccc(NC(=O)Nc2ccc3[nH]c(=O)[nH]c3c2)c(C)c1] |
| GRB030 | 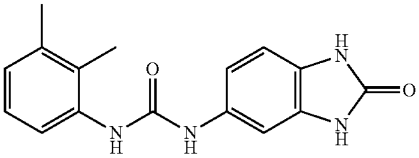 [SMILES: Cc1cccc(NC(=O)Nc2ccc3[nH]c(=O)[nH]c3c2)c1C] |
| GRB031 | 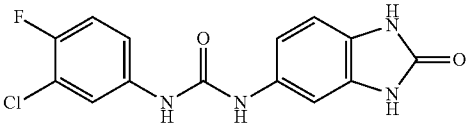 [SMILES: O=C(Nc1ccc(F)c(Cl)c1)Nc1ccc2[nH]c(=O)[nH]c2c1] |
| GRB032 | 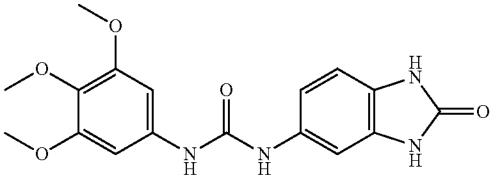 [SMILES: COc1cc(NC(=O)Nc2ccc3[nH]c(=O)[nH]c3c2)cc(OC)c1OC] |

TABLE 1-continued
| Exemplary small molecule GRB2 inhibitors. | |
|---|---|
| ID | Structure |
| GRB033 | 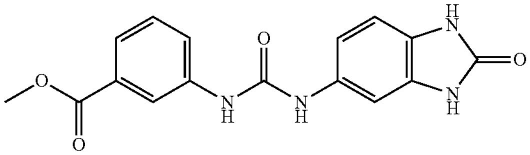 [SMILES: COC(=O)c1cccc(NC(=O)Nc2ccc3[nH]c(=O)[nH]c3c2)c1] |
| GRB034 | 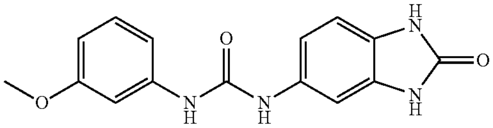 [SMILES: COc1cccc(NC(=O)Nc2ccc3[nH]c(=O)[nH]c3c2)c1] |
| GRB035 | 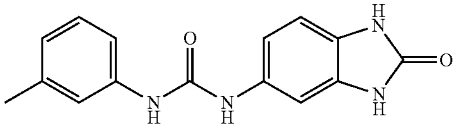 [SMILES: Cc1cccc(NC(=O)Nc2ccc3[nH]c(=O)[nH]c3c2)c1] |
| GRB036 | 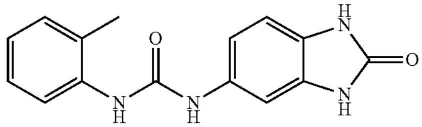 [SMILES: Cc1ccccc1NC(=O)Nc1ccc2[nH]c(=O)[nH]c2c1] |
| GRB037 | 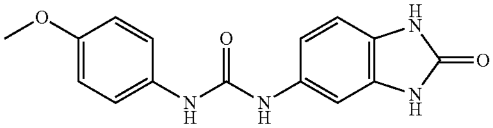 [SMILES: COc1ccc(NC(=O)Nc2ccc3[nH]c(=O)[nH]c3c2)cc1] |
| GRB038 | 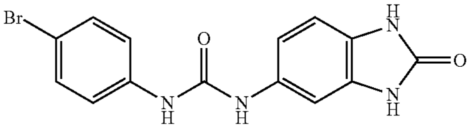 |
| GRB039 | 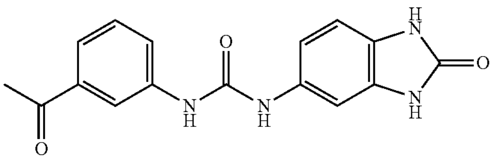 [SMILES: CC(=O)c1cccc(NC(=O)Nc2ccc3[nH]c(=O)[nH]c3c2)c1] |
| GRB040 | 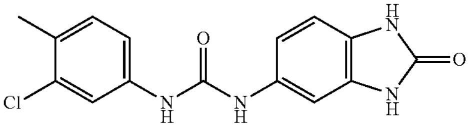 [SMILES: Cc1ccc(NC(=O)Nc2ccc3[nH]c(=O)[nH]c3c2)cc1Cl] |
| GRB041 | 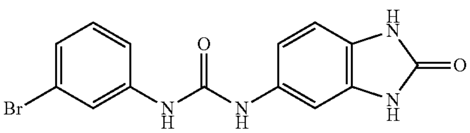 [SMILES: O=C(Nc1cccc(Br)c1)Nc1ccc2[nH]c(=O)[nH]c2c1] |
| GRB042 | 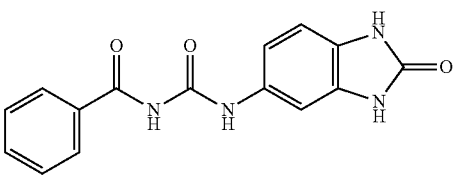 [SMILES: O=C(NC(=O)c1ccccc1)Nc1ccc2[nH]c(=O)[nH]c2c1] |

TABLE 1-continued
| Exemplary small molecule GRB2 inhibitors. | |
|---|---|
| ID | Structure |
| GRB043 | 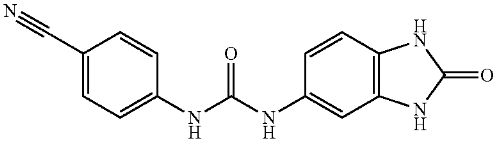 [SMILES: N#Cc1ccc(NC(=O)Nc2ccc3[nH]c(=O)[nH]c3c2)cc1] |
| GRB044 | 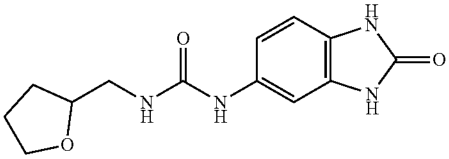 [SMILES: O=C(NCC1CCCO1)Nc1ccc2[nH]c(=O)[nH]c2c1] |
| GRB045 | 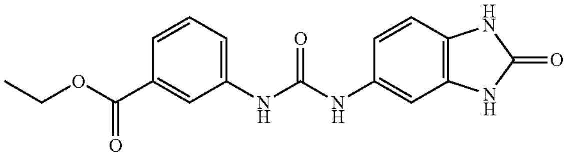 [SMILES: CCOC(=O)c1cccc(NC(=O)Nc2ccc3[nH]c(=O)[nH]c3c2)c1] |
| GRB046 | 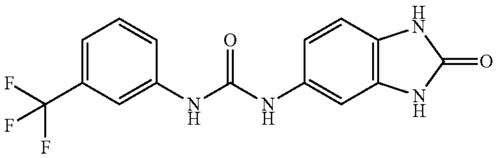 [SMILES: O=C(Nc1cccc(C(F)(F)F)c1)Nc1ccc2[nH]c(=O)[nH]c2c1] |
| GRB047 | 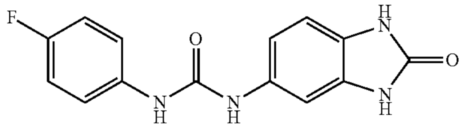 [SMILES: O=C(Nc1ccc(F)cc1)Nc1ccc2[nH]c(=O)[nH]c2c1] |
| GRB048 | 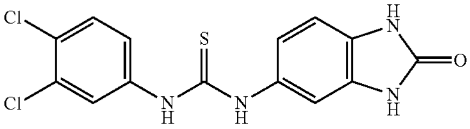 |
| GRB049 | 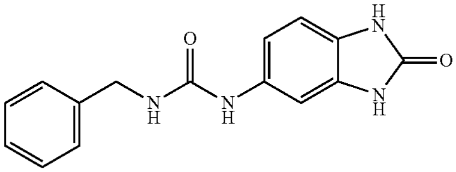 [SMILES: O=C(NCc1ccccc1)Nc1ccc2[nH]c(=O)[nH]c2c1] |
| GRB050 | 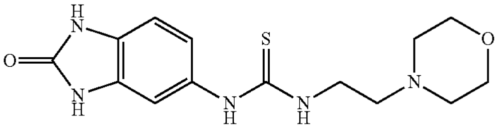 [SMILES: O=c1[nH]c2ccc(NC(=S)NCCN3CCOCC3)cc2[nH]1] |
| GRB051 | 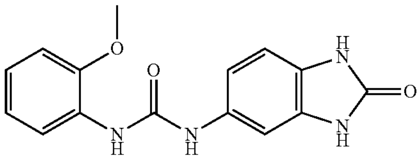 [SMILES: COc1ccccc1NC(=O)Nc1ccc2[nH]c(=O)[nH]c2c1] |

TABLE 1-continued
| Exemplary small molecule GRB2 inhibitors. | |
|---|---|
| ID | Structure |
| GRB052 | 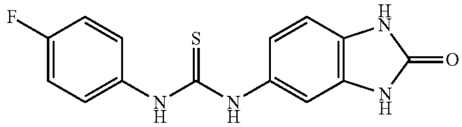 [SMILES: O=c1[nH]c2ccc(NC(=S)Nc3ccc(F)cc3)cc2[nH]1] |
| GRB053 | 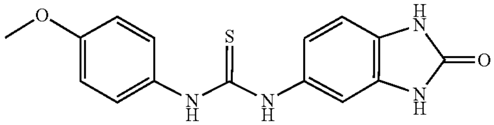 [SMILES: COc1ccc(NC(=S)Nc2ccc3[nH]c(=O)[nH]c3c2)cc1] |
| GRB054 | 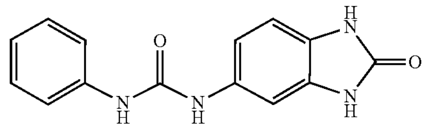 [SMILES: O=C(Nc1ccccc1)Nc1ccc2[nH]c(=O)[nH]c2c1] |
| GRB055 | 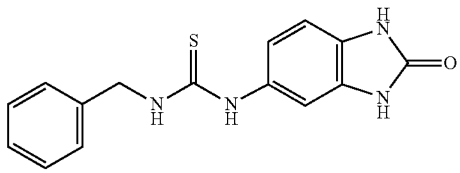 [SMILES: O=c1[nH]c2ccc(NC(=S)NCc3ccccc3)cc2[nH]1] |
| GRB056 | 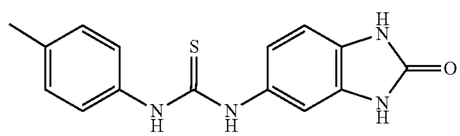 [SMILES: Cc1ccc(NC(=S)Nc2ccc3[nH]c(=O)[nH]c3c2)cc1] |
| GRB057 | 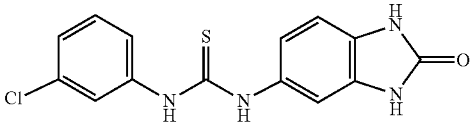 [SMILES: O=c1[nH]c2ccc(NC(=S)Nc3cccc(Cl)c3)cc2[nH]1] |
| GRB058 | 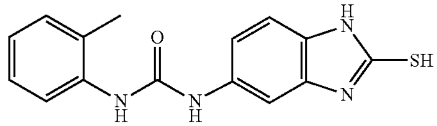 [SMILES: Cc1ccccc1NC(=O)Nc1ccc2[nH]c(S)nc2c1] |
| GRB059 | 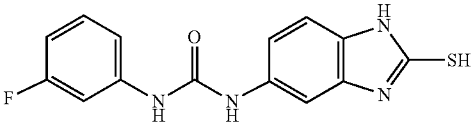 [SMILES: O=C(Nc1cccc(F)c1)Nc1ccc2[nH]c(S)nc2c1] |
| GRB060 | 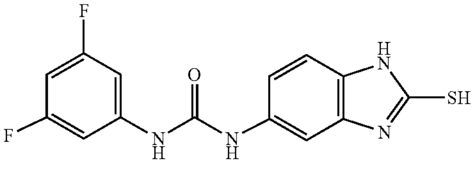 [SMILES: O=C(Nc1cc(F)cc(F)c1)Nc1ccc2[nH]c(S)nc2c1] |
| GRB061 | 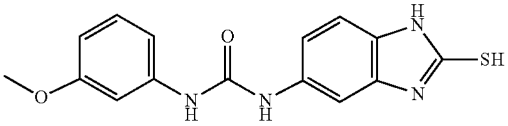 [SMILES: COc1cccc(NC(=O)Nc2ccc3[nH]c(S)nc3c2)c1] |

TABLE 1-continued
| Exemplary small molecule GRB2 inhibitors. | |
|---|---|
| ID | Structure |
| GRB062 | 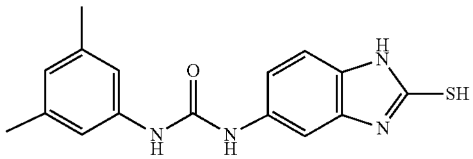 [SMILES: Cc1cc(C)cc(NC(=O)Nc2ccc3[nH]c(S)nc3c2)c1] |
| GRB063 | 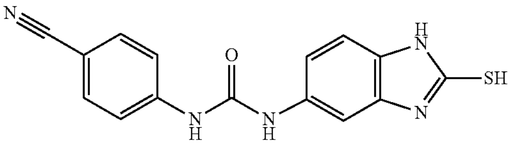 [SMILES: N#Cc1ccc(NC(=O)Nc2ccc3[nH]c(S)nc3c2)cc1] |
| GRB064 | 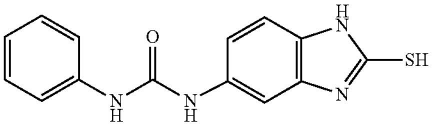 [SMILES: O=C(Nc1ccccc1)Nc1ccc2[nH]c(S)nc2c1] |
| GRB065 | 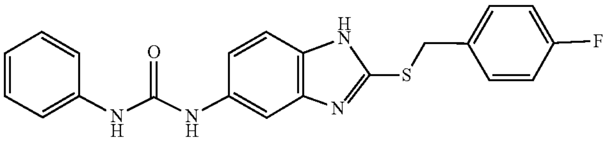 [SMILES: C=C(Nc1ccc(NC(=O)Nc2ccccc2)cc1N)SCc1ccc(F)cc1] |
| GRB066 | 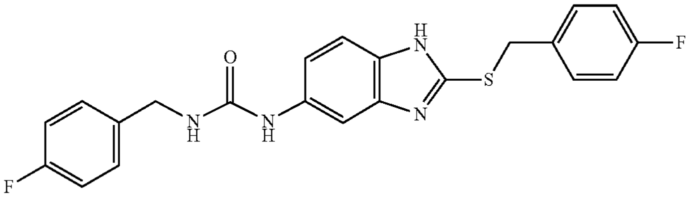 [SMILES: O=C(NCc1ccc(F)cc1)Nc1ccc2[nH]c(SCc3ccc(F)cc3)nc2c1] |
| GRB067 | 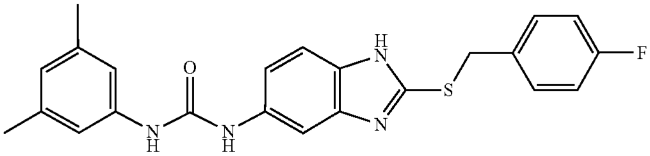 [SMILES: Cc1cc(C)cc(NC(=O)Nc2ccc3[nH]c(SCc4ccc(F)cc4)nc3c2)c1] |
| GRB068 | 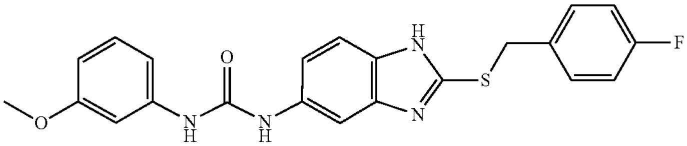 [SMILES: COc1cccc(NC(=O)Nc2ccc3[nH]c(SCc4ccc(F)cc4)nc3c2)c1] |
| GRB069 | 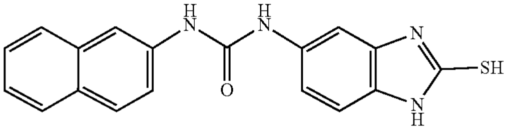 [SMILES: O=C(Nc1ccc2ccccc2c1)Nc1ccc2[nH]c(S)nc2c1] |
| GRB070 | 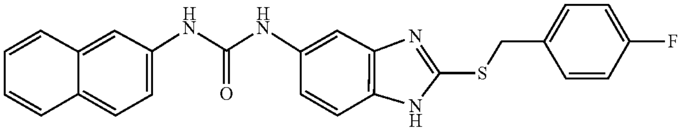 [SMILES: O=C(Nc1ccc2ccccc2c1)Nc1ccc2[nH]c(SCc3ccc(F)cc3)nc2c1] |

TABLE 1-continued
| Exemplary small molecule GRB2 inhibitors. | |
|---|---|
| ID | Structure |
| GRB071 | 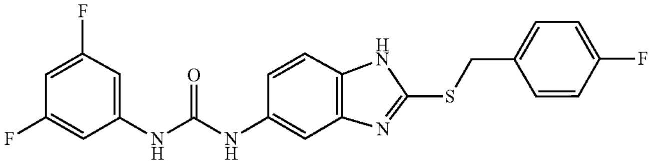 [SMILES: O=C(Nc1cc(F)cc(F)c1)Nc1ccc2[nH]c(SCc3ccc(F)cc3)nc2c1] |
| GRB072 | 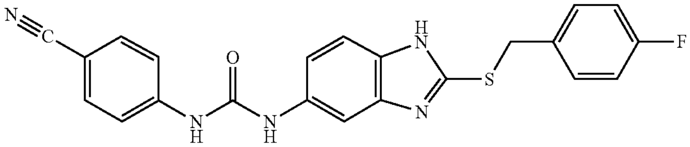 [SMILES: N#Cc1ccc(NC(=O)Nc2ccc3[nH]c(SCc4ccc(F)cc4)nc3c2)cc1] |
| GRB073 | 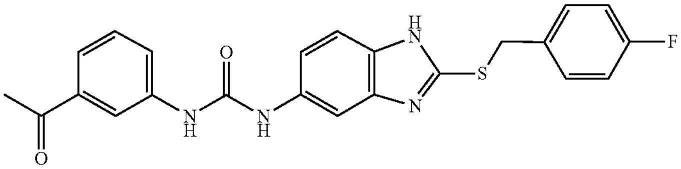 [SMILES: CC(=O)c1cccc(NC(=O)Nc2ccc3[nH]c(SCc4ccc(F)cc4)nc3c2)c1] |
| GRB074 | 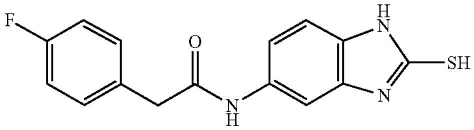 [SMILES: O=C(Cc1ccc(F)cc1)Nc1ccc2[nH]c(S)nc2c1] |
| GRB075 | 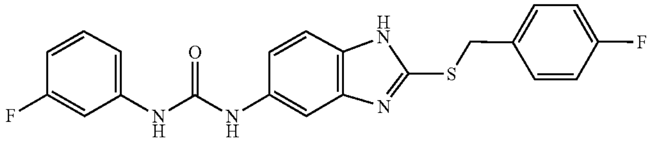 [SMILES: O=C(Nc1cccc(F)c1)Nc1ccc2[nH]c(SCc3ccc(F)cc3)nc2c1] |
| GRB076 | 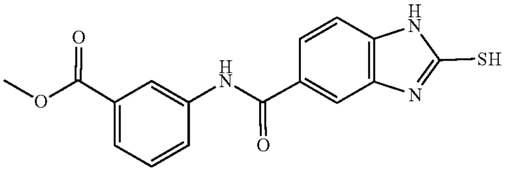 [SMILES: COC(=O)c1cccc(NC(=O)c2ccc3[nH]c(S)nc3c2)c1] |
| GRB077 | 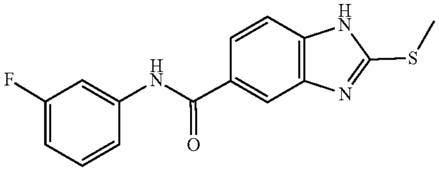 [SMILES: CSc1nc2cc(C(=O)Nc3cccc(F)c3)ccc2[nH]1] |
| GRB078 | 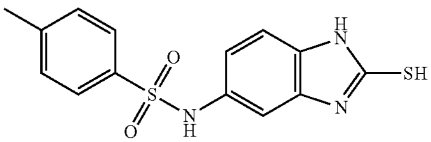 [SMILES: Cc1ccc(S(=O)(=O)Nc2ccc3[nH]c(S)nc3c2)cc1] |

TABLE 1-continued
| Exemplary small molecule GRB2 inhibitors. | |
|---|---|
| ID | Structure |
| GRB079 | 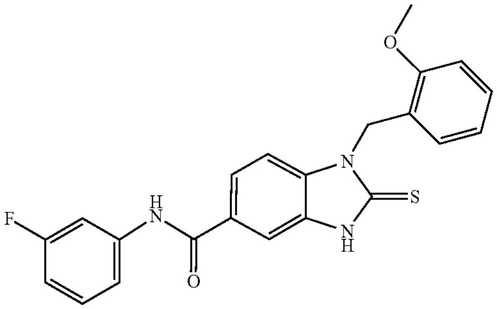 [SMILES: COc1ccccc1Cn1c(=S)[nH]c2cc(C(=O)Nc3cccc(F)c3)ccc21] |
| GRB080 | 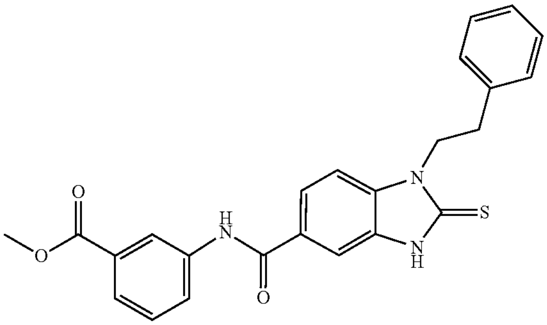 [SMILES: COC(=O)c1cccc(NC(=O)c2ccc3c(c2)[nH]c(=S)n3CCc2ccccc2)c1] |
| GRB081 | 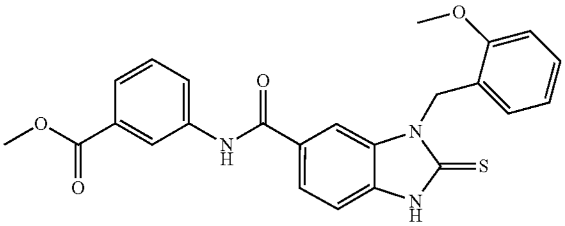 [SMILES: COC(=O)c1cccc(NC(=O)c2ccc3[nH]c(=S)n(Cc4ccccc4OC)c3c2)c1] |
| GRB082 | 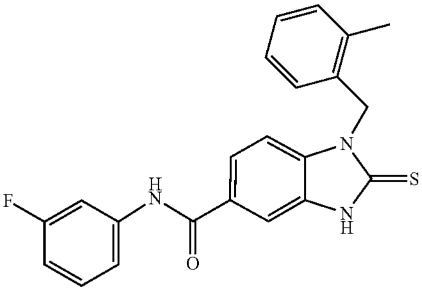 [SMILES: Cc1ccccc1Cn1c(=S)[nH]c2cc(C(=O)Nc3cccc(F)c3)ccc21] |
| GRB083 | 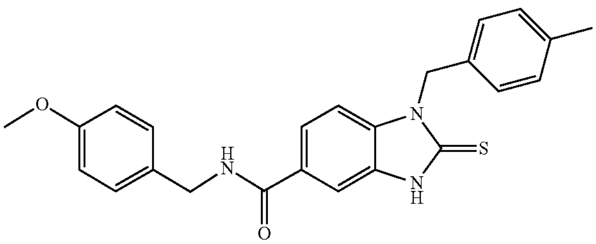 |

TABLE 1-continued
| Exemplary small molecule GRB2 inhibitors. | |
|---|---|
| ID | Structure |
| GRB084 | 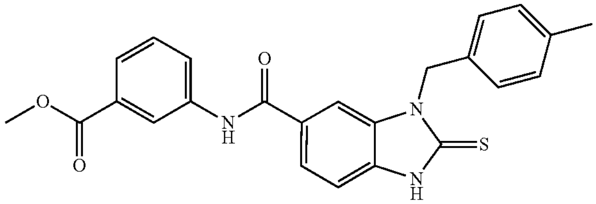 |
| GRB085 | 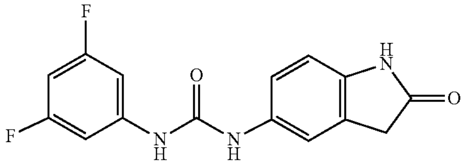 [SMILES: O=C1Cc2cc(NC(=O)Nc3cc(F)cc(F)c3)ccc2N1] |
| GRB086 | 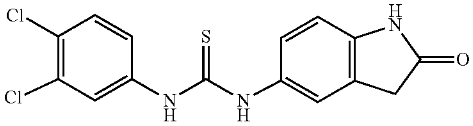 [SMILES: O=C1Cc2cc(NC(=S)Nc3ccc(Cl)c(Cl)c3)ccc2N1] |
| GRB087 | 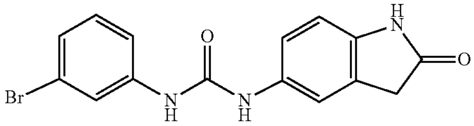 [SMILES: O=C1Cc2cc(NC(=O)Nc3cccc(Br)c3)ccc2N1] |
| GRB088 | 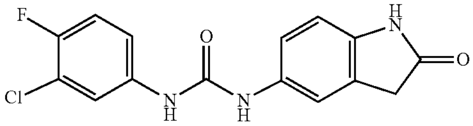 [SMILES: O=C1Cc2cc(NC(=O)Nc3ccc(F)c(Cl)c3)ccc2N1] |
| GRB089 | 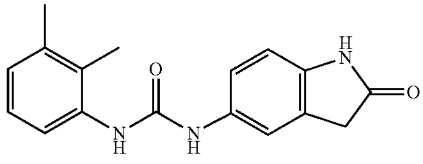 [SMILES: Cc1cccc(NC(=O)Nc2ccc3c(c2)CC(=O)N3)c1C] |
| GRB090 | 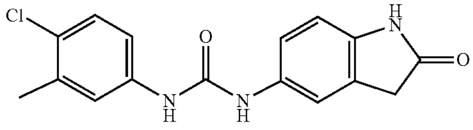 [SMILES: Cc1cc(NC(=O)Nc2ccc3c(c2)CC(=O)N3)ccc1Cl] |
| GRB091 | 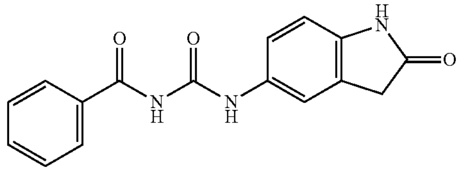 [SMILES: O=C1Cc2cc(NC(=O)NC(=O)c3ccccc3)ccc2N1] |
| GRB092 | 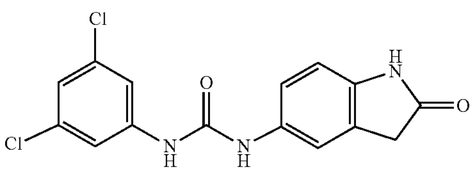 [SMILES: O=C1Cc2cc(NC(=O)Nc3cc(Cl)cc(Cl)c3)ccc2N1] |

TABLE 1-continued
| Exemplary small molecule GRB2 inhibitors. | |
|---|---|
| ID | Structure |
| GRB093 | 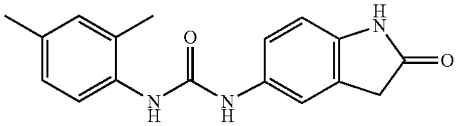 [SMILES: Cc1ccc(NC(=O)Nc2ccc3c(c2)CC(=O)N3)c(C)c1] |
| GRB094 | 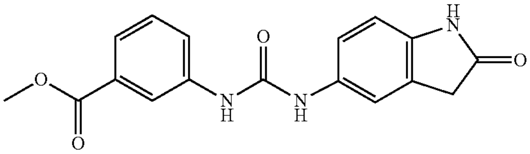 [SMILES: COC(=O)c1cccc(NC(=O)Nc2ccc3c(c2)CC(=O)N3)c1] |
| GRB095 | 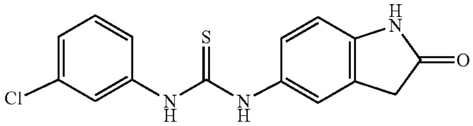 [SMILES: O=C1Cc2cc(NC(=S)Nc3cccc(Cl)c3)ccc2N1] |
| GRB096 | 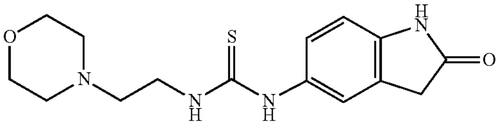 [SMILES: O=C1Cc2cc(NC(=S)NCCN3CCOCC3)ccc2N1] |
| GRB097 | 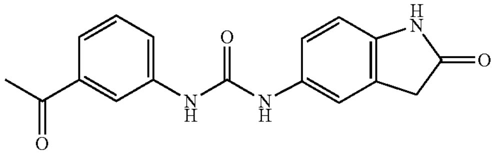 [SMILES: CC(=O)c1cccc(NC(=O)Nc2ccc3c(c2)CC(=O)N3)c1] |
| GRB098 | 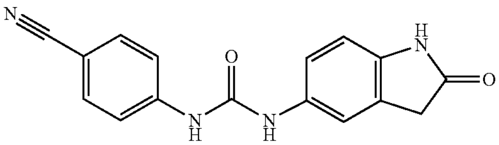 [SMILES: N#Cc1ccc(NC(=O)Nc2ccc3c(c2)CC(=O)N3)cc1] |
| GRB099 | 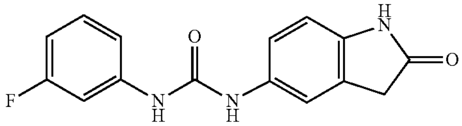 [SMILES: O=C1Cc2cc(NC(=O)Nc3cccc(F)c3)ccc2N1] |
| GRB100 | 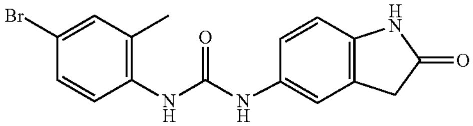 [SMILES: Cc1cc(Br)ccc1NC(=O)Nc1ccc2c(c1)CC(=O)N2] |
| GRB005 | 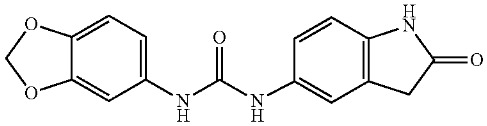 [SMILES: O=C1Cc2cc(NC(=O)Nc3ccc4c(c3)OCO4)ccc2N1] |
| GRB006 | 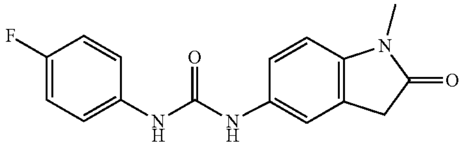 [SMILES: CN1C(=O)Cc2cc(NC(=O)Nc3ccc(F)cc3)ccc21] |

TABLE 1-continued
| Exemplary small molecule GRB2 inhibitors. | |
|---|---|
| ID | Structure |
| GRB010 | 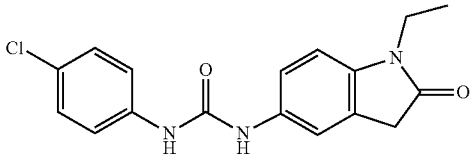 [SMILES: CCN1C(=O)Cc2cc(NC(=O)Nc3ccc(Cl)cc3)ccc21] |
| GRB012 | 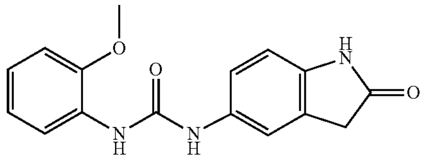 [SMILES: COc1ccccc1NC(=O)Nc1ccc2c(c1)CC(=O)N2] |
| GRB009 | 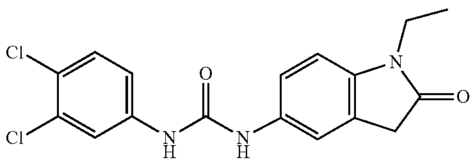 [SMILES: CCN1C(=O)Cc2cc(NC(=O)Nc3ccc(Cl)c(Cl)c3)ccc21] |
| GRB002 | 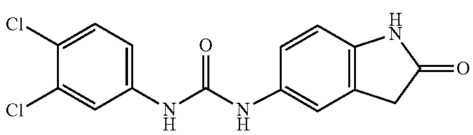 [SMILES: O=C1Cc2cc(NC(=O)Nc3ccc(Cl)c(Cl)c3)ccc2N1] |
| GRB003 | 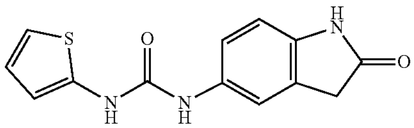 [SMILES: O=C1Cc2cc(NC(=O)Nc3cccs3)ccc2N1] |
| GRB007 | 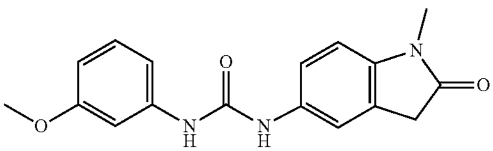 [SMILES: COc1cccc(NC(=O)Nc2ccc3c(c2)CC(=O)N3C)c1] |
| GRB004 | 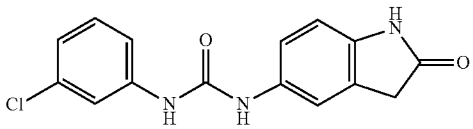 [SMILES: O=C1Cc2cc(NC(=O)Nc3cccc(Cl)c3)ccc2N1] |
| GRB001 | 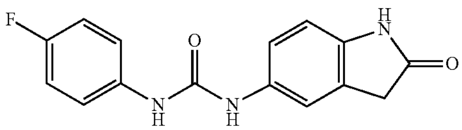 [SMILES: O=C1Cc2cc(NC(=O)Nc3ccc(F)cc3)ccc2N1] |
| GRB013 | 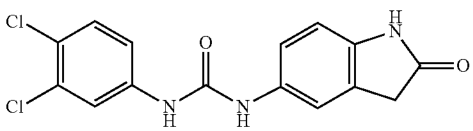 [SMILES: O=C1Cc2cc(NC(=O)Nc3ccc(Cl)c(Cl)c3)ccc2N1] |
| GRB008 | 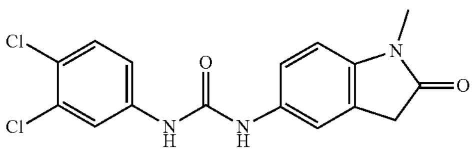 [SMILES: CN1C(=O)Cc2cc(NC(=O)Nc3ccc(Cl)c(Cl)c3)ccc21] |

TABLE 1-continued
| Exemplary small molecule GRB2 inhibitors. | |
|---|---|
| ID | Structure |
| GRB011 | 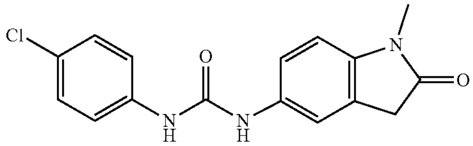 [SMILES: CN1C(=O)Cc2cc(NC(=O)Nc3ccc(Cl)cc3)ccc21] |
| GRB014 | 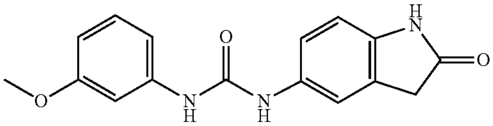 [SMILES: COc1cccc(NC(=O)Nc2ccc3c(c2)CC(=O)N3)c1] |
| GRB015 | 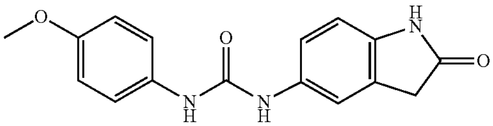 [SMILES: COc1ccc(NC(=O)Nc2ccc3c(c2)CC(=O)N3)cc1] |
| GRB016 | 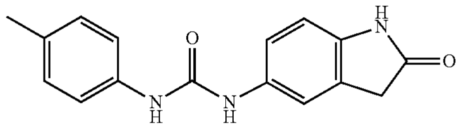 [SMILES: Cc1ccc(NC(=O)Nc2ccc3c(c2)CC(=O)N3)cc1] |
| GRB017 | 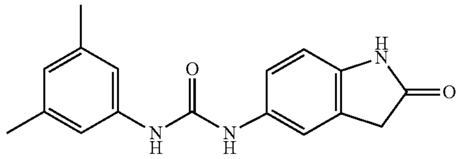 [SMILES: Cc1cc(C)cc(NC(=O)Nc2ccc3c(c2)CC(=O)N3)c1] |
| GRB018 | 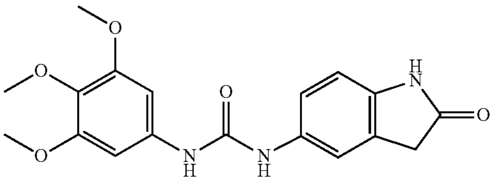 [SMILES: COc1cc(NC(=O)Nc2ccc3c(c2)CC(=O)N3)cc(OC)c1OC] |
| GRB019 | 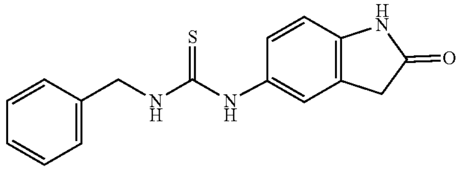 [SMILES: O=C1Cc2cc(NC(=S)NCc3ccccc3)ccc2N1] |
| GRB101 | 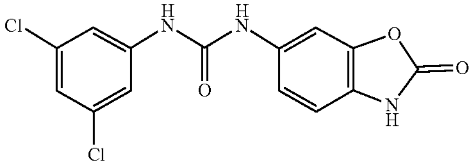 [SMILES: O=C(Nc1cc(Cl)cc(Cl)c1)Nc1ccc2[nH]c(=O)oc2c1] |
| GRB102 | 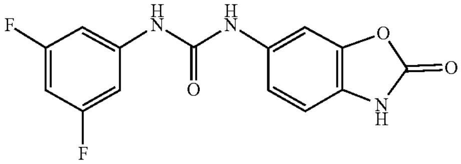 [SMILES: O=C(Nc1cc(F)cc(F)c1)Nc1ccc2[nH]c(=O)oc2c1] |

TABLE 1-continued

| Exemplary small molecule GRB2 inhibitors. | |
|---|---|
| ID | Structure |
| GRB103 | 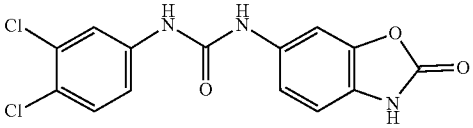 [SMILES: O=C(Nc1ccc(Cl)c(Cl)c1)Nc1ccc2[nH]c(=O)oc2c1] |
| GRB104 | 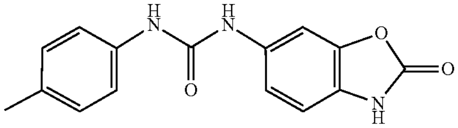 [SMILES: Cc1ccc(NC(=O)Nc2ccc3[nH]c(=O)oc3c2)cc1] |
| GRB105 | 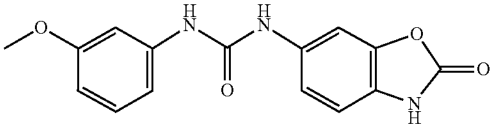 [SMILES: COc1cccc(NC(=O)Nc2ccc3[nH]c(=O)oc3c2)c1] |
| GRB106 | 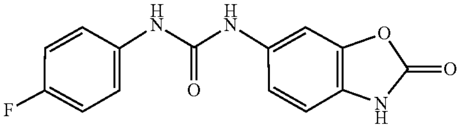 [SMILES: O=C(Nc1ccc(F)cc1)Nc1ccc2[nH]c(=O)oc2c1] |
| GRB107 | 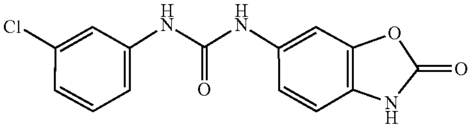 [SMILES: O=C(Nc1cccc(Cl)c1)Nc1ccc2[nH]c(=O)oc2c1] |
| GRB108 | 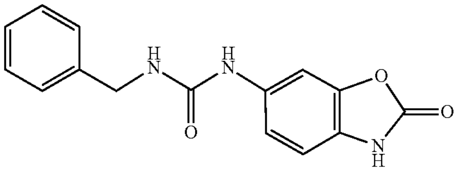 [SMILES: O=C(NCc1ccccc1)Nc1ccc2[nH]c(=O)oc2c1] |

The compounds of the present disclosure are shown, for example, above, in the summary section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

All the compounds of the present disclosure may in some embodiments be used for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all the compounds of the present disclosure are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present disclosure have the advantage that they may be more efficacious than, be less toxic than, be longer acting than, be more potent than, produce fewer side effects than, be more easily absorbed than, more metabolically stable than, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present disclosure may contain one or more asymmetrically-substituted carbon or nitrogen atom and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration. In some embodiments, the present compounds may contain two or more atoms which have a defined stereochemical orientation.

Chemical formulas used to represent compounds of the present invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, isotopes of fluorine include $^{18}F$, and isotopes of carbon include $^{13}C$ and $^{14}C$.

In some embodiments, compounds of the present disclosure function as prodrugs or can be derivatized to function as prodrugs. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

In some embodiments, compounds of the present disclosure exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

II. DNA Damaging Agents or DNA Repair Inhibitors

Poly(ADP-ribose)polymerase 1 has an essential role in facilitating DNA repair, controlling RNA transcription, mediating cell death, and regulating immune response. PARP1 inhibitors are a group of pharmacological inhibitors of the enzyme PARP1 (see NP_001609.2, which is incorporated herein by reference). In various preclinical cancer models and human clinical trials, PARP1 inhibitors have been shown to potentiate radiation and chemotherapy by increasing apoptosis of cancer cells, limiting tumor growth, decreasing metastasis, and prolonging the survival of tumor-bearing subjects (WO 2007/084532; Donawho et al., 2007; Kummar et al., 2009). By way of example, PARP1 inhibitors include, but are not limited to, olaparib (AZD-2281), veliparib (ABT-888), iniparib (BSI-201), rucaparib (AG014699, PF-01367338), niraparib, talazoparib, pamiparib, AG14361, INO-1001, A-966492, PJ34, MK-4827, CEP 9722, BNM-673, E7016, AZD2461, 3-aminobenzamide, and those disclosed in U.S. Pat. Nos. 7,928,105; 8,124,606; 8,236,802; 8,450,323; WO 2006/110816; WO 2008/083027; and WO 2011/014681.

By the term "poly-ADP-ribose glycolase inhibitor" or "PARG inhibitor" is meant an agent that decreases (e.g., at least 10%, 20%, 30%, 40%, 50%, 60%, 70%, 80%, 90%, or even 100%) the expression (e.g., protein and/or mRNA level) or one or more (e.g., 1, 2, 3, 4, or 5) biological activities of one or more (e.g., 1, 2, 3, 4, 5, 6, 7, 8, 9, or 10) PARGs. For example, a PARG inhibitor may decrease the levels of one or more (e.g., 1, 2, 3, 4, 5, 6, 7, 8, 9, or 10) nucleic acids containing a nucleic acid sequence encoding PARG or ARH3, or decrease the level of one or more (e.g., 1, 2, 3, 4, 5, 6, 7, 8, 9, or 10) polypeptides encoded by these nucleic acids. A PARG inhibitor may decrease one or more (e.g., 1, 2, 3, 4, or 5) of the biological activities of a PARG including, but not limited to, the ability to remove a ADP-ribose attached to one or more substrate(s) (e.g., a protein, RNA molecule, DNA molecule, lipid, or small molecule), the ability to remove one or more ADP-ribose molecules from a pre-existing poly-ADP-ribose molecule covalently attached to a substrate (e.g., a protein, RNA molecule, DNA molecule, lipid, or small molecule), the ability to decrease or prevent the formation or the rate of formation of a stress granule in a cell, or the ability to increase the rate of disassembly of a stress granule. Non-limiting examples of PARG inhibitors include antibodies or antibody fragments that specifically bind to PARG protein, ARH3 protein, PARG fusion protein, or ARH3 fusion protein; RNAi molecules, or small molecules (e.g., PDD 00017273, CAS 1945950-21-9; COH34; JA2131; see WO2020/023802, which is incorporated by reference herein in its entirety).

DNA-dependent protein kinase (DNA-PK) is a serine/threonine protein kinase which is activated in conjunction with DNA. Biochemical and genetic data show that DNA-PK consists (a) of a catalytic sub-unit, which is called DNA-PKcs, and (b) two regulatory components (Ku70 and Ku80). In functional terms, DNA-PK is a crucial constituent on the one hand of the repair of DNA double-strand breaks (DSBs) and on the other hand of somatic or V(D)J recombination. In addition, DNA-PK and its components are connected with a multiplicity of further physiological processes, including modulation of the chromatin structure and telomeric maintenance. Exemplary DNAPK inhibitors include those disclosed in WO2016/210046, WO2018/178040, AZD7648, MSC-2490484, and M-3814.

DNA polymerase theta (also referred to as PolQ; Gene ID No. 10721) is a DNA polymerase that also functions as an DNA-dependent ATPase. PolQ is implicated in a pathway required for the repair of double-stranded DNA breaks, referred to as the error-prone microhomology-mediated end-joining (MMEJ) pathway. As used herein, a "PolQ inhibitor" is any agent that reduces, slows, halts, and/or prevents PolQ activity in a cell relative to vehicle, or an agent that reduces or prevents expression of PolQ protein. Typically, PolQ comprises two distinct enzymatic (catalytic) domains, an N-terminal ATPase and a C-terminal polymerase domain. Thus, a PolQ inhibitor can be an agent (e.g., a small molecule, peptide or antisense molecule) that inhibits polymerase function, ATPase function, or polymerase function and ATPase function of PolQ. In some embodiments, the inhibitor reduces, slows, halts, and/or prevents the ATPase activity of PolQ. A PolQ inhibitor can be any molecule or compound that inhibits PolQ as described above, including a small molecule, antibody or antibody fragments, peptide or antisense compound, siRNA and shRNA, and DNA and RNA aptamers. In some embodiments, a PolQ inhibitor is a molecule that reduces or prevents expression of PolQ, such as one or more antisense molecules (e.g., siRNA, shRNA, dsRNA, miRNA, amiRNA, antisense oligonucleotides (ASO)) that target DNA or mRNA encoding PolQ. In some embodiments, the antisense molecule is an interfering RNA (e.g., dsRNA, siRNA, shRNA, miRNA, amiRNA, ASO). In some embodiments, a PolQ inhibitor is as disclosed WO2020160213, as disclosed in WO2020160134, or novobiocin.

Homology-dependent repair at a DNA double-strand break starts with the localization of the MRE11-RAD50-NBS1 (MRN) complex to the double stranded break. The break is resected, long-range chromatin modifications take place and the resected DNA invades the homologous sequence in a Rad51/52 dependent reaction. Additional factors are then required, including Rad paralogs and BRCA1/2 in vertebrates. Exemplary MRE11 inhibitors include Mirin; PFM01; and PFM39. Also contemplated are any of the DNA repair pathway inhibitors recited in Hengel et al. (2017), which is incorporated by reference herein in its entirety.

"ATR inhibitor" or "ATRi" refers to an inhibitor of the ATR kinase pathway, which mediates the DNA damage response. Preferably, the ATR inhibitor is a molecule that inhibits the enzymatic activity of the ATR kinase. Examples of ATR inhibitors that are useful in the treatment method, medicaments and uses of the present invention include any of the compounds described in WO 2013/049726, WO 2013/152298, WO 2013/049859, US-2013-0089625, US-2013-0115312, US-2014-0107093, US-2013-0096139, WO 2011/143426, US-2013-0095193, WO 2014/055756, WO 2011/143419, WO 2011/143422, WO 2011/143425, US-2013-0115311, US-2013-0115312, US-2013-0115313, US-2013-0115314, WO 2011/163527, WO 2012/178123, WO 2012/178124, WO 2012/178125, US-2014-0113005, WO2013/049726, WO 2013/071085, WO 2010/071837, WO 2014/089379, WO2014/143242, WO 2014/143241, WO 2015/084384, WO 2014/143240, WO 2015/187451, WO 2015/085132, WO 2014/062604, WO 2014/143240, WO 2013/071094, WO2013/071093, WO 2013/071090, WO 2013/071088, WO 2013/049859, WO 2013/049719, WO 2013/049720, WO 2013/049722, WO 2012/138,938, WO 2011/163527, WO2011/143,423, WO 2011/143,426, WO 2011/143,399, and/or WO 2010/054398.

III. Chemical Definitions

When used in the context of a chemical group: "hydrogen" means —H; "hydroxy" means —OH; "oxo" means ═O; "carbonyl" means —C(═O)—; "carboxy" means —C(═O)OH (also written as —COOH or $—CO_2H$); "halo" means independently —F, —Cl, —Br or —I; "amino" means $—NH_2$; "hydroxyamino" means —NHOH; "nitro" means $—NO_2$; imino means ═NH; "cyano" means —CN; "isocyanyl" means —N═C═O; "azido" means $—N_3$; in a monovalent context "phosphate" means $—OP(O)(OH)_2$ or a deprotonated form thereof, in a divalent context "phosphate" means —OP(O)(OH)O— or a deprotonated form thereof, "mercapto" means —SH; and "thio" means ═S; "sulfonyl" means $—S(O)_2—$; and "sulfinyl" means —S(O)—.

In the context of chemical formulas, the symbol "—" means a single bond, "═" means a double bond, and "≡" means triple bond. The symbol "----" represents an optional bond, which if present is either single or double. The symbol "═══" represents a single bond or a double bond. Thus, the formula

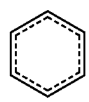

covers, for example,

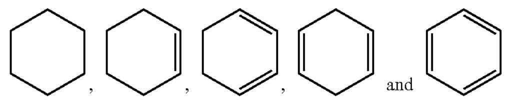

, , , and .

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⦙⦙⦙" means a single bond where the group attached to the thick end of the wedge is "into the page". The symbol "∿∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

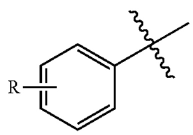

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

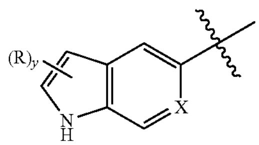

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" or "C=n" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C\leq8)}$", "cycloalkanediyl$_{(C\leq8)}$", "heteroaryl$_{(C\leq8)}$", and "acyl$_{(C\leq8)}$" is one, the minimum number of carbon atoms in the groups "alkenyl$_{(C\leq8)}$", "alkynyl$_{(C\leq8)}$", and "heterocycloalkyl$_{(C\leq8)}$" is two, the minimum number of carbon atoms in the group "cycloalkyl$_{(C\leq8)}$" is three, and the minimum number of carbon atoms in the groups "aryl$_{(C\leq8)}$" and "arenediyl$_{(C\leq8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. Except as noted below, every carbon atom is counted to determine whether the group or compound falls with the specified number of carbon atoms. For example, the group dihexylamino is an example of a dialkylamino$_{(C=12)}$ group; however, it is not an example of a dialkylamino$_{(C=6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

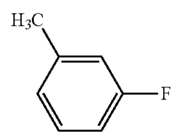

is also taken to refer to

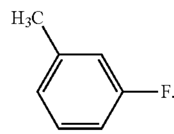

Aromatic compounds may also be depicted using a circle to represent the delocalized nature of the electrons in the fully conjugated cyclic a system, two non-limiting examples of which are shown below:

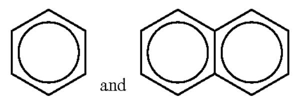

The term "alkyl" refers to a monovalent saturated aliphatic group with a carbon atom as the point of attachment, a linear or branched acyclic structure, and no atoms other than carbon and hydrogen. The groups $—CH_3$ (Me), $—CH_2CH_3$ (Et), $—CH_2CH_2CH_3$ (n-Pr or propyl), $—CH(CH_3)_2$ (i-Pr, $^i$Pr or isopropyl), $—CH_2CH_2CH_2CH_3$ (n-Bu), $—CH(CH_3)CH_2CH_3$ (sec-butyl), $—CH_2CH(CH_3)_2$ (isobutyl), $—C(CH_3)_3$ (tert-butyl, t-butyl, t-Bu or $^t$Bu), and $—CH_2C(CH_3)_3$ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups $—CH_2—$ (methylene), $—CH_2CH_2—$, $—CH_2C(CH_3)_2CH_2—$, and $—CH_2CH_2CH_2—$ are non-limiting examples of alkanediyl groups. The term "alkylidene" refers to the divalent group $=CRR'$ in which R and R' are independently hydrogen or alkyl. Non-limiting examples of alkylidene groups include: $=CH_2$, $=CH(CH_2CH_3)$, and $=C(CH_3)_2$. An "alkane" refers to the class of compounds having the formula H—R, wherein R is alkyl as this term is defined above.

The term "cycloalkyl" refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: $—CH(CH_2)_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" refers to a divalent saturated aliphatic group with two carbon atoms as points of attachment, no carbon-carbon double or triple bonds, and no atoms other than carbon and hydrogen. The group

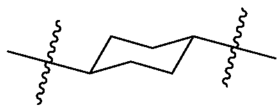 [SMILES: *C1CCC(*)CC1]

is a non-limiting example of cycloalkanediyl group. A "cycloalkane" refers to the class of compounds having the formula H—R, wherein R is cycloalkyl as this term is defined above.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, $—C_6H_4CH_2CH_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

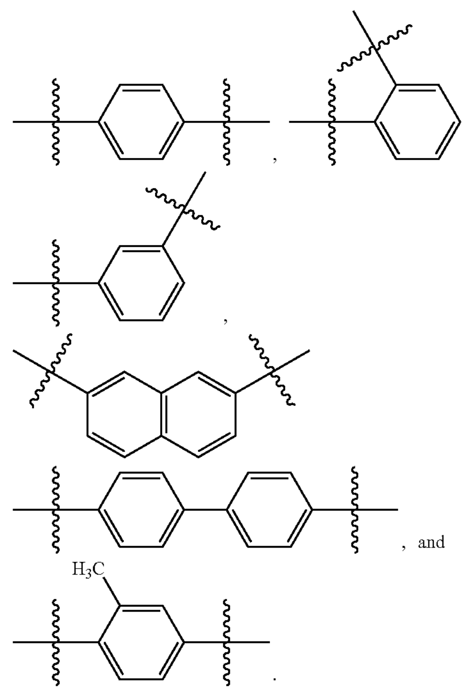

, , , , and .

An "arene" refers to the class of compounds having the formula H—R, wherein R is aryl as that term is defined above. Benzene and toluene are non-limiting examples of arenes.

The term "aralkyl" refers to the monovalent group-alkanediyl-aryl, in which the terms alkanediyl and aryl are each used in a manner consistent with the definitions provided above. Non-limiting examples are: phenylmethyl (benzyl, Bn) and 2-phenyl-ethyl.

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include benzoxazolyl, benzimidazolyl, furanyl, imidazolyl (Im), indolyl, indazolyl (Im), isoxazolyl, methylpyridinyl, oxazolyl, oxadiazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes.

The term "heterocycloalkyl" refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group.

The term "acyl" refers to the group —C(O)R, in which R is a hydrogen, alkyl, cycloalkyl, or aryl as those terms are defined above. The groups, —CHO, —$C(O)CH_3$ (acetyl, Ac), —$C(O)CH_2CH_3$, —$C(O)CH(CH_3)_2$, —$C(O)CH(CH_2)_2$, —$C(O)C_6H_5$, and —$C(O)C_6H_4CH_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group.

The term "alkoxy" refers to the group —OR, in which R is an alkyl, as that term is defined above. Non-limiting examples include: —$OCH_3$ (methoxy), —$OCH_2CH_3$ (ethoxy), —$OCH_2CH_2CH_3$, —$OCH(CH_3)_2$ (isopropoxy), or —$OC(CH_3)_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group.

When a chemical group is used with the "substituted" modifier, one or more hydrogen atom has been replaced, independently at each instance, by —OH, —F, —Cl, —Br, —I, —$NH_2$, —$NO_2$, —$CO_2H$, —$CO_2CH_3$, —$CO_2CH_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$. For example, the following groups are non-limiting examples of substituted alkyl groups: —$CH_2OH$, —$CH_2Cl$, —$CF_3$, —$CH_2CN$, —$CH_2C(O)OH$, —$CH_2C(O)OCH_3$, —$CH_2C(O)NH_2$, —$CH_2C(O)CH_3$, —$CH_2OCH_3$, —$CH_2OC(O)CH_3$, —$CH_2NH_2$, —$CH_2N(CH_3)_2$, and —$CH_2CH_2Cl$. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —$CH_2Cl$ is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —$CH_2F$, —$CF_3$, and —$CH_2CF_3$ are non-limiting examples of fluoroalkyl groups. Non-limiting examples of substituted aralkyls are: (3-chlorophenyl)-methyl, and 2-chloro-2-phenyl-eth-1-yl. The groups, —$C(O)CH_2CF_3$, —$CO_2H$ (carboxyl), —$CO_2CH_3$ (methylcarboxyl), —$CO_2CH_2CH_3$, —$C(O)NH_2$ (carbamoyl), and —$CON(CH_3)_2$, are non-limiting examples of substituted acyl groups. The groups —$NHC(O)OCH_3$ and —$NHC(O)NHCH_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

An "active ingredient" (AI) or active pharmaceutical ingredient (API) (also referred to as an active compound, active substance, active agent, pharmaceutical agent, agent, biologically active molecule, or a therapeutic compound) is the ingredient in a pharmaceutical drug that is biologically active.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient, is sufficient to effect such treatment or prevention of the disease as those terms are defined below.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug, agent, or preparation) is a composition used to diagnose, cure, treat, or prevent disease, which comprises an active pharmaceutical ingredient (API) (defined above) and optionally contains one or more inactive ingredients, which are also referred to as excipients (defined above).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contain ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

IV. Methods of Treatment and Methods of Detection

The term "subject" or "patient" as used herein refers to any individual to which the subject methods are performed. Generally the patient is human, although as will be appreciated by those in the art, the patient may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient.

"Treatment" and "treating" refer to administration or application of a therapeutic agent to a subject or performance of a procedure or modality on a subject for the purpose of obtaining a therapeutic benefit of a disease or health-related condition. For example, a treatment may include administration chemotherapy, immunotherapy, radiotherapy, performance of surgery, or any combination thereof.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

While hyperproliferative diseases can be associated with any disease which causes a cell to begin to reproduce uncontrollably, the prototypical example is cancer. Psoriasis is another example. One of the key elements of cancer is that the cell's normal apoptotic cycle is interrupted and thus agents that interrupt the growth of the cells are important as therapeutic agents for treating these diseases. In some embodiments, the caffeic acid derivatives described herein may be used to decreased cell counts and as such may be used to treat a variety of cancers or other malignancies.

The methods described herein are useful in inhibiting survival or proliferation of cells (e.g., tumor cells), treating proliferative disease (e.g., cancer, psoriasis), and treating pathogenic infection. Generally, the terms "cancer" and "cancerous" refer to or describe the physiological condition in mammals that is typically characterized by unregulated cell growth. More specifically, cancers that are treated in connection with the methods provided herein include, but are not limited to, solid tumors, metastatic cancers, or non-metastatic cancers. In certain embodiments, the cancer may originate in the lung, kidney, bladder, blood, bone, bone marrow, brain, breast, colon, esophagus, duodenum, small intestine, large intestine, colon, rectum, anus, gum, head, liver, nasopharynx, neck, ovary, pancreas, prostate, skin, stomach, testis, tongue, or uterus.

The cancer may specifically be of the following histological type, though it is not limited to these: neoplasm, malignant; carcinoma; non-small cell lung cancer; renal cancer; renal cell carcinoma; clear cell renal cell carcinoma; lymphoma; blastoma; sarcoma; carcinoma, undifferentiated; meningioma; brain cancer; oropharyngeal cancer; nasopharyngeal cancer; biliary cancer; pheochromocytoma; pancreatic islet cell cancer; Li-Fraumeni tumor; thyroid cancer; parathyroid cancer; pituitary tumor; adrenal gland tumor; osteogenic sarcoma tumor; neuroendocrine tumor; breast cancer; lung cancer; head and neck cancer; prostate cancer; esophageal cancer; tracheal cancer; liver cancer; bladder cancer; stomach cancer; pancreatic cancer; ovarian cancer; uterine cancer; cervical cancer; testicular cancer; colon cancer; rectal cancer; skin cancer; giant and spindle cell carcinoma; small cell carcinoma; small cell lung cancer; papillary carcinoma; oral cancer; oropharyngeal cancer; nasopharyngeal cancer; respiratory cancer; urogenital cancer; squamous cell carcinoma; lymphoepithelial carcinoma; basal cell carcinoma; pilomatrix carcinoma; transitional cell carcinoma; papillary transitional cell carcinoma; adenocarcinoma; gastrointestinal cancer; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma with squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; lentigo maligna melanoma; acral lentiginous melanoma; nodular melanoma; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; an endocrine or neuroendocrine cancer or hematopoietic cancer; pinealoma, malignant; chordoma; central or peripheral nervous system tissue cancer; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; B-cell lymphoma; malignant lymphoma; Hodgkin's disease; Hodgkin's; low grade/follicular non-Hodgkin's lymphoma; paragranuloma; malignant lymphoma, small lymphocytic; malignant lymphoma, large cell, diffuse; malignant lymphoma, follicular; mycosis fungoides; mantle cell lymphoma; Waldenstrom's macroglobulinemia; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; chronic lymphocytic leukemia (CLL); acute lymphoblastic leukemia (ALL); Hairy cell leukemia; chronic myeloblastic leukemia; and hairy cell leukemia.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

Likewise, an effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the treatment of disease, the appropriate dosage of a therapeutic composition will depend on the type of disease to be treated, as defined above, the severity and course of the disease, previous therapy, the patient's clinical history and response to the agent, and the discretion of the physician. The agent may be suitably administered to the patient at one time or over a series of treatments.

In certain embodiments regarding methods of treating cancer in a patient, comprising administering to the patient a pharmaceutically effective amount of a compound of the present disclosure, the pharmaceutically effective amount is 0.1-1000 mg/kg. In certain embodiments, the pharmaceutically effective amount is administered in a single dose per day. In certain embodiments, the pharmaceutically effective amount is administered in two or more doses per day. The compound may be administered by contacting a tumor cell during ex vivo purging, for example. The method of treatment may comprise any one or more of the following: a) inducing cytotoxicity in a tumor cell; b) killing a tumor cell; c) inducing apoptosis in a tumor cell; d) inducing differentiation in a tumor cell; or e) inhibiting growth in a tumor cell.

In some embodiments, treatment methods further comprise monitoring treatment progress. In some of these embodiments, the method includes the step of determining a level of changes in hematological parameters and/or diagnostic markers or diagnostic measurement (e.g., screen, assay) in a patient suffering from or susceptible to a disorder or symptoms thereof associated with cancer in which the patient has been administered a therapeutic amount of a compound or composition as described herein. The level of the marker determined in the method can be compared to known levels of marker in either healthy normal controls or in other afflicted patients to establish the patient's disease status. In some embodiments, a second level of the marker in the patient is determined at a time point later than the determination of the first level, and the two levels are compared to monitor the course of disease or the efficacy of the therapy. In some embodiments, a pre-treatment level of marker in the patient is determined prior to beginning treatment according to the methods described herein; this pre-treatment level of marker can then be compared to the level of marker in the patient after the treatment commences, to determine the efficacy of the treatment.

In some embodiments, the patient is a mammal, e.g., a primate, preferably a higher primate, e.g., a human (e.g., a patient having, or at risk of having, a disorder described herein). In some embodiments, the patient is in need of enhancing the patient's immune response. In certain embodiments, the patient is, or is at risk of being, immunocompromised. For example, in some embodiments, the patient is undergoing or has undergone a chemotherapeutic treatment and/or radiation therapy. Alternatively, or in combination, the patient is, or is at risk of being, immunocompromised as a result of an infection.

A. Breast Cancer

Breast cancer refers to cancers originating from breast tissue, most commonly from the inner lining of milk ducts or the lobules that supply the ducts with milk. Cancers originating from ducts are known as ductal carcinomas; those originating from lobules are known as lobular carcinomas. There are many different types of breast cancer, with different stages (spread), aggressiveness, and genetic makeup; survival varies greatly depending on those factors. Computerized models are available to predict survival. With best treatment and dependent on staging, 10-year disease-free survival varies from 98% to 10%. Treatment includes surgery, drugs (hormonal therapy and chemotherapy), and radiation.

Worldwide, breast cancer comprises 10.4% of all cancer incidence among women, making it the second most common type of non-skin cancer (after lung cancer) and the fifth most common cause of cancer death. In 2004, breast cancer caused 519,000 deaths worldwide (7% of cancer deaths; almost 1% of all deaths). Breast cancer is about 100 times more common in women than in men, although males tend to have poorer outcomes due to delays in diagnosis.

Some breast cancers require the hormones estrogen and progesterone to grow, and have receptors for those hormones. After surgery those cancers are treated with drugs that interfere with those hormones, usually tamoxifen, and with drugs that shut off the production of estrogen in the ovaries or elsewhere; this may damage the ovaries and end fertility. After surgery, low-risk, hormone-sensitive breast cancers may be treated with hormone therapy and radiation alone. Breast cancers without hormone receptors, or which have spread to the lymph nodes in the armpits, or which express certain genetic characteristics, are higher-risk, and are treated more aggressively. One standard regimen, popular in the U.S., is cyclophosphamide plus doxorubicin (Adriamycin), known as CA; these drugs damage DNA in the cancer, but also in fast-growing normal cells where they cause serious side effects. Sometimes a taxane drug, such as docetaxel, is added, and the regime is then known as CAT; taxane attacks the microtubules in cancer cells. An equivalent treatment, popular in Europe, is cyclophosphamide, methotrexate, and fluorouracil (CMF). Monoclonal antibodies, such as trastuzumab (Herceptin), are used for cancer cells that have the HER2 mutation. Radiation is usually added to the surgical bed to control cancer cells that were missed by the surgery, which usually extends survival, although radiation exposure to the heart may cause damage and heart failure in the following years.

While screening techniques (which are further discussed below) are useful in determining the possibility of cancer, a further testing is necessary to confirm whether a lump detected on screening is cancer, as opposed to a benign alternative such as a simple cyst.

In a clinical setting, breast cancer is commonly diagnosed using a "triple test" of clinical breast examination (breast examination by a trained medical practitioner), mammography, and fine needle aspiration cytology. Both mammography and clinical breast exam, also used for screening, can indicate an approximate likelihood that a lump is cancer, and may also identify any other lesions. Fine Needle Aspiration and Cytology (FNAC), which may be done in a doctor's office using local anaesthetic if required, involves attempting to extract a small portion of fluid from the lump. Clear fluid makes the lump highly unlikely to be cancerous, but bloody fluid may be sent off for inspection under a microscope for cancerous cells. Together, these three tools can be used to diagnose breast cancer with a good degree of accuracy.

Other options for biopsy include core biopsy, where a section of the breast lump is removed, and an excisional biopsy, where the entire lump is removed.

In addition vacuum-assisted breast biopsy (VAB) may help diagnose breast cancer among patients with a mammographically detected breast in women according to a systematic review. In this study, summary estimates for vacuum assisted breast biopsy in diagnosis of breast cancer were as follows sensitivity was 98.1% with 95% CI=0.972-0.987 and specificity was 100% with 95% CI=0.997-0.999; however, underestimate rates of atypical ductal hyperplasia (ADH) and ductal carcinoma in situ (DCIS) were 20.9% with 95% CI=0.177-0.245 and 11.2% with 95% CI=0.098-0.128 respectively.

Breast cancer screening refers to testing otherwise-healthy women for breast cancer in an attempt to achieve an earlier diagnosis. The assumption is that early detection will improve outcomes. A number of screening tests have been employed including: clinical and self breast exams, mammography, genetic screening, ultrasound, and magnetic resonance imaging.

A clinical or self breast exam involves feeling the breast for lumps or other abnormalities. Research evidence does not support the effectiveness of either type of breast exam, because by the time a lump is large enough to be found it is likely to have been growing for several years and will soon be large enough to be found without an exam. Mammographic screening for breast cancer uses x-rays to examine the breast for any uncharacteristic masses or lumps. In women at high risk, such as those with a strong family history of cancer, mammography screening is recommended at an earlier age and additional testing may include genetic screening that tests for the BRCA genes and/or magnetic resonance imaging.

Breast cancer is sometimes treated first with surgery, and then with chemotherapy, radiation, or both. Treatments are given with increasing aggressiveness according to the prognosis and risk of recurrence. Stage 1 cancers (and DCIS) have an excellent prognosis and are generally treated with lumpectomy with or without chemotherapy or radiation. Although the aggressive HER2+ cancers should also be treated with the trastuzumab (Herceptin) regime. Stage 2 and 3 cancers with a progressively poorer prognosis and greater risk of recurrence are generally treated with surgery (lumpectomy or mastectomy with or without lymph node removal), radiation (sometimes) and chemotherapy (plus trastuzumab for HER2+ cancers). Stage 4, metastatic cancer, (i.e., spread to distant sites) is not curable and is managed by various combinations of all treatments from surgery, radiation, chemotherapy and targeted therapies. These treatments increase the median survival time of stage 4 breast cancer by about 6 months.

B. Combination Treatments

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. A tissue, tumor, or cell can be contacted with one or more compositions or pharmacological formulation(s) comprising one or more of the agents or by contacting the tissue, tumor, and/or cell with two or more distinct compositions or formulations. Also, it is contemplated that such a combination therapy can be used in conjunction with radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

An anti-cancer first treatment may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient. In such instances, it is contemplated that one may provide a patient with the first therapy and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a combination of a GRB2 inhibitor and a PARP inhibitor is "A" and another anti-cancer therapy (e.g., immunotherapy) is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

i. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DFMO); retinoids, such as retinoic acid; capecitabine; carboplatin, procarbazine, plicomycin, gemcitabien, navelbine, famesyl-protein tansferase inhibitors, transplatinum, and pharmaceutically acceptable salts, acids, or derivatives of any of the above.

ii. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

iii. Immunotherapy

The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, Infection Immun., 66(11):5329-5336, 1998; Christodoulides et al., Microbiology, 144(Pt 11):3027-3037, 1998); cytokine therapy, e.g., interferons, IL-1, GM-CSF, and TNF (Bukowski et al., Clinical Cancer Res., 4(10):2337-2347, 1998; Davidson et al., J. Immunother., 21(5):389-398, 1998; Hellstrand et al., Acta Oncologica, 37(4):347-353, 1998); gene therapy, e.g., TNF, IL-1, IL-2, and p53 (Qin et al., Proc. Natl. Acad. Sci. USA, 95(24):14411-14416, 1998; Austin-Ward and Villaseca, Revista Medica de Chile, 126(7):838-845, 1998; U.S. Pat. Nos. 5,830,880 and 5,846,945); and monoclonal antibodies, e.g., anti-CD20, anti-ganglioside GM2, and anti-p185 (Hanibuchi et al., Int. J. Cancer, 78(4):480-485, 1998; U.S. Pat. No. 5,824,311). It is contemplated that one or more anti-cancer therapies may be employed with the antibody therapies described herein.

In some embodiment, the immune therapy could be adoptive immunotherapy, which involves the transfer of autologous antigen-specific T cells generated ex vivo. The T cells used for adoptive immunotherapy can be generated either by expansion of antigen-specific T cells or redirection of T cells through genetic engineering. Isolation and transfer of tumor specific T cells has been shown to be successful in treating melanoma. Novel specificities in T cells have been successfully generated through the genetic transfer of transgenic T cell receptors or chimeric antigen receptors (CARs). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T cells to be redirected against antigens expressed at the surface of tumor cells from various malignancies including lymphomas and solid tumors.

In one embodiment, the present application provides for a combination therapy for the treatment of cancer wherein the combination therapy comprises adoptive T cell therapy and a checkpoint inhibitor. In one aspect, the adoptive T cell therapy comprises autologous and/or allogenic T-cells. In another aspect, the autologous and/or allogenic T-cells are targeted against tumor antigens.

Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), programmed death-ligand 1 (PD-L1), T-cell immunoglobulin domain and mucin domain 3 (TIM-3), and V-domain Ig suppressor of T cell activation (VISTA). In particular, the immune checkpoint inhibitors target the PD-1 axis and/or CTLA-4.

The immune checkpoint inhibitors may be drugs, such as small molecules, recombinant forms of ligand or receptors, or antibodies, such as human antibodies (e.g., International Patent Publication WO2015/016718; Pardoll, *Nat Rev Cancer,* 12(4): 252-264, 2012; both incorporated herein by reference). Known inhibitors of the immune checkpoint proteins or analogs thereof may be used, in particular chimerized, humanized, or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

In some embodiments, a PD-1 binding antagonist is a molecule that inhibits the binding of PD-1 to its ligand binding partners. In a specific aspect, the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, a PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or an oligopeptide. Exemplary antibodies are described in U.S. Pat. Nos. 8,735,553, 8,354,509, and 8,008,449, all of which are incorporated herein by reference. Other PD-1 axis antagonists for use in the methods provided herein are known in the art, such as described in U.S. Patent Application Publication Nos. 2014/0294898, 2014/022021, and 2011/0008369, all of which are incorporated herein by reference.

In some embodiments, a PD-1 binding antagonist is an anti-PD-1 antibody (e.g., a human antibody, a humanized antibody, or a chimeric antibody). In some embodiments, the anti-PD-1 antibody is selected from the group consisting of Nivolumab (also known as MDX-1106-04, MDX-1106, MK-347, ONO-4538, BMS-936558, and OPDIVO®; described in WO2006/121168), Pembrolizumab (also known as MK-3475, Merck 3475, lambrolizumab, KEYTRUDA®, and SCH-900475; WO2009/114335), Pidilizumab (also known as CT-011, hBAT or hBAT-1; WO2009/101611), Cemiplimab (also known as LIBTAYO®, REGN-2810, REGN2810, SAR-439684, SAR439684), Tislelizumab (also known as BGB-A317, hu317-1/IgG4mt2; U.S. Pat. No. 8,735,553), Spartalizumab (also known as PDR001, PDR-001, NPV-PDR001, NPVPDR001; U.S. Pat. No. 9,683,048), PF-06801591, AK105, BCD-100, BI-754091, HLX10, JS001, LZM009, MEDI 0680, MGA012, Sym021, TSR-042, MGD013, AK104 (bispecific with anti-CTLA4), and XmAb20717 (bispecific with anti-CTLA4).

In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence)). For example, AMP-224 (also known as B7-DCIg) is a PD-L2-Fc fusion soluble receptor described in WO2010/027827 and WO2011/066342.

In some embodiment, a PD-L1 binding antagonist is an anti-PD-L1 antibody (e.g., a human antibody, a humanized antibody, or a chimeric antibody). In some embodiments, the anti-PD-L1 antibody is selected from the group consisting of Atezolizumab (also known as Tencentriq, MPDL3280A; described in U.S. Pat. No. 8,217,149), Avelumab (also known as BAVENCIO®, MSB-0010718C, MSB0010718C), Durvalumab (also known as IMFINZI®, MEDI-4736, MEDI4736; described in WO2011/066389), FS118, BCD-135, BGB-A333, CBT502 (also known as TQB2450), CK-301, CS1001 (also known as WBP3155), FAZ053, KN035, MDX-1105, MSB2311, SHR-1316, M7824, LY3415244, CA-170, and CX-072.

Another immune checkpoint protein that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA-4 is similar to the T-cell co-stimulatory protein, CD28, and both molecules bind to CD80 and CD86, also called B7-1 and B7-2 respectively, on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide. Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in U.S. Pat. No. 8,119,129; PCT Publn. Nos. WO 01/14424, WO 98/42752, WO 00/37504 (CP675,206, also known as tremelimumab; formerly ticilimumab); U.S. Pat. No. 6,207,156; Hurwitz et al. (1998) *Proc Natl Acad Sci USA,* 95(17): 10067-10071; Camacho et al. (2004) *J Clin Oncology,* 22(145): Abstract No. 2505 (antibody CP-675206); and Mokyr et al. (1998) *Cancer Res,* 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

An exemplary anti-CTLA-4 antibody is ipilimumab (also known as 10D1, MDX-010, MDX-101, MDX-CTLA4, and YERVOY®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2, and CDR3 domains of the VL region of ipilimumab. In another embodiment, the antibody competes for binding with and/or binds to the same epitope on CTLA-4 as the above-mentioned antibodies. In another embodiment, the antibody has an at least about 90% variable region amino acid sequence identity with the above-mentioned antibodies (e.g., at least about 90%, 95%, or 99% variable region identity with ipilimumab).

In some embodiment, a CTLA-4 binding antagonist is an anti-CTLA-4 antibody (e.g., a human antibody, a humanized antibody, or a chimeric antibody). In some embodiments, the anti-CTLA-4 antibody is selected from the group consisting of ipilimumab (also known as 10D1, MDX-010, MDX-101, MDX-CTLA4, and YERVOY®; described in WO 01/14424), Tremelimumab (also known as CP-675,206, CP-675, ticilimumab; described in WO 00/37504), BMS-986218, AK104 (bispecific with anti-PD-1), and XmAb20717 (bispecific with anti-PD-1).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

Another immune checkpoint protein that can be targeted in the methods provided herein is lymphocyte-activation gene 3 (LAG-3), also known as CD223. The complete protein sequence of human LAG-3 has the Genbank accession number NP-002277. LAG-3 is found on the surface of activated T cells, natural killer cells, B cells, and plasmacytoid dendritic cells. LAG-3 acts as an "off" switch when bound to MHC class II on the surface of antigen-presenting cells. Inhibition of LAG-3 both activates effector T cells and inhibitor regulatory T cells. In some embodiments, the immune checkpoint inhibitor is an anti-LAG-3 antibody (e.g., a human antibody, a humanized antibody, or a chimeric antibody), an antigen binding fragment thereof, an immunoadhesin, a fusion protein, or oligopeptide. Anti-human-LAG-3 antibodies (or VH and/or VL domains derived therefrom) suitable for use in the present methods can be generated using methods well known in the art. Alternatively, art recognized anti-LAG-3 antibodies can be used. An exemplary anti-LAG-3 antibody is relatlimab (also known as BMS-986016) or antigen binding fragments and variants thereof (see, e.g., WO 2015/116539). Other exemplary anti-LAG-3 antibodies include TSR-033 (see, e.g., WO 2018/201096), MK-4280, and REGN3767. MGD013 is an anti-LAG-3/PD-1 bispecific antibody described in WO 2017/019846. FS118 is an anti-LAG-3/PD-L1 bispecific antibody described in WO 2017/220569.

Another immune checkpoint protein that can be targeted in the methods provided herein is V-domain Ig suppressor of T cell activation (VISTA), also known as C10orf54. The complete protein sequence of human VISTA has the Genbank accession number NP_071436. VISTA is found on white blood cells and inhibits T cell effector function. In some embodiments, the immune checkpoint inhibitor is an anti-VISTA3 antibody (e.g., a human antibody, a humanized antibody, or a chimeric antibody), an antigen binding fragment thereof, an immunoadhesin, a fusion protein, or oligopeptide. Anti-human-VISTA antibodies (or VH and/or VL domains derived therefrom) suitable for use in the present methods can be generated using methods well known in the art. Alternatively, art recognized anti-VISTA antibodies can be used. An exemplary anti-VISTA antibody is JNJ-61610588 (also known as onvatilimab) (see, e.g., WO 2015/097536, WO 2016/207717, WO 2017/137830, WO 2017/175058). VISTA can also be inhibited with the small molecule CA-170, which selectively targets both PD-L1 and VISTA (see, e.g., WO 2015/033299, WO 2015/033301).

Another immune checkpoint protein that can be targeted in the methods provided herein is CD38. The complete protein sequence of human CD38 has Genbank accession number NP_001766. In some embodiments, the immune checkpoint inhibitor is an anti-CD38 antibody (e.g., a human antibody, a humanized antibody, or a chimeric antibody), an antigen binding fragment thereof, an immunoadhesin, a fusion protein, or oligopeptide. Anti-human-CD38 antibodies (or VH and/or VL domains derived therefrom) suitable for use in the present methods can be generated using methods well known in the art. Alternatively, art recognized anti-CD38 antibodies can be used. An exemplary anti-CD38 antibody is daratumumab (see, e.g., U.S. Pat. No. 7,829,673).

Another immune checkpoint protein that can be targeted in the methods provided herein is T cell immunoreceptor with Ig and ITIM domains (TIGIT). The complete protein sequence of human TIGIT has Genbank accession number NP_776160. In some embodiments, the immune checkpoint inhibitor is an anti-TIGIT antibody (e.g., a human antibody, a humanized antibody, or a chimeric antibody), an antigen binding fragment thereof, an immunoadhesin, a fusion protein, or oligopeptide. Anti-human-TIGIT antibodies (or VH and/or VL domains derived therefrom) suitable for use in the present methods can be generated using methods well known in the art. Alternatively, art recognized anti-TIGIT antibodies can be used. An exemplary anti-TIGIT antibody is MK-7684 (see, e.g., WO 2017/030823, WO 2016/028656).

Co-stimulatory molecules are ligands that interact with receptors on the surface of the immune cells, e.g., CD28, 4-1BB, OX40 (also known as CD134), ICOS, and GITR. As an example, the complete protein sequence of human OX40 has Genbank accession number NP_003318. In some embodiments, the immunomodulatory agent is an anti-OX40 antibody (e.g., a human antibody, a humanized antibody, or a chimeric antibody), an antigen binding fragment thereof, an immunoadhesin, a fusion protein, or oligopeptide. Anti-human-OX40 antibodies (or VH and/or VL domains derived therefrom) suitable for use in the present methods can be generated using methods well known in the art. Alternatively, art recognized anti-OX40 antibodies can be used. An exemplary anti-OX40 antibody is PF-04518600 (see, e.g., WO 2017/130076). ATOR-1015 is a bispecific antibody targeting CTLA4 and OX40 (see, e.g., WO 2017/182672, WO 2018/091740, WO 2018/202649, WO 2018/002339).

Another co-stimulatory molecule that can be targeted in the methods provided herein is ICOS, also known as CD278. The complete protein sequence of human ICOS has Genbank accession number NP_036224. In some embodiments, the immune checkpoint inhibitor is an anti-ICOS antibody (e.g., a human antibody, a humanized antibody, or a chimeric antibody), an antigen binding fragment thereof, an immunoadhesin, a fusion protein, or oligopeptide. Anti-human- ICOS antibodies (or VH and/or VL domains derived therefrom) suitable for use in the present methods can be generated using methods well known in the art. Alternatively, art recognized anti-ICOS antibodies can be used. Exemplary anti-ICOS antibodies include JTX-2011 (see, e.g., WO 2016/154177, WO 2018/187191) and GSK3359609 (see, e.g., WO 2016/059602).

Yet another co-stimulatory molecule that can be targeted in the methods provided herein is glucocorticoid-induced tumour necrosis factor receptor-related protein (GITR), also known as TNFRSF18 and AITR. The complete protein sequence of human GITR has Genbank accession number NP_004186. In some embodiments, the immunomodulatory agent is an anti-GITR antibody (e.g., a human antibody, a humanized antibody, or a chimeric antibody), an antigen binding fragment thereof, an immunoadhesin, a fusion protein, or oligopeptide. Anti-human-GITR antibodies (or VH and/or VL domains derived therefrom) suitable for use in the present methods can be generated using methods well known in the art. Alternatively, art recognized anti-GITR antibodies can be used. An exemplary anti-GITR antibody is TRX518 (see, e.g., WO 2006/105021).

Other immune inhibitory molecules that can be targeted for immunomodulation include STAT3 and indoleamine 2,3-dioxygenase (IDO). By way of example, the complete protein sequence of human IDO has Genbank accession number NP_002155. In some embodiments, the immunomodulatory agent is a small molecule IDO inhibitor. Exemplary small molecules include BMS-986205, epacadostat (INCB24360), and navoximod (GDC-0919).

iv. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

v. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

C. Detection

In some aspects, the present disclosure concerns immunodetection methods for detecting expression of GRB2 and/or MRE11. In some aspects, the present disclosure concerns detection of 'Signature 3' mutations, which correspond to a defect in the homologous recombination (HR) machinery. This signature is observed in tumors with complete inactivation of BRCA1/2. This inactivation can occur by germline and somatic point mutations, loss of heterozygosity (LOH) due to structural variations, hyper-methylation of BRCA1 promoters, or loss-of-function mutations of PALB2 and RAD51D. See WO2020/068506, which is incorporated by reference herein in its entirety.

A wide variety of assay formats are contemplated for detecting protein products, including immunohistochemistry, enzyme linked immunosorbent assay (ELISA), radioimmunoassay (RIA), immunoradiometric assay, fluoroimmunoassay, chemiluminescent assay, bioluminescent assay, dot blotting, FACS analyses, and Western blot to mention a few. The steps of various useful immunodetection methods have been described in the scientific literature. In general, the immunobinding methods include obtaining a sample of the cancer, and contacting the sample with an antibody specific for the protein to be detected, as the case may be, under conditions effective to allow the formation of immunocomplexes. In general, the detection of immunocomplex formation is well known in the art and may be achieved through the application of numerous approaches. These methods are generally based upon the detection of a label or marker, such as any of those radioactive, fluorescent, biological and enzymatic tags. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

With regard to detecting expression of mRNA products, or a corresponding cDNA, mRNA is first extracted from the cancer cells. The extracted mRNA may be amplified prior to detection. Alternatively, the extracted mRNA may be reverse transcribed to cDNA prior to amplification of the cDNA. Any nucleic acid amplification assay which can be utilized, including but not limited to the polymerase chain reaction (RT-PCR), branched DNA signal amplification, ligase chain reaction, isothermal nucleic acid sequence based amplification (NASBA), Q-beta replication, transcription-based amplification, amplifiable RNA reporters, boomerang DNA amplification, strand displacement activation, cycling probe technology, and other self-sustained sequence replication assays, as well as variations on these including methods for nucleic acid enrichment such as by using restriction digestion with polymerase chain reaction and the use of nested primers. Similarly, any method capable of detecting an amplified nucleic acid product, including but not limited to agarose gel electrophoresis, fluorescence-based detection methods, real-time PCR, ELISA detection methods, electrochemiluminescence, high performance liquid chromatography, reverse dot blot methods, and nucleic acid sequencing methods, may be used.

As used herein, the term "sample" refers to any sample suitable for the detection methods provided by the present invention. The sample may be any sample that includes material suitable for detection or isolation. Sources of samples include blood, pleural fluid, peritoneal fluid, urine, saliva, malignant ascites, broncho-alveolar lavage fluid, synovial fluid, and bronchial washes. In one aspect, the sample is a blood sample, including, for example, whole blood or any fraction or component thereof. A blood sample suitable for use with the present invention may be extracted from any source known that includes blood cells or components thereof, such as venous, arterial, peripheral, tissue, cord, and the like. For example, a sample may be obtained and processed using well-known and routine clinical methods (e.g., procedures for drawing and processing whole blood). In one aspect, an exemplary sample may be peripheral blood drawn from a subject with cancer. In some aspects, the biological sample comprises a plurality of cells. In certain aspects, the biological sample comprises fresh or frozen tissue. In specific aspects, the biological sample comprises formalin fixed, paraffin embedded tissue. In some aspects, the biological sample is a tissue biopsy, fine needle aspirate, blood, serum, plasma, cerebral spinal fluid, urine, stool, saliva, circulating tumor cells, exosomes, or aspirates and bodily secretions, such as sweat. In some aspects, the biological sample contains cell-free DNA.

V. Pharmaceutical Formulations

In another aspect, for administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound disclosed herein formulated with one or more excipients and/or drug carriers appropriate to the indicated route of administration. In some embodiments, the compounds disclosed herein are formulated in a manner amenable for the treatment of human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain drug carriers and/or excipients such as preservatives, stabilizers, wetting agents, emulsifiers, encapsulating agents such as lipids, dendrimers, polymers, proteins such as albumin, nucleic acids, and buffers.

Pharmaceutical formulations may be administered by a variety of methods, e.g., orally or by injection (e.g. subcutaneous, intravenous, and intraperitoneal). Depending on the route of administration, the compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. In some embodiments, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds disclosed herein can be administered orally, for example, with an inert diluent or an assimilable edible carrier. The compounds and other ingredients may also be enclosed in a hard or soft-shell gelatin capsule, compressed into tablets, or incorporated directly into the patient's diet. For oral therapeutic administration, the compounds disclosed herein may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical carrier. In some embodiments, the specification for the dosage unit forms of the disclosure are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In some embodiments, the human equivalent dose (HED) in mg/kg can be calculated in accordance with the following formula (see, e.g., Reagan-Shaw et al., *FASEB J.,* 22(3):659-661, 2008, which is incorporated herein by reference):

$$\text{HED (mg/kg)}=\text{Animal dose (mg/kg)}\times(\text{Animal } K_m/\text{Human } K_m)$$

Use of the $K_m$ factors in conversion results in HED values based on body surface area (BSA) rather than only on body mass. $K_m$ values for humans and various animals are well known. For example, the $K_m$ for an average 60 kg human (with a BSA of 1.6 $m^2$) is 37, whereas a 20 kg child (BSA 0.8 $m^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are specific to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the disclosure provides that the agent(s) may be taken orally and that the timing of which is or is not dependent upon food intake. Thus, for example, the agent can be taken every morning and/or every evening, regardless of when the patient has eaten or will eat.

The following abbreviations are used in the present disclosure: GRB2, growth factor receptor-bound protein 2; mGRB2, monomeric growth factor receptor-bound protein 2; dGRB, dimeric growth factor receptor-bound protein 2; SOS, son of sevenless; RTK, Receptor tyrosine kinases;

MAP, mitogen-activated protein; SH2, Src homology 2; SH3, SRC homology 3; EGFR, epidermal growth factor receptor; TNBC, triple-negative breast cancer; NMR, nuclear magnetic resonance; LRMS, low-resolution mass spectrometry; GEF, guanine exchange factor; and ESC, early signaling complex.

VI. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Results and Discussion

Figure 1C:
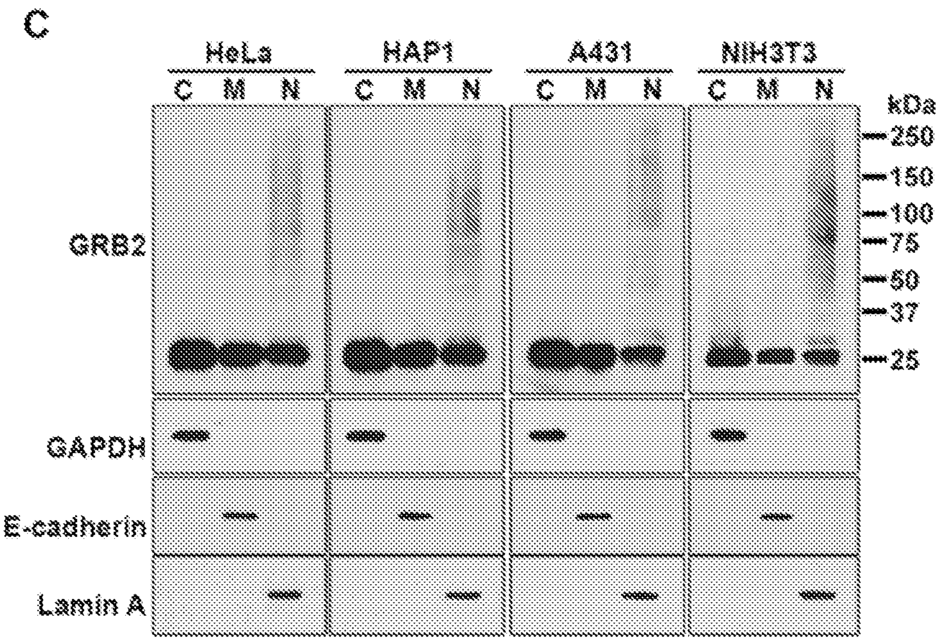
Figures 10A, 10B:
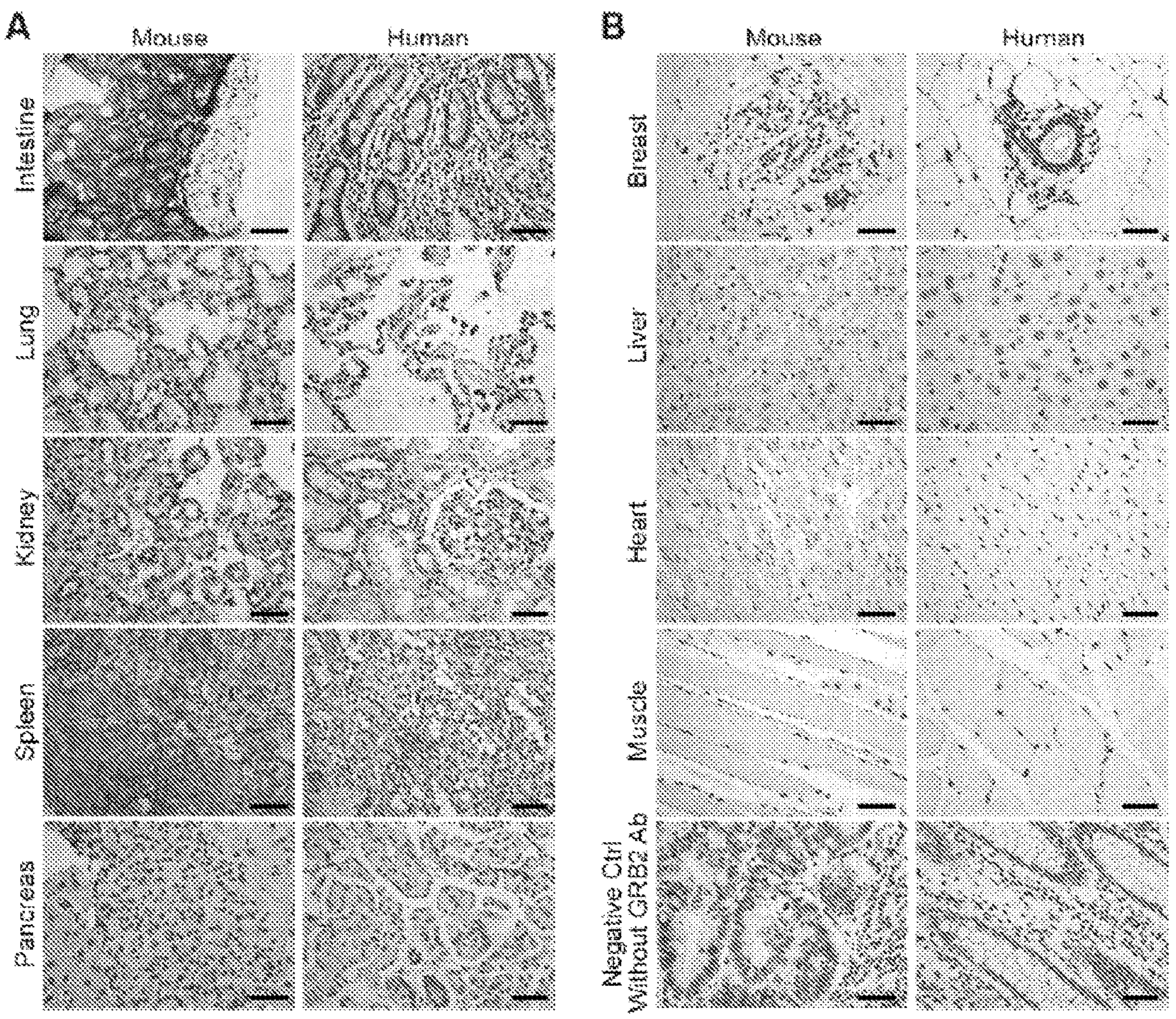
FIGS. 10A-10C. Immunohistochemical and immunofluorescence analyses of GRB2 expression.
Figure 10C:
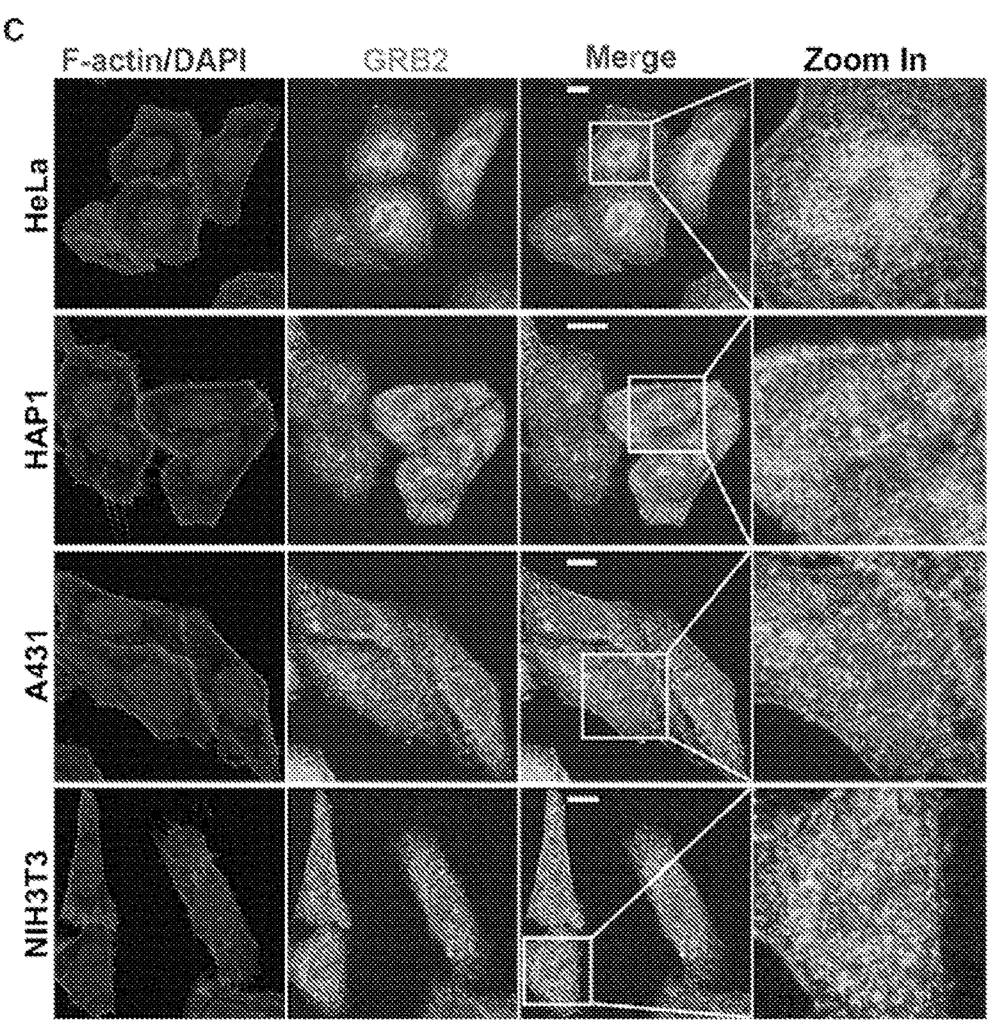

DNA double-strand break (DSB) repair is initiated by MRE11 nuclease for both homology-directed repair (HDR) and alternative end joining (Alt-EJ). GRB2, crucial to timely proliferative RAS/MAPK pathway activation, unexpectedly forms a biophysically validated GRB2-MRE11 (GM) complex for efficient HDR initiation. Importantly, GRB2-SH2 domain targets the GM complex to phosphorylated H2AX at DSBs. GRB2 K109 ubiquitination by E3 ubiquitin ligase RBBP6 releases MRE11 promoting HDR. RBBP6 depletion results in prolonged GM complex and HDR defects. GRB2 knockout increased MRE11-XRCC1 complex and Alt-EJ. Reconstitution with separation-of-function GRB2 mutant caused HDR-deficiency and synthetic lethality with PARP inhibitor. Cell and cancer genome analyses suggest biomarkers of low GRB2 for non-canonical HDR-deficiency, and high MRE11 and GRB2 expression for worse survival in HDR-proficient patients. These findings establish GRB2's role in binding, targeting, and releasing MRE11 to promote efficient HDR over Alt-EJ DSB repair with implications for genome stability and cancer biology.

nGRB2 is poly-ubiquitinated at K109. To robustly test potential for significant GRB2 nuclear function, the inventors used systematic immunohistochemistry (IHC) analysis on representative mouse and human tissues to determine its localization. The inventors found differential GRB2 nuclear localization with broad tissue type specificity. This observation supports and extends reports of GRB2 in the nucleus in some cells (Verbeek et al., 1997; Yamazaki et al., 2002). Although ubiquitous in the cytoplasm, the nuclear localization of GRB2 interestingly showed apparent tissue type specificity: nGRB2 was highly detected in brain, colon, stomach and intestine, while rarely observed in breast, liver, heart and muscle (FIGS. 1A, 1B, 10A, 10B). Importantly, immunofluorescence (IF) and cell fractionation analyses in representative cancer cell lines also indicated GRB2 presence in nuclei (FIGS. 1C & 10C). Intriguingly, nGRB2 showed an apparent higher-molecular-weight pattern stereotypical of ubiquitination.

Figures 1D, 1E:
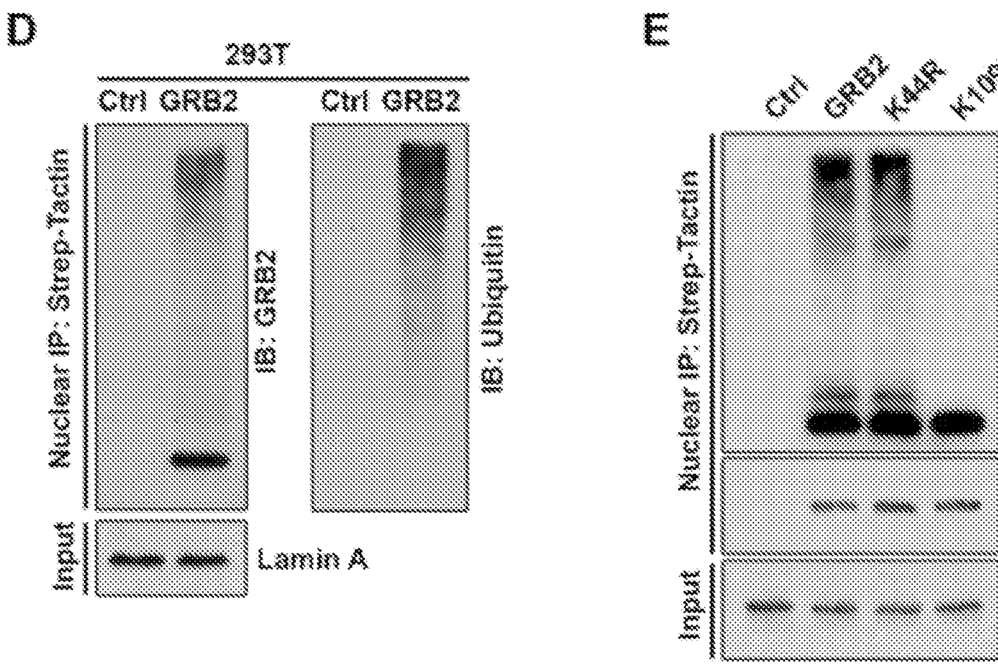

Therefore, the inventors employed Strep-tagged nGRB2 affinity purification and western blotting and found a strong correlation in nGRB2 migration patterns with proteins detected by anti-ubiquitin antibody, supporting nGRB2 ubiquitination (FIG. 1D). PhosphoSite database analysis revealed 61 independent mass spectrometry (MS) studies reporting potential GRB2 ubiquitination on lysine 109 (K109) and five reporting ubiquitination on lysine 44 (K44). The inventors created lysine-to-arginine K44R and K109R GRB2 mutants and tested ubiquitination potentials. Only the K109R mutation eliminated nGRB2 high-molecular-weight protein bands (FIG. 1E), supporting K109 as the major ubiquitin conjugation site.

Figures 1F, 1G:
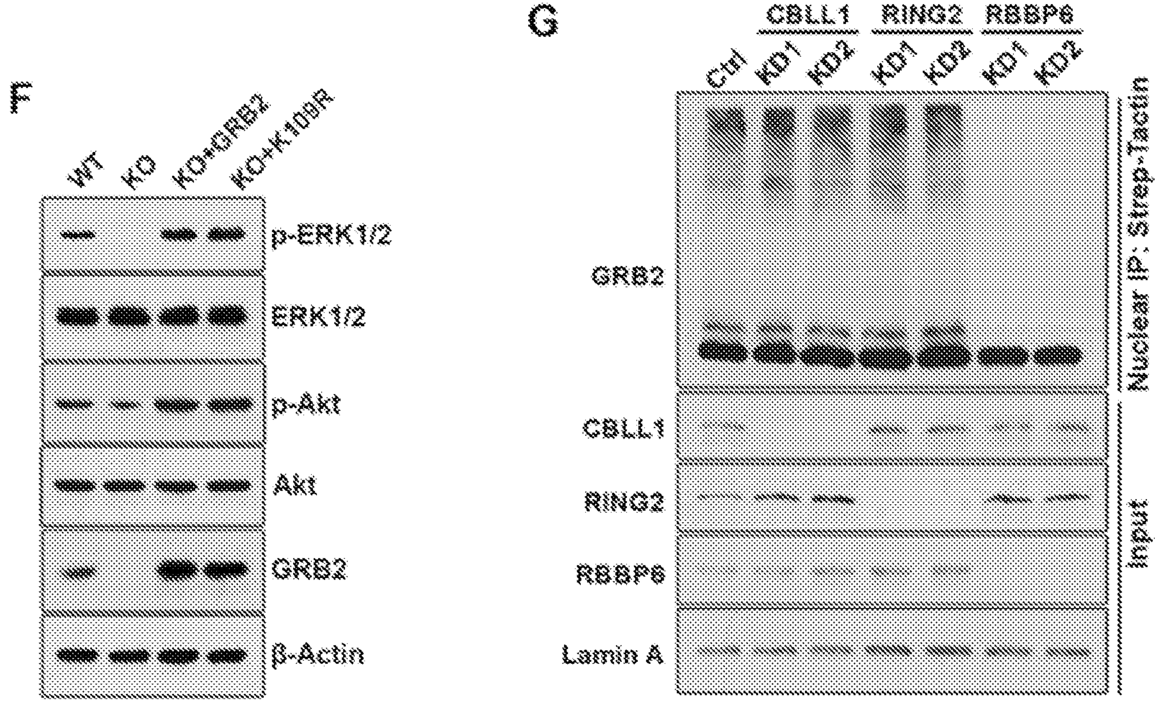
Figure 11A:
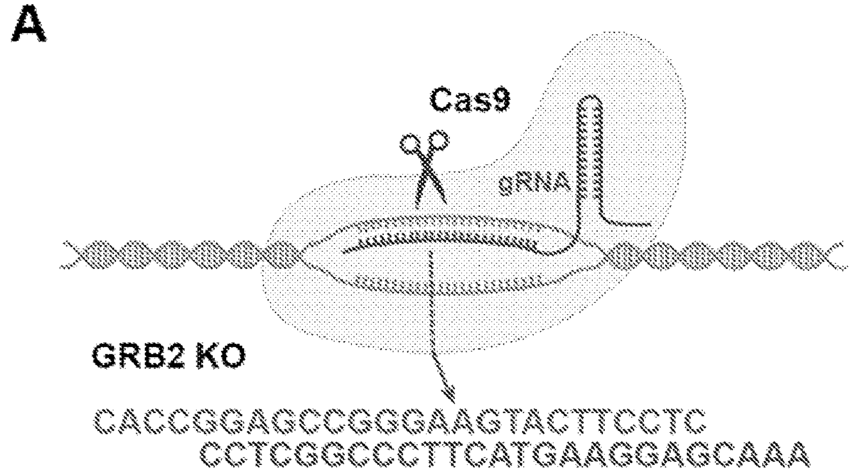
Figures 11F, 11G:
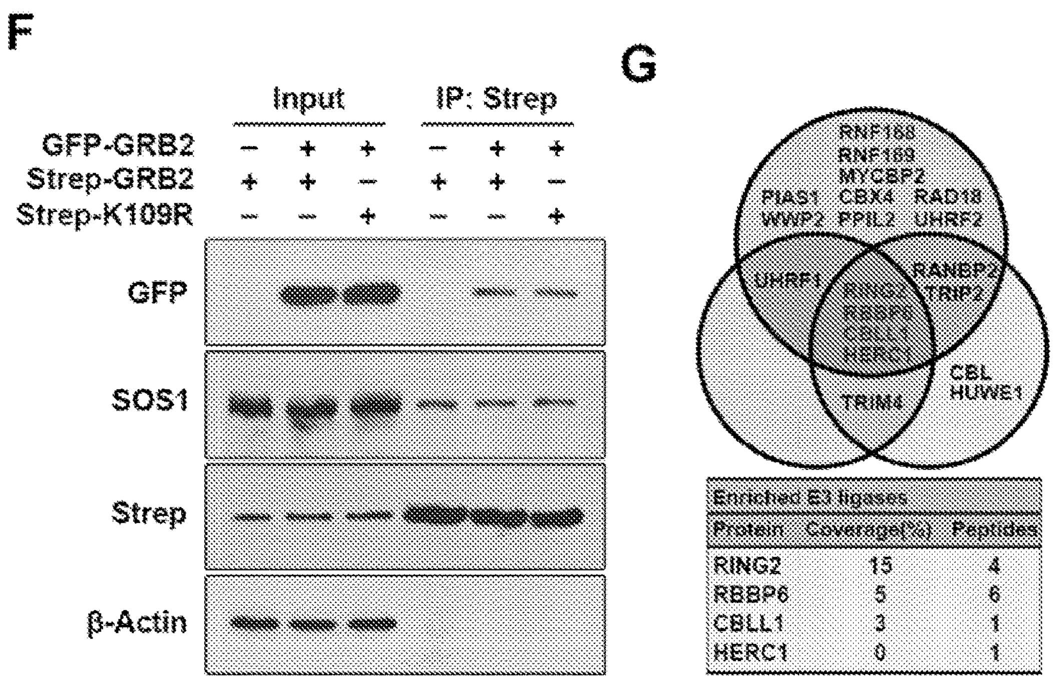

To test the function of K109R, the inventors generated CRISPR/Cas9 GRB2-knockout (KO) cells (FIGS. 11A & 11B) reconstituted with either $^{WT}$GRB2 or $^{K109R}$GRB2 and measured RAS/MAPK or PI3K activity under normal growth condition and following RTK activation (FIGS. 1F,11C,11D). The $^{K109R}$GRB2 showed ubiquitination loss, but no measurable difference in GRB2 dimerization in cells, SOS binding or cellular localization (FIGS. 11F & 11E). Thus, $^{K109R}$GRB2 had no quantifiable effect on cytoplasmic signaling and is empirically a separation-of-function mutant for nuclear activity.

Figures 1H, 1I, 1J:
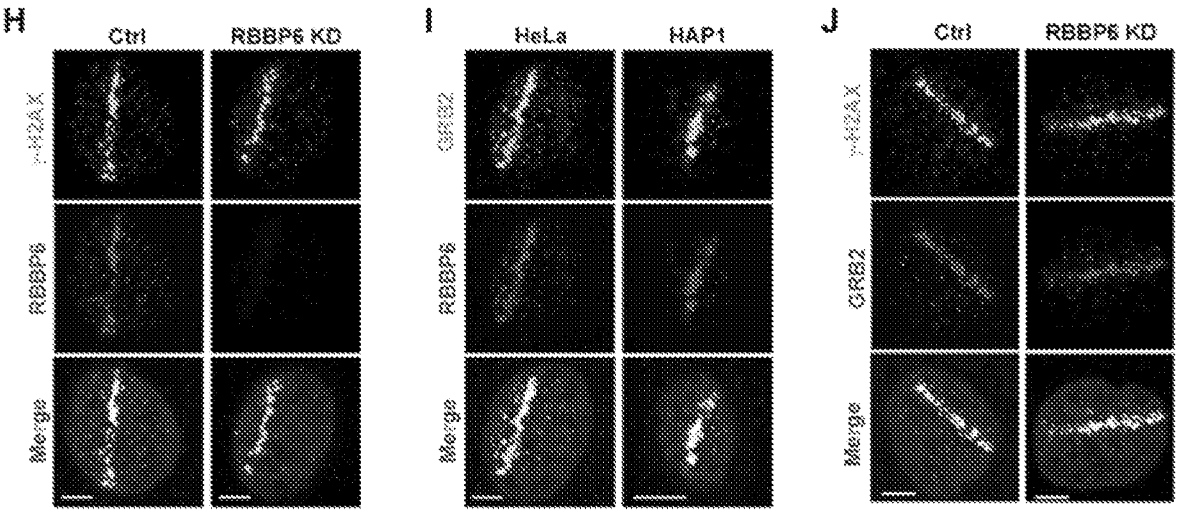
Figures 11H, 11I:
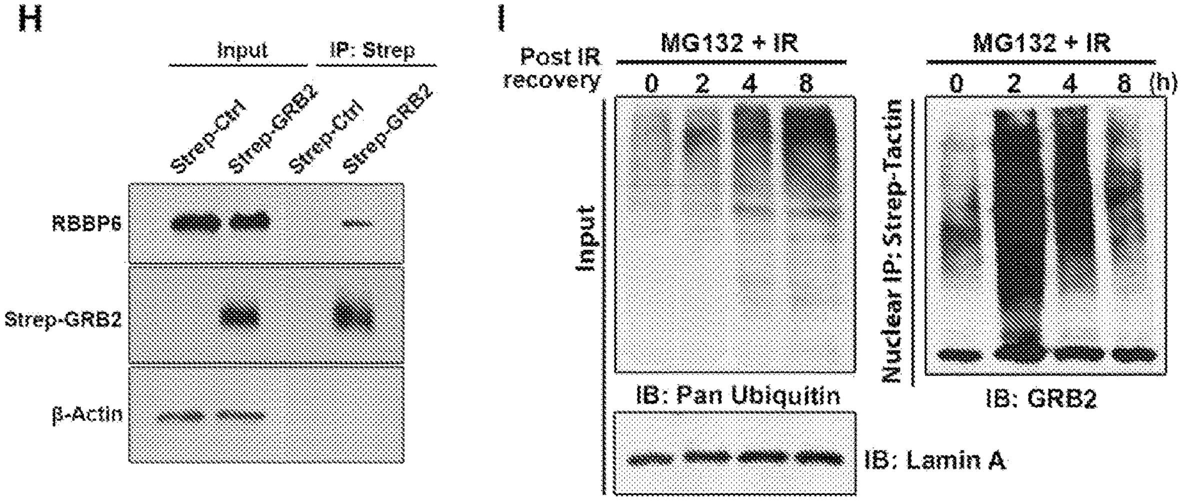
Figure 12A:
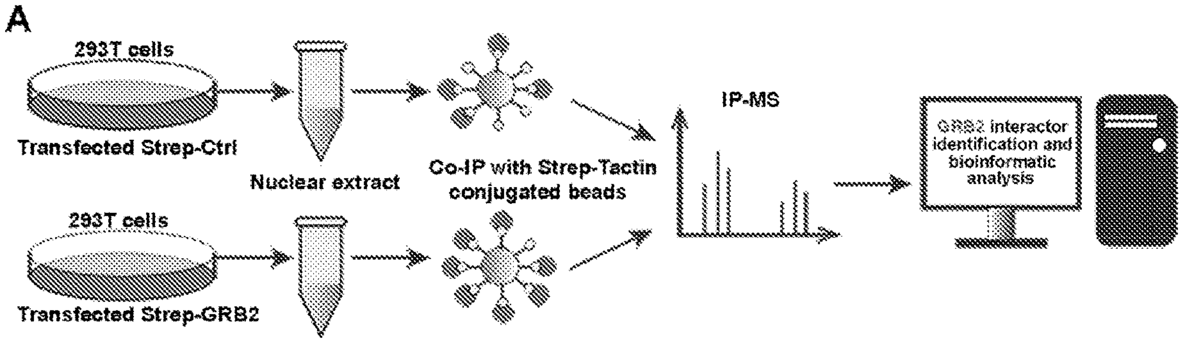
FIGS. 12A-12D. Identification of nuclear GRB2 interaction network.
Figure 12B:
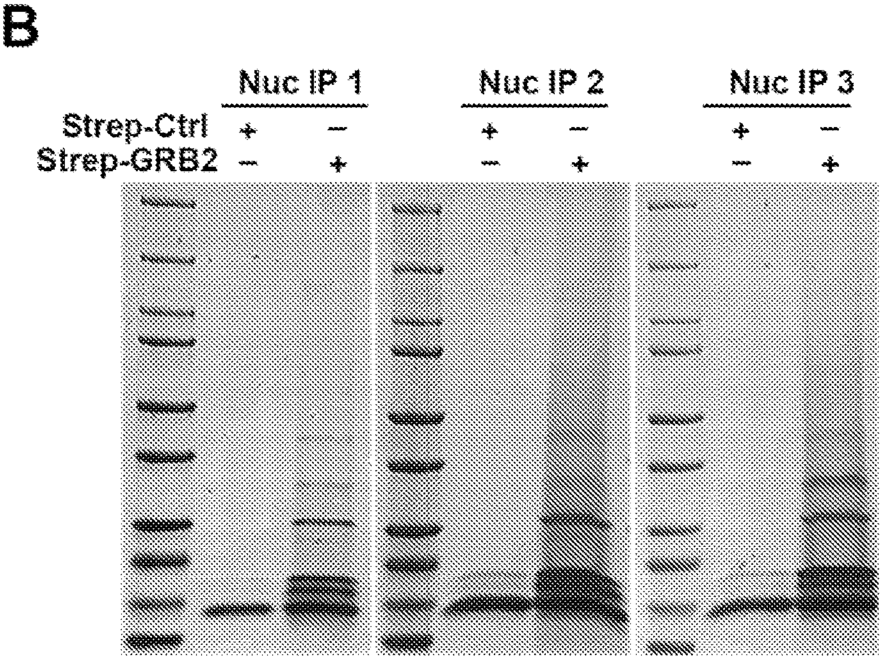
Figure 12C:
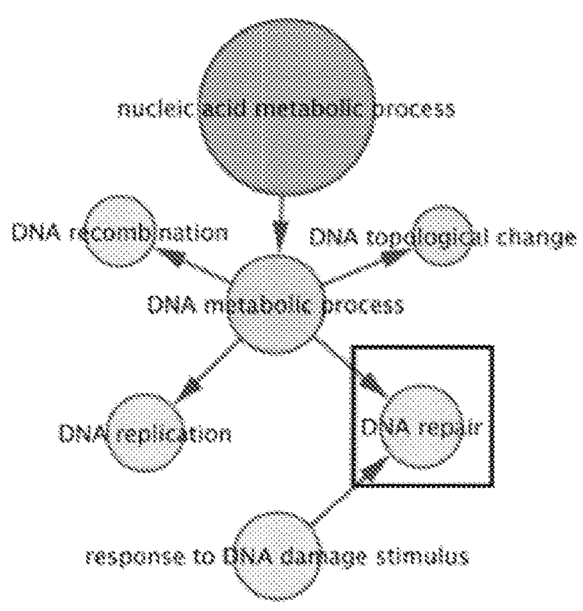

RBBP6 ubiquitinates nGRB2 at DNA damage sites. Strep-tagged nGRB2 affinity purification followed by MS identified multiple coprecipitating E3 ubiquitin ligases, RING2, RBBP6 and CBLL1 being precipitated with nGRB2 in three independent MS experiments (FIGS. 11G, 12A & 12B). Knockdown of each E3 ligase with two different shRNAs, followed by nuclear extraction, affinity precipitation and western blotting, identified RBBP6 as the E3 ubiquitin ligase responsible for nGRB2 ubiquitination (FIG. 1G). Co-immunoprecipitation further verified the interaction between GRB2 and RBBP6 (FIG. 11H). Notably, RBBP6 acts in maintenance of genome stability and retention of common fragile sites (Miotto et al., 2014), which are DNA damage hotspots (Donovan et al., 1994). UV laser microirradiation (UV-LMI) coupled immunofluorescence analysis showed an obvious enrichment of endogenous RBBP6 at the DNA damage site marked by γH2AX (FIG. 1H), an early DNA damage indicator (Celeste et al., 2002; Rogakou et al., 1998). Moreover, nGRB2 also accumulated and co-localized with RBBP6 at the DNA break site where ubiquitination most likely occurs (FIG. 1I).

Figure 1K:
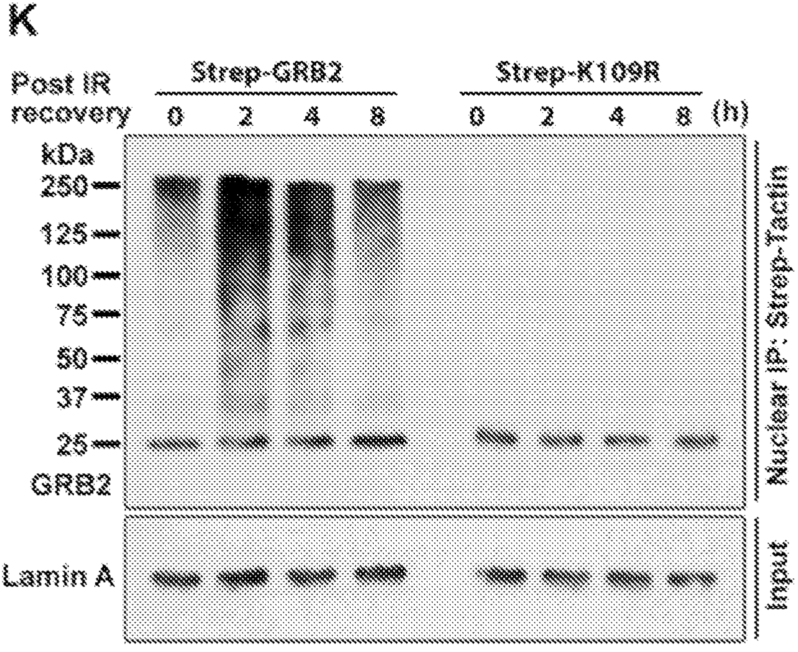

The inventors examined recruitment kinetics using RBBP6 knockdown and UV-LMI. The results showed that RBBP6 does not facilitate GRB2 recruitment to the DNA damage site (FIG. 1J). Instead, Strep-tagged affinity purification and immunoblotting revealed ionizing radiation (IR)-induced transient ubiquitination of $^{WT}$GRB2 that peaked at 2 h but no ubiquitination of $^{K109R}$GRB2 at all the tested time periods (FIG. 1K). Investigation with the proteasomal inhibitor MG132 indicated that the IR-induced ubiquitinated GRB2 (ubGRB2) was not degraded by the proteasome (FIG. 11I). As PSMD14 de-ubiquitinates GRB2 (Butler et al., 2012; Lv et al., 2019), it is most likely responsible for GRB2 deubiquitination. Notably, the detection of ubGRB2 without DNA damage required long exposure times, which can be correlated to the relative intensities of the non-ubiquitinated 25-kDa GRB2.

Figures 2A, 2B:
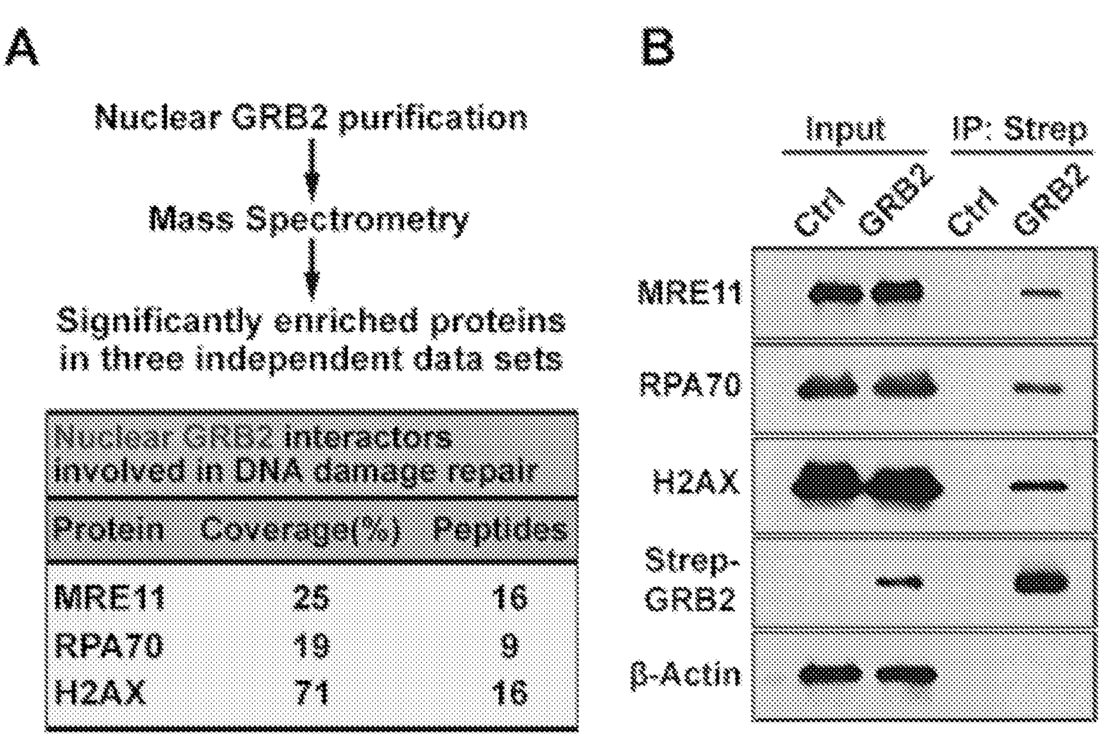
FIGS. 2A-2H. Interactions of nGRB2 with DNA damage response factors.
Figure 2C:
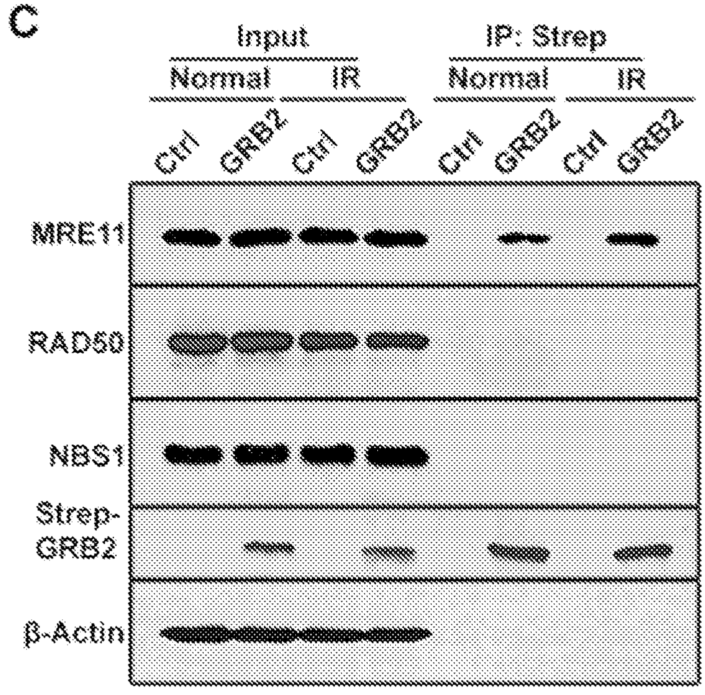
Figures 2D, 2E:
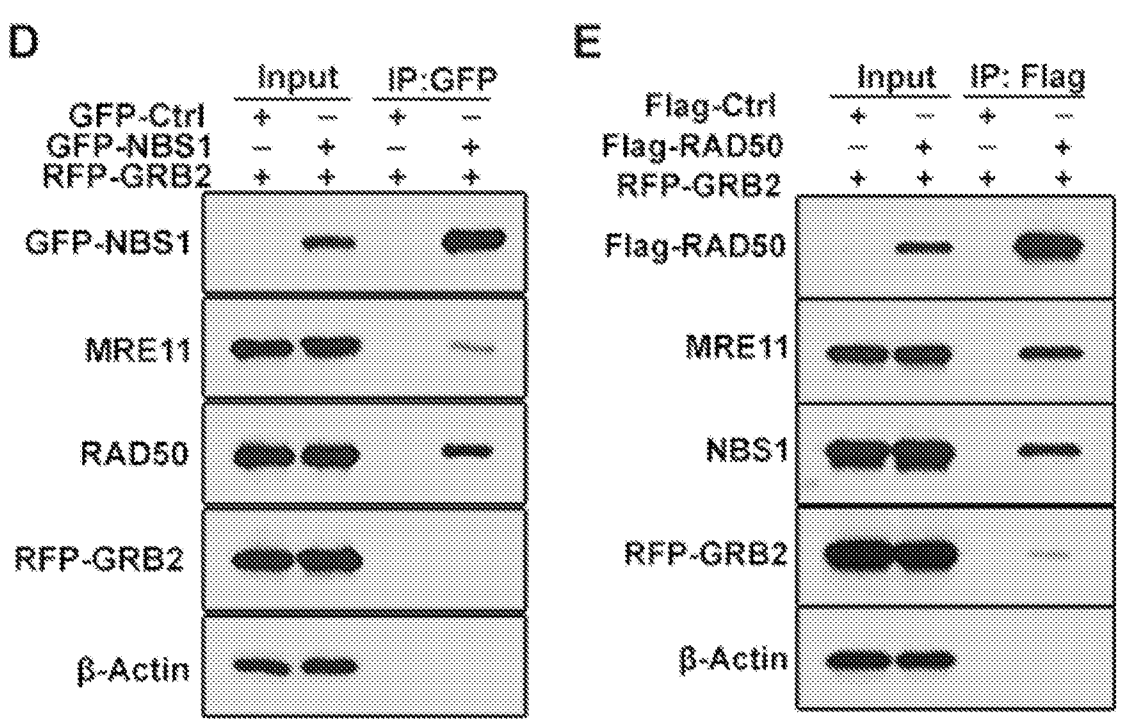
Figure 2F:
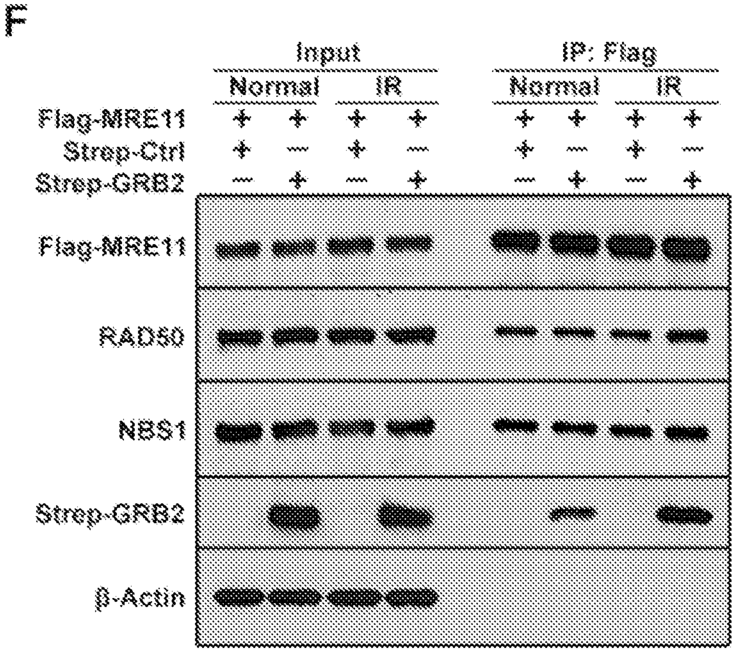

These collective results show that GRB2 localizes to the cell nucleus, and nGRB2 is primarily ubiquitinated at K109. Under normal cell-growth conditions, there is a steady-state basal level of nGRB2 ubiquitination, possibly as a result of endogenous DNA damage. However, exogenous DNA damage stimulates a transient increase in ubGRB2 that is deubiquitinated. RBBP6 E3-ubiquitin ligase, which co-localizes with GRB2 at DNA damage sites, ubiquitinates nGRB2.

nGRB2 forms a GRB2-MRE11 (GM) complex. To examine nGRB2 function, the inventors analyzed its nuclear interactome by MS. The inventors identified binding partners acting in the DNA damage response (DDR) (FIGS. 2A and 12A-12C). Co-immunoprecipitation confirmed top DDR-related proteins MRE11, RPA70 (also called RPA1), and γH2AX as nGRB2 interactors, supporting the MS data (FIG. 2B). Interestingly, the immunoprecipitation couples with MS did not identify RAD50 or NBS1 as co-precipitants. Consistently, GRB2 precipitation and western blotting also identified MRE11, but not RAD50 or NBS1 (FIG. 2C). The inventors investigated this further by NBS1 and RAD50 precipitation followed by western analysis and found the MRN complex but little or no GRB2 (FIGS. 2D & 2E). The inventors also performed MRE11 precipitation and found RAD50 and NBS1 in addition to GRB2 (FIG. 2F). Provocatively, these data imply that GRB2 associated MRE11 is not bound to NBS1 and RAD50. In other words, nGRB2-bound MRE11 may be a separate pool of MRE11 from that in MRN complex. Indeed, in several cultured cell lines, RAD50 knockdown only induced a proportional loss of NBS1 but not MRE11 (Chang et al., 2019; Millet et al., 2015; Zhong et al., 2007) suggesting MRE11 can exist separately from MRN.

Figure 2G:
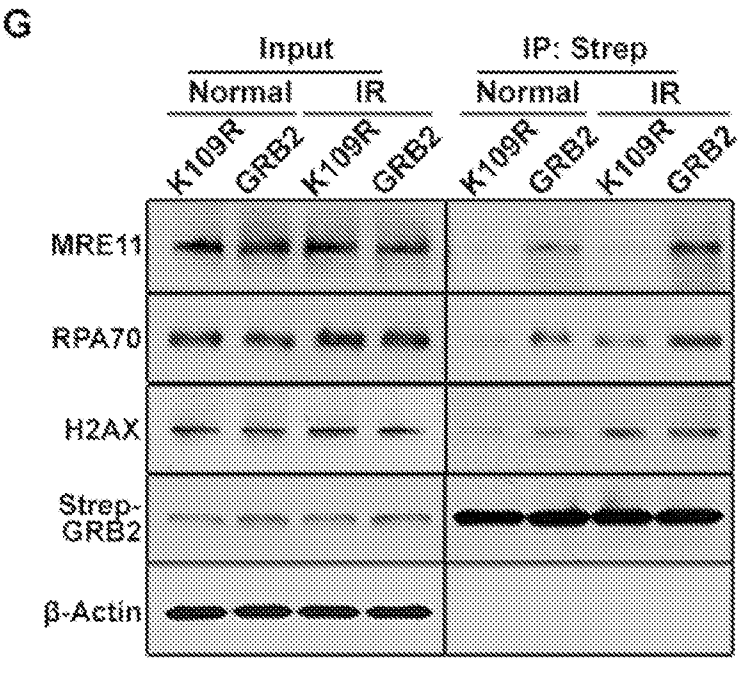

Since $^{WT}$GRB2 can be ubiquitinated while $^{K109R}$GRB2 cannot, the inventors investigated the role of GRB2 ubiquitination in MRE11 binding and differential protein interaction functions. Strep-tagged $^{WT}$GRB2 and $^{K109R}$GRB2 were affinity purified from cells treated with or without IR and the co-precipitants were analyzed by western blotting. IR treatment without a recovery period transiently increased MRE11, RPA70, and H2AX association with $^{WT}$GRB2. In contrast, $^{K109R}$GRB2 showed a drastic reduction in MRE11 co-precipitation while retaining unaltered RPA70 and H2AX levels (FIG. 2G). Notably, the $^{K109R}$GRB2 mutant did not affect GRB2 dimerization, SOS binding or MAP kinase signaling (FIG. 1F,11C-11F).

Figure 2H:
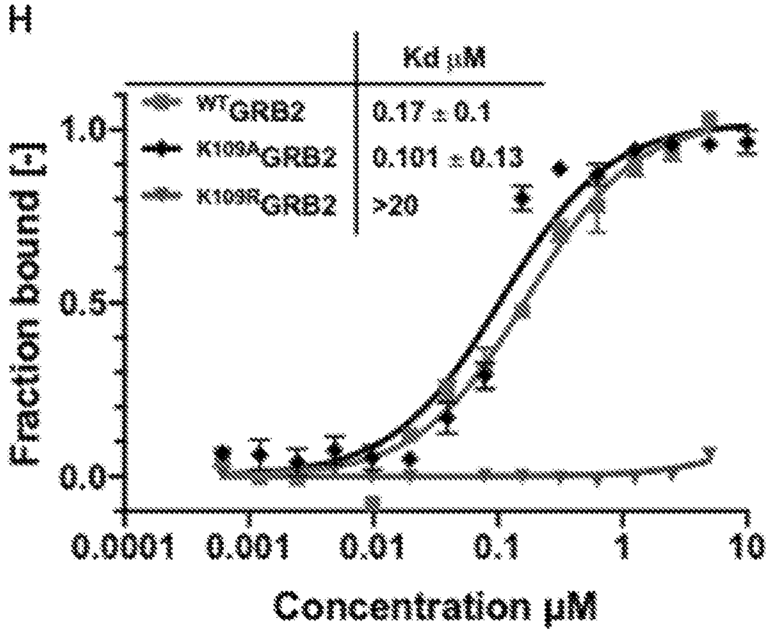

To test if ubiquitination is required for GRB2-MRE11 interaction, the inventors performed microscale thermophoresis (MST), an in vitro binding assay, by using bacterially expressed and purified proteins (FIG. 12D) that lack ubiquitination. The binding isotherms revealed that non-ubiquitinated GRB2 interacted with MRE11 with a dissociation constant (Kd) of 0.17±0.1 μM while the K109R mutant showed no binding. Thus, the K109R mutation itself, independent of ubiquitination status prevents GM complex formation (FIG. 2H). While a lysine to arginine mutation maintains the charge, the bulky arginine guanidinium was sufficient to block GRB2 interaction with MER11 independent of ubiquitination status (FIG. 2H). This finding uncovered the specificity of the GM binding interface and the expectation that K109 site ubiquitination would certainly be sufficient to disrupt GM interaction (see below). In contrast, the K109A mutant, which is ubiquitination-defective without steric blocking, showed intact MRE11 binding (FIG. 2H).

Figure 3A:
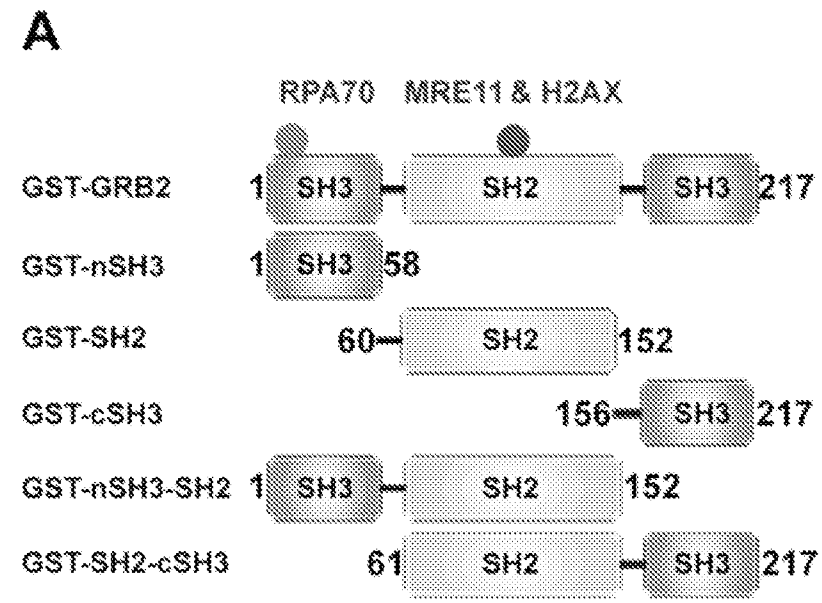
FIGS. 3A-3I. Identification of GRB2 binding interfaces on MRE11, RPA70 and H2AX.
Figures 3B, 3C:
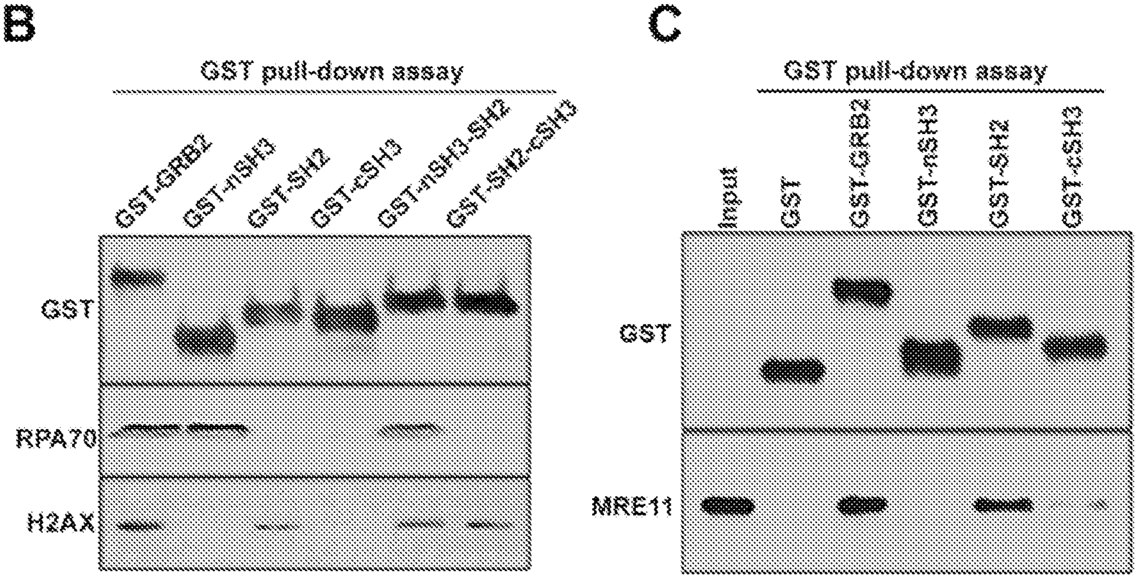
Figures 3D, 3E:
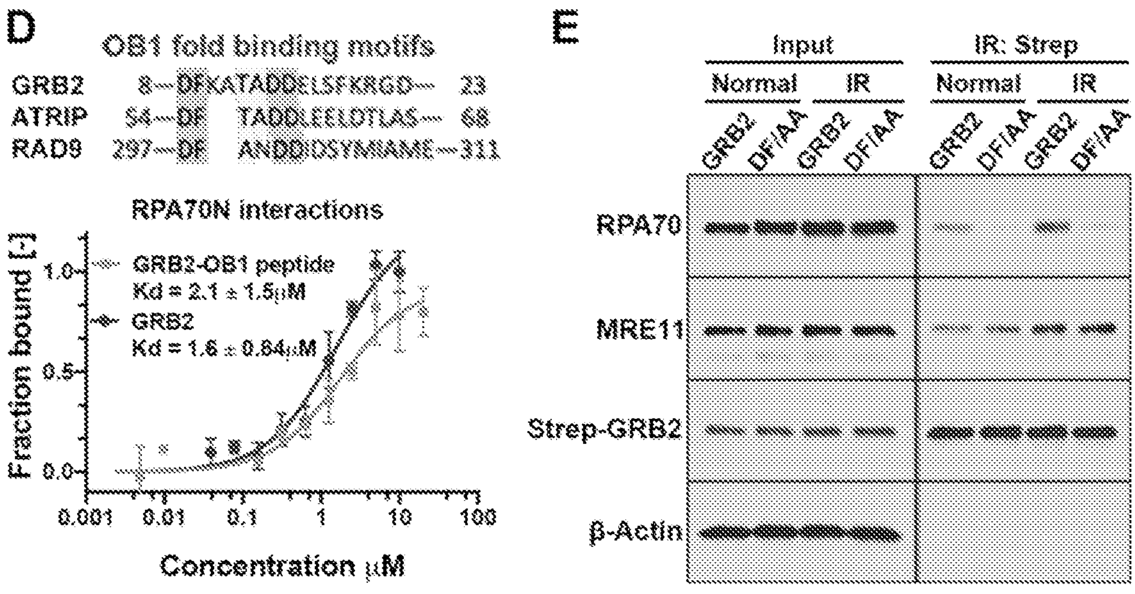
Figure 4A:
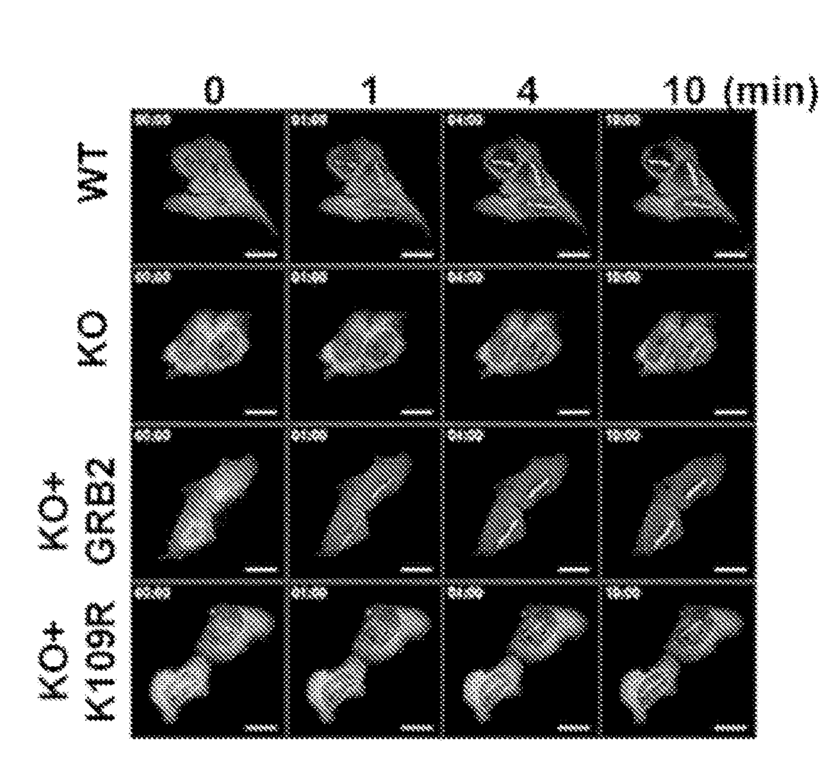
FIGS. 4A-4E. GRB2 recruits MRE11 to the DNA damage sites.
Figures 4B, 4C:
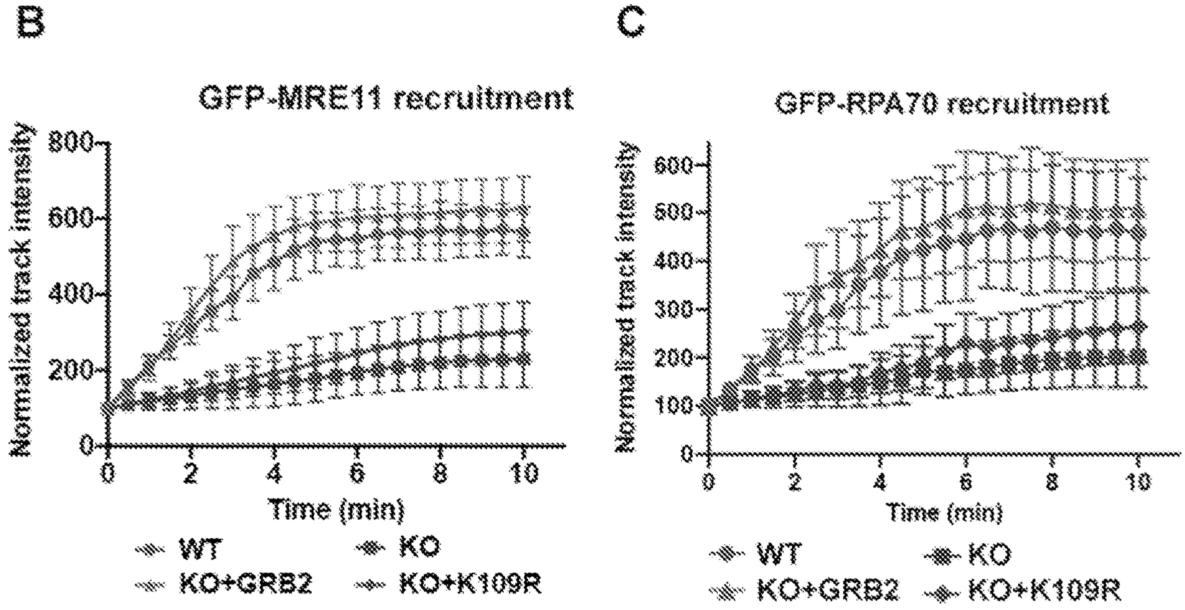
Figure 4D:
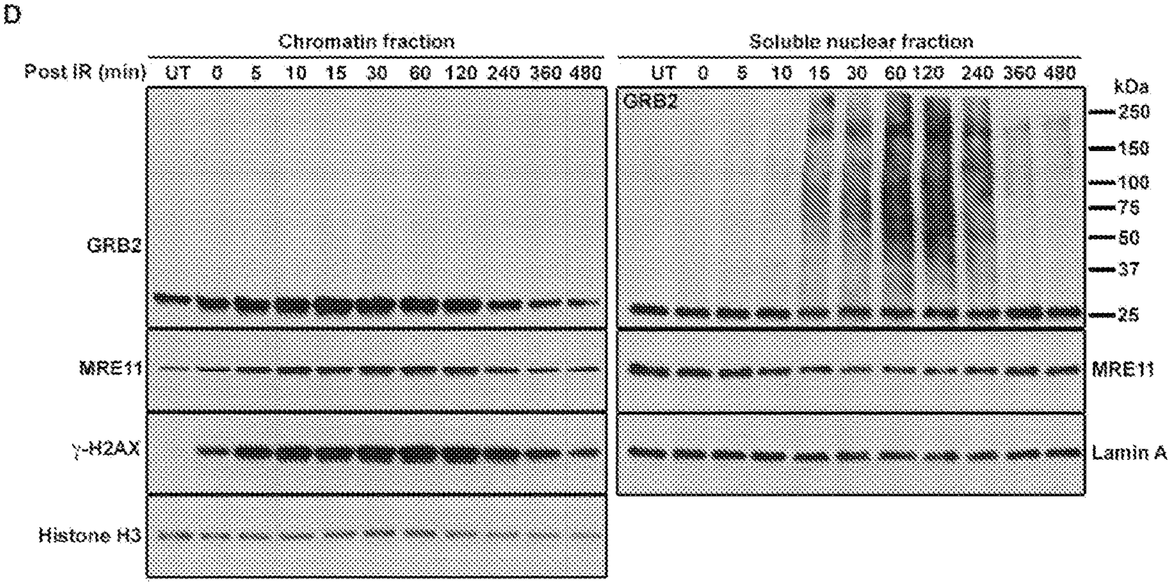

Novel GRB2 binding interfaces are specific for DNA repair proteins. GRB2 consists of an SH2 domain flanked by two SH3 domains specializing in protein-protein interactions. To identify individual domains responsible for the observed DDR protein binding, the inventors used a glutathione S-transferase (GST) fused SH domain (FIG. 3A) to precipitate nuclear proteins. The N-terminal SH3 (nSH3) domain engaged RPA70, while the SH2 domain precipitated H2AX (FIG. 3B). Multiple DDR proteins interact with MRE11, such as the reported direct interaction between PCNA and MRE11 (Hogrel et al., 2018); the inventors therefore used bacterially purified MRE11 for the GST pulldown assay and identified the GRB2-SH2 domain as the primary MRE11 interacting domain (FIG. 3C). The C-terminal (cSH3) domain also precipitated MRE11, albeit with lower efficiency. Interestingly, nSH3 sequence analyses revealed a conserved OB1 fold domain binding motif (DFKATADDE; SEQ ID NO: 3) embedded within the nSH3 domain as a suitable docking site for RPA70 (FIG. 4D, sequence alignment). Using MST, the inventors confirmed direct binding and a comparable Kd for RPA70 N-terminal OB1 domain (RPA70N) interaction with full-length GRB2. Furthermore, synthetic peptides corresponding to the putative OB1 sequence of GRB2 interacted with RPA70N (FIG. 3D). Furthermore, double aspartic acid and phenylalanine mutations of GRB2 to alanine (DF/AA) within the GRB2-OB1 binding motif at positions 8 and 9 drastically reduced RPA70 co-precipitation with GRB2. These data support a novel GRB2-RPA70 interaction site in the GRB2 nSH3 domain (FIG. 3E).

Figure 3F:
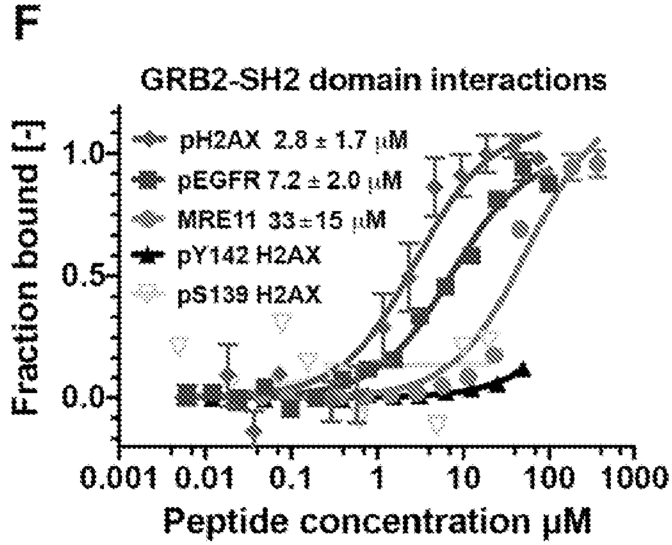

The GRB2-MRE11 complex targets phosphorylated histone H2AX. GRB2 SH2 domain interacts with tyrosine-phosphorylated motifs in the context of a pYxNx motif, where asparagine at the +2 position provides specificity (Songyang et al., 1994). As the pulldown experiments showed the GRB2-SH2 domain precipitated H2AX (FIG. 3B) and phosphorylated-H2AX is a marker for DNA damage (Rogakou et al., 1998; Xiao et al., 2009), the inventors investigated whether H2AX forms a GRB2-SH2 domain binding site. Since dually S139 and Y142 phosphorylated H2AX (pH2AX) dominates early signaling events (Xiao et al., 2009) and GRB2 is known for its involvement in early signaling complexes (ESCs), the inventors used a double phosphorylated peptide for MST binding measurements. These results revealed that the pH2AX peptide [PSGGK-KATQA(pS)QE(pY); SEQ ID NO: 4] binds the GRB2-SH2 domain with a Kd of 2.8±3.3 μM. Notably, this Kd resembles canonical EGFR-derived phosphopeptide (pEGFR) binding (7.2±2.0 μM) (FIG. 4E; (Ahmed et al., 2015)). However, using a H2AX peptide containing single phosphorylation at pS139 or pY142 failed to produce a binding isotherm (FIG. 3F; pS139 H2AX and pY142 H2AX).

Having found the GRB2-SH2 domain also binds MRE11, the inventors sought to identify the interaction site on MRE11. SH2 domains are classically known for their affinity for tyrosine phosphorylated protein binding, yet GRB2 interacted with unphosphorylated MRE11 (FIGS. 2H and 3C). Focusing upon GRB2's binding to unstructured flexible regions, the inventors analyzed the human MRE11 crystal structure (PDB 3T1I). The inventors identified the WVNYQDGNLN (SEQ ID NO: 5) sequence missing in the atomic structure due to flexibility (Park et al., 2011), and tested whether GRB2-SH2 would bind to the corresponding synthetic peptide. Indeed, in vitro MST binding studies confirmed the GRB2-SH2 domain bound WVNYQDGNLN (SEQ ID NO: 5) with a 33±15 μM affinity (FIG. 3F), similar to the reported binding Kd for GRB2-SOS peptides (McDonald et al., 2009; Ahmed et al., 2015). That this binding is weaker than fully folded MRE11 suggests possible added stabilizing contacts with the cSH3 domain, with likely sites being solvent-exposed PxxP motifs within residues 323-326 and 358-361.

Figure 3G:
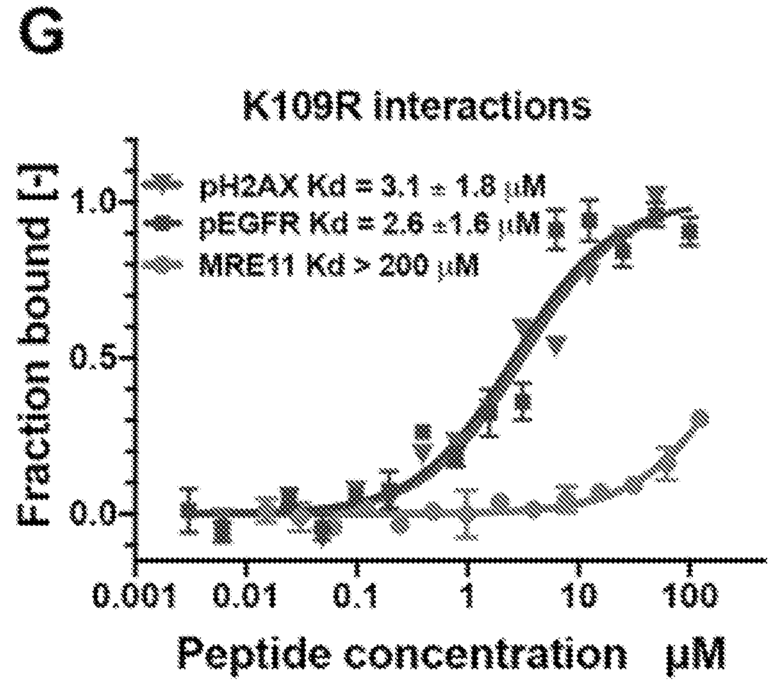
Figure 13A:
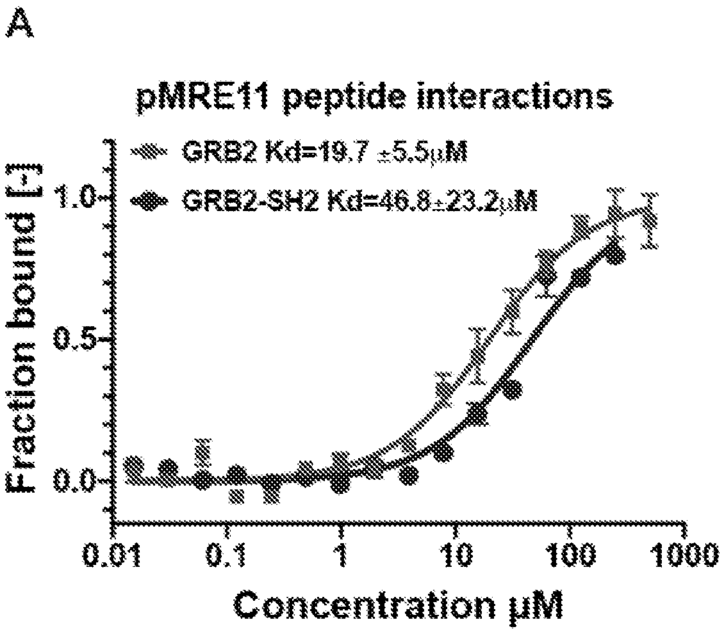
FIGS. 13A-13E. HDR protein foci formation in wild-type and GRB2 KO cells.

As the MRE11 peptide contains a tyrosine, the inventors tested a tyrosine phosphorylated peptide (WVNpYQDGNLN (SEQ ID NO: 6) to both full-length GRB2 and the SH2 domain. The inventors found that phosphorylation had a limited impact on its binding affinity for the GRB2-SH2 domain (FIG. 13A). This suggests that GRB2-SH2 domain interaction with MRE11 is outside the typical SH2 domain phosphotyrosine binding mode. As K109R abrogated GRB2-MRE11 interactions (FIG. 2G), the inventors tested the $^{K109R}$GRB2 binding affinity for MRE11 peptide. The measured binding affinity was at least two orders of magnitude weaker. In contrast, binding of $^{K109R}$GRB2 to the pEGFR and pH2AX peptides was comparable to that of $^{WT}$GRB2 (FIG. 3G).

Figures 3H, 3I:
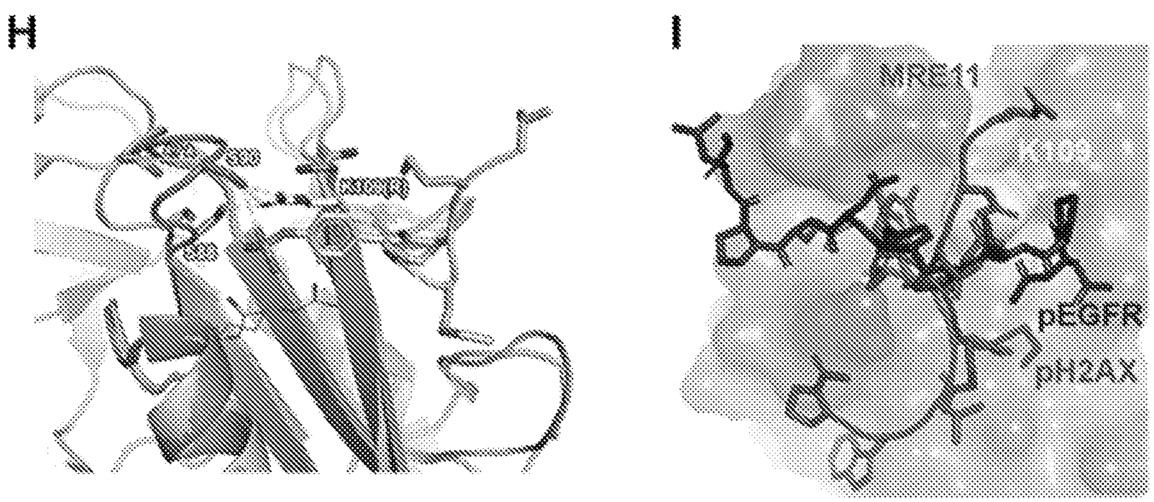
Figure 13B:
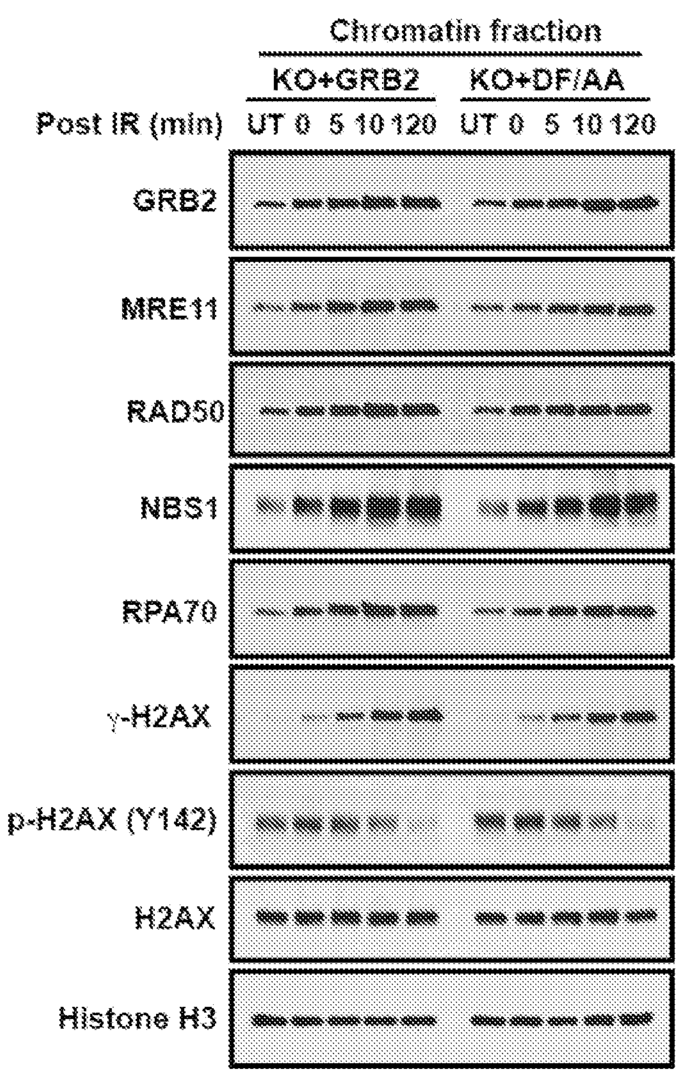

The GRB2 structure suggests K109R is likely to engage a loop through interactions with S88 and S90, which would obstruct the predicted MRE11-binding groove in the molecular docking model where MRE11 peptide adopted a perpendicular pose, placing it directly above K109 (FIGS. 3H & 3I). Thus, ubiquitin at K109, like $^{K109R}$GRB2, would sterically block the MRE11 binding grove. Collectively, these data defined individual GRB2 interactions, identified reciprocal binding interfaces and determined relative binding affinities that establish GRB2 as a nuclear adapter suitable to link MRE11 to H2AX and RPA70.

nGRB2 links MRE11 to phosphorylated H2AX marked DNA damage sites. As MRE11 is a key nuclease for HDR initiation (Shibata et al., 2014), the inventors investigated whether GRB2 directs GFP-MRE11 to DNA damage sites using UV-LMI and live-cell imaging. In control cells, GFP-MRE11 was recruited to the UV laser damage site within 1 min (FIGS. 4A & 4B). However, GFP-MRE11 recruitment was delayed in GRB2-KO cells, appearing later (after 4 min) and at much lower levels than in control cells (FIGS. 4A & 4B; KO). Reconstitution of $^{WT}$GRB2, but not $^{K109R}$GRB2, restored GFP-MRE11 recruitment kinetics to control levels, indicating GRB2-MRE11 interaction enables efficient MRE11 recruitment to the DNA damage site (FIGS. 4A & 4B, KO+GRB2 versus KO+K109R). The inventors also tested RPA70 recruitment using UV-LMI and found that it mirrored the MRE11 recruitment profile (FIG. 4C). Since MRE11 is not recruited to the DNA damage site, ssDNA is not generated by MRE11 nuclease activity, thereby causing defective recruitment of RPA70. In other words, since MRE11 is evidently recruited to pH2AX rather than to DSBs per se, we postulate that GRB2 acts in both MRE11 and RPA recruitment as single-stranded DNA is not yet generated by MRE11. Notably, reconstitution of $^{WT}$GRB2 but not the MRE11 interaction-defective $^{K109R}$GRB2 rescued the RPA70 recruitment (FIG. 4C). Furthermore, restoration of MRE11 recruitment was sufficient for RPA70 chromatin loading independent of GRB2 binding (FIG. 13B).

Figure 13C:
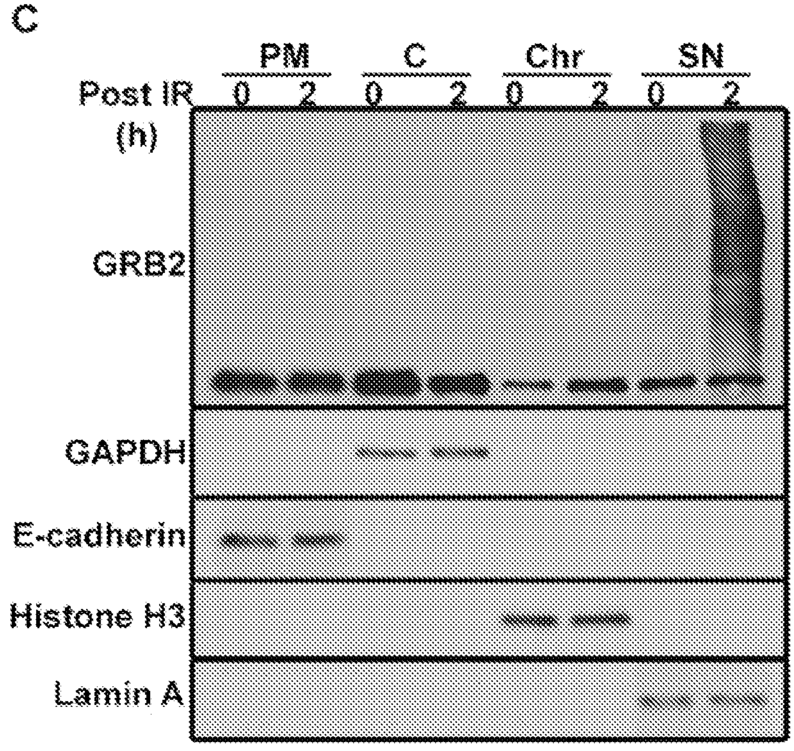
Figure 13D:
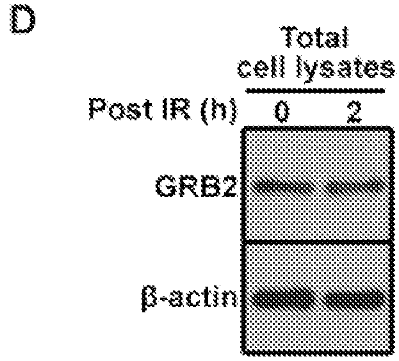
Figure 13E:
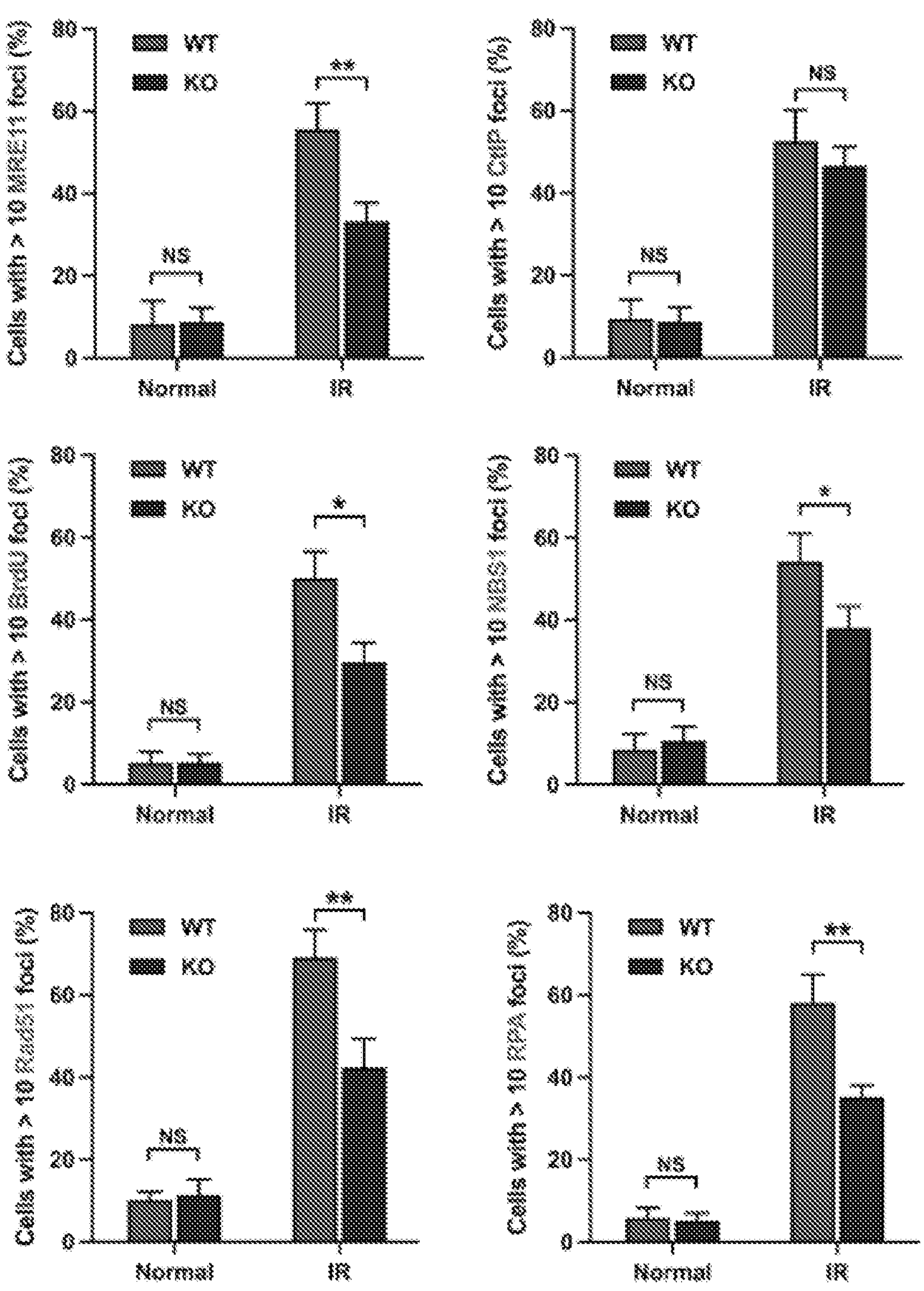

Since UV-LMI was conducted in GFP-MRE11 overexpression, the inventors next investigated whether IR-induced endogenous MRE11 recruitment to DNA damage sites on chromatin recapitulates the live cell findings. Chromatin fractions of IR-treated HeLa cells were prepared and analyzed by western blotting. The results revealed IR-induced transient GRB2 and MRE11 accumulation onto chromatin at the early DDR stage, which coincided with γH2AX phosphorylation (FIG. 4D; chromatin fractions). An adjustment of immunoblot exposure time also revealed that IR-induced transient GRB2 ubiquitination reached a maximum level at 2 h before subsiding (FIG. 4D, long exposure). Analysis of the nucleoplasmic proteins revealed that ubGRB2 was readily detectable 15 min after IR, and ubiquitination reached the maximum level at 2 h before subsiding (FIG. 4D, soluble nuclear fractions). Notably, increased MRE11 on chromatin correlated with a measurable and proportional decrease in the nucleoplasm (FIG. 4D, second panel). However, changes in GRB2 levels were less clear. The inventors therefore conducted additional cell fractionations to include cytoplasm and plasma membrane. These results uncovered a measurable redistribution of the cytoplasmic GRB2 in response to IR. The observed GRB2 increase on chromatin following IR correlated with a proportional decrease in cytoplasmic GRB2 (FIG. 13C). Immunoblotting of total cell extracts showed no change in overall GRB2 level between control and IR-treated samples (FIG. 13D), indicating the observed reduction in the cytoplasmic GRB2 was indeed due to a redistribution of proteins.

To further understand the role of GRB2 in MRE11 chromatin loading, the inventors directly compared HDR-related protein loading on chromatin between control and GRB2-KO HeLa cells. In control cells, time-dependent accumulation of MRE11 and GRB2 onto chromatin was induced by IR. However, in GRB2-KO cells IR-induced MRE11 recruitment to chromatin was abrogated (FIG. 4E; GRB2-KO left column). The chromatin loading of DNA damage marker γH2AX and the other MRN complex components NBS1 and RAD50 were unaffected by the loss of GRB2. In agreement with our UV-LMI, RPA70 chromatin recruitment was delayed in GRB2-KO cells (FIG. 4E; RPA70). Thus, GRB2 plays an indispensable role in timely IR-induced MRE11 recruitment to the DNA damage site.

Figure 4E:
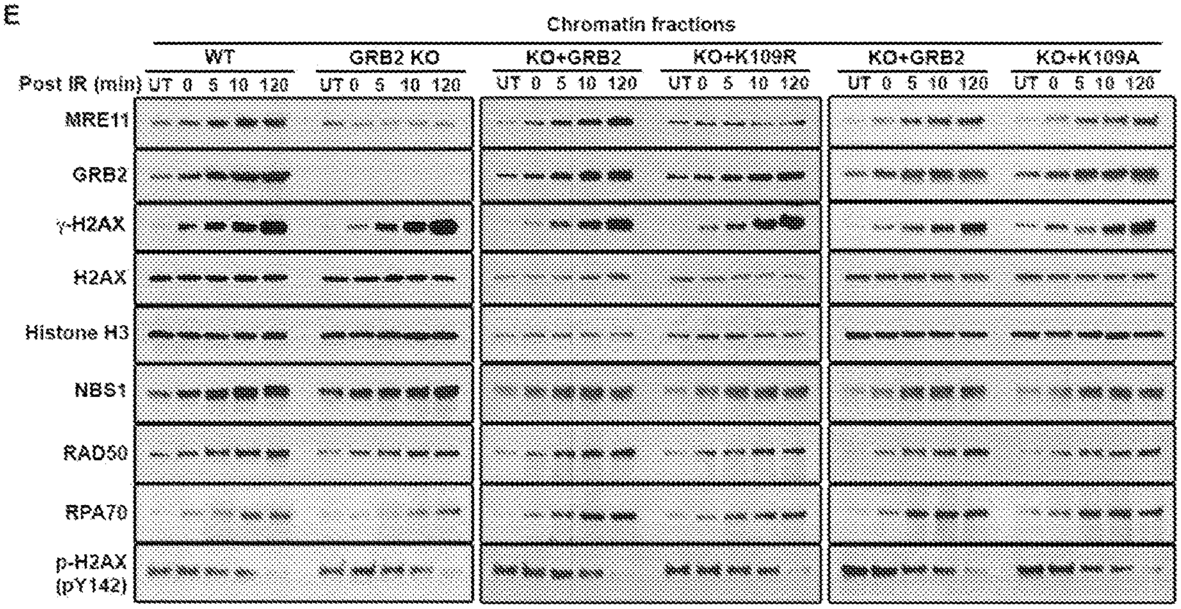

Since the K109R mutant cannot bind to MRE11 but retains H2AX binding capacity (FIG. 3G), the inventors directly compared the effect of this mutation in MRE11 recruitment. In a reconstitution experiment, the $^{WT}$GRB2 (KO+GRB2), but not $^{K109R}$GRB2 mutant (KO+K109R), rescued MRE11 recruitment to the chromatin in a manner parallel to the $^{WT}$GRB2 (FIG. 4E; right column and see below). Thus, the formation of the GRB2-MRE11 complex is vital for efficient MRE11 loading onto chromatin. These results are consistent with the cellular pulldown experiments (FIGS. 2C-2F) showing an exclusive GM complex, the observed MRE11 non-binding to $^{K109R}$GRB2 (FIGS. 2G & 2H) and the failure to recruit MRE11 to the UV-LMI site in GRB2 knockout and K109R reconstituted cells (FIGS. 4A & 4B).

Figure 12D:
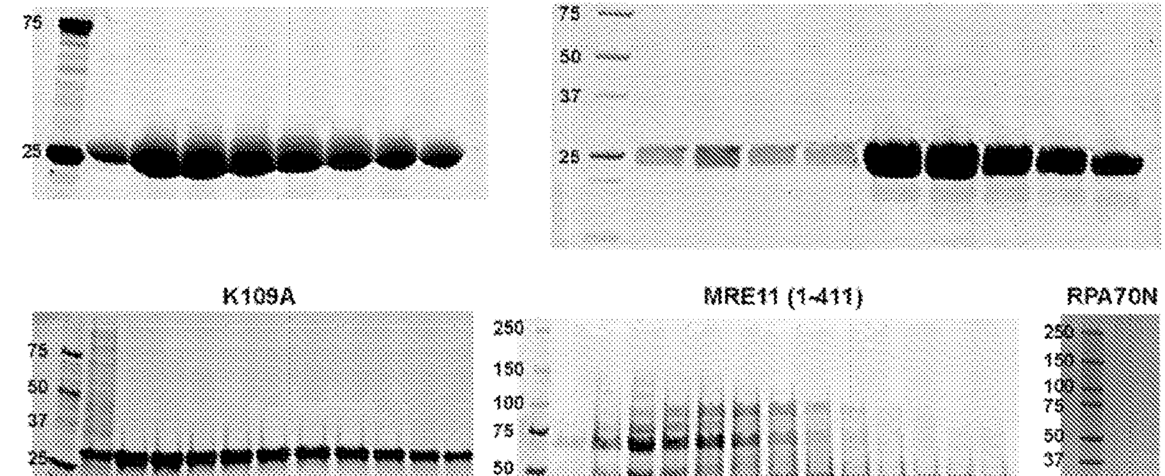

The inventors also investigated IR-induced endogenous MRE11 foci formation along with RPA70, NBS1, RAD51, CtIP and BrdU between the control groups and GRB2-KO cells. Cells were either untreated (normal) or IR treated and allowed to recover for 120 min (Post IR) before collection (FIG. 12D). Under normal conditions, all tested proteins formed a limited number of foci, but no significant difference between the WT and KO cells was observed. However, following IR treatment, the number of DNA damage foci detected per cell increased in both groups. Quantification analysis of foci-positive cells revealed a measurable reduction in MRE11, NBS1, BrdU, RPA70 and RAD51 foci formation in GRB2-KO cells. However, no difference of CtIP foci formation was observed in these two cell groups (FIG. 12D; histograms). Thus, these data support the idea that defective MRE11 recruitment impedes efficient resection and subsequent ssDNA accumulation at damage sites in GRB2-KO cells.

Figure 5A:
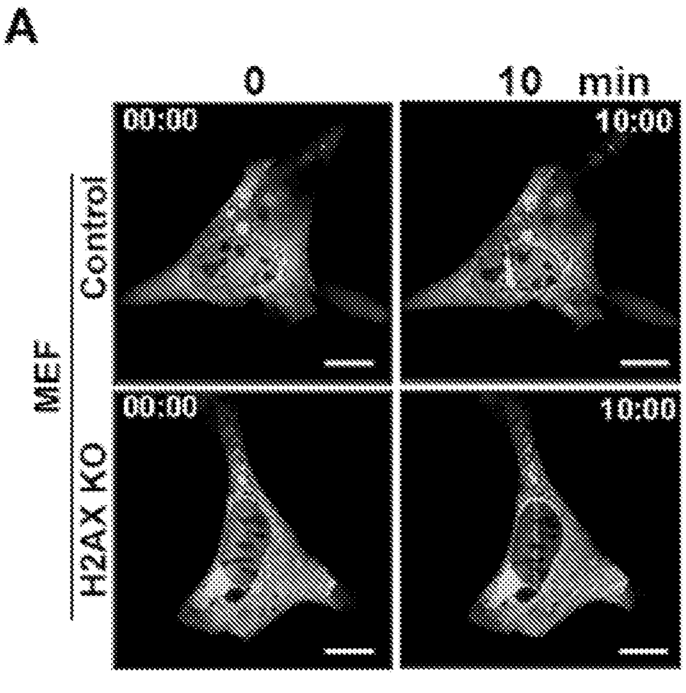
FIGS. 5A-5F. pH2AX creates a platform for GRB2-MRE11 complex recruitment.
Figure 5B:
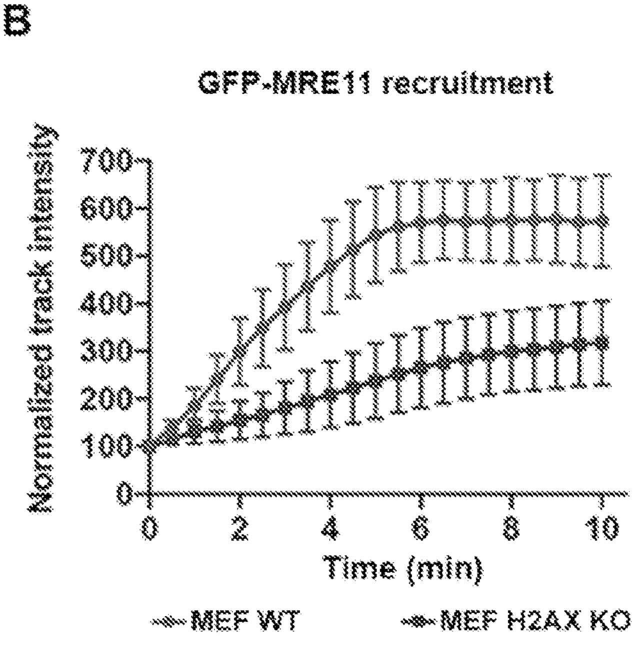
Figure 5C:
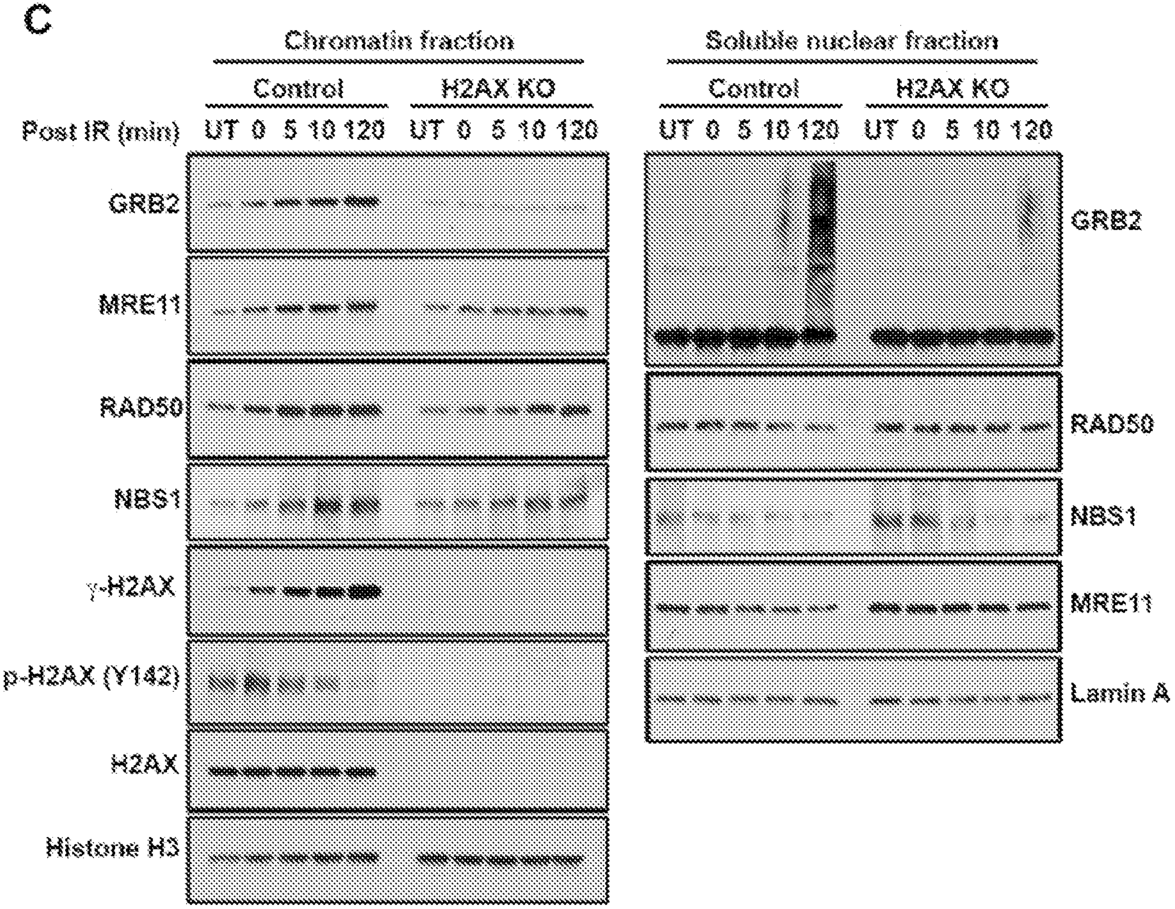

Phosphorylated H2AX is a docking site for GRB2. Having measured high-affinity interaction between the GRB2-SH2 domain and pH2AX (FIG. 3F), the inventors tested the requirement of H2AX for GRB2-mediated MRE11 recruitment onto chromatin. UV-LMI of H2AX-KO mouse embryonic fibroblasts (MEFs) with matched controls (WT) showed that the H2AX-KO MEF cells were defective in MRE11 recruitment to the DNA damage site (FIGS. 5A & 5B). Furthermore, the inventors performed comparative chromatin fractionation time-course experiments that showed a time-dependent incremental increase in IR-induced GRB2 on chromatin mirrored by MRE11 and H2AX phosphorylation in control cells (FIG. 5C, Control lanes). These data correlate with the observed pattern of IR-induced GRB2 accumulation on chromatin in HeLa cells (FIGS.

Figure 5D:
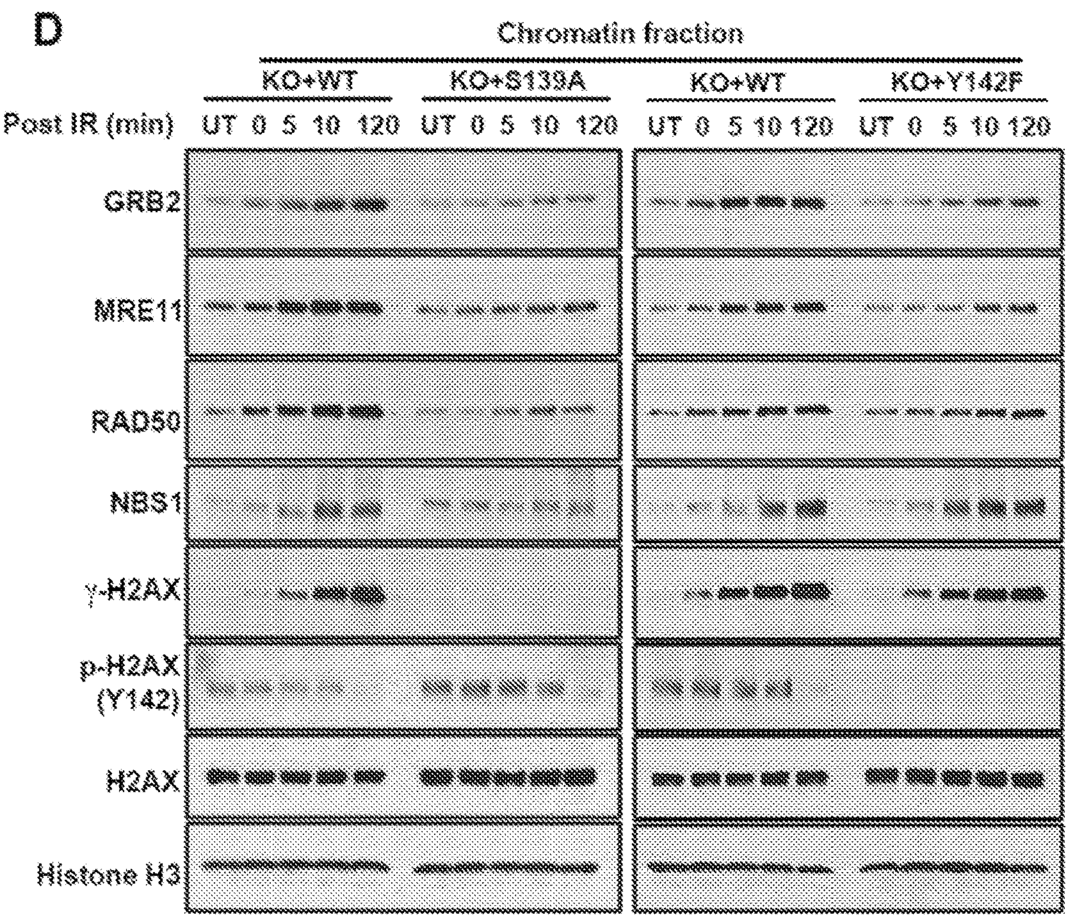
Figure 5E:
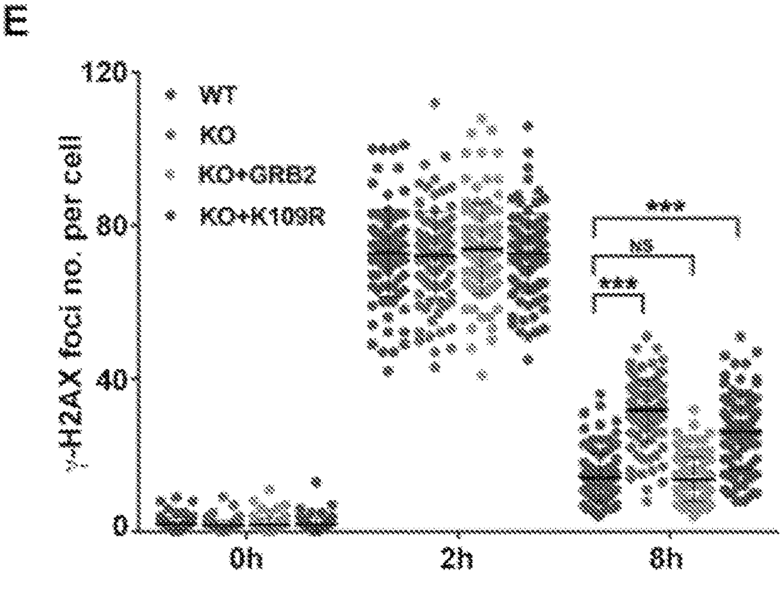

4D-4E). However, in H2AX-KO MEFs, IR-induced GRB2 and MRE11 enrichment were severely compromised at all tested time periods (FIG. 5C, H2AX KO), suggesting H2AX is required for GM assembly on chromatin. The MRN complex recruitment was also measurably decreased in H2AX-KO MEFs. Reconstitution of the wild-type H2AX (KO+WT) restored GRB2 and MRN recruitment patterns similar to the control. However, reconstitution of S139A or Y142F H2AX mutant only partially rescued IR-induced GRB2 and MRE11 accumulation on chromatin. NBS1 recruitment was abrogated in S139A but not in Y142F reconstituted cells (FIG. 5D) Thus, these collective data demonstrate that H2AX is required for GM complex recruitment following DNA damage and that dual phosphorylation of H2AX on S139 and Y142 is important for efficient GRB2 docking.

nGRB2 promotes DNA damage repair. Through direct interactions, the inventors found that GRB2 links MRE11 to the pH2AX (FIG. 3). UV-LMI treatment of live HeLa cells followed by indirect immunofluorescence revealed enrichment of endogenous GRB2 together with γH2AX at laser-induced damage sites (FIG. 1J). The inventors therefore investigated the consequence of low intracellular GRB2 by focusing on the spatiotemporal regulation of DNA damage foci. Using γH2AX as a marker, control and GRB2-knockdown (GRB2-KD) cells were IR-treated and foci longevity was compared. At 2 h after IR, no measurable difference was observed between control and GRB2-KD cells. However, lingering γH2AX foci in GRB2-KD cells remained at 8 h after IR (FIGS. 14A-14E) suggesting that reduced intracellular GRB2 was sufficient to delay DNA repair.

Figure 14A:
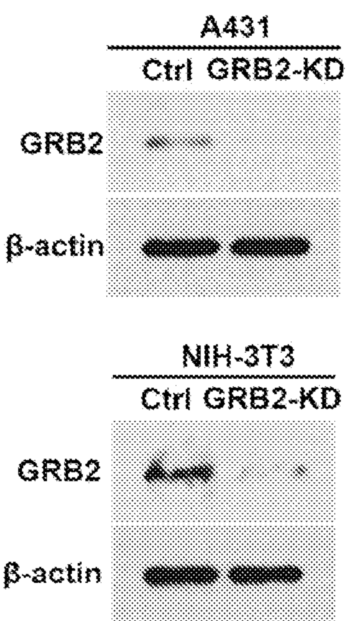
FIGS. 14A-14J. GRB2 knockdown delays DNA damage repair.
Figure 14B:
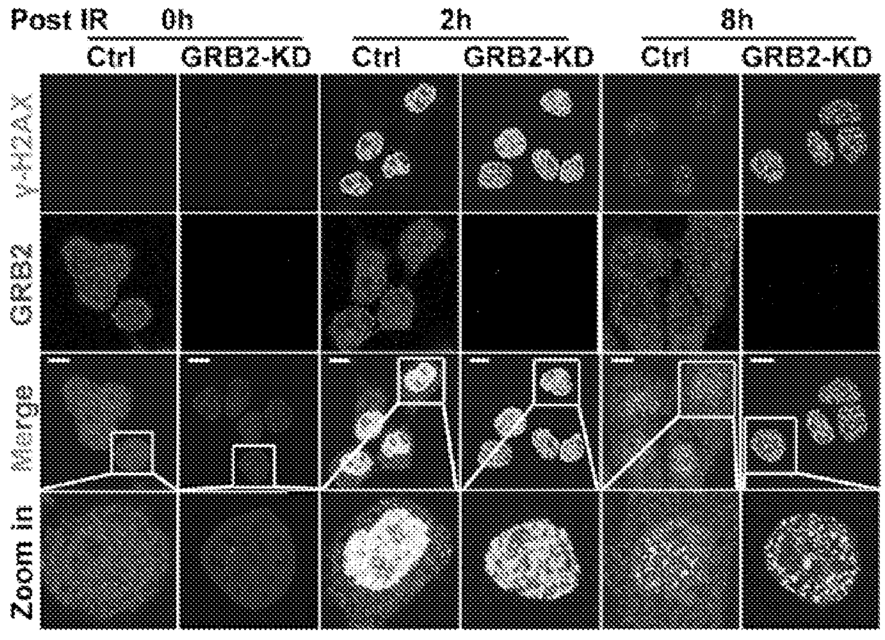
Figure 14C:
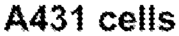
Figure 14C:
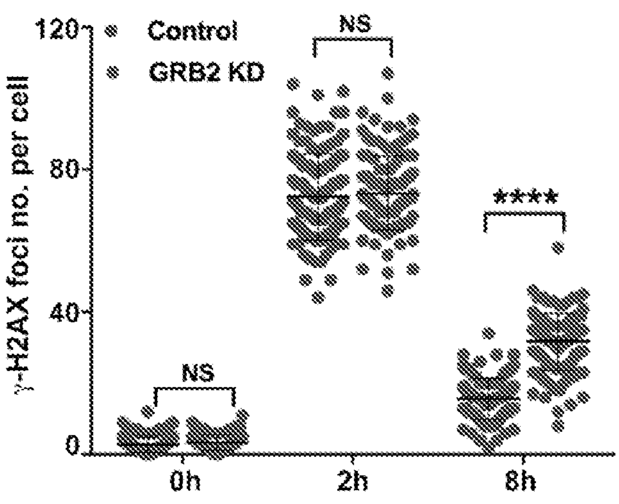
Figure 14D:
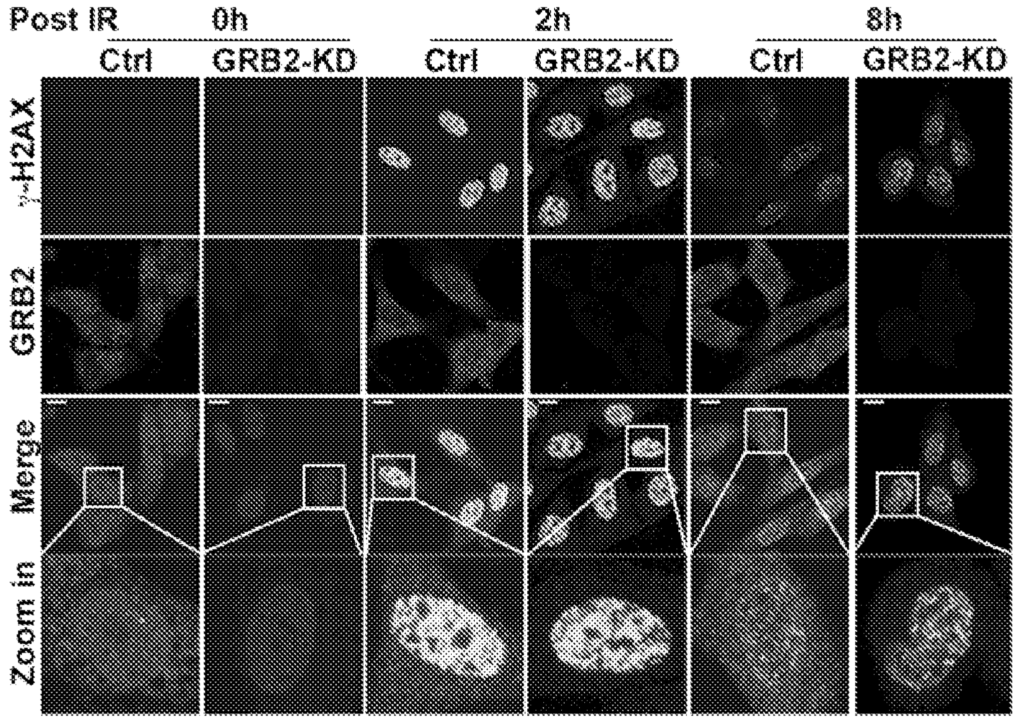
Figure 14E:
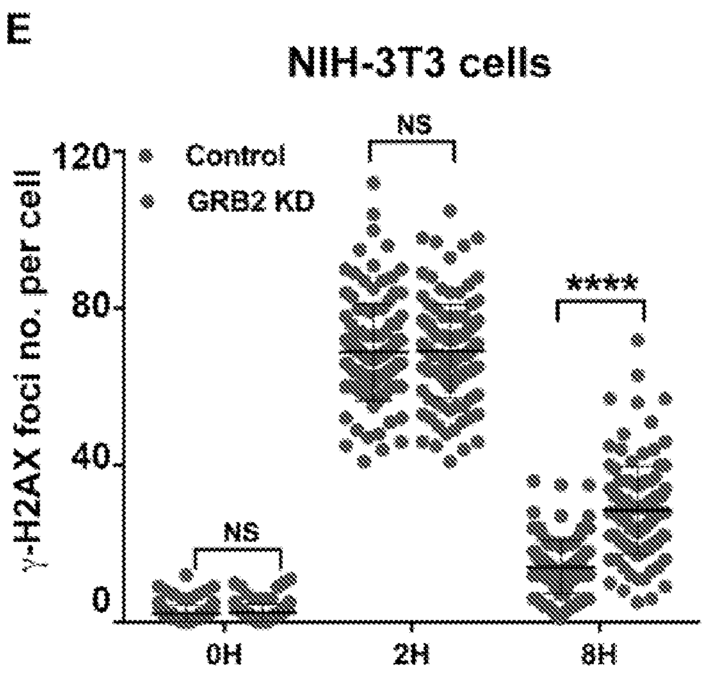
Figure 14F:
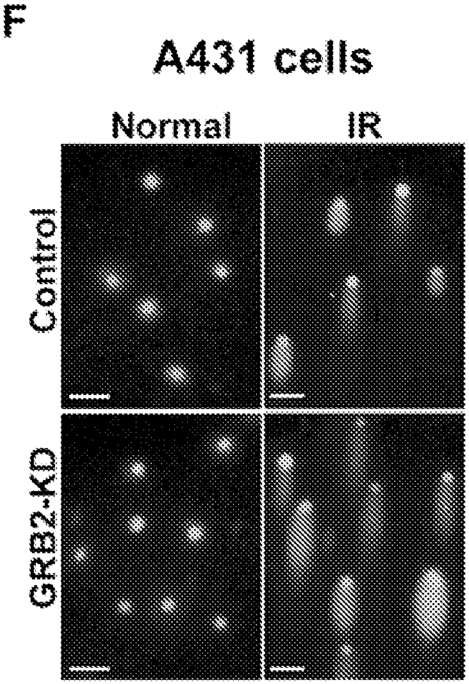
Figure 14G:
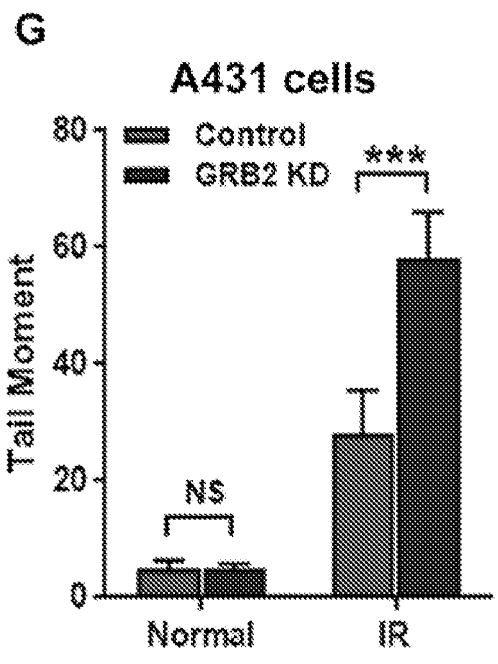
Figures 14H, 14I:
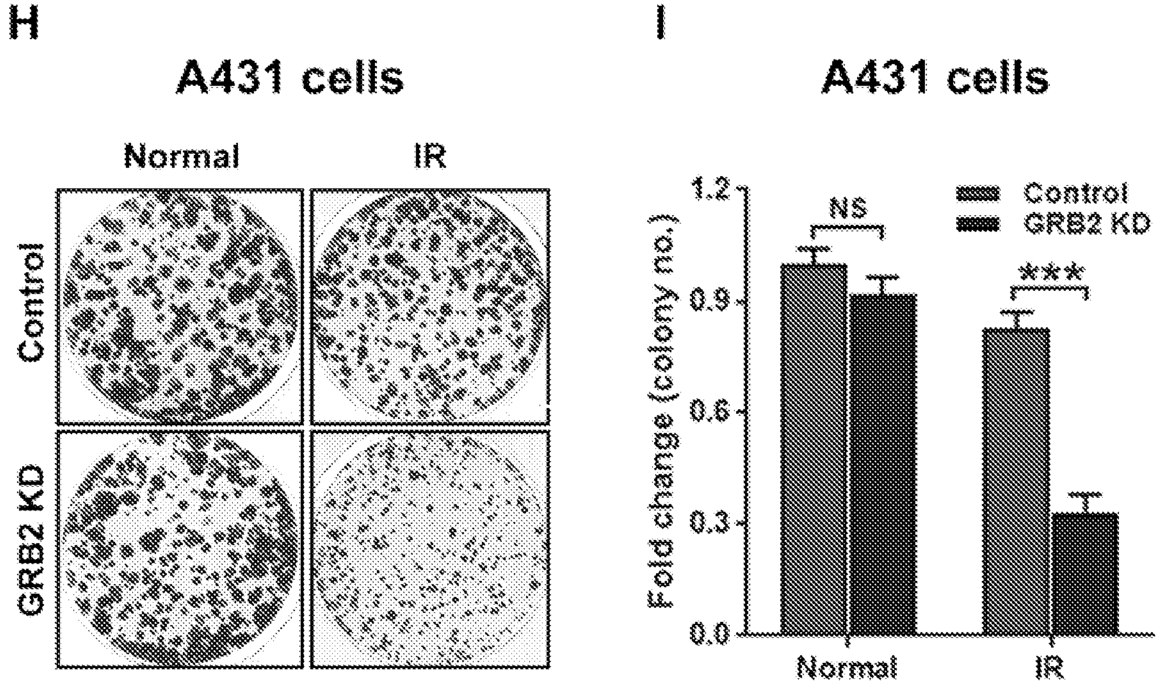
Figure 14J:
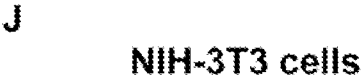
Figure 14J:
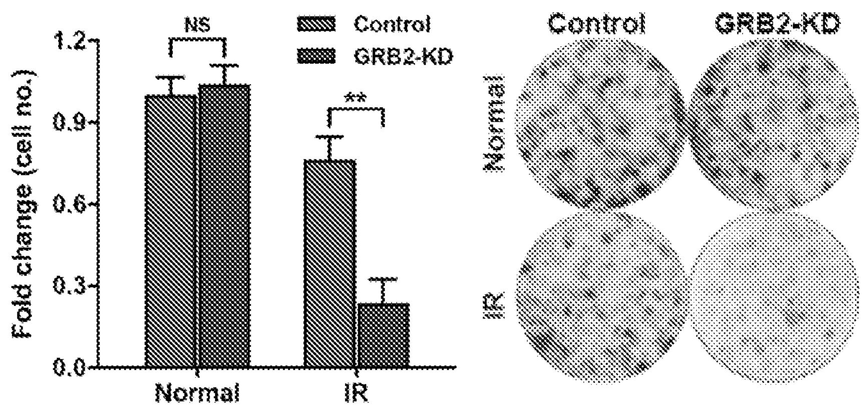

To further investigate this delay, the inventors utilized the MRE11 non-binding $^{K109R}$GRB2. GRB2-KO (KO) cells reconstituted with either $^{WT}$GRB2 (KO+GRB2) or $^{K109R}$GRB2 (KO+K109R) together with the control cells (WT) were IR-treated and allowed to recover for designated times. GRB2-KO cells mirrored GRB2-KD results. Reconstitution of $^{WT}$GRB2 restored cells to the control γH2AX foci phenotype. However, $^{K109R}$GRB2 reconstitution failed to rescue the GRB2-KO phenotype (FIG. 5E), suggesting GRB2-mediated MRE11 recruitment is indispensable for a timely DNA repair process. The inventors therefore tested the consequence of this delayed repair on fragmented genomic DNA. Comet assay showed substantial unrepaired damaged DNA in IR-treated GRB2-KD cells, as seen by longer DNA tail moment compared with controls (FIGS. 14F & 14G), as consistent with the observed prolonged γH2AX foci in GRB2-KD and GRB2-KO cells (FIGS. 5E,14B-14E). Thus, these collective data indicate that robust completion of DSB repair by HDR requires GM interactions.

Figure 5F:
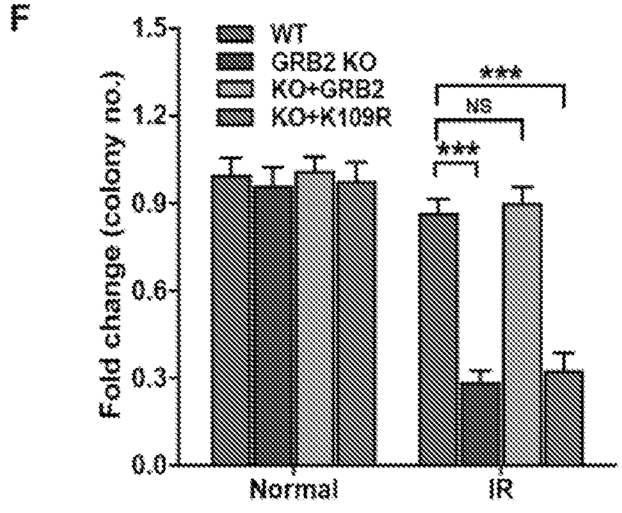

To further test the functional significance of reduced GM complex formation and consequent prolonged DNA repair, the inventors performed clonogenic cell survival assays. GRB2-KD or GRB2-KO cells exposed to IR showed a drastic reduction in colony survival (FIGS. 5F,14H-14J). Clonogenic assays also linked delayed repair to reduced cell survival in $^{K109R}$GRB2 reconstituted cells following IR treatment (FIG. 5F). These results showed that nGRB2 improves DNA repair efficiency and that nGRB2 deficiency reduces overall cell viability. Notably, the finding that the K109R mutant, which has intact canonical cytoplasmic functions, failed to rescue GRB2-KO cell survival establishes the biological importance of nGRB2 for genome stability impacting survival.

Figures 6A, 6B:
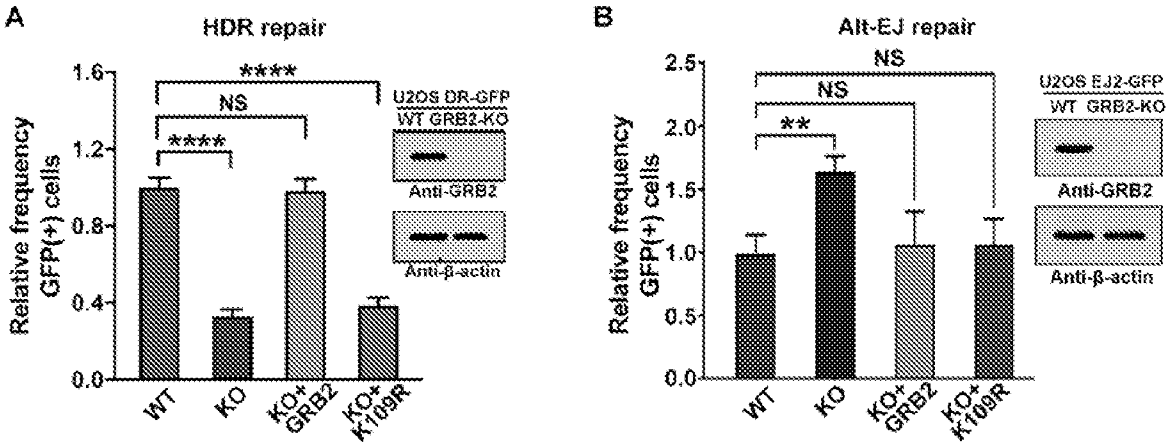
Figure 15A:
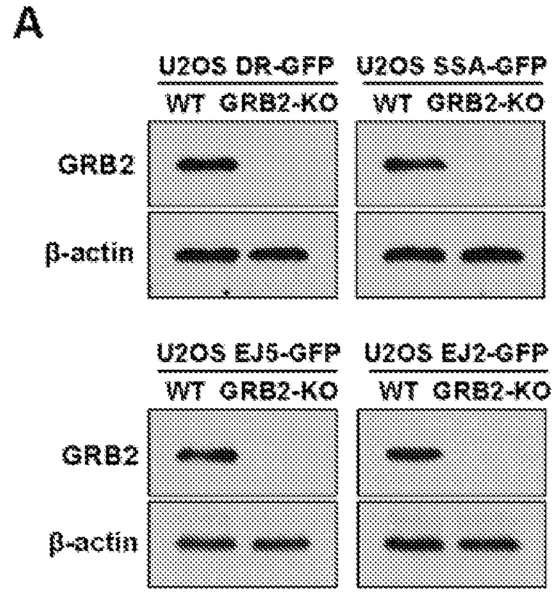
FIGS. 15A-15I. The effect of GRB2 on DSB repair.
Figures 15B, 15C:
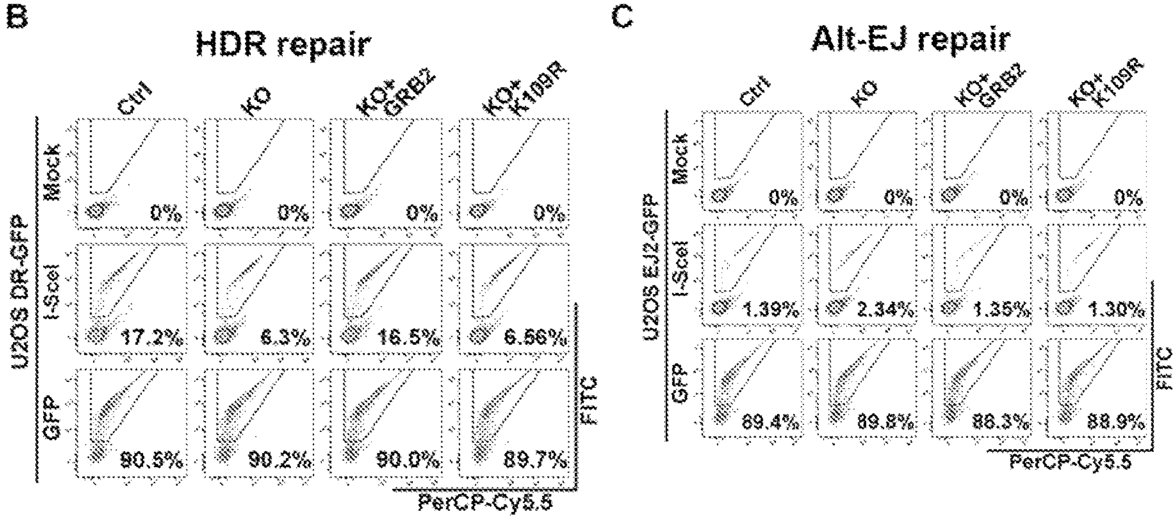
Figures 15D, 15E:
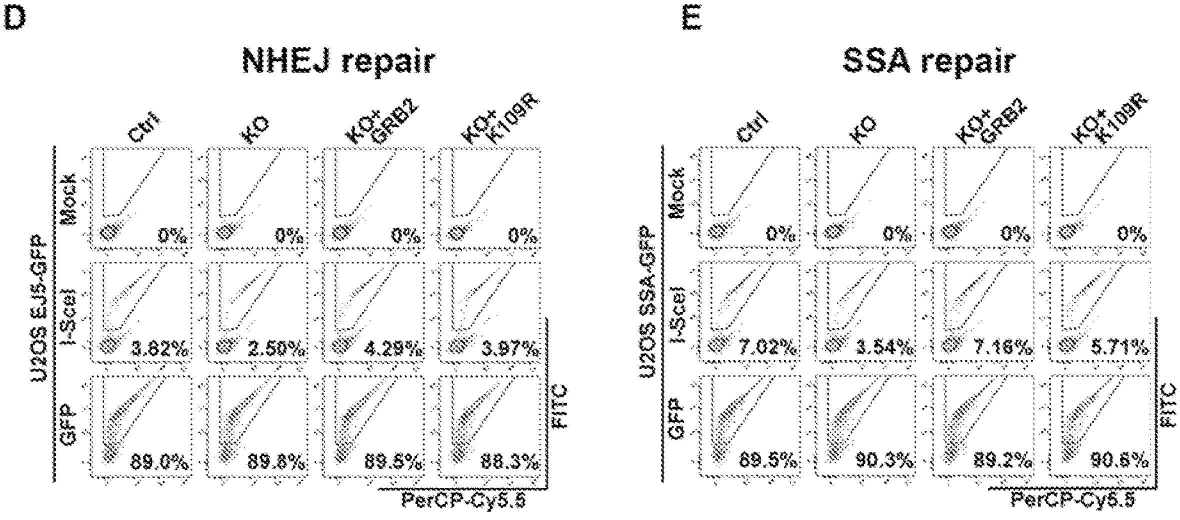

GRB2 promotes HDR while suppressing Alt-EJ. To further test nGRB2's role in cellular DNA repair and its importance for HDR in particular, the inventors performed I-SceI-based assays for all major DSB repair processes (Gunn & Stark, 2012). GRB2-KO of stable DR-GFP U2OS cells were generated and then reconstituted with either $^{WT}$GRB2 or $^{K109R}$GRB2 followed by a comparison of repair efficiency between the four cell lines (FIG. 15A). GRB2-KO had an immediate effect on all tested repair processes, most-likely due to a lack of growth factor stimulation. The inventors used the K109R reconstitution mutant to separate the GRB2s' DNA repair-related function from the loss of RAS/MAPK signaling. Notably, a significant reduction in HDR occurred in GRB2-KO cells, which was rescued by wild-type but not $^{K109R}$GRB2 (FIGS. 6A and 15B). Importantly, the observed HDR reduction coincided with an increase in alternative NHEJ (Alt-EJ) (Sfeir and Symington, 2015), the overall repair could be rescued by either $^{WT}$GRB2 or $^{K109R}$GRB2 (FIG. 6B and FIG. 15C), suggesting that the GM complex is channeled towards HDR, whereas GRB2-free MRE11 is shunted towards alternative NHEJ (i.e., Alt-EJ) by interactions with XRCC1 (Dutta et al., 2017; Eckelmann et al., 2020). MRE11 complex with XRCC1 and polymerase theta (also known as POLQ) is important for the initiation of Alt-EJ repair at breaks and forks (Dutta et al., 2017; Eckelmann et al., 2020). The inventors therefore immunoprecipitated POLQ, and detected MRE11 and XRCC1 but not GRB2 in the complex (FIG. 6C). The inventors then directly tested the nature of the XRCC1/MRE11 complex in control, GRB2-KO, and KO cells either reconstituted with $^{WT}$GRB2 (KO+GRB2) or $^{K109R}$GRB2 mutant. The results revealed that lack of GRB2 expression in GRB2-KO cells promoted XRCC1/MRE11 complex formation, which was reduced by reconstitution of $^{WT}$GRB2 (FIG. 6D). Unexpectedly, $^{K109R}$GRB2, which does not bind MRE11, also partially suppressed the XRCC1/MRE11 complex, in agreement with the Alt-EJ suppression measured by I-SceI based assay (FIGS. 6B and 6D). How K109R suppresses the XRCC1/MRE11 complex requires further investigation. Nonetheless, these data provide insight into how GRB2 can promote molecular complexes and dictate pathway choices and outcomes.

Figure 7A:
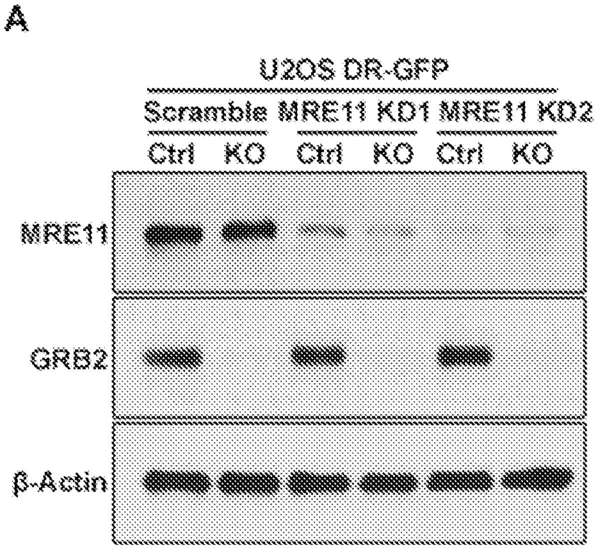
FIGS. 7A-7F. GRB2 KO sensitizes cells to PARPi.
Figures 7B, 7C:
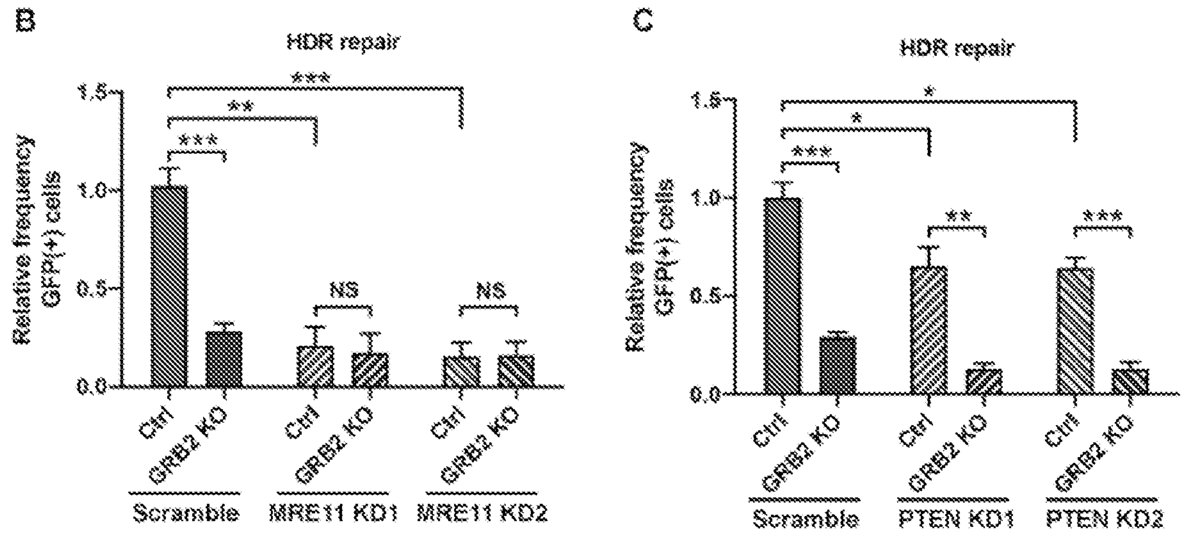
Figure 15F:
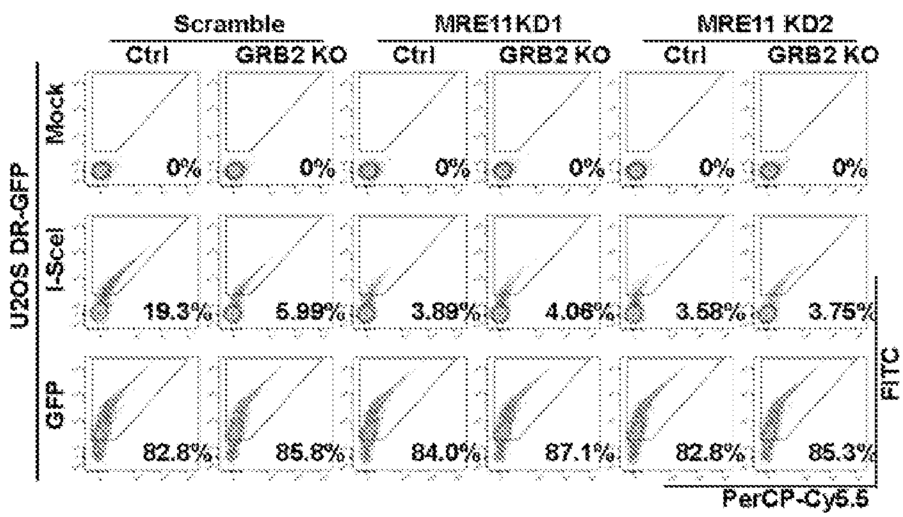

Interestingly, GRB2-KO cells also showed reduced single-stranded annealing (SSA) and NHEJ repair. Like Alt-EJ, reconstitution with either $^{WT}$GRB2 or $^{K109R}$GRB2 was sufficient to restore of NHEJ; yet, the mutant only partially activated SSA (FIGS. 6E,6F,15D,15E). These data suggest GRB2, through its interaction with MRE11, preferentially promotes HDR and that GRB2-deficient cells are HDR deficient. To further test if GRB2 and MRE11 are part of the same repair axis, the inventors performed an HDR repair assay in MRE11-knockdown (MRE11-KD) cells with or without GRB2 using two different shRNAs (FIG. 7A). MRE11-KD showed a drastic reduction in GFP-positive cells, indicating HDR repair deficiencies matching those seen with GRB2-KO cells (FIGS. 7B and 15F). MRE11-KD in a GRB2-KO background showed no further reduction in HDR repair efficiency, suggesting both proteins function in the same repair pathway and a reduction in either one is sufficient to significantly impair HDR.

Figure 15G:
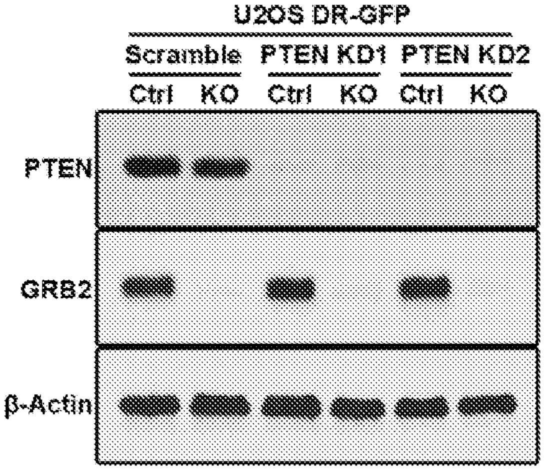
Figure 15H:
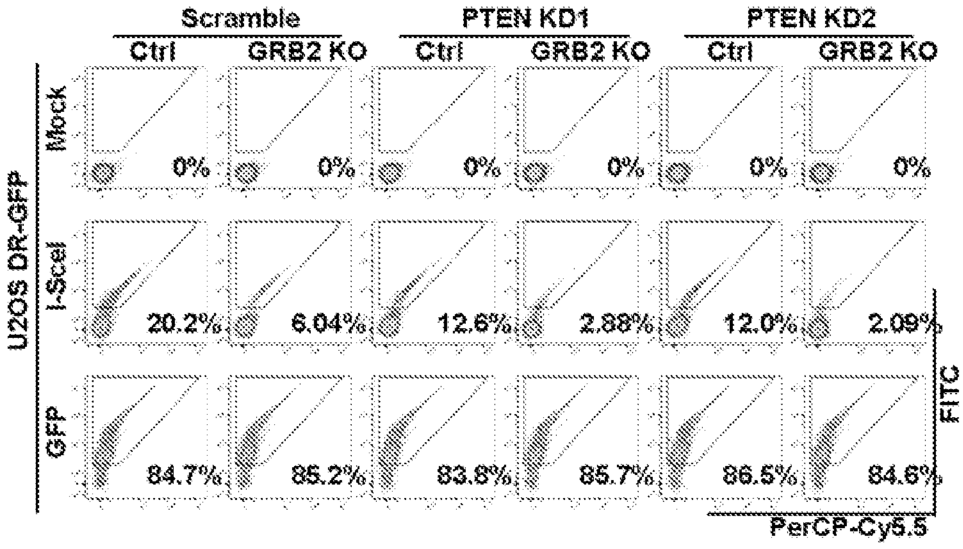

Recently, GRB2 was suggested to induce PTEN nuclear translocation to suppress micronucleus formation (Hou et al., 2019). To test if this proposal is related to these data, the inventors knocked down PTEN (PTEN-KD) in control and GRB2-KO U2OS cells (FIG. 15G) and tested HDR repair. Unlike GRB2-KO, which showed a staggering 80% reduction in HDR repair, PTEN-KD had a modest 20% decease. Notably, KO of GRB2 in PTEN-KD cells induced further suppression of HDR (FIGS. 7C and 15H), suggesting PTEN is not required for the GRB2-mediated HDR, and they are not in the same repair axis. The observed 20% reduction in HDR in PTEN-KD cells could reflect defective global phosphoinositide 3-kinase signaling or the prior observation that nuclear PTEN regulates RAD51 expression (Shen et al., 2007).

Figure 7D:
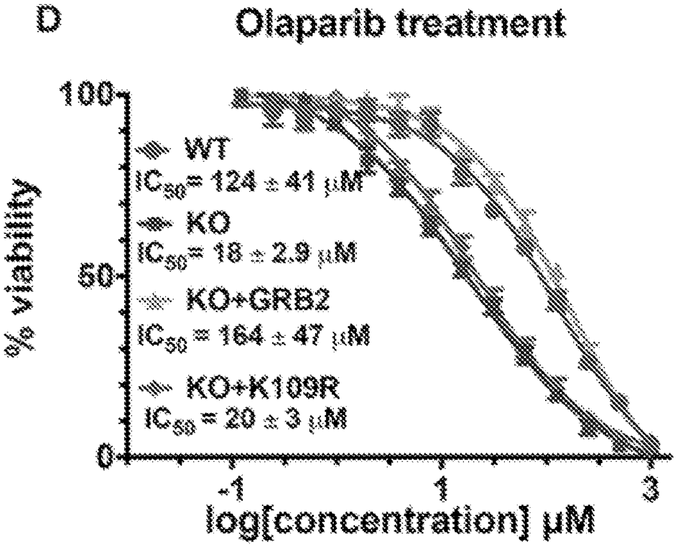
Figures 7E, 7F:
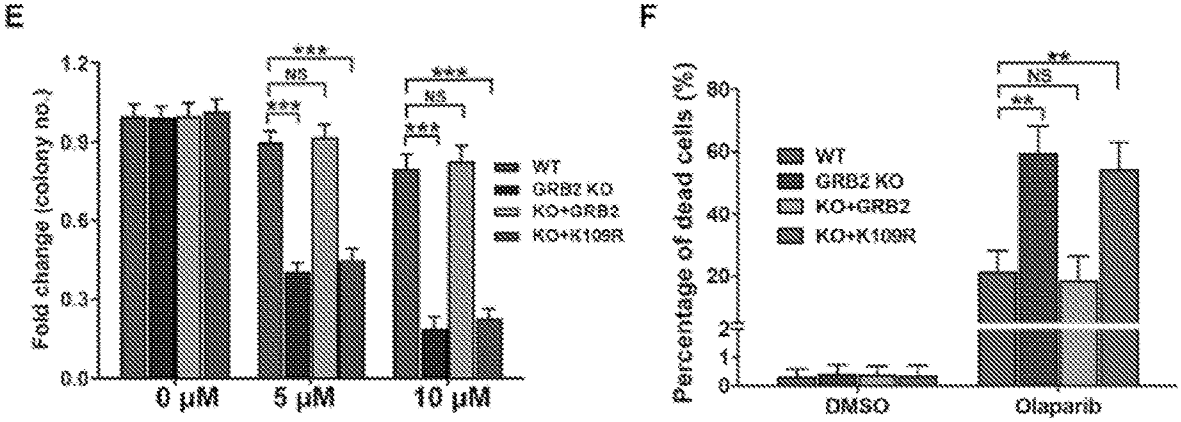
Figure 15I:
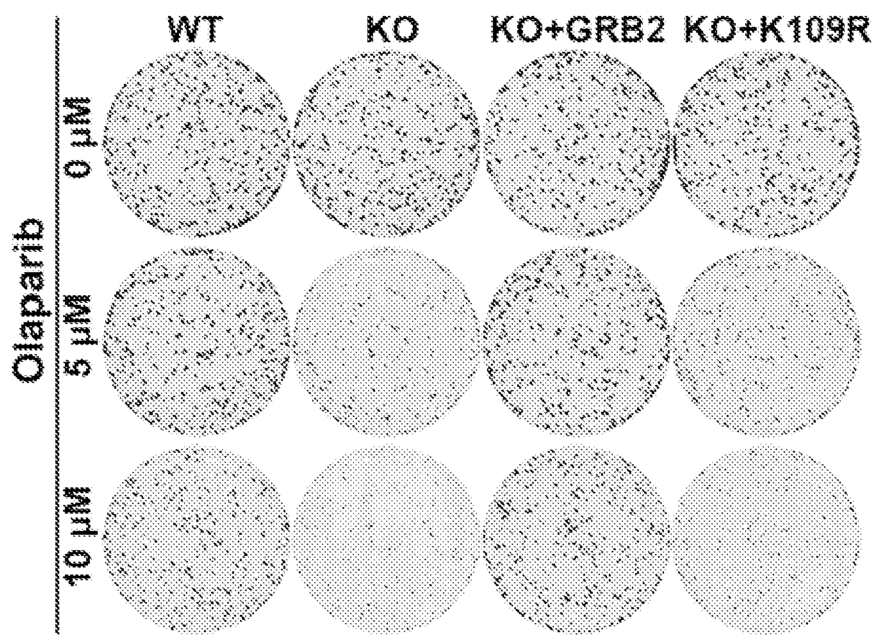
Figure 16A:
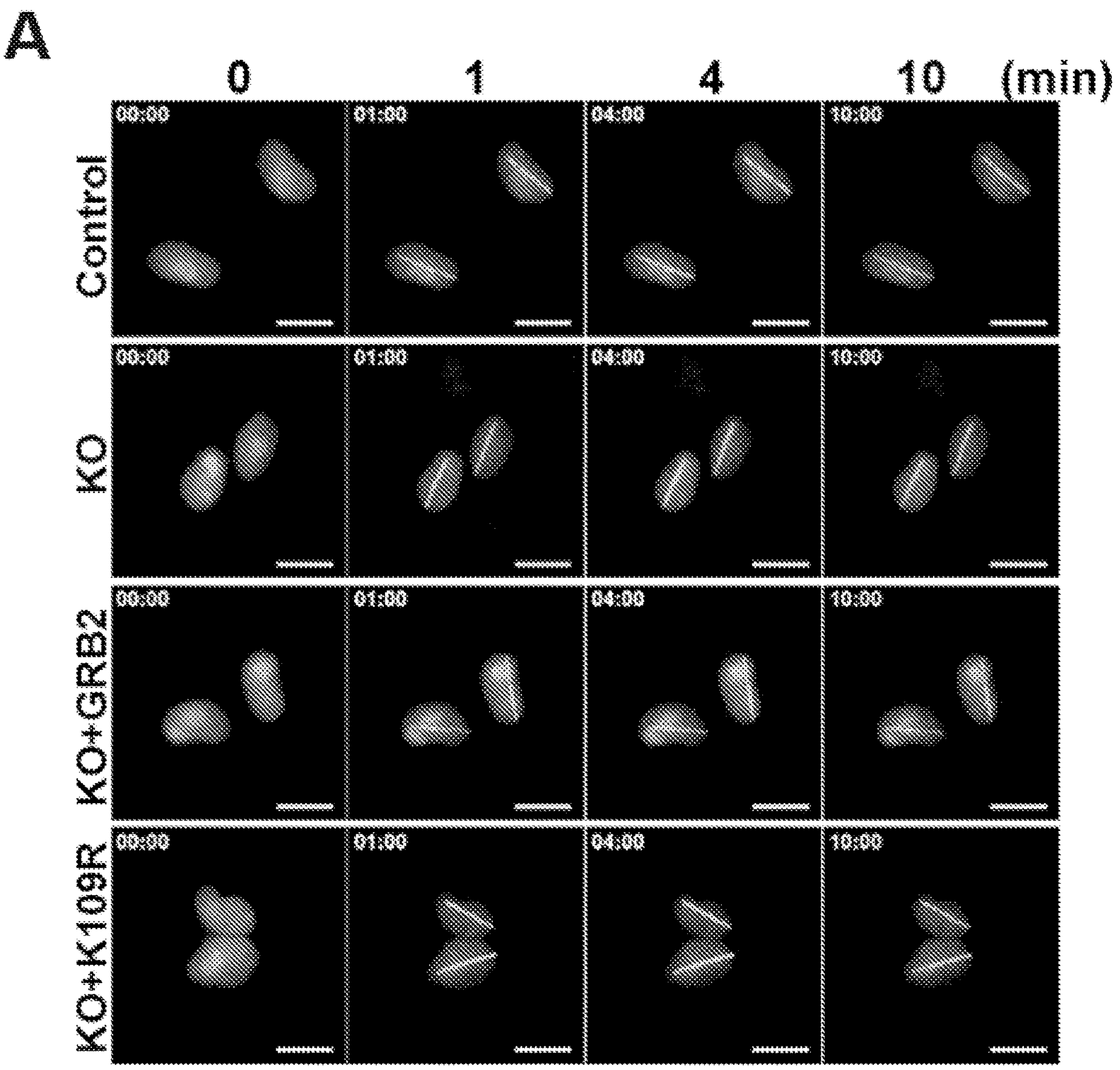
FIGS. 16A-16D. GRB2-KO sensitizes cells to PARP inhibitor Olaparib.
Figure 16B:
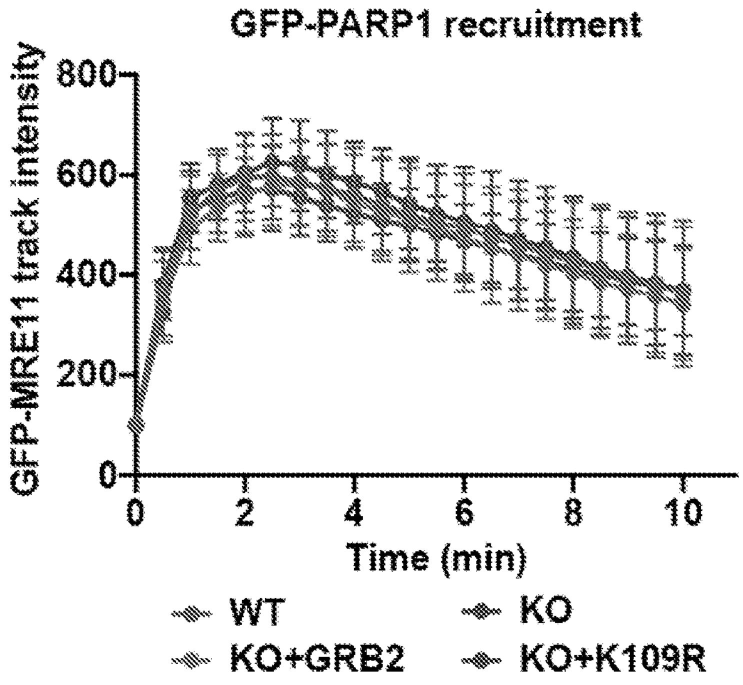
Figure 16C:
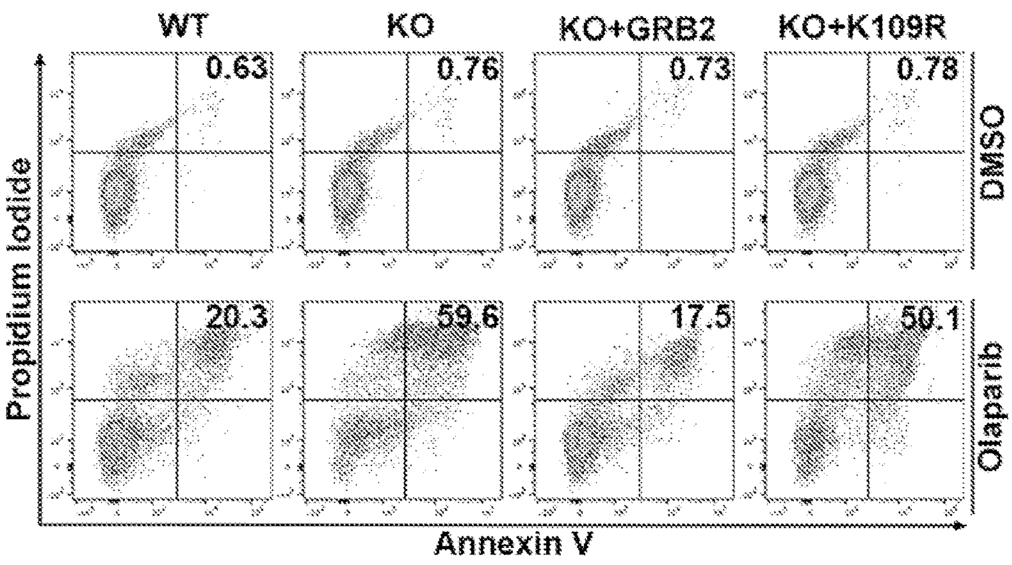
Figure 16D:
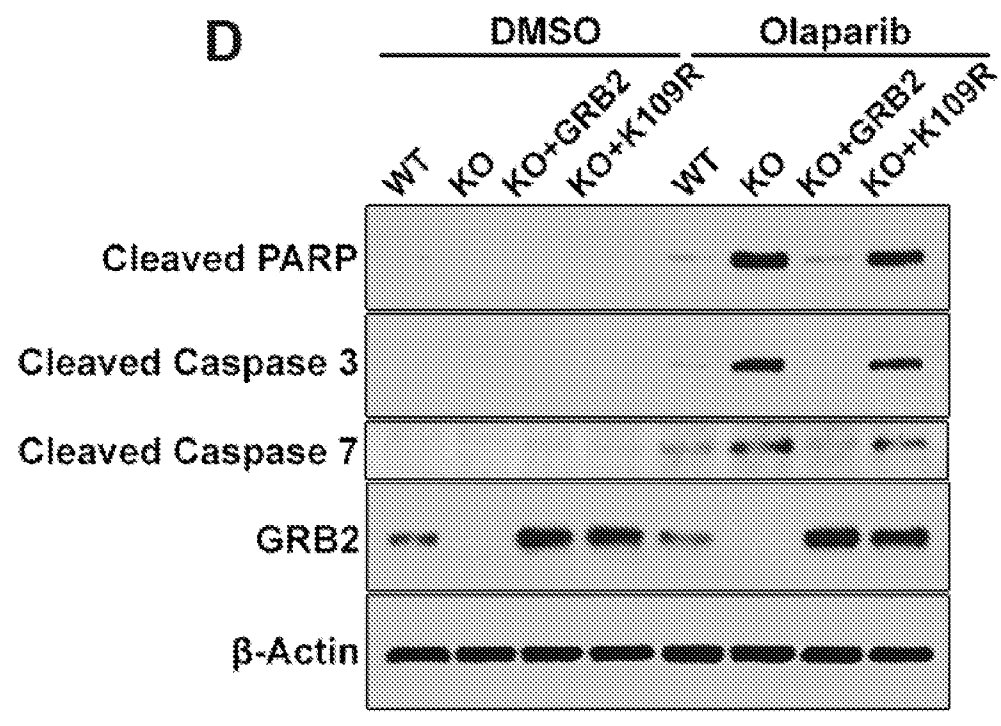

Combined GRB2 and PARP defects are synthetically lethal. As HDR deficiency causes synthetic lethality with PARP inhibitors (PARPi) (Ashworth and Lord, 2018) and GRB2-KO cells are HDR defective (FIG. 6A), the inventors reasoned that if GRB2 plays a key role in HDR then GRB2-KO cells would be PARPi sensitive. Therefore, the inventors compared PARPi olaparib sensitivity between control and GRB2-KO cells along with GRB2-KO cells reconstituted with either $^{WT}$GRB2 or $^{K109R}$GRB2. Sulforhodamine B assays revealed GRB2-KO cells were 7-times more sensitive to olaparib treatment ($IC_{50}$ 18±2.9 μM) than WT control cells ($IC_{50}$ 124±41 μM). Moreover, reconstitution of $^{WT}$GRB2 ($IC_{50}$ 164±47 μM), but not $^{K109R}$GRB2 ($IC_{50}$ 20±3 μM), caused desensitization (FIG. 7D). Additionally, in clonogenic survival assays, only the GRB2-KO and $^{K109R}$GRB2 reconstituted cells showed a severe reduction in colony formation in response to olaparib treatment (FIGS. 15I & 7E). UV-LMI experiments demonstrated that PARP1 recruitment to DNA damage sites was unaffected by GRB2 expression levels (FIGS. 16A & 16B). Annexin V/propidium iodide (PI) staining followed by fluorescence-activated cell sorting (FACS) analysis showed olaparib-induced apoptosis in 20% of the control (WT) cells, increasing to a staggering 60% in GRB2-KO cells, and reconstitution of $^{K109R}$GRB2 failed to rescue the phenotype (FIGS. 16C & 7F). These results correlated with measured PARP, caspase-3 and caspase-7 cleavage in GRB2-KO and $^{K109R}$GRB2 reconstituted cells (FIG. 16D). Thus, GRB2-KO is synthetically lethal with loss of PARP function, confirming GRB2's critical role in HDR.

Figure 8A:
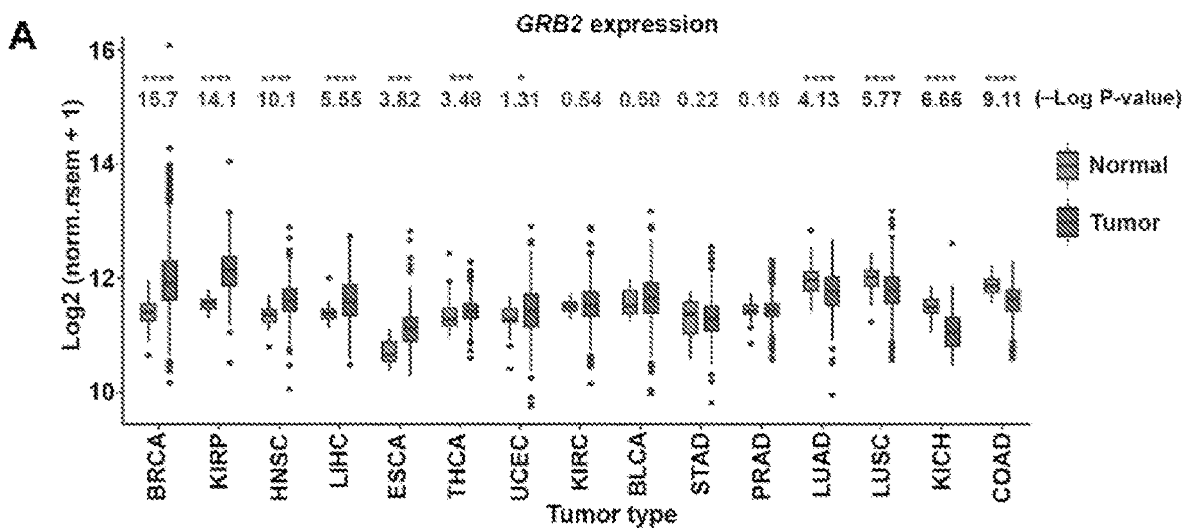
FIGS. 8A-8F. GRB2 expression affects survival upon high expression of MRE11 in an HDR-proficient cohort.
Figure 8B:
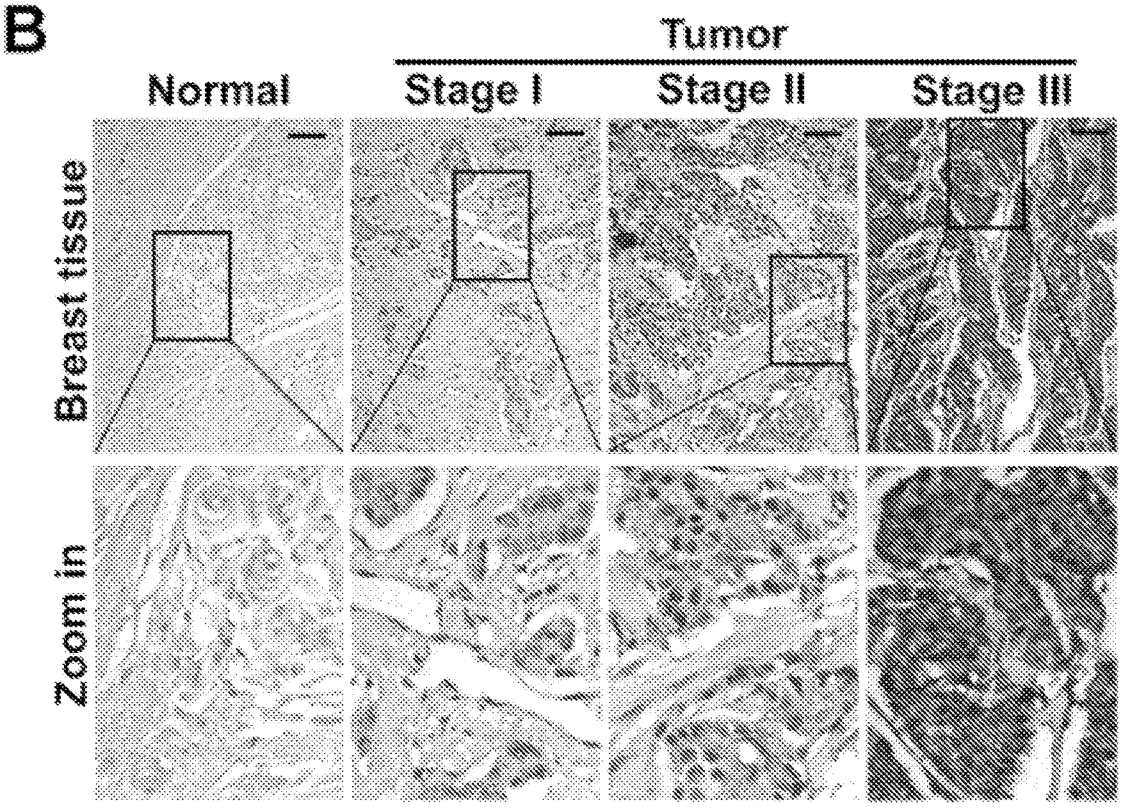
Figure 8C:
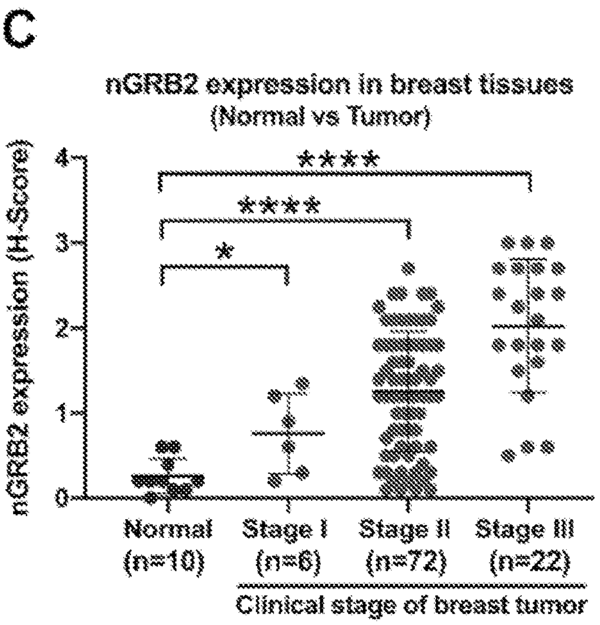

The GRB2-MRE11 axis correlates with cancer progression and survival. The inventors analyzed The Cancer Genome Atlas (TCGA) database to investigate whether a functional GRB2-MRE11 axis can be discerned in the clinical setting and if efficiency in GM-complex formation can translate into cancer patient outcome. GRB2 expression was upregulated in about half of the tumor types (FIG. 8A). As mentioned, in normal breast tissues nGRB2 expression was very low (FIG. 1B), and upregulation is therefore an indication of malignancy. The inventors further investigated nGRB2 expression with IHC using a human breast cancer tissue array containing clinical tumor samples at different stages (FIG. 8B). Analysis of 100 patient and 10 normal breast tissue samples revealed a correlation between protein expression and nuclear localization with disease progression. In late-stage diseases, more GRB2 expression and nuclear localization were observed compared to early stages or normal tissue (FIG. 8C). This incremental increase of GRB2 expression/nuclear localization suggests a potential predictive biomarker for tracking breast cancer progression.

Figure 8D:
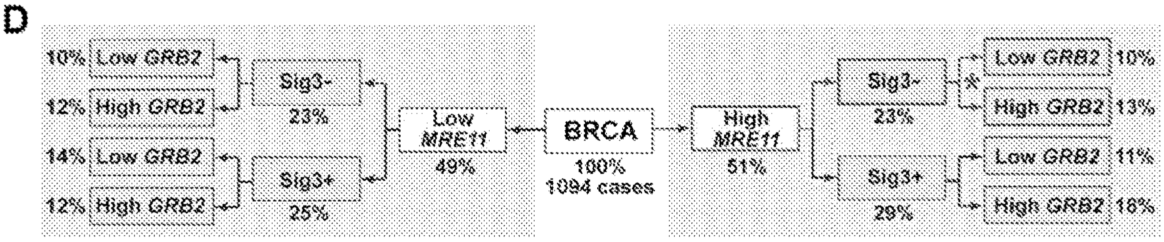
Figures 8E, 8F:
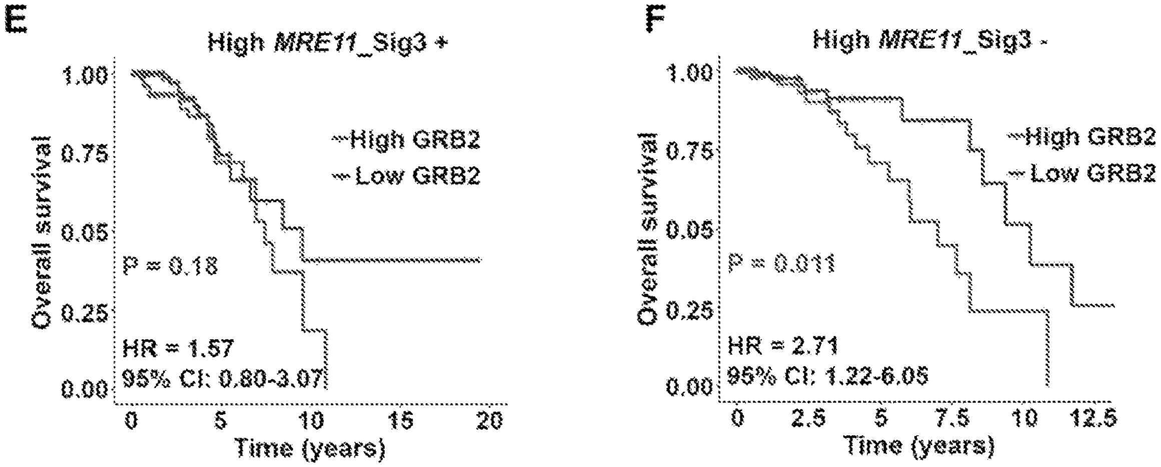
Figures 17A, 17B:
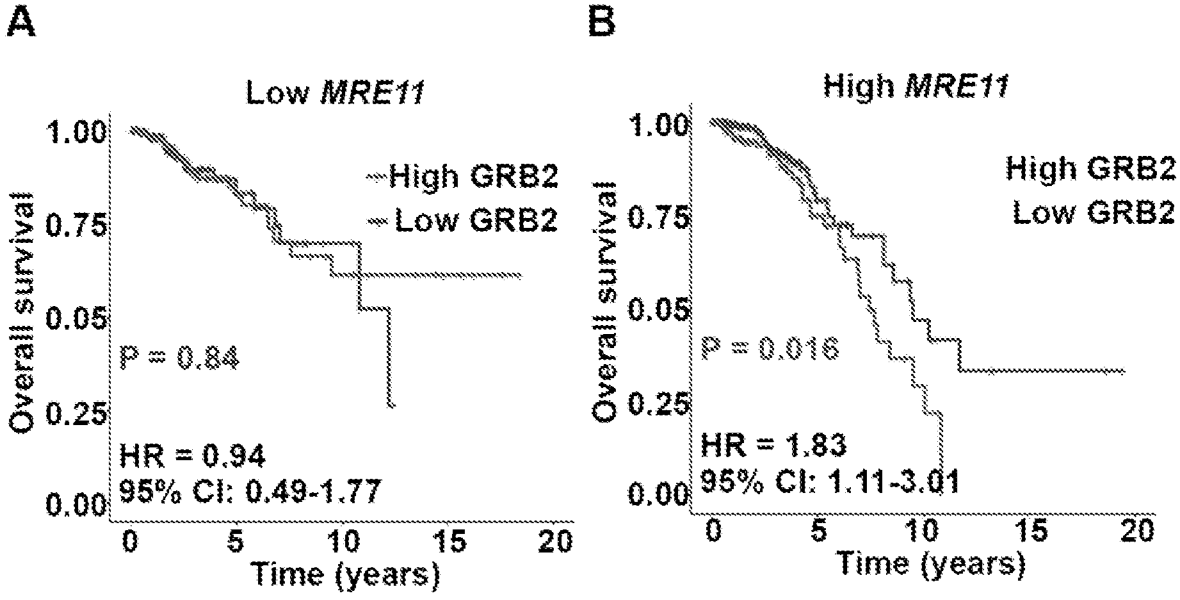
FIGS. 17A-17F. GRB2 gene expression does not affect the survival of patients with low MRE11 expression.
Figures 17C, 17D:
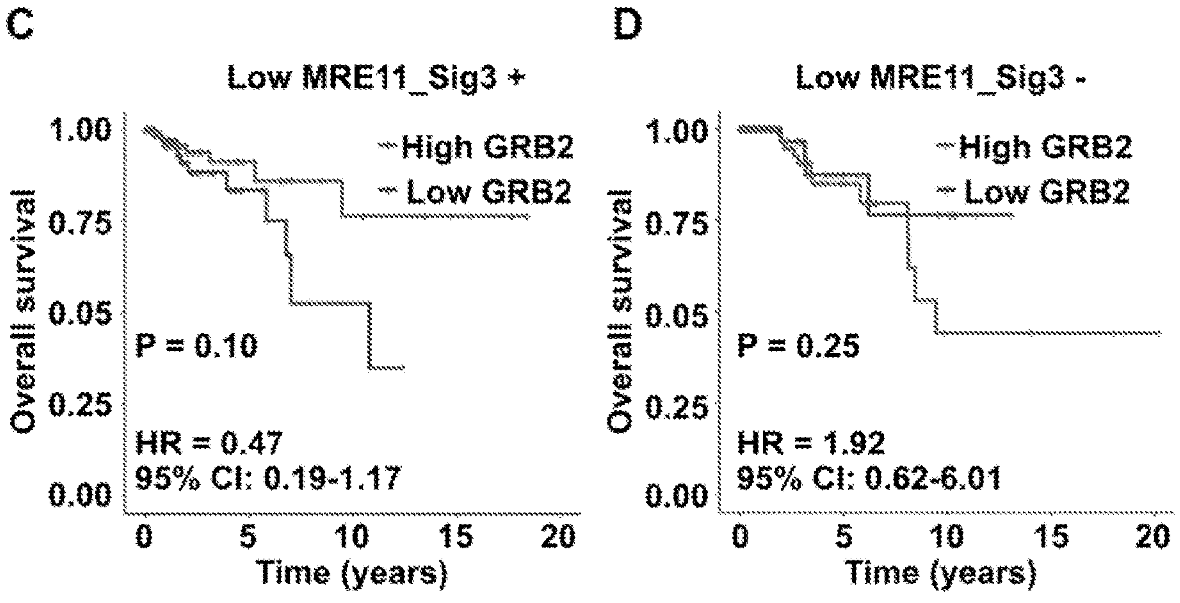
Figures 17E, 17F:
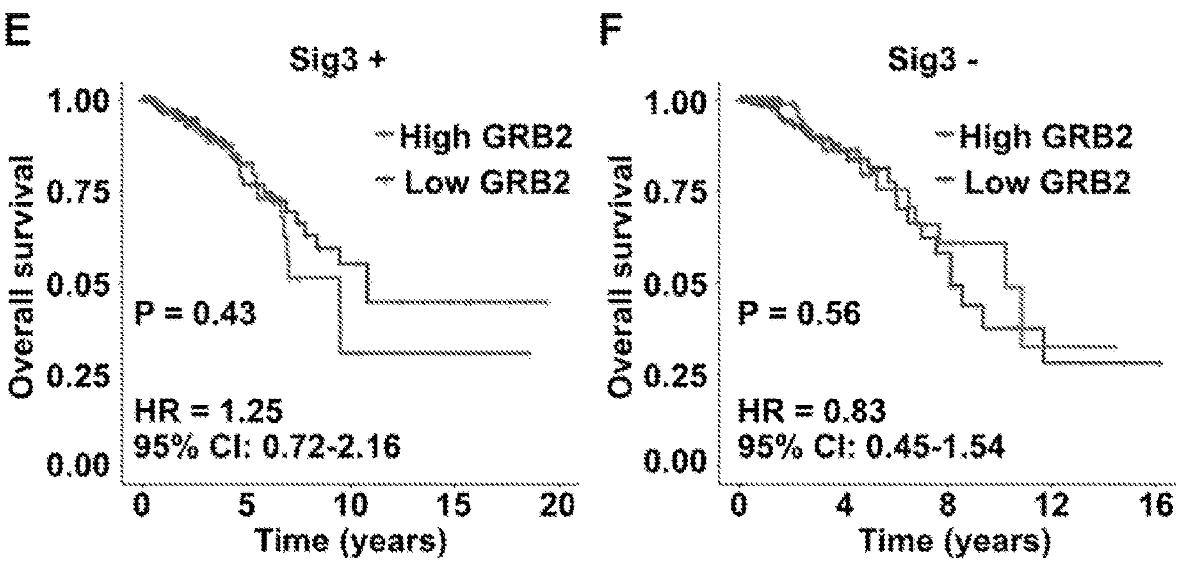

In breast cancer patients, where GRB2 was most upregulated relative to matched controls, co-upregulation of MRE11 with GRB2 was associated with worse clinical outcome (FIGS. 8D,17A,17B). Importantly, this poor prognosis was exquisitely dependent on patients' HDR status. Indeed, when breast cancer patients were stratified as HDR-proficient and HDR-deficient based on their signature 3 mutations (FIG. 8D), a pattern of single base substitution mutations strongly associated with BRCAness (Angus et al., 2019), only patients with no signature 3 mutations (HDR-proficient) combined with high MRE11 and high GRB2 expression exhibited increased risk. By contrast, survival was not affected in HDR-defective patients (signature 3 positive) with high MRE11 and high GRB2 (FIGS. 8E & 8F). Thus, in this context, GRB2 expression alone does not confer poor outcome unless it is correlated with MRE11 expression and HDR status. Importantly, these data imply upregulated GRB2 expression acting with MRE11 on the DDR specifically impacts survival of breast cancer patients. Likewise, survival was independent of HDR status in high- and low-GRB2-expressing patients when either MRE11 expression was low (FIGS. 17C & 17D) or when patients were not stratified according to MRE11 expression (FIGS. 17E & 17F). The collective experimental and bioinformatics data imply that MRE11 and GRB2 are partners in the DDR in cancer, where cells with fully operational HDR may utilize the GM complex pathway to recover from oncogenic replication stress and DSBs, providing benefit to tumor growth at the expense of patients' lives. These observations reinforce our molecular findings and suggest that disruption of the GRB2-MRE11 signaling axis may be therapeutically beneficial to the subpopulation of HDR proficient breast cancer patients with co-upregulated GRB2 and MRE11.

In addition, FIG. 16 shows that GRB2 inhibitors having an effect on the DNA repair pathway. H1299 cells, which are highly resistant to radiation, were treated with small molecule GRB2 inhibitors and then exposed to radiation or not. It can be seen that a number of the small molecules tested specifically sensitized the cells to ionizing radiation, only showing specific cell-killing when combined with radiation.

Figure 9A:
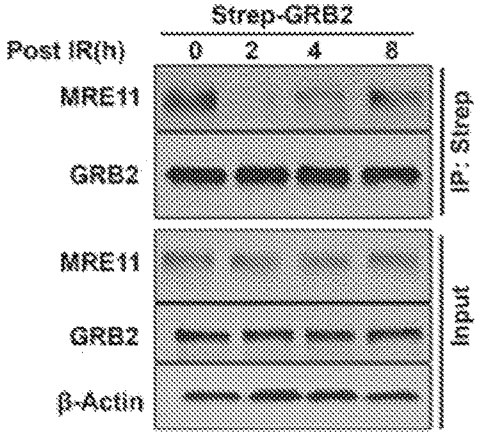
FIGS. 9A-9F. Ubiquitinated GRB2 releases MRE11 at the DSB sites.

GRB2 is a key regulator of MRE11 recruitment and release for HDR function. GRB2 chromatin recruitment begins immediately following IR, and peaks at 15-30 min (FIGS. 4D, left panel and 4E). Ubiquitination of GRB2, on the other hand, first detected in the nucleoplasm of cells at 15 min and reaching maxima at 120 min (FIG. 4D, right panel). Furthermore, IR-induced increase in nGRB2 correlated with an apparent proportional decrease of GRB2 in the cytoplasm (FIG. 13C). These data indicate a dynamic temporal regulation of GRB2 concentration across cellular compartments and the disruption of GRB2-MRE11 interaction by ubiquitination of GRB2. The inventors therefore tested the effect of GRB2 ubiquitination on MRE11 interaction by co-complex analysis. Strep-tagged GRB2 precipitations were performed in cells treated with IR (time '0') and then recovered for 2, 4 or 8 h, and MRE11 1 co-precipitation was monitored by western blotting. The results revealed that at the height of GRB2 ubiquitination at 2 h post-IR (FIGS. 1K,4D,13C), the GM complex was drastically reduced (FIG. 9A). At 4 and 8 h post-IR, when the level of ubGRB2 was decreasing, the GM complex began to recover. Thus, ubGRB2 releases MRE11 and non-ubGRB2 promotes GM complex formation.

Figure 18:
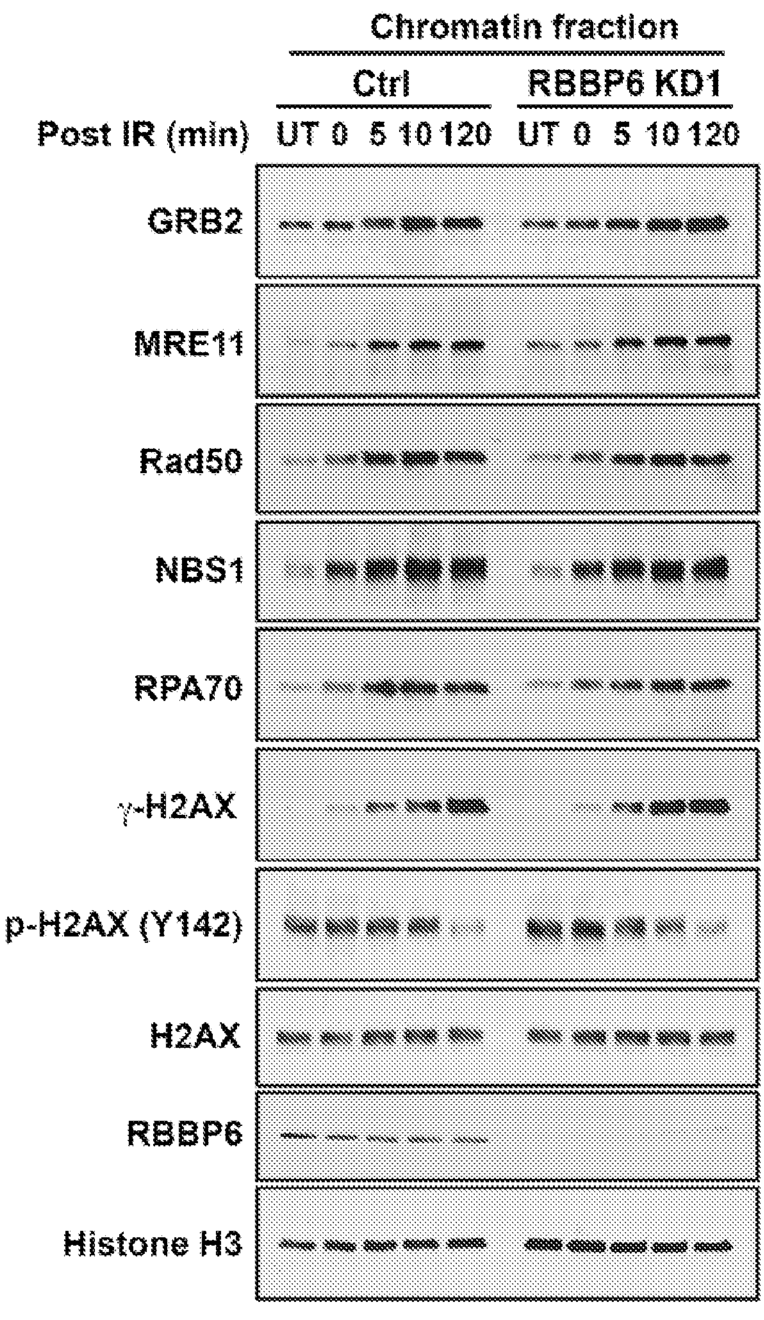
FIG. 18. The impact of RBBP6 on chromatin uploading of HDR proteins. Direct comparison of HDR protein recruitment onto chromatin between WT and RBBP6-KD HeLa cells. Cells were either untreated (UT) or irradiated with 5 Gy IR (152 sec), then lysed immediately (0 min) or allowed to recover for the indicated time. Chromatin fractions were analyzed by western blot with the indicated antibody.
Figure 19:
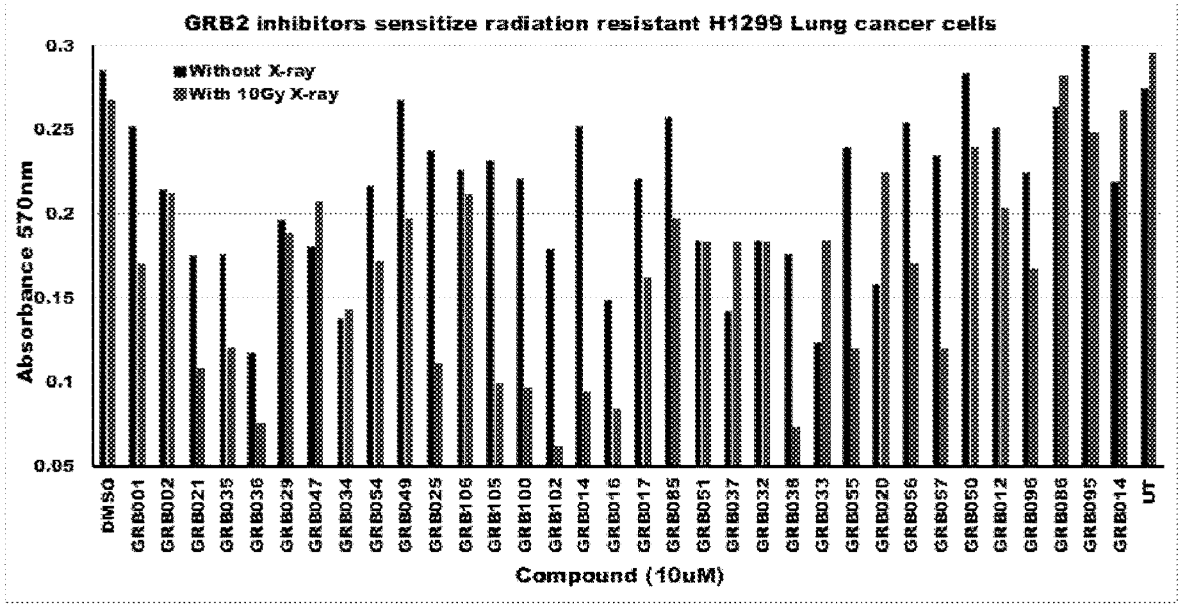
FIG. 19. MTT cell viability assay. GRB2-inhibitor-treated cells were either left untreated or irradiated with 10 Gy x-ray and allowed to recover for 48 hours. Cell viability was quantified with MTT assay reagents.

To further test the role of ubiquitination in GM interaction, the inventors knocked down RBBP6 (RBBP6-KD) from cells and performed the same strep-GRB2 co-immunoprecipitation study. In wild-type cells, following IR, the GM complex decreased incrementally over time to its lowest level at 2 h post-IR. In RBBP6-KD cells, on the other hand, the GM complex persisted for an extended period of time and was readily detectable at 1 and 2 h post-IR (FIG. 9B; upper two panels, MRE11 levels indicated by *). RBBP6 depletion caused no change in IR-induced GRB2, MRE11 and other HDR protein recruitment to chromatin (FIG. 18). Additional co-precipitation experiments with ubiquitination-defective $^{K109A}$GRB2 mutant revealed that lack of ubiquitination maintained the GM complex at 2 h after IR treatment (FIG. 9C).

Figure 9B:
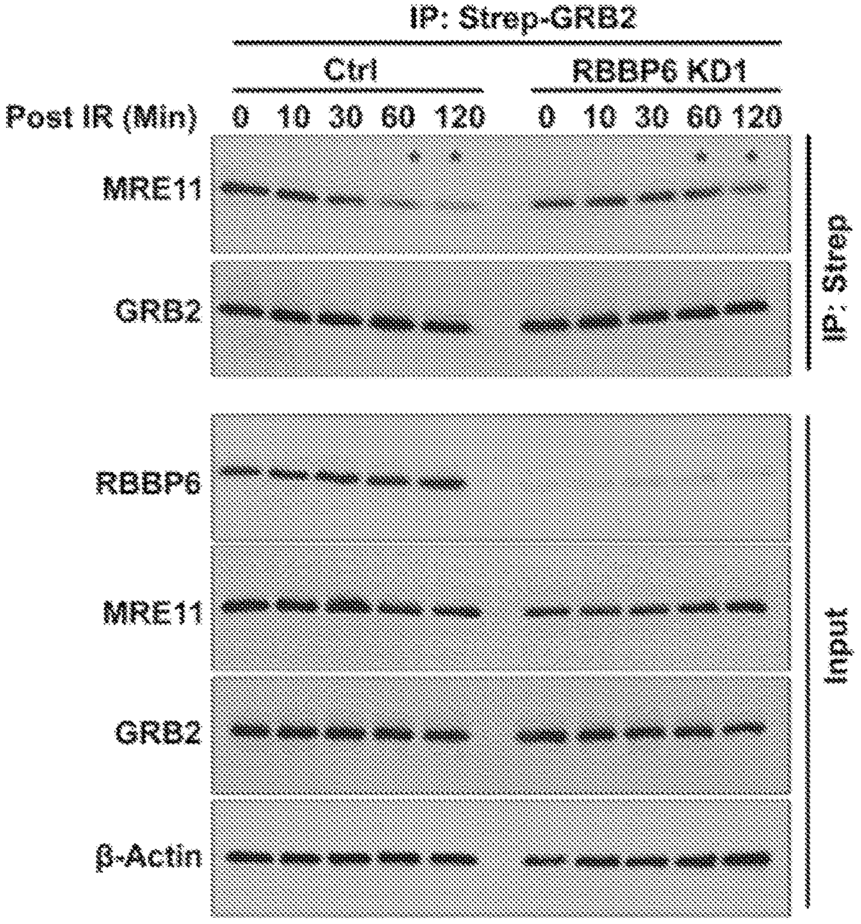
Figure 9C:
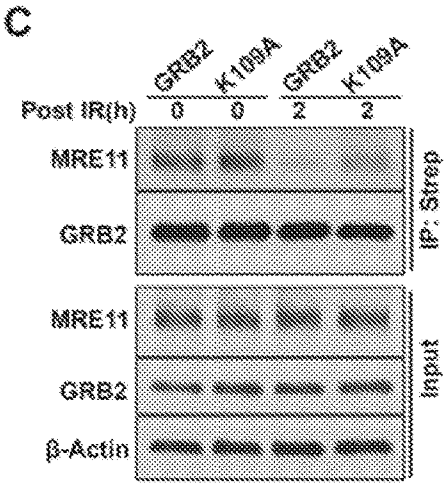
Figures 9D, 9E:
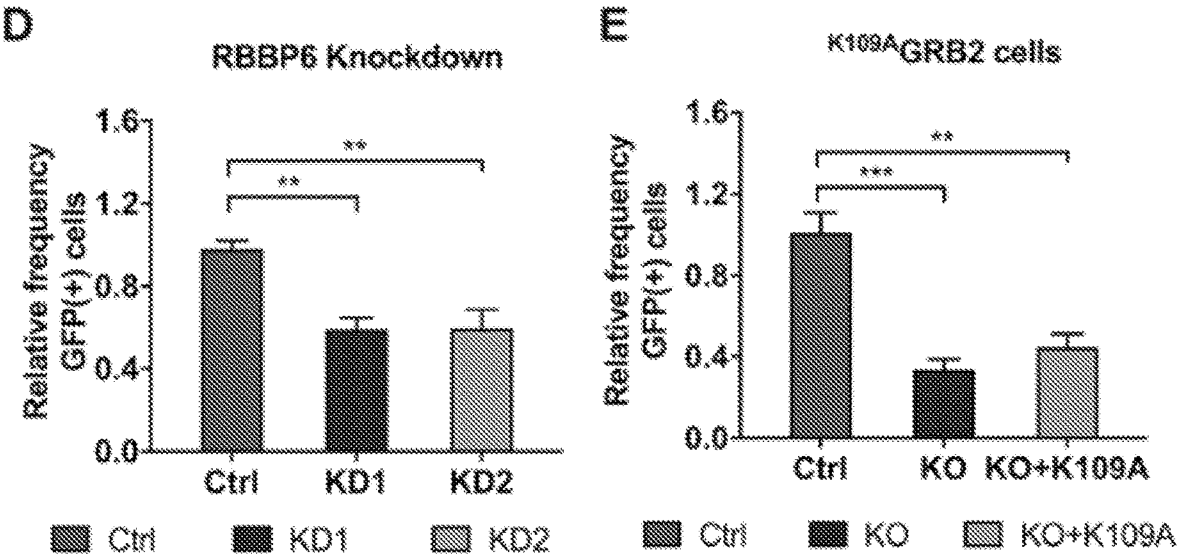
Figure 9F:
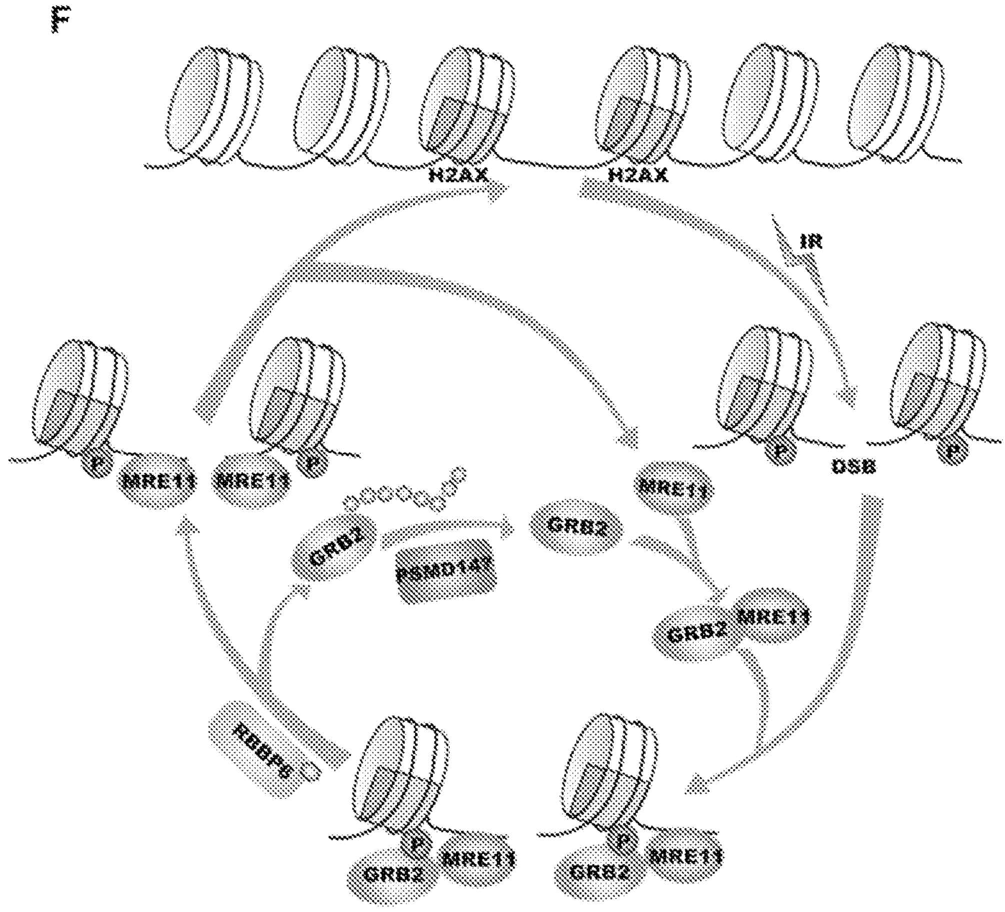

In the absence of RBBP6 ubiquitin ligase, GRB2 ubiquitination was abrogated (FIG. 1G), resulting in lingering GM complexes (FIG. 9B). The inventors investigated the consequence of the prolonged GM complexes in DSB repair using I-SceI-based assays for HDR (Gunn et al., 2012) in RBBP6 knocked-down (KD) cells. The results from two different RBBP6 shRNA knockdowns (KD1 and KD2) revealed significant HDR reduction (FIG. 9D). To further test if the observed HDR reduction in RBBP6-KD cells was due to GRB2 ubiquitination defects, the inventors used the $^{K09A}$GRB2 mutant reconstituted GRB2-KO cells to measure HDR efficiency. Consistent with the RBBP6-KD results, $^{K109A}$GRB2 failed to rescue the HDR defect caused by GRB2-KO (FIG. 9E), suggesting ubiquitination-mediated MRE11 release at DSBs is important for error-free HDR repair. Collectively, these data revealed a pool of MRE11 in the nucleoplasm bound to GRB2 (the GM complex), which appear to be separate from MRE11 in the canonical MRN complex (Syed & Tainer, 2018). Immediately following DNA damage, GRB2 efficiently recruits MRE11 to pH2AX-marked DNA damage sites, where MRE11 is released for HDR by ubiquitination of GRB2 at K109 by RBBP6, whereas deubiquitination re-enables the GM complex formation (FIG. 9F).

Discussion Timely recruitment and site-specific assembly of proteins is fundamental to effective cellular responses in all aspects of cell biology. DNA repair and genome fidelity critically depend on timely recruitment and regulated release or handoffs of damage excision enzymes, as initially shown for APE1 in base excision repair (BER) (Mol et al., 2000). For DSBs, the inventors collective findings unveil an GRB2 adapter complex for recruitment and release of MRE11 for efficient HDR. GRB2's cytoplastic role in proliferative RAS/MAPK/ERK kinase pathway activation is unexpectedly complemented by a nuclear role in targeting MRE11 for the repair of the DSB's, as expected to be associated with replication and proliferative stress. The GRB2-SH2 domain binds MRE11 through a novel binding interface tailored to GRB2 DDR function. As RPA70 binds to a conserved OB1 fold in the nSH3 domain of GRB2, which occurs in many DNA repair proteins (e.g. BRCA2, BLM-complex proteins and Ligase-1 (Flynn & Zou, 2010)), further studies may test and uncover GRB2 as an adapter for recruitment of other DNA repair proteins. Currently, GRB2 targeting of MRE11 and RPA to □H2AX for efficient HDR has apparent analogies to recruitment of NEIL glycosylase to oxidation-susceptible open chromatin sites for efficient BER, as revealed by the striking correspondence between NEIL1 occupancy and mutation rates along the genome (Bacolla et al., 2021).

The present results provide mechanistic insight into GRB2-mediated temporal regulation of MRE11 recruitment to DSB sites, with profound functional consequences for HDR and implied relevance to human cancer and treatment choice. We reveal a pool of MRE11 in the nucleoplasm that is bound to GRB2 (GM complex) independent of RAD50 and NBS1. Following DNA damage, GRB2 efficiently recruits MRE11 to pH2AX marked DNA damage sites. GRB2 ubiquitination at K109 by RBBP6 blocks GM complex formation, and deubiquitination re-enables complex re-association (FIG. 10). The GRB2-SH2 domain binds MRE11 but through a novel binding interface tailored to the DNA damage response function of GRB2. In addition, RPA70 binds to a conserved OB1 fold in the nSH3 domain of GRB2. The OB1 fold domain module is present in many DNA repair proteins including BRCA2, BLM and Ligase-1 (Flynn and Zou, 2010); therefore, GRB2 may have the ability to act as an adapter for other DNA repair proteins.

GRB2 promotes HDR and suppresses Alt-EJ, suggesting GRB2 has an important role for maintaining genome integrity. GRB2-KO cells show an immediate measurable down-regulation of DNA repair activity except for the Alt-EJ. While one might argue this impact is due to loss of RAS/MAPK signaling in GRB2-KO cells, it is unclear why Alt-EJ would be upregulated under the same condition unless nGRB2 adaptor targeting GM to pH2AX is competing with XRCC1 adaptor, which forms an active alt-EJ repair complex with MRE11 and POLQ that supports alt-EJ activity (Dutta et al., 2017; Eckelmann et al., 2020). Also, the adapter protein XRCC1, which forms a repair complex with MRE11 and POLQ that supports Alt-EJ activity (Dutta et al., 2017; Eckelmann et al., 2020), is upregulated in GRB2-depleted cells. Thus the interplay between nuclear and cytosolic GRB2 function and the possibility that MRE11 switches between GM complexes for HDR and XRCC1 complex for Alt-EJ merits future investigation. Furthermore, the reconstitution of our separation-of-function K109R mutant GRB2 provides an MRE11-dependency in each pathway. Notably, the K109R mutant retains all cytoplasmic function but cannot bind its DDR protein partners and is therefore unable to recruit MRE11 to the DNA damage site. The GFP reporter assays show that NHEJ is downregulated by GRB2-KO and can be fully rescued by the mutant K109R reconstitution, which also suppressed the elevated Alt-EJ to normal levels. The K109R mutant only partially rescues SSA. In the absence of MRE11, EXO1 could provide the necessary resection required for SSA repair (Symington, 2016; Williams et al., 2008). Most importantly, the $^{K109R}$GRB2, which is defective in MRE11 binding, and $^{K109A}$GRB2, which is defective in MRE11 release, both failed to rescue HDR highlighting the importance of GM complex for this pathway.

In sum, GRB2 nuclear functions revealed here provide mechanistic insight into MRE11 recruitment to DSB sites with functional consequences for HDR and human cancer. GRB2 only impacting the survival of HDR-proficient patients with high MRE11 expression was seen in the TCGA database analysis. These results unveil indispensable GRB2 nuclear functions aside from its canonical RTK-RAS signaling axis. BRCA-proficient patients with high MRE11 and low GRB2 are a non-canonical HDR-deficient group with cancer progression vulnerability; this profile thus could serve as a potential biomarker to guide PARPi patient selection. Furthermore BRCA-proficient patients with high MRE11 and low GRB2 are a non-canonical HDR-deficient group with cancer progression vulnerability. Indeed, both GRB2-KD and GRB2-KO cells are HDR deficient, which causes synthetic lethality to PARPi-treated cells. Indeed, both GRB2-KD and GRB2-KO cells are HDR deficient, which causes synthetic lethality to PARPi-treated cells. Overall, these results unveil GRB2's critical role for DDR by efficiently recruiting MRE11 to initiate HDR rather than Atl-EJ and provide broader implications for cancer biology and for targeting synthetic lethality in clinical anti-cancer efforts.

Example 2—Materials and Methods

Reagents. Antibodies against p-ERK1/2 (4370S), ERK1/2 (4695S), p-Akt (S473) (4060S), Akt (4685S), Ubiquitin (3936S), Ubiquitin (3933S), Cleaved PARP (Asp214) (5625S), Cleaved Caspase-3 (Asp175) (D3R6Y) (9664S), Cleaved Caspase-7 (Asp198) (D2Q3L) (8438S), MRE11 (4847S), RPA70 (2267S), H2AX (7631S), p-H2AX (S139X20E3) (9718S), RAD50 (3427S), NBS1(14956S), XRCC1 (2735S), Histone H3 (4499S) and β-Actin (3700S) were ordered from Cell Signaling. Antibodies against GRB2 (C-23) (sc-255), GAPDH (sc-47724), E-cadherin (sc-21791), Lamin A (sc-71481), CBLL1 (sc-517157), RING2 (sc-101109), RBBP6 (M56) (sc-9962), GST (sc-138), GFP (sc-9996) and SOS1(sc-10803) were purchased from Santa Cruz Biotechnology. Antibodies against γH2AX (S139) (05-636) and p-H2AX (Y142) (07-1590) were ordered from Millipore Sigma. Antibodies against MRE11 (ab214), NBS1 (ab181729) and RAD50 (ab124682) were purchased from abcam. Antibodies against Strep-tag (A00626), RFP-tag (A00682) and Flag-tag (A00187) were ordered from GenScript. Antibody against Rad51 (GTX100469) was from GeneTex. Antibody against CtIP (61141) was from Active Motif. Antibody against BrdU (347580) was from BD Biosciences and antibody against RBBP6 (NBP1-49535) was from Novus Biologicals. CBLL1 shRNA1 (V2LHS_157953), CBLL1 shRNA2 (V3LHS_319113), RING2 shRNA1 (V2LHS_188269), RING2 shRNA2 (V3LHS_640474), RBBP6 shRNA1 (V2LHS_255063), RBBP6 shRNA2 (V3LHS_353550), MRE11 shRNA1 (V2LHS_202468), MRE11 shRNA2 (V2LHS_202464), PTEN shRNA1 (V2LHS_231477), PTEN shRNA2 (V2LHS_192536) and GRB2 shRNA (V2LHS_137365) were ordered from Dharmacon. Flag-MRE11, Flag-RAD50 and Flag-H2AX plasmids were purchased from Origene. Mutants H2AX S139A, H2AX Y142, GRB2 K109R, GRB2 K109A, GRB2 DF/AA were generated by site-directed mutagenesis. GFP-MRE11 plasmid was a gift from Stephen Jackson (University of Cambridge, UK). gRNA sequence "CCTCGGCCCTTCATGAAGGAGCAAA" (SEQ ID NO: 2) was synthesized by Integrated DNA Technologies. pEGFP-MRE11 was a gift from Stephen Jackson (University of Cambridge, UK). NBS1-GFP plasmid was a gift from Jiri Lukas (University of Copenhagen, Denmark). GFP-RPA70 plasmid was kindly provided by Marc S. Wold (University of Iowa, USA). Flag-XRCC1 and Flag-POLQ plasmids were kindly provided by Sankar Mitra (Houston Methodist, USA). Phosphorylated EGFR synthetic peptide FLPVPE(pY)INQSVPKR (SEQ ID NO: 7), MRE11 peptide PWVNYQDGNLN (SEQ ID NO: 8), tyrosine-phosphorylated MRE11 peptide PWVN(pY)QDGNLN (SEQ ID NO: 9), phosphorylated H2AX (pH2AX) peptide PSGGK-KATQA(pS)QEY (SEQ ID NO: 10), phosphorylated H2AX (pH2AX) peptide PSGGKKATQASQE(pY) (SEQ ID NO: 11), dual phosphorylated H2AX (pH2AX) peptide PSGGK-KATQA(pS)QE(pY) (SEQ ID NO: 4) and GRB2 OB1 peptide KYDFKATADDELSFKRG (SEQ ID NO: 12) were purchased from GenScript. GFP-trap, FLAG agarose beads and Strep-Tactin beads were purchased from Chromotek (gta-10), Millipore Sigma (A2220), Millipore Sigma (71613) respectively.

Cell culture. HEK293T, NIH3T3 and A431 cells (purchased from ATCC) and mouse embryonic fibroblasts (MEFs) and H2AX-KO MEFs (gifts from Andre Nussenzweig, Center for Cancer Research, National Cancer Institute) were maintained in Dulbecco's modified Eagle's high-glucose medium (DMEM). HeLa cells (ATCC) were maintained in RPMI 1640 medium, HAP1 cells (Horizon Discovery) were maintained in Iscove's Modified Dulbecco's medium. U2OS cells (ATCC) were maintained in McCoy's 5A medium. Media were supplemented with 10% (vol/vol) fetal bovine serum (FBS) and 1% antibiotic/antimycotic (Lonza) in a humidified incubator with 10% $CO_2$. Stable HEK293T cells containing Strep-tagged GRB2 or GRB2 mutants were produced as described previously (Ahmed et al., 2013). The I-SecI reporter assay (a generous gift from Jeremy Stark, City of Hope) was performed as described previously(Gunn and Stark, 2012). The sulforhodamine B (SRB) cytotoxicity and colony formation assays were performed as described previously(Houl et al., 2019).

CRISPR/Cas9-mediated GRB2 knockout. GRB2 was knocked out by using the CRISPR/Cas9 system according to the protocol described previously (Sanjana et al., 2014; Shalem et al., 2014). The guide RNA targeting GRB2 was designed using an online tool available at crispr.mit.edu. DNA primers (forward primer 5'-CACCGGAGCCG-GAAGTCTTCCTC-3' (SEQ ID NO: 16); reverse primer 5'-AAACGAGGAAGTACTTCCCGGCTCC-3' (SEQ ID NO: 17)) for the GRB2 gRNA and reverse complement sequence plus adapters needed for ligation were synthesized from IDT and ligated into the LentiCRISPR v2 (Addgene #52961) or LentiCRISPR v2-Blast (Addgene #83480). Correct insertion of GRB2 gRNA was confirmed by sequencing the constructs. Lentivirus particles were generated in HEK293T cells. Cells were infected with lentivirus and then selected with puromycin or blasticidin. Single clones were picked up and GRB2 knockout was verified by western blotting. Mixture pools of different clones were used for experiments.

Western blots. Cells were seeded onto 10-cm dishes and grown for at least 24 h before experiments. Cells were lysed with RIPA buffer (20 mM Tris-HCl [pH 7.5], 150 mM NaCl, 1 mM $Na_2EDTA$, 1 mM EGTA, 1% IGPAL, 1% sodium deoxycholate, 2.5 mM sodium pyrophosphate, 1 mM p-glycerophosphate, 1 mM $Na_3VO_4$, 1 μg/ml leupeptin) supplemented with Protease Inhibitor Cocktail Set III (EMD Millipore) to obtain total proteins. Cell fractionation was done using a Subcellular Protein Fractionation Kit for Cultured Cells (ThermoFisher) according to the manufacturer's instructions.

Protein expression and purification. Expression and purification of GRB2 from bacteria have been described previously (Ahmed et al., 2015). The K109R and K109A mutant GRB2 was generated by site-directed mutagenesis and purified similarly as the wild type. Human MRE11 core (residues 1-411) purification was described previously (Park et al., 2011). The generation of individual GRB2 domains was as described before (Ahmed et al., 2010). The purification of RPA70N (1-120) was performed according to the published procedure(Souza-Fagundes et al., 2012).

Immunofluorescence. Designated cells were grown on coverslips, fixed with the addition of 4% (w/vol) paraformaldehyde (pH 8.0) with or without pre-extraction and washed four times with PBS (pH 8.0). After permeabilization with 0.5% Triton X-100 on ice for 5 min, cells were washed three times with PBS and incubated blocking buffer (PBS, 3% bovine serum albumin [BSA], 5% FBS and 0.5% Triton X-100) for 2 h at room temperature or overnight at 4° C. Following a further three washes with PBS, cells were incubated with primary antibody overnight in PBS, 3% BSA and 0.5% Triton X-100. Cells were then washed five or six times with PBS and incubated with the fluorescent conjugated secondary antibody for 2-3 h. Following another PBS wash, coverslips were mounted onto a slide with mounting medium (0.1% p-phenylenediamine and 75% glycerol in PBS at pH 7.5-8.0). For pre-extraction before fixation, cells were treated with cytoskeleton buffer (10 mM PIPES [pH 6.8], 100 mM NaCl, 300 mM Sucrose, 3 mM $MgCl_2$, 1 mM EGTA and 0.5% Triton X-100) for 5 min on ice and followed by washed by stripping buffer (10 mM Tris-HCl at [pH 7.4], 10 mM NaCl, 3 mM $MgCl_2$, 1% Tween 20 and 0.25% sodium deoxycholate) for 5 min on ice. Cells were imaged using either a Leica SP5 II or Zeiss LSM710 confocal microscope.

Ultraviolet laser microirradiation (UV-LMI). UV-LMI was performed as described previously (Feng and Chen, 2012): Cells were grown on 35-mm glass-bottom dishes (Matsunami), micro-irradiated with a MicroPoint ablation system (Photonics Instruments) with 60% laser output, and visualized with a Nikon Eclipse TE2000-U inverted microscope.

Alkaline comet assay. Untreated and IR-treated cells embedded in low-melting-point agarose were layered over a slide with a thin film of agarose. Cell were then lysed overnight at 4° C. in lysis buffer (10 mM Tris-HCl [pH 10], 2.5 M NaCl, 100 mM EDTA, 5% DMSO, 1% Triton X-100). After equilibration in electrophoresis buffer (300 mM NaOH, 1 mM EDTA [pH >13]) for 40 min at 4° C., electrophoresis was performed to identify DNA damage by the migration of small fragments of broken DNA away from the nucleus, forming a "tail" to the dense circular comet head of undamaged DNA. Nuclear DNA was visualized by staining with SYBR Gold solution, and images were captured using a Leica SP5 II microscope. The tail moment of each cell was analyzed by OpenComet software.

Annexin V/PI staining assay. To determine the percentage of olaparib-induced apoptotic cells, an Annexin V-propidium iodide (PI) staining assay was used according to the standard protocol (Life Technologies). Briefly, cells were cultured and treated with DMSO or 50 μM olaparib for 72 h. Then cells were trypsinized, washed and resuspended in Annexin-binding buffer. Cells were labeled by adding Annexin V-Alexa647 and PI to each sample. After incubation for 15 min at room temperature in the dark, samples were analyzed on a flow cytometer (FACSCanto IL, BD Biosciences) for the detection of Annexin V- and PI-positive subpopulations. DMSO-treated cells were used as a control, and each experiment was performed in triplicate. Further data analysis was performed with FlowJo V10 software.

Microscale thermophoresis. The MST method has been described in detail elsewhere (Seidel et al., 2013). The Kd values were measured using the Monolith NT.115 system (Nano Temper). Proteins were fluorescently labeled with Atto 488 according to the manufacturer's protocol. Labeling efficiency was determined to be 1:1 (protein:dye) by measuring the absorbance at 280 and 488 nm. A solution of peptides or proteins in 0.01 M HEPES (pH 7.4), 0.15 M NaCl and 0.005% v/v Surfactant P20 was serially diluted, typically from about 100 μM to 30 nM in the presence of 100 nM labeled protein. The samples were loaded into silica capillaries (Polymicro Technologies) after incubation at room temperature for 15 min. Measurements were performed at 22° C. using 20% LED power and 40% IR-laser power. Measurements were also carried out using 20% and 60% IR-laser power for comparison. Data analyses were performed using Nano Temper Analysis software using the Kd curve fitting function. Raw data were exported and fitting curves were generated using Prism 8 (GraphPad Software) for presentation.

Molecular docking. The inventors used the available GRB2 structure from the Protein Data Bank (PDB ID: 1GRI). The structure was prepared for docking by eliminating water and cofactors; a monomeric unit was used. The GRB2 coordinates were prepared and minimized using Protein Preparation Wizard (Schrödinger Suite 2019-2). The inventors aimed the molecular docking to the K109 site. The inventors docked ligands (in this specific experimental peptide) with length ≤20 Å with cubic box dimensions of 15 Å. The inventors also generated a mutant of GRB2, K109R, using the function "simply mutate" in Coot model-building software. In this structure, we aimed the docking to $R_{109}$. The inventors used the peptide docking utility implemented in the Schrödinger Suite; the peptides were added as a sequence in the specific section "Define peptide to dock." The inventors used the following peptide-derived sequences for MRE11, EGFR and γH2AX: Mre11-PWVNYQDGN (SEQ ID NO: 13), EGFR-NPVYHNQPL (SEQ ID NO: 14) and H2AX-SQEY (SEQ ID NO: 15), respectively. For the docking experiments, the inventors used Glide (Schrödinger Release 2019-2). The best docking results were selected and compared in superimposed sessions in the PyMOL molecular graphics system (PyMOL 2.0; Schrödinger).

Immunohistochemistry (IHC) and staining quantification. Breast cancer tumor tissue array slides (BC081116d; Biomax), normal human tissue array slides (MNO961; US Biomax) and the paraffin-embedded tissue sections of different mouse tissues were collected for determination of GRB2 distribution. Sections were dewaxed and rehydrated following a standard dewaxing protocol. Then the samples were exposed to 10 mM citric acid buffer (pH 6.0 for 20 min at 105° C.) for heat antigen retrieval, and exposed to 3% $H_2O_2$ for 12 min to block endogenous peroxidase activity. Subsequently, the samples were blocked with goat serum for 1 h and incubated with anti-GRB2 primary antibody (1:100) overnight. The VECTASTAIN® ABC HRP Kit (Peroxidase, Rabbit IgG) and DAB Substrate Kit (Peroxidase, HRP) were used to develop color, followed by a nuclear counterstaining with hematoxylin. Finally, the slides were mounted and visualized. Representative regions were selected and photographed. Two pathologists were tasked with evaluating IHC staining, and the H-score method was applied for calculating the staining score of each sample. In brief, each sample was assessed by staining intensity (negative: 0, weak: 1, moderate: 2, strong: 3) and staining extent (0%-100%), with H-score=[1×(staining extent of weak staining)+2×(staining extent of moderate staining)+3×(staining extent of strong staining)]. Three samples were used to quantify H-score for each tissue, and the average of H-score and standard deviation for all the cases were calculated and presented.

Mass spectrometry. To identify proteins associated with GRB2 in the nucleus, GRB2 was immunoprecipitated with Strep-Tactin beads (MilliporeSigma #GE28-9355-99) from the nuclear extracts of 293T cells expressing Strep-GRB2 or Strep-Ctrl. Three experimental samples and three matched negative controls were prepared independently for mass spectrometry. The MS spectra by using the Myrimatch and Sequest search engines were matched to the human protein database. Scaffold 3 was used to analyze the fold-enrichment values of each sample compared to the matched negative control sample. Proteins enriched at least 1.5 fold with a p-value less than 0.05 (Fisher test) as computed by Scaffold 3 were selected and listed. The proteins in the list were used to conduct the pathway and network analysis by BINGO in Cytoscape 3.7.2 (Maere et al., 2005). Hypergeometric tests were performed and corrected by Benjamini and Hochberg false discovery rate correction. A p-value of less than 0.05 was considered significant.

Statistical analysis. All statistical analyses were performed using GraphPad Prism 8 utilizing multiple 1-test function.

TCGA data analysis. The inventors retrieved the gene expression and clinical patient data to estimate the Kaplan-Meier survival curved from TCGA using the TCGA-Assembler suite available at github.com/compgenome365/TCGA- Assembler-2. For gene expression analyses between tumor and matched controls we selected the datasets with at least 10 matched controls. Data were plotted with the R packages ggpllot2 and ggpubr. Survival curves and hazard ratios were obtained with the survminer, survival and dplyr R packages. Signature 3 mutations are available at synapse.org/#!Synapse:syn11801497.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Anderson, *Practical Process Research & Development—A Guide for Organic Chemists,* 2nd ed., Academic Press, New York, 2012.

*Handbook of Pharmaceutical Salts: Properties, and Use*, Stahl and Wermuth Eds., Verlag Helvetica Chimica Acta, 2002.

Reagan-Shaw et al., *FASEB J.,* 22(3):659-661, 2008.

Smith, *March's Advanced Organic Chemistry: Reactions, Mechanisms, and Structure,* 7th Ed., Wiley, 2013.

International Patent Application No. PCT/US2020/022722

Ahmed, R. George, C. C. Lin, K. M. Suen, J. A. Levitt, K. Suhling, J. E. Ladbury, Direct binding of Grb2 SH3 domain to FGFR2 regulates SHP2 function. Cell Signal 22, 23-33 (2010).

Ahmed, C. C. Lin, K. M. Suen, F. A. Melo, J. A. Levitt, K. Suhling, J. E. Ladbury, Grb2 controls phosphorylation of FGFR2 by inhibiting receptor kinase and Shp2 phosphatase activity. J Cell Biol 200, 493-504 (2013).

Ahmed, Z. Timsah, K. M. Suen, N. P. Cook, G. R. t. Lee, C. C. Lin, M. Gagea, A. A. Marti, J. E. Ladbury, Grb2 monomer-dimer equilibrium determines normal versus oncogenic function. Nat Commun 6, 7354 (2015).

Angus, M. Smid, S. M. Wilting, J. van Riet, A. Van Hoeck, L. Nguyen, S. Nik-Zainal, T. G. Steenbruggen, V. C. G. Tjan-Heijnen, M. Labots, J. van Riel, H. J. Bloemendal, N. Steeghs, M. P. Lolkema, E. E. Voest, H. J. G. van de Werken, A. Jager, E. Cuppen, S. Sleijfer, J. W. M. Martens, The genomic landscape of metastatic breast cancer highlights changes in mutation and signature frequencies. Nat Genet 51, 1450-1458 (2019).

Aoki, M. Yamada, K. Kunida, S. Yasuda, M. Matsuda, Processive phosphorylation of ERK MAP kinase in mammalian cells. *Proc Natl Acad Sci USA* 108, 12675-12680 (2011).

Ashworth, C. J. Lord, Synthetic lethal therapies for cancer: what's next after PARP inhibitors? Nat Rev Clin Oncol 15, 564-576 (2018).

Bacolla, S. Sengupta, Z. Ye, C. Yang, J. Mitra, R. B. De-Paula, M. L. Hegde, Z. Ahmed, M. Mort, D. N. Cooper, S. Mitra, J. A. Tainer, Heritable pattern of oxidized DNA base repair coincides with pre-targeting of repair complexes to open chromatin. Nucleic Acids Res 49, 221-243 (2021).

Bai, W. Wang, S. Li, J. Zhan, H. Li, M. Zhao, X. A. Zhou, S. Li, X. Li, Y. Huo, Q. Shen, M. Zhou, H. Zhang, J. Luo, P. Sung, W. G. Zhu, X. Xu, J. Wang, C1QBP Promotes Homologous Recombination by Stabilizing MRE11 and Controlling the Assembly and Activation of MRE11/RAD50/NBS1 Complex. *Mol Cell* 75, 1299-1314 e1296 (2019).

A. N. Blackford, S. P. Jackson, ATM, ATR, and DNA-PK: The Trinity at the Heart of the DNA Damage Response. Mol Cell 66, 801-817 (2017).

Buday et al., *J. Biol. Chem.,* 269:9019-9023, 1994.

Butler et al. *EMBO J.,* 31:3918-3934, 2012.

Celeste et al., *Science,* 296:922-927, 2002.

Chang, S. Tsai, M. J. Aristizabal, J. P. Wells, Y. Coulombe, F. F. Busatto, Y. A. Chan, A. Kumar, Y. Dan Zhu, A. Y. Wang, L. A. Fournier, P. Hieter, M. S. Kobor, J. Y. Masson, P. C. Stirling, MRE11-RAD50-NBS1 promotes Fanconi Anemia R-loop suppression at transcription-replication conflicts. Nat Commun 10, 4265 (2019).

Chapman, S. P. Jackson, Phospho-dependent interactions between NBS1 and MDC1 mediate chromatin retention of the MRN complex at sites of DNA damage. EMBO Rep 9, 795-801 (2008).

Chardin, J. H. Camonis, N. W. Gale, L. van Aelst, J. Schlessinger, M. H. Wigler, D. Bar-Sagi, Human Sos1: a guanine nucleotide exchange factor for Ras that binds to GRB2. *Science* 260, 1338-1343 (1993).

Cheng, T. M. Saxton, R. Sakai, S. Kulkarni, G. Mbamalu, W. Vogel, C. G. Tortorice, R. D. Cardiff, J. C. Cross, W. J. Muller, T. Pawson, Mammalian Grb2 regulates multiple steps in embryonic development and malignant transformation. *Cell* 95, 793-803 (1998).

Cook, B. G. Ju, F. Telese, X. Wang, C. K. Glass, M. G. Rosenfeld, Tyrosine dephosphorylation of H2AX modulates apoptosis and survival decisions. Nature 458, 591-596 (2009).

Dearth et al., *Cell Cycle,* 6:705-713, 2007.

Deshpande et al., *EMBO J.,* 33:482-500, 2014.

Donovan et al., *J. Biol. Chem.,* 269:22921-22924, 1994.

Dutta, B. Eckelmann, S. Adhikari, K. M. Ahmed, S. Sengupta, A. Pandey, P. M. Hegde, M. S. Tsai, J. A. Tainer, M. Weinfeld, M. L. Hegde, S. Mitra, Microhomology-mediated end joining is activated in irradiated human cells due to phosphorylation-dependent formation of the XRCC1 repair complex. Nucleic Acids Res 45, 2585-2599 (2017).

Eckelmann, A. Bacolla, H. Wang, Z. Ye, E. N. Guerrero, W. Jiang, R. El-Zein, M. L. Hegde, A. E. Tomkinson, J. A. Tainer, S. Mitra, XRCC1 promotes replication restart, nascent fork degradation and mutagenic DNA repair in BRCA2-deficient cells. NAR Cancer 2, zcaa013 (2020).

Feng, J. Chen, The E3 ligase RNF8 regulates KU80 removal and NHEJ repair. Nat Struct Mol Biol 19, 201-206 (2012).

Fernandez-Capetillo et al., *DNA Repair,* 3:959-967, 2004.

Flynn, L. Zou, Oligonucleotide/oligosaccharide-binding fold proteins: a growing family of genome guardians. Crit Rev Biochem Mol Biol 45, 266-275 (2010).

Gale et al., *Nature,* 363:88-92, 1993.

Giubellino et al., *Expert Opin. Ther. Targets,* 12:1021-1033, 2008.

Gunn, J. M. Stark, I-SceI-based assays to examine distinct repair outcomes of mammalian chromosomal double strand breaks. Methods Mol Biol 920, 379-391 (2012).

Hengel et al., Cell Chem. Biol., 24:1101-1119, 2017.

Hogrel, Y. Lu, S. Laurent, E. Henry, C. Etienne, D. K. Phung, R. Dulermo, A. Bosse, P. F. Pluchon, B. Clouet-d'Orval, D. Flament, Physical and functional interplay between PCNA DNA clamp and Mre11-Rad50 complex from the archaeon *Pyrococcus furiosus*. Nucleic Acids Res 46, 5651-5663 (2018).

Hou, S. Xu, Y. Xu, Q. Gao, C. Zhang, L. Liu, H. Yang, X. Jiang, Y. Che, Grb2 binds to PTEN and regulates its nuclear translocation to maintain the genomic stability in DNA damage response. *Cell Death Dis* 10, 546 (2019).

Houl, Z. Ye, C. A. Brosey, L. P. F. Balapiti-Modarage, S. Namjoshi, A. Bacolla, D. Laverty, B. L. Walker, Y. Pourfarjam, L. S. Warden, N. Babu Chinnam, D. Moiani, R. A. Stegeman, M. K. Chen, M. C. Hung, Z. D. Nagel, T. Ellenberger, I. K. Kim, D. E. Jones, Z. Ahmed, J. A. Tainer, Selective small molecule PARG inhibitor causes replication fork stalling and cancer cell death. Nat Commun 10, 5654 (2019).

Li et al., *Nature,* 363:85-88, 1993.

Lloyd, J. R. Chapman, J. A. Clapperton, L. F. Haire, E. Hartsuiker, J. Li, A. M. Carr, S. P. Jackson, S. J. Smerdon, A supramodular FHA/BRCT-repeat architecture mediates Nbs1 adaptor function in response to DNA damage. *Cell* 139, 100-111 (2009).

Lowenstein, R. J. Daly, A. G. Batzer, W. Li, B. Margolis, R. Lammers, A. Ullrich, E. Y. Skolnik, D. Bar-Sagi, J. Schlessinger, The SH2 and SH3 domain-containing protein GRB2 links receptor tyrosine kinases to ras signaling. *Cell* 70, 431-442 (1992).

Lv, S. Zhang, H. Wu, J. Lu, Y. Lu, F. Wang, W. Zhao, P. Zhan, J. Lu, Q. Fang, C. Xie, Z. Yin, Deubiquitinase PSMD14 enhances hepatocellular carcinoma growth and metastasis by stabilizing GRB2. Cancer Lett 469, 22-34 (2019).

Maere et al., *Bioinformatics,* 21:3448-3449, 2005.

McDonald et al., *Biochemistry,* 48:4074-4085, 2009.

Melander, S. Bekker-Jensen, J. Falck, J. Bartek, N. Mailand, J. Lukas, Phosphorylation of SDT repeats in the MDC1 N terminus triggers retention of NBS1 at the DNA damage-modified chromatin. J Cell Biol 181, 213-226 (2008).

Millet, N. Jolinon, X. N. Nguyen, G. Berger, A. Cimarelli, A. Greco, P. Bertrand, M. Odenthal, H. Buning, A. Salvetti, Impact of the MRN Complex on Adeno-Associated Virus Integration and Replication during Coinfection with Herpes Simplex Virus 1. J Virol 89, 6824-6834 (2015).

Miotto, M. Chibi, P. Xie, S. Koundrioukoff, H. Moolman-Smook, D. Pugh, M. Debatisse, F. He, L. Zhang, P. A. Defossez, The RBBP6/ZBTB38/MCM10 axis regulates DNA replication and common fragile site stability. Cell Rep 7, 575-587 (2014).

Mol, T. Izumi, S. Mitra, J. A. Tainer, DNA-bound structures and mutants reveal abasic DNA binding by APE1 and DNA repair coordination [corrected]. Nature 403, 451-456 (2000).

Park, J. Chae, Y. C. Kim, Y. Cho, Crystal structure of human Mre11: understanding tumorigenic mutations. Structure 19, 1591-1602 (2011).

T. T. Paull, R. A. Deshpande, The Mre11/Rad50/Nbs1 complex: recent insights into catalytic activities and ATP-driven conformational changes. Exp Cell Res 329, 139-147 (2014).

Paull, *Mol. Cell,* 71:419-427, 2018.

Paull, E. P. Rogakou, V. Yamazaki, C. U. Kirchgessner, M. Gellert, W. M. Bonner, A critical role for histone H2AX in recruitment of repair factors to nuclear foci after DNA damage. Curr Biol 10, 886-895 (2000).

Rogakou et al., *J. Cell. Biol.,* 146:905-916, 1999.

Rogakou, D. R. Pilch, A. H. Orr, V. S. Ivanova, W. M. Bonner, DNA double-stranded breaks induce histone H2AX phosphorylation on serine 139. J Biol Chem 273, 5858-5868 (1998).

Sakai et al., *Genomics,* 30:98-101, 1995.

Sanjana, O. Shalem, F. Zhang, Improved vectors and genome-wide libraries for CRISPR screening. Nat Methods 11, 783-784 (2014).

Seidel et al., *Methods,* 59:301-315, 2013.

Sfeir, L. S. Symington, Microhomology-Mediated End Joining: A Back-up Survival Mechanism or Dedicated Pathway? Trends Biochem Sci 40, 701-714 (2015).

Shalem, N. E. Sanjana, E. Hartenian, X. Shi, D. A. Scott, T. Mikkelson, D. Heckl, B. L. Ebert, D. E. Root, J. G. Doench, F. Zhang, Genome-scale CRISPR-Cas9 knockout screening in human cells. Science 343, 84-87 (2014).

Shen, A. S. Balajee, J. Wang, H. Wu, C. Eng, P. P. Pandolfi, Y. Yin, Essential role for nuclear PTEN in maintaining chromosomal integrity. Cell 128, 157-170 (2007).

Shibata, D. Moiani, A. S. Arvai, J. Perry, S. M. Harding, M. M. Genois, R. Maity, S. van Rossum-Fikkert, A. Kertokalio, F. Romoli, A. Ismail, E. Ismalaj, E. Petricci, M. J. Neale, R. G. Bristow, J. Y. Masson, C. Wyman, P. A. Jeggo, J. A. Tainer, DNA double-strand break repair pathway choice is directed by distinct MRE11 nuclease activities. Mol Cell 53, 7-18 (2014).

Simon et al., *Cell,* 67:701-716, 1991.

Songyang, S. E. Shoelson, J. McGlade, P. Olivier, T. Pawson, X. R. Bustelo, M. Barbacid, H. Sabe, H. Hanafusa, T. Yi, et al., Specific motifs recognized by the SH2 domains of Csk, 3BP2, fps/fes, GRB-2, HCP, SHC, Syk, and Vav. Mol Cell Biol 14, 2777-2785 (1994).

Souza-Fagundes, A. O. Frank, M. D. Feldkamp, D. C. Dorset, W. J. Chazin, O. W. Rossanese, E. T. Olejniczak, S. W. Fesik, A high-throughput fluorescence polarization anisotropy assay for the 70N domain of replication protein A. Anal Biochem 421, 742-749 (2012).

Spycher, E. S. Miller, K. Townsend, L. Pavic, N. A. Morrice, P. Janscak, G. S. Stewart, M. Stucki, Constitutive phosphorylation of MDC1 physically links the MRE11-RAD50-NBS1 complex to damaged chromatin. J Cell Biol 181, 227-240 (2008).

Stucki, J. A. Clapperton, D. Mohammad, M. B. Yaffe, S. J. Smerdon, S. P. Jackson, MDC1 directly binds phosphorylated histone H2AX to regulate cellular responses to DNA double-strand breaks. Cell 123, 1213-1226 (2005).

A. Syed, J. A. Tainer, The MRE11-RAD50-NBS1 Complex Conducts the Orchestration of Damage Signaling and Outcomes to Stress in DNA Replication and Repair. Annu Rev Biochem 87, 263-294 (2018).

Symington, Mechanism and regulation of DNA end resection in eukaryotes. Crit Rev Biochem Mol Biol 51, 195-212 (2016).

Timsah et al., *Oncogene,* 35:2186-2196, 2016.

Verbeek, S. S. Adriaansen-Slot, G. Rijksen, T. M. Vroom, Grb2 overexpression in nuclei and cytoplasm of human breast cells: a histochemical and biochemical study of normal and neoplastic mammary tissue specimens. *J Pathol* 183, 195-203 (1997).

Wagner et al., *Perspect. Biol.,* 5:a008987, 2013.

Wang, M. Goldstein, P. Alexander, T. P. Wakeman, T. Sun, J. Feng, Z. Lou, M. B. Kastan, X. F. Wang, Rad17 recruits the MRE11-RAD50-NBS1 complex to regulate the cellular response to DNA double-strand breaks. *EMBO J* 33, 862-877 (2014).

Williams, G. Moncalian, J. S. Williams, Y. Yamada, O. Limbo, D. S. Shin, L. M. Groocock, D. Cahill, C. Hitomi, G. Guenther, D. Moiani, J. P. Carney, P. Russell, J. A. Tainer, Mre11 dimers coordinate DNA end bridging and nuclease processing in double-strand-break repair. Cell 135, 97-109 (2008).

Williams et al., *DNA Repair,* 9:1299-1306, 2010.

Wu, K. Luo, Z. Lou, J. Chen, MDC1 regulates intra-S-phase checkpoint by targeting NBS1 to DNA double-strand breaks. Proc Natl Acad Sci USA 105, 11200-11205 (2008).

A. Xiao, H. Li, D. Shechter, S. H. Ahn, L. A. Fabrizio, H. Erdjument-Bromage, S. Ishibe-Murakami, B. Wang, P. Tempst, K. Hofmann, D. J. Patel, S. J. Elledge, C. D. Allis, WSTF regulates the H2A.X DNA damage response via a novel tyrosine kinase activity. Nature 457, 57-62 (2009).

Yamazaki, K. Zaal, D. Hailey, J. Presley, J. Lippincott-Schwartz, L. E. Samelson, Role of Grb2 in EGF-stimulated EGFR internalization. *J Cell Sci* 115, 1791-1802 (2002).

Zhong, W. Q. Jiang, A. J. Cesare, A. A. Neumann, R. Wadhwa, R. R. Reddel, Disruption of telomere maintenance by depletion of the MRE11/RAD50/NBS1 complex in cells that use alternative lengthening of telomeres. J Biol Chem 282, 29314-29322 (2007).

What is claimed:

1. A method of treating a homology-directed repair (HDR) proficient breast cancer in a patient, the method comprising determining that the cancer is homology-directed repair (HDR) proficient, and administering to the patient a combined effective amount of a GRB2 inhibitor and a DNA damaging agent or DNA repair inhibitor, wherein the DNA damaging agent or DNA repair inhibitor is a PARP inhibitor and wherein the patient's cancer is HDR proficient.

2. The method of claim 1, further comprising determining if the cancer is expressing high levels of MRE11 relative to a reference level.

3. The method of claim 1, further comprising determining if the cancer is expressing high levels of GRB2 relative to a reference level.

4. The method of claim 1, further comprising determining if the cancer is expressing high levels of GRB2 and high levels of MRE11 relative to reference levels.

5. The method of claim 2, 3, or 4, wherein the reference level is a level in a sample sourced from healthy or non-cancerous tissue from the patient.

6. The method of claim 2, 3, or 4, wherein the reference level is a level in a sample sourced from a healthy subject.

7. The method of claim 1, wherein the GRB2 inhibitor is a small molecule GRB2 inhibitor or an anti-GRB2 inhibitory nucleic acid.

8. The method of claim 1, wherein the PARP inhibitor is olaparib, ABT-888, BSI-201, BMN 673, AG-014699, PF-01367338, AG14361, INO-1001, A-966492, PJ34, MK-4827, or Fluzoparib.

9. The method of claim 1, wherein the GRB2 inhibitor and the DNA damaging agent or DNA repair inhibitor are administered concurrently or essentially simultaneously.

10. The method of claim 1, wherein the GRB2 inhibitor is administered before the DNA damaging agent or DNA repair inhibitor.

11. The method of claim 1, further comprising administering ionizing radiation to the subject.

* * * * *

SEQUENCE LISTING

```
<160> NUMBER OF SEQ ID NOS: 17

<210> SEQ ID NO 1
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 1

ctccttcatg aagggccgag gccac                                             25


<210> SEQ ID NO 2
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 2

cctcggccct tcatgaagga gcaaa                                             25


<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Asp Phe Lys Ala Thr Ala Asp Asp Glu
1               5


<210> SEQ ID NO 4
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: Xaa is phosphorylated serine
<220> FEATURE:
<221> NAME/KEY: MISC_FEATURE
<222> LOCATION: (14)..(14)
<223> OTHER INFORMATION: Xaa is phosphorylated tyrosine

<400> SEQUENCE: 4

Pro Ser Gly Gly Lys Lys Ala Thr Gln Ala Xaa Gln Glu Xaa
1               5                   10


<210> SEQ ID NO 5
```

-continued

<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Trp Val Asn Tyr Gln Asp Gly Asn Leu Asn
1 5 10

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is phosphorylated tyrosine

<400> SEQUENCE: 6

Trp Val Asn Xaa Gln Asp Gly Asn Leu Asn
1 5 10

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is phosphorylated tyrosine

<400> SEQUENCE: 7

Phe Leu Pro Val Pro Glu Xaa Ile Asn Gln Ser Val Pro Lys Arg
1 5 10 15

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

Pro Trp Val Asn Tyr Gln Asp Gly Asn Leu Asn
1 5 10

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is phosphorylated tyrosine

<400> SEQUENCE: 9

Pro Trp Val Asn Xaa Gln Asp Gly Asn Leu Asn
1 5 10

<210> SEQ ID NO 10
<211> LENGTH: 14
<212> TYPE: PRT

<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: Xaa is phosphorylated serine

<400> SEQUENCE: 10

Pro Ser Gly Gly Lys Lys Ala Thr Gln Ala Xaa Gln Glu Tyr
1 5 10

<210> SEQ ID NO 11
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: Xaa is phosphorylated tyrosine

<400> SEQUENCE: 11

Pro Ser Gly Gly Lys Lys Ala Thr Gln Ala Ser Gln Glu Xaa
1 5 10

<210> SEQ ID NO 12
<211> LENGTH: 17
<212> TYPE: PRT
<213> ORGANISM: Artificial Sequence
<220> FEATURE:
<223> OTHER INFORMATION: Synthetic peptide

<400> SEQUENCE: 12

Lys Tyr Asp Phe Lys Ala Thr Ala Asp Asp Glu Leu Ser Phe Lys Arg
1 5 10 15

Gly

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Pro Trp Val Asn Tyr Gln Asp Gly Asn
1 5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Asn Pro Val Tyr His Asn Gln Pro Leu
1 5

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide -continued

```
<400> SEQUENCE: 15

Ser Gln Glu Tyr
1


<210> SEQ ID NO 16
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 16

caccggagcc ggaagtcttc ctc                                    23


<210> SEQ ID NO 17
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 17

aaacgaggaa gtacttcccg gctcc                                  25
```